US011124835B2

(12) United States Patent
Ziesche

(10) Patent No.: US 11,124,835 B2
(45) **Date of Patent: *Sep. 21, 2021**

(54) METHODS OF DIAGNOSING CHRONIC OBSTRUCTIVE PULMONARY DISEASE (COPD) USING NOVEL MOLECULAR BIOMARKERS

(71) Applicant: Transgenion—International Institute for Regenerative Translational Medicine GmbH, Vienna (AT)

(72) Inventor: Rolf Ziesche, Neusiedl am See (AT)

(73) Assignee: Transgenion—International Institute for Regenerative Translational Medicine GmbH, Vienna (AT)

( * ) Notice: Subject to any disclaimer, the term of this patent is extended or adjusted under 35 U.S.C. 154(b) by 19 days.

This patent is subject to a terminal disclaimer.

(21) Appl. No.: 16/507,945

(22) Filed: Jul. 10, 2019

(65) Prior Publication Data

US 2020/0017914 A1 Jan. 16, 2020

Related U.S. Application Data

(62) Division of application No. 15/316,105, filed as application No. PCT/EP2015/062431 on Jun. 3, 2015, now Pat. No. 10,508,307.

(30) Foreign Application Priority Data

Jun. 5, 2014 (EP) .................................... 14171388

(51) Int. Cl.

*C12Q 1/6883* (2018.01)
*G01N 33/68* (2006.01)
*A61K 31/44* (2006.01)

(52) U.S. Cl.

CPC ............ *C12Q 1/6883* (2013.01); *A61K 31/44* (2013.01); *G01N 33/6893* (2013.01); *C12Q 2600/112* (2013.01); *C12Q 2600/118* (2013.01); *C12Q 2600/158* (2013.01); *G01N 2333/47* (2013.01); *G01N 2800/122* (2013.01); *G01N 2800/50* (2013.01)

(58) Field of Classification Search

CPC ............ C12Q 1/6883; C12Q 2600/118; C12Q 2600/158; G01N 2800/50; G01N 2800/122

See application file for complete search history.

(56) References Cited

U.S. PATENT DOCUMENTS

| | | | |
|---|---|---|---|
| 2005/0208496 | A1 | 9/2005 | Ohtani et al. |
| 2013/0095110 | A1 | 4/2013 | Yoshida et al. |
| 2013/0165343 | A1 | 6/2013 | Robinson et al. |
| 2013/0324428 | A1 | 12/2013 | Ryu et al. |
| 2017/0335393 | A1 | 11/2017 | Ziesche |
| 2017/0349947 | A1 | 12/2017 | Ziesche |

FOREIGN PATENT DOCUMENTS

| | | |
|---|---|---|
| JP | 2013-35871 | 2/2013 |
| WO | WO 2008/003701 | 1/2008 |
| WO | WO 2010/064702 | 6/2010 |
| WO | WO 2013/104990 | 7/2013 |

(Continued)

OTHER PUBLICATIONS

Palmer et al. BMC Genomics. 2006. 7:115. (Year: 2006).*
Min et al. BMC Genomics. 2010. 11:96. (Year: 2010).*
Chen et al. Journal of Proteomics. 2012. 75:2835-2843. (Year: 2012).*
Affymetrix Inc. Human Genome U95 Set. GeneChip® Human Genome U95 Set, available via URL: <tools.thermofisher.com/content/sfs/brochures/hgu95_datasheet.pdf>, 2001-2003, printed on Jan. 8, 2019, pp. 1-2.
Affymetrix NetAffx. Expression Probeset Details for Human Genome U95 Sets for the KIA 1199, TMSB15A, and DMBT1 genes, available via URL: <affymetrix.com/analysis/netaffx/xmlquery.affx?netaffx=netaffx4_annot>, printed on Jan. 8, 2019, 14 pages.

(Continued)

*Primary Examiner* — Joseph G. Dauner
(74) *Attorney, Agent, or Firm* — Parker Highlander PLLC

(57) ABSTRACT

The present invention relates to in vitro methods for the diagnosis of chronic obstructive pulmonary disease (COPD), wherein the expression of the marker gene DMBT1 is determined. In particular, the invention relates to an in vitro diagnostic method of assessing the susceptibility of a subject to develop progressive COPD involving the appearance of irreversible lung damage, wherein the expression of the marker gene DMBT1 and optionally one or more further marker genes selected from KIAA1199, TMSB15A, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL is determined. The invention also relates to an in vitro method of diagnosing stable COPD or assessing the susceptibility of a subject to develop stable COPD, wherein the expression of DMBT1 and optionally one or more further marker genes selected from KIAA1199, TMSB15A, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL is determined. Furthermore, the invention relates to the use of primers for transcripts of the aforementioned marker genes, the use of nucleic acid probes to transcripts of these marker genes, the use of microarrays comprising nucleic acid probes to transcripts of these marker genes, and the use of antibodies against the proteins expressed from these marker genes in corresponding in vitro methods. In vitro methods of monitoring the progression of COPD are also provided, in which the expression of marker genes according to the invention is determined.

10 Claims, 28 Drawing Sheets

Figure 1:
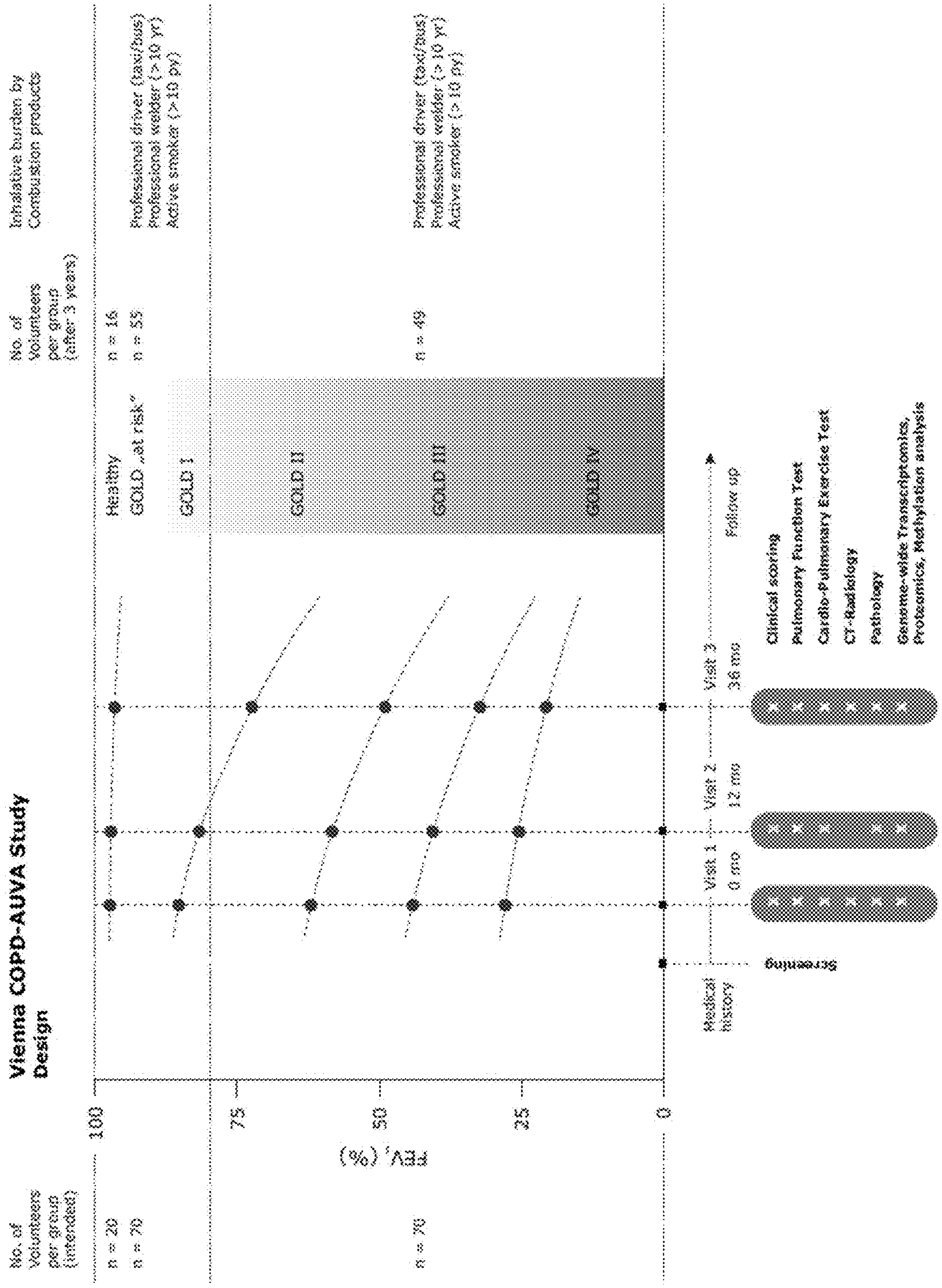

Specification includes a Sequence Listing.

(56) References Cited

FOREIGN PATENT DOCUMENTS

| | | |
|---|---|---|
| WO | WO 2013/177060 | 11/2013 |
| WO | WO 2013/190092 | 12/2013 |

OTHER PUBLICATIONS

Bahr et al. "Peripheral blood mononuclear cell gene expression in chronic obstructive pulmonary disease." *American Journal of Respiratory Cell and Molecular Biology*, 49(2) (2013): 316-323.
Banyard et al., "Differential regulation of human thymosin beta 15 isoforms by transforming growth factor beta 1", *Genes Chromosomes Cancer*, 48(6):502-509, 2009.
Baye, "Roflumilast (daliresp): a novel phosphodiesterase-4 inhibitor for the treatment of severe chronic obstructive pulmonary disease." *Pharmacy and Therapeutics*, 37.3 (2012): 149-161.
Bhattacharya et al., "Molecular biomarkers for quantitative and discrete COPD phenotypes," *American Journal of Respiratory and Cell and Molecular Biology*, 40(3):359-367, 2009.
Calverley et al. "Effect of 1-year treatment with roflumilast in severe chronic obstructive pulmonary disease." *American Journal of Respiratory and Critical Care Medicine*, 176.2 (2007): 154-161.
Calverley, et al. "Roflumilast in symptomatic chronic obstructive pulmonary disease: two randomised clinical trials." *The Lancet*, 374.9691 (2009): 685-694.
Chan, "Integrating transcriptomics and proteomics," *G&P Magazine*, 6(3):20-26, 2006.
Chen et al., "Discordant protein and mRNA expression in lung adenocarcinomas", *Mol. Cell. Proteomics*, 1:304-313, 2002.
Coleman, "Of mouse and man—what is the value of the mouse in predicting gene expression in humans?", *Drug Discov. Today*, 8(6):233-235, 2003.
Gosselink et al., "Differential expression of tissue repair genes in the pathogenesis of chronic obstructive pulmonary disease," *American Journal of Respiratory and Critical Care Medicine*, 181(12):1329-1335, 2010.
Haynes et al., "Proteome analysis: biological assay or data archive?" *Electrophoresis*, 19:1862-1871, 1998.
Hoshikawa, et al. "Hypoxia induces different genes in the lungs of rats compared with mice." *Physiological Genomics*, 12.3 (2003): 209-219.
Kendrick, "A gene's mRNA level does not usually predict its protein level." *Madison: Kendricklabscom* (2014).
Liu et al., "Comparison of differentially expressed genes in T lymphocytes between human autoimmune disease and murine models of autoimmune disease", *Clin. Immunol.*, 112:225-230, 2004.
Llinàs et al. "Similar gene expression profiles in smokers and patients with moderate COPD." *Pulmonary Pharmacology & Therapeutics* 24.1 (2011): 32-41.
Maier et al., "Correlation of mRNA and protein in complex biological samples." *FEBS letters* 583.24 (2009): 3966-3973.
Min et al., "Variability of gene expression profiles in human blood and lymphoblastoid cell lines", *BMC Genomics*, 11:96, 2010.
Office Action issued in Japanese Application No. 2017-516196, dated Jun. 4, 2019.
Office Action issued in U.S. Appl. No. 15/316,105, dated May 29, 2018.
Office Action issued in U.S. Appl. No. 15/316,105, dated Dec. 27, 2018.
Palmer, "Cell-type specific gene expression profiles of leukocytes in human peripheral blood", *BMC Genomics*, 7:115, 2006.
Pascal et al. "Correlation of mRNA and protein levels: cell type-specific gene expression of cluster designation antigens in the prostate." *BMC Genomics* 9.1 (2008): 246.
PCT International Preliminary Report on Patentability issued in International Application No. PCT/EP2015/062431, dated Dec. 15, 2016.
PCT International Search Report and Written Opinion issued in International Application No. PCT/EP2015/062431, dated Sep. 14, 2015.
Rabe et al. "Roflumilast—an oral anti-inflammatoity treatment for chronic obstructive pulmonary disease: a randomised controlled trial," *The Lancet*, 366.9485 (2005): 563-571.
Renner et al. "DMBT1 confers mucosal protection in vivo and a deletion variant is associated with Crohn's disease." *Gastroenterology* 133.5 (2007): 1499-1509.
Richens et al., "Systems biology coupled with label-free high-throughput detection as a novel approach for diagnosis of chronic obstructive pulmonary disease," *Respiratory Research*, 10(1):29, 2009.
Saito-Hisaminato et al. "Genome-wide profiling of gene, expression in 29 normal human tissues with a cDNA microarray." *DNA Research*, 9.2 (2002): 35-45.
Savarimuthu et al., "Genes and gene ontologies common to airflow obstruction and emphysema in the lungs of patients with COPD," *PLOS ONE*, 6(3):e17442, 2011.
Spira et al. "Gene expression profiling of human lung tissue from smokers with severe emphysema." *American Journal of Respiratory Cell and Molecular Biology* 31.6 (2004): 601-610.
Steiling et al., "A dynamic bronchial airway gene expression signature of chronic obstructive pulmonary disease and lung function impairment," *American Journal of Respiratory and Critical Care Medicine*, 187(9):933-942, 2013.
Steiling et al., "Personalized management of chronic obstructive pulmonary disease via transcriptomic profiling of the airway and lung." *Annals of the American Thoracic Society* 10. Supplement (2013): S190-S196.
Van den Berge et al. "Airway gene expression in COPD is dynamic with inhaled corticosteroid treatment and reflects biological pathways associated with disease activity." *Thorax*, 69.1 (2014): 14-23.
Vogel et al., "Insights into the regulation of protein abundance from proteomic and transcriptomic analyses", *Nat. Rev. Genet.*, 13(4):227-232, 2012.
Whitehead and Crawford, "Variation in tissue-specific gene expression among natural populations." *Genome Biology* 6.2 (2005): R13.

* cited by examiner

Fig. 3A

Healthy participants

| | | | Clinical strata | Age | GOLD | | | Bronchitis & Phlegm | | | Pack Years | Smoking habits | | |
|---|---|---|---|---|---|---|---|---|---|---|---|---|---|---|
| Initials | Gender | ID | Healthy controls | | V1 | V2 | V3 | V1 | V2 | V3 | Total | V1 | V2 | V3 |
| AC | F | 145 | Healthy | 40.2 | 0 | 0 | 0 | n.a. | n.a. | n.a. | n.a. | -1 | -1 | -1 |
| BR | M | 24 | Healthy | 38.3 | 0 | 0 | 0 | n.a. | n.a. | n.a. | n.a. | -1 | -1 | -1 |
| GI | F | 159 | Healthy | 24.2 | 0 | 0 | 0 | n.a. | n.a. | n.a. | n.a. | -1 | -1 | -1 |
| HO | F | 44 | Healthy | 33.0 | 0 | 0 | 0 | n.a. | n.a. | n.a. | n.a. | -1 | -1 | -1 |
| KH | M | 35 | Healthy | 62.7 | 0 | 0 | 0 | n.a. | n.a. | n.a. | n.a. | -1 | -1 | -1 |
| LR | F | 161 | Healthy | 33.3 | 0 | 0 | 0 | n.a. | n.a. | n.a. | n.a. | -1 | -1 | -1 |
| MA | F | 158 | Healthy | 24.2 | 0 | 0 | 0 | n.a. | n.a. | n.a. | n.a. | -1 | -1 | -1 |
| MO | F | 31 | Healthy | 43.5 | 0 | 0 | 0 | n.a. | n.a. | n.a. | n.a. | -1 | -1 | -1 |
| SE | M | 57 | Healthy | 35.6 | 0 | 0 | 0 | n.a. | n.a. | n.a. | n.a. | -1 | -1 | -1 |
| SH | M | 23 | Healthy | 45.2 | 0 | 0 | 0 | n.a. | n.a. | n.a. | n.a. | -1 | -1 | -1 |
| SS | M | 34 | Healthy | 27.2 | 0 | 0 | 0 | n.a. | n.a. | n.a. | n.a. | -1 | -1 | -1 |
| TK | F | 163 | Healthy | 24.6 | 0 | 0 | 0 | n.a. | n.a. | n.a. | n.a. | -1 | -1 | -1 |
| TT | M | 50 | Healthy | 58.9 | 0 | 0 | 0 | n.a. | n.a. | n.a. | n.a. | -1 | -1 | -1 |
| WH | M | 123 | Healthy | 27.0 | 0 | 0 | 0 | n.a. | n.a. | n.a. | n.a. | -1 | -1 | -1 |
| WW | M | 155 | Healthy | 28.2 | 0 | 0 | 0 | n.a. | n.a. | n.a. | n.a. | -1 | -1 | -1 |
| ZB | M | 128 | Healthy | 28.0 | 0 | 0 | 0 | n.a. | n.a. | n.a. | n.a. | -1 | -1 | -1 |
| | n | 16 | Age (yrs, mean) | 36.4 | | | | | | | | | | |

Fig. 3B

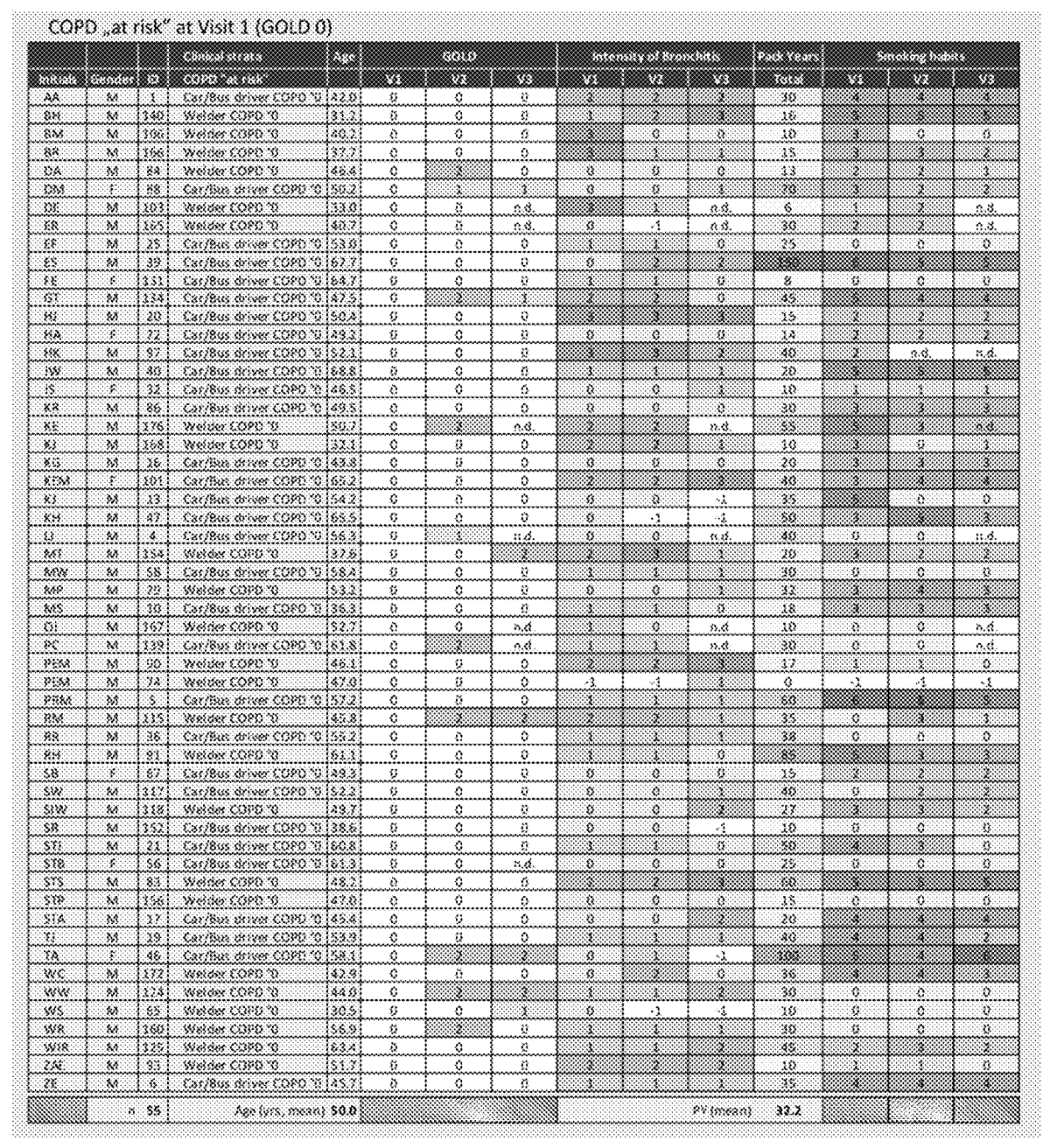

COPD „at risk" at Visit 1 (GOLD 0)

| | | | Clinical strata | Age | GOLD | | | Intensity of Bronchitis | | | Pack Years | Smoking habits | | |
|---|---|---|---|---|---|---|---|---|---|---|---|---|---|---|
| Initials | Gender | ID | COPD "at risk" | | V1 | V2 | V3 | V1 | V2 | V3 | Total | V1 | V2 | V3 |
| AA | M | 1 | Car/Bus driver COPD °0 | 42.0 | 0 | 0 | 0 | 3 | 2 | 3 | 30 | 4 | 4 | 4 |
| BH | M | 140 | Welder COPD °0 | 31.2 | 0 | 0 | 0 | 1 | 2 | 3 | 16 | 3 | 3 | 3 |
| BM | M | 196 | Welder COPD °0 | 40.2 | 0 | 0 | 0 | 3 | 0 | 0 | 10 | 3 | 0 | 0 |
| BR | M | 166 | Welder COPD °0 | 37.7 | 0 | 0 | 0 | 3 | 1 | 1 | 15 | 3 | 3 | 2 |
| DA | M | 84 | Welder COPD °0 | 46.4 | 0 | 1 | 0 | 0 | 0 | 0 | 13 | 2 | 1 | 1 |
| DM | F | 88 | Car/Bus driver COPD °0 | 50.2 | 0 | 1 | 1 | 0 | 0 | 1 | 38 | 3 | 2 | 2 |
| DE | M | 103 | Welder COPD °0 | 33.0 | 0 | 0 | n.d. | 3 | 1 | n.d. | 6 | 1 | 2 | n.d. |
| ER | M | 165 | Welder COPD °0 | 40.7 | 0 | 0 | n.d. | 0 | -1 | n.d. | 30 | 2 | 2 | n.d. |
| EF | M | 25 | Car/Bus driver COPD °0 | 53.0 | 0 | 0 | 0 | 1 | 1 | 0 | 25 | 0 | 0 | 0 |
| ES | M | 39 | Car/Bus driver COPD °0 | 67.7 | 0 | 0 | 0 | 0 | 2 | 2 | 100 | 3 | 3 | 3 |
| FE | F | 131 | Car/Bus driver COPD °0 | 64.7 | 0 | 0 | 0 | 1 | 1 | 0 | 8 | 0 | 0 | 0 |
| GT | M | 134 | Car/Bus driver COPD °0 | 47.5 | 0 | 2 | 1 | 2 | 2 | 0 | 45 | 3 | 4 | 3 |
| HI | M | 20 | Car/Bus driver COPD °0 | 50.4 | 0 | 0 | 0 | 3 | 3 | 3 | 15 | 2 | 2 | 2 |
| HA | F | 72 | Car/Bus driver COPD °0 | 49.3 | 0 | 0 | 0 | 0 | 0 | 0 | 14 | 2 | 2 | 2 |
| HK | M | 97 | Car/Bus driver COPD °0 | 52.3 | 0 | 0 | 0 | 3 | 3 | 2 | 40 | 2 | n.d. | n.d. |
| JW | M | 40 | Car/Bus driver COPD °0 | 68.8 | 0 | 0 | 0 | 1 | 1 | 1 | 20 | 3 | 3 | 3 |
| JS | F | 32 | Car/Bus driver COPD °0 | 46.5 | 0 | 0 | 0 | 0 | 0 | 1 | 10 | 1 | 1 | 1 |
| KR | M | 86 | Car/Bus driver COPD °0 | 49.5 | 0 | 0 | 0 | 0 | 0 | 0 | 30 | 3 | 3 | 3 |
| KE | M | 176 | Welder COPD °0 | 50.7 | 0 | 3 | n.d. | 2 | 3 | n.d. | 55 | 3 | 3 | n.d. |
| KJ | M | 168 | Welder COPD °0 | 37.1 | 0 | 0 | 0 | 2 | 2 | 1 | 10 | 3 | 0 | 1 |
| KG | M | 16 | Car/Bus driver COPD °0 | 43.8 | 0 | 0 | 0 | 0 | 0 | 0 | 20 | 3 | 3 | 3 |
| KEM | F | 101 | Car/Bus driver COPD °0 | 65.2 | 0 | 0 | 0 | 2 | 2 | 3 | 40 | 3 | 4 | 4 |
| KJ | M | 13 | Car/Bus driver COPD °0 | 54.2 | 0 | 0 | 0 | 0 | 0 | -1 | 35 | 3 | 0 | 0 |
| KH | M | 47 | Car/Bus driver COPD °0 | 65.5 | 0 | 0 | 0 | 0 | -1 | -1 | 50 | 3 | 3 | 3 |
| LJ | M | 4 | Car/Bus driver COPD °0 | 56.3 | 0 | 1 | n.d. | 0 | 0 | n.d. | 40 | 0 | 0 | n.d. |
| MT | M | 154 | Welder COPD °0 | 37.6 | 0 | 0 | 2 | 2 | 3 | 1 | 20 | 3 | 2 | 2 |
| MW | M | 58 | Car/Bus driver COPD °0 | 58.4 | 0 | 0 | 0 | 1 | 1 | 1 | 30 | 0 | 0 | 0 |
| MP | M | 79 | Welder COPD °0 | 53.3 | 0 | 0 | 0 | 0 | 0 | 1 | 33 | 3 | 4 | 3 |
| MS | M | 10 | Car/Bus driver COPD °0 | 36.3 | 0 | 0 | 0 | 1 | 1 | 0 | 18 | 3 | 3 | 3 |
| OI | M | 167 | Welder COPD °0 | 52.7 | 0 | 0 | n.d. | 1 | 0 | n.d | 10 | 0 | 0 | n.d. |
| PC | M | 139 | Car/Bus driver COPD °0 | 61.8 | 0 | 2 | n.d. | 1 | 1 | n.d | 30 | 0 | 0 | n.d. |
| PEM | M | 90 | Welder COPD °0 | 46.1 | 0 | 0 | 0 | 2 | 3 | 3 | 17 | 1 | 1 | 0 |
| PEM | M | 74 | Welder COPD °0 | 47.0 | 0 | 0 | 0 | -1 | -1 | 1 | 0 | -1 | -1 | -1 |
| PRM | M | 5 | Car/Bus driver COPD °0 | 57.2 | 0 | 0 | 0 | 1 | 1 | 1 | 60 | 4 | 3 | 3 |
| RM | M | 115 | Welder COPD °0 | 45.8 | 0 | 2 | 2 | 2 | 2 | 1 | 35 | 0 | 3 | 1 |
| RR | M | 36 | Car/Bus driver COPD °0 | 55.2 | 0 | 0 | 0 | 1 | 1 | 1 | 38 | 0 | 0 | 0 |
| RH | M | 91 | Welder COPD °0 | 61.1 | 0 | 0 | 0 | 1 | 1 | 0 | 85 | 3 | 3 | 3 |
| SB | F | 67 | Car/Bus driver COPD °0 | 49.3 | 0 | 0 | 0 | 0 | 0 | 0 | 15 | 2 | 2 | 2 |
| SW | M | 117 | Car/Bus driver COPD °0 | 52.2 | 0 | 0 | 0 | 0 | 0 | 1 | 40 | 0 | 2 | 2 |
| SIW | M | 118 | Welder COPD °0 | 49.7 | 0 | 0 | 0 | 0 | 0 | 2 | 27 | 3 | 3 | 2 |
| SR | M | 152 | Car/Bus driver COPD °0 | 38.6 | 0 | 0 | 0 | 0 | 0 | -1 | 10 | 0 | 0 | 0 |
| STI | M | 21 | Car/Bus driver COPD °0 | 60.8 | 0 | 0 | 0 | 1 | 1 | 0 | 50 | 4 | 3 | 0 |
| STB | F | 56 | Car/Bus driver COPD °0 | 61.3 | 0 | 0 | n.d. | 0 | 0 | 0 | 25 | 0 | 0 | 0 |
| STS | M | 83 | Welder COPD °0 | 48.2 | 0 | 0 | 0 | 3 | 2 | 3 | 60 | 3 | 3 | 3 |
| STP | M | 156 | Welder COPD °0 | 47.0 | 0 | 0 | 0 | 0 | 0 | 0 | 15 | 0 | 0 | 0 |
| STA | M | 17 | Car/Bus driver COPD °0 | 45.4 | 0 | 0 | 0 | 0 | 0 | 2 | 20 | 4 | 4 | 4 |
| TJ | M | 19 | Car/Bus driver COPD °0 | 53.3 | 0 | 0 | 0 | 1 | 1 | 1 | 40 | 4 | 4 | 2 |
| TA | F | 46 | Car/Bus driver COPD °0 | 58.1 | 0 | 2 | 2 | 0 | 1 | -1 | 100 | 3 | 4 | 4 |
| WC | M | 172 | Welder COPD °0 | 42.9 | 0 | 0 | 0 | 0 | 2 | 0 | 36 | 4 | 4 | 3 |
| WW | M | 124 | Welder COPD °0 | 44.0 | 0 | 2 | 2 | 1 | 1 | 2 | 30 | 0 | 0 | 0 |
| WS | M | 65 | Welder COPD °0 | 30.5 | 0 | 0 | 1 | 0 | -1 | -1 | 10 | 0 | 0 | 0 |
| WR | M | 160 | Welder COPD °0 | 56.9 | 0 | 2 | 0 | 1 | 1 | 1 | 30 | 0 | 0 | 0 |
| WIR | M | 125 | Welder COPD °0 | 63.4 | 0 | 0 | 0 | 1 | 1 | 2 | 45 | 2 | 3 | 2 |
| ZAE | M | 93 | Welder COPD °0 | 51.7 | 0 | 0 | 0 | 3 | 2 | 2 | 10 | 1 | 1 | 0 |
| ZE | M | 6 | Car/Bus driver COPD °0 | 45.7 | 0 | 0 | 0 | 1 | 1 | 1 | 35 | 4 | 3 | 4 |
| | n | 55 | Age (yrs, mean) | 50.0 | | | | | | PY (mean) | 32.2 | | | |

Fig. 3C

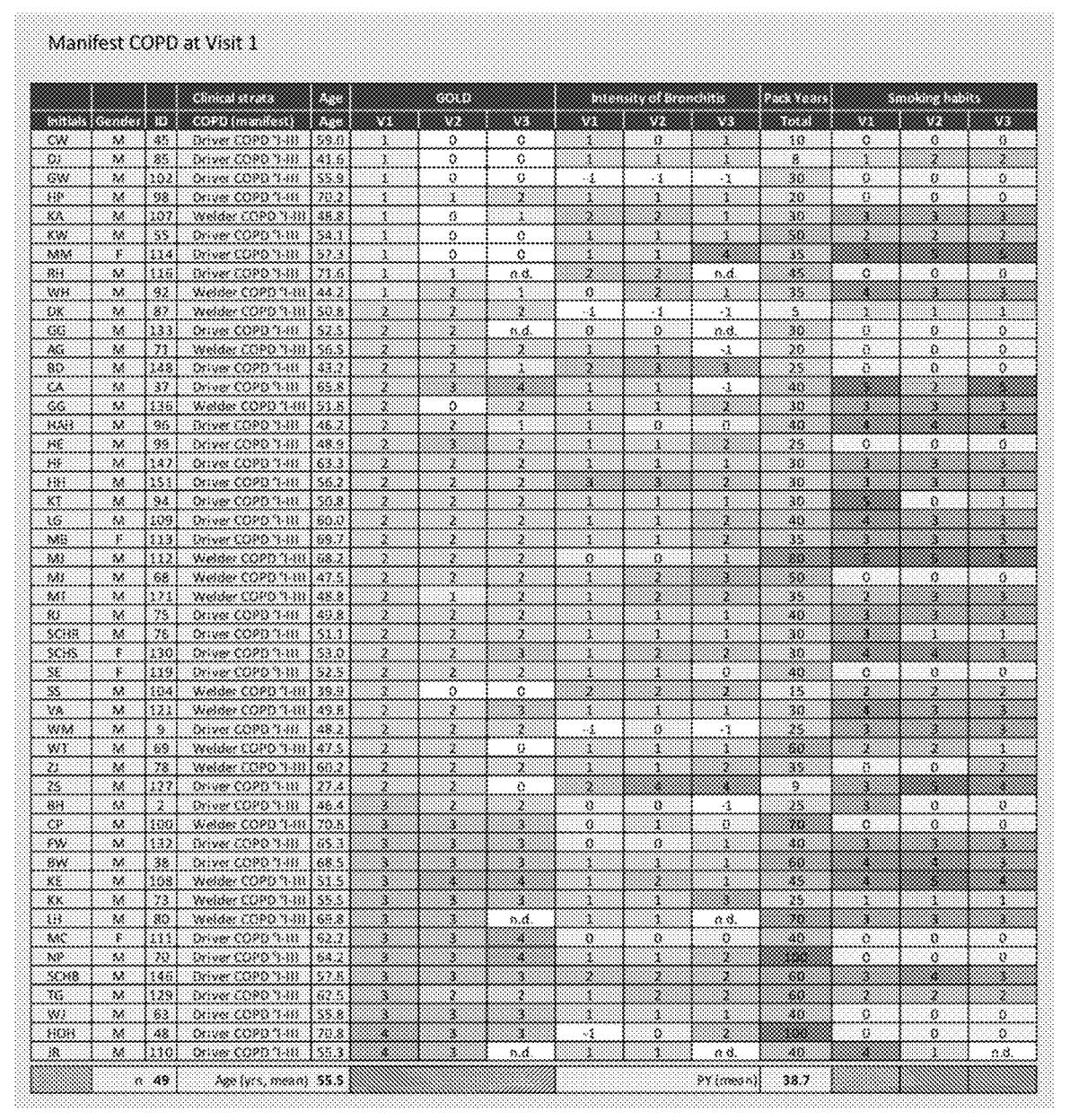

Manifest COPD at Visit 1

| | | | Clinical strata | Age | GOLD | | | Intensity of Bronchitis | | | Pack Years | Smoking habits | | |
|---|---|---|---|---|---|---|---|---|---|---|---|---|---|---|
| Initials | Gender | ID | COPD (manifest) | Age | V1 | V2 | V3 | V1 | V2 | V3 | Total | V1 | V2 | V3 |
| CW | M | 45 | Driver COPD I-III | 59.0 | 1 | 0 | 0 | 1 | 0 | 1 | 10 | 0 | 0 | 0 |
| DJ | M | 85 | Driver COPD I-III | 41.6 | 1 | 0 | 0 | 1 | 1 | 1 | 8 | 1 | 2 | 2 |
| GW | M | 102 | Driver COPD I-III | 55.9 | 1 | 0 | 0 | -1 | -1 | -1 | 30 | 0 | 0 | 0 |
| HP | M | 98 | Driver COPD I-III | 70.2 | 1 | 1 | 2 | 1 | 1 | 1 | 20 | 0 | 0 | 0 |
| KA | M | 107 | Welder COPD I-III | 48.8 | 1 | 0 | 1 | 2 | 2 | 1 | 30 | 3 | 3 | 3 |
| KW | M | 55 | Driver COPD I-III | 54.1 | 1 | 0 | 0 | 1 | 1 | 1 | 50 | 2 | 2 | 2 |
| MM | F | 114 | Driver COPD I-III | 57.3 | 1 | 0 | 0 | 1 | 1 | 4 | 35 | 4 | 4 | 4 |
| RH | M | 116 | Driver COPD I-III | 71.6 | 1 | 1 | n.d. | 2 | 2 | n.d. | 45 | 0 | 0 | 0 |
| WH | M | 92 | Welder COPD I-III | 44.2 | 1 | 2 | 1 | 0 | 2 | 1 | 35 | 4 | 3 | 3 |
| DK | M | 87 | Welder COPD I-III | 50.8 | 2 | 2 | 2 | -1 | -1 | -1 | 5 | 1 | 1 | 1 |
| GG | M | 133 | Driver COPD I-III | 52.5 | 2 | 2 | n.d. | 0 | 0 | n.d. | 30 | 0 | 0 | 0 |
| AG | M | 71 | Welder COPD I-III | 56.5 | 2 | 2 | 2 | 1 | 1 | -1 | 20 | 0 | 0 | 0 |
| BD | M | 148 | Driver COPD I-III | 43.2 | 2 | 2 | 1 | 2 | 3 | 3 | 25 | 0 | 0 | 0 |
| CA | M | 37 | Driver COPD I-III | 65.8 | 2 | 3 | 4 | 1 | 1 | -1 | 40 | 4 | 2 | 4 |
| GG | M | 136 | Welder COPD I-III | 51.8 | 2 | 0 | 2 | 1 | 1 | 2 | 30 | 3 | 3 | 3 |
| HAH | M | 96 | Driver COPD I-III | 46.2 | 2 | 2 | 1 | 1 | 0 | 0 | 30 | 4 | 4 | 4 |
| HE | M | 99 | Driver COPD I-III | 48.9 | 2 | 3 | 2 | 1 | 1 | 2 | 25 | 0 | 0 | 0 |
| HF | M | 147 | Driver COPD I-III | 63.3 | 2 | 2 | 2 | 1 | 1 | 1 | 30 | 3 | 3 | 3 |
| HH | M | 151 | Driver COPD I-III | 56.2 | 2 | 2 | 2 | 3 | 3 | 2 | 30 | 3 | 3 | 3 |
| KT | M | 94 | Driver COPD I-III | 50.8 | 2 | 2 | 2 | 1 | 1 | 1 | 30 | 4 | 0 | 1 |
| LG | M | 109 | Driver COPD I-III | 60.0 | 2 | 2 | 2 | 1 | 1 | 2 | 40 | 3 | 3 | 3 |
| MB | F | 113 | Driver COPD I-III | 69.7 | 2 | 2 | 2 | 1 | 1 | 2 | 35 | 3 | 3 | 3 |
| MJ | M | 112 | Welder COPD I-III | 68.2 | 2 | 2 | 2 | 0 | 0 | 1 | 80 | 4 | 4 | 4 |
| MJ | M | 68 | Welder COPD I-III | 47.5 | 2 | 2 | 2 | 1 | 2 | 3 | 50 | 0 | 0 | 0 |
| MT | M | 171 | Welder COPD I-III | 48.8 | 2 | 1 | 2 | 1 | 2 | 2 | 35 | 3 | 3 | 3 |
| RJ | M | 75 | Driver COPD I-III | 49.8 | 2 | 2 | 2 | 1 | 1 | 1 | 40 | 3 | 3 | 3 |
| SCHR | M | 76 | Driver COPD I-III | 51.1 | 2 | 2 | 2 | 1 | 1 | 1 | 30 | 3 | 1 | 1 |
| SCHS | F | 130 | Driver COPD I-III | 53.0 | 2 | 2 | 3 | 1 | 2 | 2 | 30 | 3 | 4 | 3 |
| SE | F | 119 | Driver COPD I-III | 52.5 | 2 | 2 | 2 | 1 | 1 | 0 | 40 | 0 | 0 | 0 |
| SS | M | 104 | Welder COPD I-III | 39.9 | 2 | 0 | 0 | 2 | 2 | 2 | 15 | 2 | 2 | 2 |
| VA | M | 121 | Welder COPD I-III | 49.8 | 2 | 2 | 3 | 1 | 1 | 1 | 30 | 3 | 3 | 3 |
| WM | M | 9 | Driver COPD I-III | 48.2 | 2 | 2 | 2 | -1 | 0 | -1 | 25 | 3 | 3 | 3 |
| WT | M | 69 | Welder COPD I-III | 47.5 | 2 | 2 | 0 | 1 | 1 | 1 | 60 | 2 | 3 | 1 |
| ZJ | M | 78 | Welder COPD I-III | 60.2 | 2 | 2 | 2 | 1 | 1 | 2 | 35 | 0 | 0 | 2 |
| ZS | M | 177 | Driver COPD I-III | 27.4 | 2 | 2 | 0 | 2 | 3 | 4 | 9 | 3 | 4 | 3 |
| BH | M | 2 | Driver COPD I-III | 46.4 | 3 | 2 | 2 | 0 | 0 | -1 | 25 | 3 | 0 | 0 |
| CP | M | 100 | Welder COPD I-III | 70.6 | 3 | 3 | 3 | 0 | 1 | 0 | 70 | 0 | 0 | 0 |
| FW | M | 132 | Driver COPD I-III | 65.3 | 3 | 3 | 3 | 0 | 0 | 1 | 40 | 3 | 3 | 3 |
| BW | M | 38 | Driver COPD I-III | 68.5 | 3 | 3 | 3 | 1 | 1 | 1 | 60 | 3 | 3 | 3 |
| KE | M | 108 | Welder COPD I-III | 51.5 | 3 | 4 | 4 | 1 | 2 | 1 | 45 | 3 | 4 | 4 |
| KK | M | 73 | Welder COPD I-III | 55.5 | 3 | 3 | 3 | 1 | 1 | 3 | 25 | 1 | 1 | 1 |
| LH | M | 80 | Welder COPD I-III | 69.8 | 3 | 3 | n.d. | 1 | 1 | n.d. | 70 | 3 | 3 | 3 |
| MC | F | 111 | Driver COPD I-III | 62.7 | 3 | 3 | 4 | 0 | 0 | 0 | 40 | 0 | 0 | 0 |
| NP | M | 70 | Driver COPD I-III | 64.2 | 3 | 3 | 4 | 1 | 1 | 2 | 100 | 0 | 0 | 0 |
| SCHB | M | 146 | Driver COPD I-III | 57.6 | 3 | 3 | 3 | 2 | 2 | 2 | 60 | 3 | 4 | 3 |
| TG | M | 129 | Driver COPD I-III | 67.5 | 3 | 3 | 2 | 1 | 2 | 2 | 60 | 2 | 2 | 2 |
| WJ | M | 63 | Driver COPD I-III | 55.8 | 3 | 3 | 3 | 1 | 1 | 1 | 40 | 0 | 0 | 0 |
| HOH | M | 48 | Driver COPD I-III | 70.8 | 4 | 3 | 3 | -1 | 0 | 2 | 100 | 0 | 0 | 0 |
| JR | M | 110 | Driver COPD I-III | 55.3 | 4 | 3 | n.d. | 1 | 1 | n.d. | 40 | 4 | 1 | n.d. |
| | n | 49 | Age (yrs, mean) | 55.5 | | | | | | PY (mean) | 38.7 | | | |

| No. of participants | | Healthy 16 | GOLD at risk 55 | GOLD I 9 | | GOLD II 26 | | GOLD III 12 | | GOLD IV 2 | | | Total 120 |
|---|---|---|---|---|---|---|---|---|---|---|---|---|---|
| Age | | 36 ± 12.2 | 50 ± 9.5 | 56 ± 10.4 | p=0.083 | 52 ± 9.0 | p=0.304 | 61 ± 7.6 | p= 0.0004 | 63 ± 11.0 | p=0.054 | | |
| Packyears | | 0 | 32 ± 26 | 29 ± 15 | p=0.729 | 33 ± 15 | p=0.815 | 53 ± 21 | p=0.004 | 70 ± 42 | p=0.022 | | |
| Gender | F | 7 (44%) | 8 (15%) | 1 (11%) | | 3 (12%) | | 1 (88%) | | 0 | | p=0.931 | 20 (17%) |
| | M | 9 (56%) | 47 (85%) | 8 (89%) | | 23 (88%) | | 11 (92%) | | 2 (100%) | | | 100 (83%) |
| Occupation | Control (healthy) | 16 | 0 | 0 | | 0 | | 0 | | 0 | | p=0.594 | 16 (13%) |
| | Taxi/Bus driver | 0 | 31 (56%) | 7 (78%) | | 16 (62%) | | 8 (67%) | | 2 (100%) | | | 64 (53%) |
| | Welder | 0 | 24 (44%) | 2 (22%) | | 10 (38%) | | 4 (33%) | | 0 | | | 40 (33%) |
| Symptoms of chronic bronchitis (Cough & Phlegm) | No symptoms | 16 (100%) | 0 | 0 | | 0 | | 0 | | 0 | | p=0.054 | 16 (13%) |
| | frequently dry | 0 | 24 (44%) | 2 (22%) | | 4 (15%) | | 4 (33%) | | 1 (50%) | | | 35 (29%) |
| | productive | 0 | 16 (29%) | 5 (56%) | | 18 (69%) | | 7 (58%) | | 1 (50%) | | | 47 (39%) |
| | discolored | 0 | 15 (27%) | 2 (22%) | | 4 (15%) | | 1 (8%) | | 0 | | | 22 (18%) |
| **Changes between baseline and visit 3** | | | | | | | | | | | | | |
| GOLD stage | deterioration | 0 | 7 (13%) | 1 (11%) | | 3 (12%) | | 3 (25%) | | 0 | | p=0.001 | 14 (12%) |
| | stable | 16 (100%) | 48 (87%) | 3 (33%) | | 18 (69%) | | 7 (58%) | | 1 (50%) | | | 93 (78%) |
| | improvement | 0 | 0 | 5 (56%) | | 5 (19%) | | 2 (17%) | | 1 (50%) | | | 13 (11%) |
| Cough & Phlegm | deterioration | 0 | 11 (20%) | 2 (22%) | | 9 (35%) | | 4 (33%) | | 1 (50%) | | p=0.058 | 27 (23%) |
| | stable | 16 (100%) | 26 (47%) | 5 (56%) | | 12 (46%) | | 7 (58%) | | 0 | | | 66 (55%) |
| | improvement | 0 | 18 (33%) | 2 (22%) | | 5 (19%) | | 1 (8%) | | 1 (50%) | | | 27 (23%) |
| Exacerbations (month 1-12) | yes | 0 | 12 (22%) | 3 (33%) | | 4 (15%) | | 5 (42%) | | 1 (50%) | | p=0.308 | 25 (21%) |
| | no | 16 (100%) | 43 (78%) | 6 (67%) | | 22 (85%) | | 7 (58%) | | 1 (50%) | | | 95 (79%) |
| Exacerbations (month 12-36) | yes | 0 | 10 (18%) | 3 (33%) | | 14 (54%) | | 5 (42%) | | 0 | | p=0.008 | 32 (27%) |
| | no | 16 (100%) | 45 (82%) | 6 (67%) | | 12 (46%) | | 7 (58%) | | 2 (100%) | | | 88 (73%) |

Fig. 3D

SEQUENCE LISTING

```
<160> NUMBER OF SEQ ID NOS: 59

<210> SEQ ID NO 1
<211> LENGTH: 2471
<212> TYPE: DNA
<213> ORGANISM: Homo sapiens

<400> SEQUENCE: 1

agaaagcgag cagccaccca gctccccgcc accgccatgg tccccgacac cgcctgcgtt      60

cttctgctca ccctggctgc cctcggcgcg tccggacagg gccagagccc gttgggctca     120

gacctgggcc cgcagatgct tcgggaactg caggaaacca acgcggcgct gcaggacgtg     180

cgggagctgc tgcggcagca ggtcagggag atcacgttcc tgaaaaacac ggtgatggag     240

tgtgacgcgt gcgggatgca gcagtcagta cgcaccggcc tacccagcgt gcggcccctg     300

ctccactgcg cgcccggctt ctgcttcccc ggcgtggcct gcatccagac ggagagcggc     360

gcgcgctgcg gcccctgccc cgcgggcttc acgggcaacg gctcgcactg caccgacgtc     420

aacgagtgca acgcccaccc ctgcttcccc cgagtccgct gtatcaacac cagcccgggg     480

ttccgctgcg aggcttgccc gccggggtac agcggcccca cccaccaggg cgtggggctg     540

gctttcgcca aggccaacaa gcaggtttgc acggacatca acgagtgtga gaccgggcaa     600

cataactgcg tccccaactc cgtgtgcatc aacacccggg gctccttcca gtgcggcccg     660

tgccagcccg gcttcgtggg cgaccaggcg tccggctgcc agcggcgcgc acagcgcttc     720

tgccccgacg gctcgcccag cgagtgccac gagcatgcag actgcgtcct agagcgcgat     780

ggctcgcggt cgtgcgtgtg tgccgttggc tgggccggca acgggatcct ctgtggtcgc     840

gacactgacc tagacggctt cccggacgag aagctgcgct gcccggagcg ccagtgccgt     900

aaggacaact gcgtgactgt gcccaactca gggcaggagg atgtggaccg cgatggcatc     960

ggagacgcct gcgatccgga tgccgacggg gacggggtcc ccaatgaaaa ggacaactgc    1020

ccgctggtgc ggaacccaga ccagcgcaac acggacgagg acaagtgggg cgatgcgtgc    1080

gacaactgcc ggtcccagaa gaacgacgac caaaaggaca cagaccagga cggccggggc    1140

gatgcgtgcg acgacgacat cgacggcgac cggatccgca accaggccga caactgccct    1200

agggtaccca actcagacca gaaggacagt gatggcgatg gtatagggga tgcctgtgac    1260

aactgtcccc agaagagcaa cccggatcag gcggatgtgg accacgactt tgtgggagat    1320

gcttgtgaca gcgatcaaga ccaggatgga gacggacatc aggactctcg ggacaactgt    1380
```

-continued cccacggtgc ctaacagtgc ccaggaggac tcagaccacg atggccaggg tgatgcctgc 1440
gacgacgacg acgacaatga cggagtccct gacagtcggg acaactgccg cctggtgcct 1500
aaccccggcc aggaggacgc ggacagggac ggcgtgggcg acgtgtgcca ggacgacttt 1560
gatgcagaca aggtggtaga caagatcgac gtgtgtccgg agaacgctga agtcacgctc 1620
accgacttca gggccttcca gacagtcgtg ctggacccgg agggtgacgc gcagattgac 1680
cccaactggg tggtgctcaa ccagggaagg gagatcgtgc agacaatgaa cagcgaccca 1740
ggcctggctg tgggttacac tgccttcaat ggcgtggact tcgagggcac gttccatgtg 1800
aacacggtca cggatgacga ctatgcgggc ttcatctttg gctaccagga cagctccagc 1860
ttctacgtgg tcatgtggaa gcagatggag caaacgtatt ggcaggcgaa ccccttccgt 1920
gctgtggccg agcctggcat ccaactcaag gctgtgaagt cttccacagg ccccggggaa 1980
cagctgcgga acgctctgtg gcatacagga gacacagagt cccaggtgcg gctgctgtgg 2040
aaggacccgc gaaacgtggg ttggaaggac aagaagtcct atcgttggtt cctgcagcac 2100
cggccccaag tgggctacat cagggtgcga ttctatgagg gccctgagct ggtggccgac 2160
agcaacgtgg tcttggacac aaccatgcgg ggtggccgcc tgggggtctt ctgcttctcc 2220
caggagaaca tcatctgggc caacctgcgt taccgctgca atgacaccat cccagaggac 2280
tatgagaccc atcagctgcg gcaagcctag ggaccagggt gaggacccgc cggatgacag 2340
ccaccctcac cgcggctgga tgggggctct gcacccagcc ccaaggggtg gccgtcctga 2400
gggggaagtg agaagggctc agagaggaca aaataaagtg tgtgtgcagg gaaaaaaaaa 2460
aaaaaaaaaa a 2471

<210> SEQ ID NO 2
<211> LENGTH: 5160
<212> TYPE: DNA
<213> ORGANISM: Homo sapiens

<400> SEQUENCE: 2
aaaacccgga ggagcgggat ggcgcgcttt gactctggag tgggagtggg agcgagcgct 60
tctgcgactc cagttgtgag agccgcaagg gcatgggaat tgacgccact caccgacccc 120
cagtctcaat ctcaacgctg tgaggaaacc tcgactttgc caggtcccca agggcagcgg 180
ggctcggcga gcgaggcacc cttctccgtc cccatcccaa tccaagcgct cctggcactg 240
acgacgccaa gagactcgag tgggagttaa agcttccagt gagggcagca ggtgtccagg 300
ccgggcctgc gggttcctgt tgacgtcttg ccctaggcaa aggtcccagt tccttctcgg 360
agccggctgt cccgcgccac tggaaaccgc acctccccgc agcatgggca ccagcctcag 420
cccgaacgac ccttggccgc taaacccgct gtccatccag cagaccacgc tcctgctact 480
cctgtcggtg ctggccactg tgcatgtggg ccagcggctg ctgaggcaac ggaggcggca 540
gctccggtcc gcgcccccgg gcccgtttgc gtggccactg atcggaaacg cggcggcggt 600
gggccaggcg gctcacctct cgttcgctcg cctggcgcgg cgctacggcg acgttttcca 660
gatccgcctg ggcagctgcc ccatagtggt gctgaatggc gagcgcgcca tccaccaggc 720
cctggtgcag cagggctcgg ccttcgccga ccggccggcc ttcgcctcct tccgtgtggt 780
gtccggcggc cgcagcatgg ctttcggcca ctactcggag cactggaagg tgcagcggcg 840
cgcagcccac agcatgatgc gcaacttctt cacgcgccag ccgcgcagcc gccaagtcct 900
cgagggccac gtgctgagcg aggcgcgcga gctggtggcg ctgctggtgc gcggcagcgc 960

-continued

```
ggacggcgcc ttcctcgacc cgaggccgct gaccgtcgtg gccgtggcca acgtcatgag   1020
tgccgtgtgt ttcggctgcc gctacagcca cgacgacccc gagttccgtg agctgctcag   1080
ccacaacgaa gagttcgggc gcacggtggg cgcgggcagc ctggtggacg tgatgccctg   1140
gctgcagtac ttccccaacc cggtgcgcac cgttttccgc gaattcgagc agctcaaccg   1200
caacttcagc aacttcatcc tggacaagtt cttgaggcac tgcgaaagcc ttcggcccgg   1260
ggccgccccc cgcgacatga tggacgcctt tatcctctct gcggaaaaga aggcggccgg   1320
ggactcgcac ggtggtggcg cgcggctgga tttggagaac gtaccggcca ctatcactga   1380
catcttcggc gccagccagg acaccctgtc caccgcgctg cagtggctgc tcctcctctt   1440
caccaggtat cctgatgtgc agactcgagt gcaggcagaa ttggatcagg tcgtggggag   1500
ggaccgtctg ccttgtatgg gtgaccagcc caacctgccc tatgtcctgg ccttccttta   1560
tgaagccatg cgcttctcca gctttgtgcc tgtcactatt cctcatgcca ccactgccaa   1620
cacctctgtc ttgggctacc acattcccaa ggacactgtg gtttttgtca accagtggtc   1680
tgtgaatcat gacccactga agtggcctaa cccggagaac tttgatccag ctcgattctt   1740
ggacaaggat ggcctcatca acaaggacct gaccagcaga gtgatgattt tttcagtggg   1800
caaaaggcgg tgcattggcg aagaactttc taagatgcag ctttttctct tcatctccat   1860
cctggctcac cagtgcgatt tcagggccaa cccaaatgag cctgcgaaaa tgaatttcag   1920
ttatggtcta accattaaac ccaagtcatt taaagtcaat gtcactctca gagagtccat   1980
ggagctcctt gatagtgctg tccaaaattt acaagccaag gaaacttgcc aataagaagc   2040
aagaggcaag ctgaaatttt agaaatattc acatcttcgg agatgaggag taaaattcag   2100
tttttttcca gttcctcttt tgtgctgctt ctcaattagc gtttaaggtg agcataaatc   2160
aactgtccat caggtgaggt gtgctccata cccagcggtt cttcatgagt agtgggctat   2220
gcaggagctt ctgggagatt tttttgagtc aaagacttaa agggcccaat gaattattat   2280
atacatactg catcttggtt atttctgaag gtagcattct ttggagttaa aatgcacata   2340
tagacacata cacccaaaca cttacaccaa actactgaat gaagcagtat tttggtaacc   2400
aggccatttt tggtgggaat ccaagattgg tctcccatat gcagaaatag acaaaaagta   2460
tattaaacaa agtttcagag tatattgttg aagagacaga gacaagtaat ttcagtgtaa   2520
agtgtgtgat tgaaggtgat aagggaaaag ataaagacca gaaattccct tttcaccttt   2580
tcaggaaaat aacttagact ctagtattta tgggtggatt tatccttttg ccttctggta   2640
tacttcctta cttttaagga taaatcataa agtcagttgc tcaaaaagaa atcaatagtt   2700
gaattagtga gtatagtggg gttccatgag ttatcatgaa ttttaaagta tgcattatta   2760
aattgtaaaa ctccaaggtg atgttgtacc tcttttgctt gccaaagtac agaatttgaa   2820
ttatcagcaa agaaaaaaaa aaaagccagc caagctttaa attatgtgac cataatgtac   2880
tgatttcagt aagtctcata ggttaaaaaa aaaagtcacc aaatagtgtg aaatatatta   2940
cttaactgtc cgtaagcagt atattagtat tatcttgttc aggaaaaggt tgaataatat   3000
atgccttgta taatattgaa aattgaaaag tacaactaac gcaaccaagt gtgctaaaaa   3060
tgagcttgat taaatcaacc acctattttt gacatggaaa tgaagcaggg tttcttttct   3120
tcactcaaat tttggcgaat ctcaaaatta gatcctaaga tgtgttctta tttttataac   3180
atctttattg aaattctatt tataatacag aatcttgttt tgaaaataac ctaattaata   3240
tattaaaatt ccaaattcat ggcatgctta aattttaact aaattttaaa gccattctga   3300
ttattgagtt ccagttgaag ttagtggaaa tctgaacatt ctcctgtgga aggcagagaa   3360
```

atctaagctg tgtctgccca atgaataatg gaaaatgcca tgaattacct ggatgttctt 3420
tttacgaggt gacaagagtt ggggacagaa ctcccattac aactgaccaa gtttctcttc 3480
tagatgattt tttgaaagtt aacattaatg cctgcttttt ggaaagtcag aatcagaaga 3540
tagtcttgga agctgtttgg aaaagacagt ggagatgagg tcagttgtgt tttttaagat 3600
ggcaattact ttggtagctg ggaaagcata aagctcaaat gaaatgtatg cattcacatt 3660
tagaaaagtg aattgaagtt tcaagtttta aagttcattg caattaaact tccaaagaaa 3720
gttctacagt gtcctaagtg ctaagtgctt attacatttt attaagcttt ttggaatctt 3780
tgtaccaaaa ttttaaaaaa gggagttttt gatagttgtg tgtatgtgtg tgtggggtgg 3840
ggggatggta agagaaaaga gagaaacact gaaaagaagg aaagatggtt aaacattttc 3900
ccactcattc tgaattaatt aatttggagc acaaaattca aagcatggac atttagaaga 3960
aagatgtttg gcgtagcaga gttaaatctc aaataggcta ttaaaaaagt ctacaacata 4020
gcagatctgt tttgtggttt ggaatattaa aaaacttcat gtaattttat tttaaaattt 4080
catagctgta cttcttgaat ataaaaaatc atgccagtat ttttaaaggc attagagtca 4140
actacacaaa gcaggcttgc ccagtacatt taaatttttt ggcacttgcc attccaaaat 4200
attatgcccc accaaggctg agacagtgaa tttgggctgc tgtagcctat ttttttagat 4260
tgagaaatgt gtagctgcaa aaataatcat gaaccaatct ggatgcctca ttatgtcaac 4320
caggtccaga tgtgctataa tctgttttta cgtatgtagg cccagtcgtc atcagatgct 4380
tgcggcaaaa ggaaagctgt gtttatatgg aagaaagtaa ggtgcttgga gtttacctgg 4440
cttatttaat atgcttataa cctagttaaa gaaaggaaaa gaaaacaaaa aacgaatgaa 4500
aataactgaa tttggaggct ggagtaatca gattactgct ttaatcagaa accctcattg 4560
tgtttctacc ggagagagaa tgtatttgct gacaaccatt aaagtcagaa gttttactcc 4620
aggttattgc aataaagtat aatgtttatt aaatgcttca tttgtatgtc aaagctttga 4680
ctctataagc aaattgcttt tttccaaaac aaaaagatgt ctcaggtttg ttttgtgaat 4740
tttctaaaag ctttcatgtc ccagaactta gcctttacct gtgaagtgtt actacagcct 4800
taatattttc ctagtagatc tatattagat caaatagttg catagcagta tatgttaatt 4860
tgtgtgtttt tagctgtgac acaactgtgt gattaaaagg tatactttag tagacattta 4920
taactcaagg ataccttctt atttaatctt ttcttatttt tgtactttat catgaatgct 4980
tttagtgtgt gcataatagc tacagtgcat agttgtagac aaagtacatt ctggggaaac 5040
aacatttata tgtagccttt actgtttgat ataccaaatt aaaaaaaaat tgtatctcat 5100
tacttatact gggacaccat taccaaaata ataaaaatca ctttcataat cttgaaaaaa 5160

<210> SEQ ID NO 3
<211> LENGTH: 2608
<212> TYPE: DNA
<213> ORGANISM: Homo sapiens

<400> SEQUENCE: 3
ctcaccctga aggtgacagt tccttggaac cttccctgat ccttgtgatc ccaggctcca 60
agagtccacc cttcccagct cagctcagta cctcagccac ctccaagatc cctacactga 120
tcatgctttt cccaatctcc atgtcggcca cggagtttct tctggcctct gtcatcttct 180
gtctggtatt ctgggtaatc agggcctcaa gacctcaggt ccccaaaggc ctgaagaatc 240
caccagggcc atggggctgg cctctgattg ggcacatgct gaccctggga aagaacccgc 300

-continued

```
acctggcact gtcaaggatg agccagcagt atggggacgt gctgcagatc cgaattggct    360
ccacacccgt ggtggtgctg agcggcctgg acaccatccg gcaggccctg gtgcggcagg    420
gcgatgattt caagggccgg cccgacctct acaccttcac cctcatcagt aatggtcaga    480
gcatgtcctt cagcccagac tctggaccag tgtgggctgc ccgccggcgc ctggcccaga    540
atggcctgaa aagtttctcc attgcctctg acccagcctc ctcaacctcc tgctacctgg    600
aagagcatgt gagcaaggag gctgaggtcc tgataagcac gttgcaggag ctgatggcag    660
ggcctgggca ctttaacccc tacaggtatg tggtggtatc agtgaccaat gtcatctgtg    720
ccatttgctt tggccggcgc tatgaccaca accaccaaga actgcttagc ctagtcaacc    780
tgaataataa tttcggggag gtggttggct ctggaaaccc agctgacttc atccctattc    840
ttcgctacct acccaaccct tccctgaatg ccttcaagga cctgaatgag aagttctaca    900
gcttcatgca gaagatggtc aaggagcact acaaaacctt tgagaagggc cacatccggg    960
acatcacaga cagcctgatt gagcactgtc aggagaagca gctggatgag aacgccaatg   1020
tccagctgtc agatgagaag atcattaaca tcgtcttgga cctctttgga gctgggtttg   1080
acacagtcac aactgctatc tcctggagcc tcatgtattt ggtgatgaac cccagggtac   1140
agagaaagat ccaagaggag ctagacacag tgattggcag gtcacggcgg ccccggctct   1200
ctgacagatc ccatctgccc tatatggagg ccttcatcct ggagaccttc cgacactctt   1260
ccttcgtccc cttcaccatc ccccacagca caacaagaga cacaagtttg aaaggctttt   1320
acatccccaa ggggcgttgt gtctttgtaa accagtggca gatcaaccat gaccagaagc   1380
tatgggtcaa cccatctgag ttcctacctg aacggtttct caccccctgat ggtgctatcg   1440
acaaggtgtt aagtgagaag gtgattatct ttggcatggg caagcggaag tgtatcggtg   1500
agaccattgc ccgctgggag gtctttctct tcctggctat cctgctgcaa cgggtggaat   1560
tcagcgtgcc actgggcgtg aaggtggaca tgacccccat ctatgggcta accatgaagc   1620
atgcctgctg tgagcacttc caaatgcagc tgcgctctta ggtgcttgag agccctgagg   1680
cctagactct gtctacctgg tctggttggg cagccagacc agcaggctgg cctatgtggt   1740
ctaaggttca gcctgaaact catagacact gatctggctg cagttttgct atctgggctg   1800
tgggcaagcc taagggatcc tgcctgcccc taccctggac ttgcctctgc acaccctcca   1860
gagacaacag gtaaaacagg gccacataga tgctgatgga gccttcccaa gttgtgcttg   1920
agccaggagg cctgctaggg ttaggaggtc cttaggcctc tgagaagctc tgaagaactc   1980
tctggaagcc cctgggccca gtacctagct ggctctgtga gggtgctgac tggcttcagc   2040
aagttagaac tagccaaacc aggaccctgt ccaatctttg acaattggga gctgccaaga   2100
gtgaagggaa gagacagccc aggatactgg cacagaggta gtctcactgc ttgaactagg   2160
ctgagcaatc tgaccctatg ggtctaggac acagttcctg ggaacatcac attcctctgc   2220
ccttcctgca ggcaggaaca aacagggctg ccttctggcc ttgtaagacc cttattgctg   2280
tcctggaggg gctggggact tgtgtctgcg gggatcagag cgcacaggga gtgcacatat   2340
ccaggcacca ggactagggc tggagtgagg ggggggtatt tcaattacct tctattggtc   2400
tcccttctct acactcttgt aataaaatgt ctatttttaa tgtttgtaca caacaatcct   2460
tctattctag cctgcattga gcttgcatgc ttgcataaga gcttaagaac cattgattta   2520
atgtaatagg gaaaattcta acccaggtat ccaaaaatgt gtaagaacaa ctacctgagc   2580
taaataaaga tattgttcag aaatccta                                      2608
```

<210> SEQ ID NO 4
<211> LENGTH: 1665
<212> TYPE: DNA
<213> ORGANISM: Homo sapiens

<400> SEQUENCE: 4
cttctggtaa ggaggccccg tgatcagctc cagccatttg cagtcctggc tatcccagga 60
gcttacataa agggacaatt ggagcctgag aggtgacagt gctgacacta caaggctcgg 120
agctccgggc actcagacat catgagttgg tccttgcacc cccggaattt aattctctac 180
ttctatgctc ttttatttct ctcttcaaca tgtgtagcat atgttgctac cagagacaac 240
tgctgcatct tagatgaaag attcggtagt tattgtccaa ctacctgtgg cattgcagat 300
ttcctgtcta cttatcaaac caaagtagac aaggatctac agtctttgga agacatctta 360
catcaagttg aaaacaaaac atcagaagtc aaacagctga taaaagcaat ccaactcact 420
tataatcctg atgaatcatc aaaaccaaat atgatagacg ctgctacttt gaagtccagg 480
aaaatgttag aagaaattat gaaatatgaa gcatcgattt taacacatga ctcaagtatt 540
cgatatttgc aggaaatata taattcaaat aatcaaaaga ttgttaacct gaaagagaag 600
gtagcccagc ttgaagcaca gtgccaggaa ccttgcaaag acacggtgca aatccatgat 660
atcactggga aagattgtca agacattgcc aataagggag ctaaacagag cgggctttac 720
tttattaaac ctctgaaagc taaccagcaa ttcttagtct actgtgaaat cgatgggtct 780
ggaaatggat ggactgtgtt tcagaagaga cttgatggca gtgtagattt caagaaaaac 840
tggattcaat ataaagaagg atttggacat ctgtctccta ctggcacaac agaattttgg 900
ctgggaaatg agaagattca tttgataagc acacagtctg ccatcccata tgcattaaga 960
gtggaactgg aagactggaa tggcagaacc agtactgcag actatgccat gttcaaggtg 1020
ggacctgaag ctgacaagta ccgcctaaca tatgcctact tcgctggtgg ggatgctgga 1080
gatgcctttg atggctttga ttttggcgat gatcctagtg acaagttttt cacatcccat 1140
aatggcatgc agttcagtac ctgggacaat gacaatgata agtttgaagg caactgtgct 1200
gaacaggatg gatctggttg gtggatgaac aagtgtcacg ctggccatct caatggagtt 1260
tattaccaag gtggcactta ctcaaaagca tctactccta atggttatga taatggcatt 1320
atttgggcca cttggaaaac ccggtggtat tccatgaaga aaaccactat gaagataatc 1380
ccattcaaca gactcacaat tggagaagga cagcaacacc acctgggggg agccaaacag 1440
gctggagacg tttaaaagac cgtttcaaaa gagatttact tttttaaagg actttatctg 1500
aacagagaga tataatattt ttcctattgg acaatggact tgcaaagctt cacttcattt 1560
taagagcaaa agaccccatg ttgaaaactc cataacagtt ttatgctgat gataatttat 1620
ctacatgcat ttcaataaac cttttgtttc ctaagactag aaaaa 1665

<210> SEQ ID NO 5
<211> LENGTH: 840
<212> TYPE: DNA
<213> ORGANISM: Homo sapiens

<400> SEQUENCE: 5
agacccagag ccaatgcgtg gattagtccc tcctcctagt tgcagtctgg tagttgtcgc 60
tggccgtgtg acggctcgct gttgccctga aggcaggcga gccagctgcc caggaaaggt 120
ggaaagtggt agaagctgac ccctgagccc tggcaggtct ttaagtgcgt ttgtgcagcc 180
gatttcaagg ctaagagaga aagactgcct ctgatccctg aaggaagaaa aaaaaaaaaa 240

-continued

```
aaacaggaaa aaaactcaac atggaaaatg tccccaagga aaacaaagtt gtggagaagg    300
ccccagtgca gaatgaagcc cccgctttag gaggtggtga ataccaggag cctggaggaa    360
atgttaaagg ggtttgggct ccacctgccc cgggttttgg agaggatgtg cccaataggc    420
ttgtcgataa cattgatatg atagatggag atggagatga tatggaacgg ttcatggagg    480
agatgagaga gctaaggagg aaaattaggg aacttcagtt gaggtacagt ctgcgcattc    540
ttatagggga ccctcctcac catgatcatc atgatgagtt ttgccttatg ccttgaatct    600
tgaggttaat aatcataaaa tccctgcttt ctaaattcgc atttttcctg gtgtaccttt    660
aatgtgaacc ttttggcatt cttctgcaat tttctgattg gagattgcat tttgacctag    720
tctgtaagtt tttctgtcag aagaggactt tcatcaactt tcatggaaag atgtttattg    780
catactgtaa agttaataaa gcaatttaaa agcagtctaa aaaaaaaaaa aaaaaaaaaa    840
```

<210> SEQ ID NO 6
<211> LENGTH: 8340
<212> TYPE: DNA
<213> ORGANISM: Homo sapiens

<400> SEQUENCE: 6

```
actaatttc  tggagtttct gcccctgctc tgcgtcagcc ctcacgtcac ttcgccagca     60
gtagcagagg cggcggcggc ggctcccgga attgggttgg agcaggagcc tcgctggctg    120
cttcgctcgc gctctacgcg ctcagtcccc ggcggtagca ggagcctgga cccaggcgcc    180
gccggcgggc gtgaggcgcc ggagcccggc ctcgaggtgc ataccggacc cccattcgca    240
tctaacaagg aatctgcgcc ccagagagtc ccgggagcgc cgccggtcgg tgcccggcgc    300
gccgggccat gcagcgacgg ccgccgcgga gctccgagca gcggtagcgc ccccctgtaa    360
agcggttcgc tatgccgggg ccactgtgaa ccctgccgcc tgccggaaca ctcttcgctc    420
cggaccagct cagcctctga taagctggac tcggcacgcc cgcaacaagc accgaggagt    480
taagagagcc gcaagcgcag ggaaggcctc cccgcacggg tgggggaaag cggccggtgc    540
agcgcgggga caggcactcg ggctggcact ggctgctagg gatgtcgtcc tggataaggt    600
ggcatggacc cgccatggcg cggctctggg gcttctgctg gctggttgtg ggcttctgga    660
gggccgcttt cgcctgtccc acgtcctgca aatgcagtgc ctctcggatc tggtgcagcg    720
acccttctcc tggcatcgtg gcatttccga gattggagcc taacagtgta gatcctgaga    780
acatcaccga aattttcatc gcaaaccaga aaaggttaga aatcatcaac gaagatgatg    840
ttgaagctta tgtgggactg agaaatctga caattgtgga ttctggatta aaatttgtgg    900
ctcataaagc atttctgaaa aacagcaacc tgcagcacat caattttacc cgaaacaaac    960
tgacgagttt gtctaggaaa catttccgtc accttgactt gtctgaactg atcctggtgg   1020
gcaatccatt tacatgctcc tgtgacatta tgtggatcaa gactctccaa gaggctaaat   1080
ccagtccaga cactcaggat ttgtactgcc tgaatgaaag cagcaagaat attcccctgg   1140
caaacctgca gatacccaat tgtggtttgc catctgcaaa tctggccgca cctaacctca   1200
ctgtggagga aggaaagtct atcacattat cctgtagtgt ggcaggtgat ccggttccta   1260
atatgtattg ggatgttggt aacctggttt ccaaacatat gaatgaaaca agccacacac   1320
agggctcctt aaggataact aacatttcat ccgatgacag tgggaagcag atctcttgtg   1380
tggcggaaaa tcttgtagga gaagatcaag attctgtcaa cctcactgtg cattttgcac   1440
caactatcac atttctcgaa tctccaacct cagaccacca ctggtgcatt ccattcactg   1500
tgaaaggcaa ccccaaacca gcgcttcagt ggttctataa cggggcaata ttgaatgagt   1560
```

```
ccaaatacat ctgtactaaa atacatgtta ccaatcacac ggagtaccac ggctgcctcc   1620
agctggataa tcccactcac atgaacaatg gggactacac tctaatagcc aagaatgagt   1680
atgggaagga tgagaaacag atttctgctc acttcatggg ctggcctgga attgacgatg   1740
gtgcaaaccc aaattatcct gatgtaattt atgaagatta tggaactgca gcgaatgaca   1800
tcggggacac cacgaacaga agtaatgaaa tcccttccac agacgtcact gataaaaccg   1860
gtcgggaaca tctctcggtc tatgctgtgg tggtgattgc gtctgtggtg ggattttgcc   1920
ttttggtaat gctgtttctg cttaagttgg caagacactc caagtttggc atgaaagatt   1980
tctcatggtt tggatttggg aaagtaaaat caagacaagg tgttggccca gcctccgtta   2040
tcagcaatga tgatgactct gccagcccac tccatcacat ctccaatggg agtaacactc   2100
catcttcttc ggaaggtggc ccagatgctg tcattattgg aatgaccaag atccctgtca   2160
ttgaaaatcc ccagtacttt ggcatcacca acagtcagct caagccagac acatggccca   2220
gaggttcccc caagaccgcc tgataataat ttggtatttg gaggctcctg tgtcactgca   2280
ggaactaaag gaggctaaat ccatgcctga tggaggagaa gagttctatg gttatctgca   2340
aattctggcc agacaacatc ttgacgtcac tccttagctt ccataaccta gccaagcaag   2400
aagttgcctt tccaagacaa agcagtgtgc tctaatgact aacccctcaa agtactatgc   2460
cactttaact atagacccat ctcctcgatc aatcaggatg gcaagatgga gctgaggagc   2520
tcagcaacat caagtctgga gttggtcttt aactcaacta gctcgtttag acgtgtctga   2580
acaccacatc acctgacagc acggggtggt ttcccagtaa aatttacaaa ctcagctcaa   2640
gggcagctgt gttgctttcc tttccttgac tgctgagaaa ctttttgaca gggaacaatg   2700
gaaacacacc ttctgagctg aaacaaacaa acagaaacaa aacatactaa ccagcaaaat   2760
ccccaaatca tcaatcttgg gttctcttga agggcaggag tgtgttttat cttctcccgt   2820
cggagcaaac actatagatg tcctccctaa aattctgtct tccctagagc agccttgtaa   2880
attagctagg gtcctagggt tgaggcctaa atcaacttaa aattgtctct aaatatgtac   2940
ctggatgtgt ttgtacttgc agagcatgcc ctcttcatgt gcctagggct agtaactccc   3000
tgtggcagag gcatgtaaag tattctgact tttttttttt caacttaatt ccatttccaa   3060
tgaaatggat ttttaaaaat tttctccaga gtgtgccata cttctccagc tattatagtt   3120
aatgtgtgtg tatccttgtg tatatgtgtg tttgtgtgtg catatgtgtt ttcctagtgg   3180
ttacatgctt actaggcaat tatgtaaata agcacagatt cataggccag ctaggcctga   3240
ggaaagaaga cattataaag ggagggagta ttttaacatt agctaaagct atcacacaag   3300
gcacccattc tgctcccctc aacagccaca gcccacttcg tccttgtctt accaataagg   3360
ggaaaggctg gaggtgatat ttttcacaga accgcagagg ttttgaacat atttgcaaca   3420
ttactttgag tacacatgag caaaaattct gaattacatc caggacccca gaagctcatt   3480
agatcaaaga gtgcggggcc cctcagagtt accagagatt atctgcagac ttcagtgcaa   3540
tcgaatgacc atggtccatt ttgatggtca gaggtaggac tgaaaaacgg gtagaaacaa   3600
ttgctttagc gcttccttct gtactttgcc tattaatgtt ttgtctttca aaaatatatt   3660
ttctcctaat tgtttaattg gccaaataat ggctgctttg ggagttgttt gtatgccttg   3720
gaaggccatg gcctgcactt taaaaataag ctaagtccat tctgcccagc acgagcatta   3780
ggacagagaa tgcacttatt tttaggatcct taaaaattgc ttcttttatg gcacactggg   3840
ttgacgactc atctcgtggg agccttcatg gcacattgct gctgttctgc aggtcccaat   3900
```

```
acaattcctt ccccctctca gtgccacggc ccccccattg ctagctacaa caatttgata   3960
tcatattccc ttttcaactc caaaggagat gataagaagc tatcaaataa tgctttaaaa   4020
aagcaacttg agtttcttaa aagaaaggaa atgaatacat gctgcataat tacatttaaa   4080
atgtaagcca tgttattata agccgcactg agatgaagat ttgttagcaa accagtttca   4140
agcacactca cagtgaagta aaatcatgtt tttagcatct gaccattggg taatattatt   4200
ctttgttatc aaaagagaaa tatcacccaa gtatagtata cttagacctc ctagaggaaa   4260
cactccagtc ctaagcttgg tgtctgaaaa gaaaaacaaa aataaagatt atggatttag   4320
gtcagggaga cagagtgata ttctgaagac tgtgtttact ccctcatcat cggccaacca   4380
agatggagtt ctgcatcctg cacatatcag acatttcagt ccaatttcac caaagcatca   4440
gtgatgttct agaagcatcc cagcagatgg aggatcctaa tgtatttgtt ctgggtattt   4500
cccaaggccc agcctgactg gagtgtgtgt accaacagga tgaatccaat caagctacgc   4560
ccccatttg gtttcggatt ggccactctt gcatgtgcta gtagattgtg gaccaggacc   4620
agctgagcaa acacagttgc agagtagcct cctatgttgc taagaagctc ctgctaccca   4680
ggtgctttga acaattgagt gctccctctg gttaagtaga gatggcacca ccggagtttt   4740
tcttggatgt gaggctcaat cctttacggc agctattata acaaagtgaa ggttttctcc   4800
ctgggaaatg cagcttttct ctgtctttac taattctgcc agcctgtgag agtaaccacc   4860
gtagctgggc ttcttctcag attaattgtc atgccaggtc tccttcctgg ggagctgtga   4920
tgctgctctg aggttgattg ctgaggttgt agtgggtttt tgtttgtttt tgtttagttt   4980
ttcttgattg ttcttctttc tcttgaatgg caagagaaga aacactttct ctaacccacg   5040
gccaggaagg aaatggggag agagctactt cttagttcaa cctggttgcc acataaagga   5100
atctctctcc ttggactcag cccctaactg gaagcaagag ccactgccct ctgagactga   5160
gagagcagcc cgaggaggag atgaatccat tctgcccttt gtttgggttt gcttcctgtc   5220
agtgagagaa tgctgaggca gttcctgtta tgtgaaactt tcatttttaa aaccaggaca   5280
gtcctaaaca gactggaatg agttggtcaa tcccagttgg tataggccca atgatttttg   5340
ctagtaagat aggattgtct tcctcaccca aaatgccttc aagtgcccta aaatgggtat   5400
tttaaaataa gaataaataa tgtagattta gtagaaaacc tggaaaacat aagaaacaaa   5460
gatgaaacga aaagtcccat gtaattccac cagttagagt taaccactga tatcgtttgg   5520
atatatggct ttctagtctt gtggatatcc ttttaatctc ttgtaatata aagtctgacc   5580
atatgtgtcc ttgcatttgt ttgtactgga ctctgttaat atttctatag taatggctca   5640
ctttggggag attgtgctgc acagtgtgta ggaagcacat tgggtgtatt attcccagtt   5700
ttgtattttg tatttccttg gagatgtgca ggggttaaga gcgggggtct ggccatagct   5760
ggccacgtca gactctcata tggtaagtat cacagagcac atgaggcctg tgttatgcgc   5820
tggaaagact caggaaatga gaggctctct tgttctgaca aggcaggctg agagctctca   5880
tttagggtca tcactccaga taactccaaa tgcagtttat tgctcaactg aagcagatga   5940
tcactttttg cctccaagtt cttcacccta gctagctcct ttcaaagagc cgagtatgct   6000
ggatcttaaa gggccaaact agttacatct catacatttc ctgatgttta gggatgcctt   6060
cacttccatc aaggatacct tggctgtgca aggacctctg atagctggag tctccttttg   6120
gtcactccca gctttgctta aacttgatgg agtttgctgt ccagtgatcc ccggatcttt   6180
catcatgaaa gccttccttc ctctcctgat gtctcaggcc tctagaccta gactggggtt   6240
ctggcaagga ggcctctatc aatagtatga catccaataa tatgttagtg ttgatatttt   6300
```

gcacagtaat attaagttta agagattata aaaatgagtt caaatgaata agttcctgtg 6360
atgtaagaga ttagatatgt gtgatttcag aaccaaaggc agggggaat cccagaaaga 6420 aaacaataat ataatcctag tttctatata ttatttttat tcattactgt atatgggtag 6480
agatcaatat tctttcttat gctgttacta ttaattaaca catttttaa ccatgccatt 6540 gaacttttgg gtgcattaaa gtggaaccca agctcctcat tagataataa tggcatttgg 6600
actgagtgcc atattcctaa atttccaata aagtggttga tatagagagg acaggataaa 6660
gccctatagt gtgcagttat atcaaaacag ctagtctcca ctttagggaa tgcctttact 6720
agagattaca tgaaatgtct gcttataaaa taagcagaga tggcaccact aagcagccac 6780
ctgaattgtt ttcctacagg aatgattact tttcagatcc atttatgttt tcatgctcaa 6840
tacttactcc ccttccctgc aacacccaaa gagtttactt ttgcaagtca tttggtcttc 6900
agtctactac tgaggaatag agaggcacta actgctttac ccaggatcag aactcatgtt 6960
cttaccttct attaatagag tacttgagcc agatggacta actggtctca cattttctct 7020
atcttggttt tacttccata aacatcaata tctttaccca catgattttt ccatcctccc 7080 attttttcc atatgtatta gggttcagga actatgatgc taatgatcac atttcttcct 7140
agttcctaat ttcattagtg ccatttcctg atatctacag aaacaattat caatacatgt 7200
agctgcttga gccttattta gaaggctagc ctttcttttc caagtgctgt cagaatgtat 7260
acatttagtc tgtctttttc ccttttagga gtctttgttc tgggttgatg gcaaaattcc 7320
tctttttaca tgtgagattt ttgatttcac tgaattctac ctagattttt atggacattg 7380
gattttaaag aggaaaacac tcattttctt agtaagatat tggtgataca tagctatgcc 7440
attgatttcc atactcctga gctttgggga gggagacagt ggccaagtag caggcagaat 7500
aagatcatca ctcatgtcct gaatcaatca cactttcctt ctcggattgt gtatatgctc 7560
tgccacttcc tacatattac atcctgagtt tttaagtaaa gtggatctta gccagatttg 7620
agtctaatgg ctgattcatc ggcatagttc ttggcgttaa catctcagtg tcctctttag 7680
ttctctttga ggattcatgt cattgagggc ctttgtgcct ccacttgtct cagtatgagg 7740
aagaactttg gtgtgagggc ggagctatgt gaagggttgc tgggttgggg gattagttca 7800
tatggtcccc atgccatcta tttacttttg gagagagggg actttgagtg ggtgggtatg 7860
gatagatgtt cctcaaggaa accctgctgg ctaatgggca ctacatctgt gtattactgt 7920
gattctctct gtaagctccc catgtggcca aggacccccc tcctaccagg gcacttcctg 7980
ccacctcatt gcactggtct caaccattca gcctgctgct gctgcaccat gttgggctgc 8040
ggtaggatag ggaaggggtt ctgttgattg ctaaatgttg cctaacttta tttccctctc 8100
ccacatttca tgcaagggag cggacctaac acatgacttg cattctcttc ctatgttcag 8160
aaactccagg gcttgcccac gtgtatgtat gagtgaccaa tggagcttgg aattctttat 8220
ctatatgatc tgtccgaaaa tgagatcttt tgtactggaa tttgtgatgt agttgatcat 8280
tcagagccaa acgcatatac caataaagac aagactgtca tataaaaaaa aaaaaaaaaa 8340

<210> SEQ ID NO 7
<211> LENGTH: 8292
<212> TYPE: DNA
<213> ORGANISM: Homo sapiens

<400> SEQUENCE: 7 actaatttc tggagtttct gcccctgctc tgcgtcagcc ctcacgtcac ttcgccagca 60

-continued

```
gtagcagagg cggcggcggc ggctcccgga attgggttgg agcaggagcc tcgctggctg    120
cttcgctcgc gctctacgcg ctcagtcccc ggcggtagca ggagcctgga cccaggcgcc    180
gccggcgggc gtgaggcgcc ggagcccggc ctcgaggtgc ataccggacc cccattcgca    240
tctaacaagg aatctgcgcc ccagagagtc ccgggagcgc cgccggtcgg tgcccggcgc    300
gccgggccat gcagcgacgg ccgccgcgga gctccgagca gcggtagcgc ccccctgtaa    360
agcggttcgc tatgccgggg ccactgtgaa ccctgccgcc tgccggaaca ctcttcgctc    420
cggaccagct cagcctctga taagctggac tcggcacgcc cgcaacaagc accgaggagt    480
taagagagcc gcaagcgcag ggaaggcctc cccgcacggg tgggggaaag cggccggtgc    540
agcgcgggga caggcactcg ggctggcact ggctgctagg gatgtcgtcc tggataaggt    600
ggcatggacc cgccatggcg cggctctggg gcttctgctg gctggttgtg ggcttctgga    660
gggccgcttt cgcctgtccc acgtcctgca aatgcagtgc ctctcggatc tggtgcagcg    720
acccttctcc tggcatcgtg gcatttccga gattggagcc taacagtgta gatcctgaga    780
acatcaccga aatttcatc gcaaaccaga aaaggttaga aatcatcaac gaagatgatg    840
ttgaagctta tgtgggactg agaaatctga caattgtgga ttctggatta aaatttgtgg    900
ctcataaagc atttctgaaa aacagcaacc tgcagcacat caattttacc cgaaacaaac    960
tgacgagttt gtctaggaaa catttccgtc accttgactt gtctgaactg atcctggtgg   1020
gcaatccatt tacatgctcc tgtgacatta tgtggatcaa gactctccaa gaggctaaat   1080
ccagtccaga cactcaggat ttgtactgcc tgaatgaaag cagcaagaat attcccctgg   1140
caaacctgca gatacccaat tgtggtttgc catctgcaaa tctggccgca cctaacctca   1200
ctgtggagga aggaaagtct atcacattat cctgtagtgt ggcaggtgat ccggttccta   1260
atatgtattg ggatgttggt aacctggttt ccaaacatat gaatgaaaca agccacacac   1320
agggctcctt aaggataact aacatttcat ccgatgacag tgggaagcag atctcttgtg   1380
tggcggaaaa tcttgtagga gaagatcaag attctgtcaa cctcactgtg cattttgcac   1440
caactatcac atttctcgaa tctccaacct cagaccacca ctggtgcatt ccattcactg   1500
tgaaaggcaa ccccaaacca gcgcttcagt ggttctataa cggggcaata ttgaatgagt   1560
ccaaatacat ctgtactaaa atacatgtta ccaatcacac ggagtaccac ggctgcctcc   1620
agctggataa tcccactcac atgaacaatg gggactacac tctaatagcc aagaatgagt   1680
atgggaagga tgagaaacag atttctgctc acttcatggg ctggcctgga attgacgatg   1740
gtgcaaaccc aaattatcct gatgtaattt atgaagatta tggaactgca gcgaatgaca   1800
tcggggacac cacgaacaga agtaatgaaa tcccttccac agacgtcact gataaaaccg   1860
gtcgggaaca tctctcggtc tatgctgtgg tggtgattgc gtctgtggtg ggattttgcc   1920
ttttggtaat gctgtttctg cttaagttgg caagacactc caagtttggc atgaaaggcc   1980
cagcctccgt tatcagcaat gatgatgact ctgccagccc actccatcac atctccaatg   2040
ggagtaacac tccatcttct tcggaaggtg gcccagatgc tgtcattatt ggaatgacca   2100
agatccctgt cattgaaaat ccccagtact ttggcatcac caacagtcag ctcaagccag   2160
acacatggcc cagaggttcc cccaagaccg cctgataata atttggtatt tggaggctcc   2220
tgtgtcactg caggaactaa aggaggctaa atccatgcct gatggaggag aagagttcta   2280
tggttatctg caaattctgg ccagacaaca tcttgacgtc actccttagc ttccataacc   2340
tagccaagca agaagttgcc tttccaagac aaagcagtgt gctctaatga ctaacccctc   2400
aaagtactat gccactttaa ctatagaccc atctcctcga tcaatcagga tggcaagatg   2460
```

-continued gagctgagga gctcagcaac atcaagtctg gagttggtct ttaactcaac tagctcgttt 2520
agacgtgtct gaacaccaca tcacctgaca gcacggggtg gtttcccagt aaaatttaca 2580
aactcagctc aagggcagct gtgttgcttt cctttccttg actgctgaga aactttttga 2640
cagggaacaa tggaaacaca ccttctgagc tgaaacaaac aaacagaaac aaaacatact 2700
aaccagcaaa atccccaaat catcaatctt gggttctctt gaagggcagg agtgtgtttt 2760
atcttctccc gtcggagcaa acactataga tgtcctccct aaaattctgt cttccctaga 2820
gcagccttgt aaattagcta gggtcctagg gttgaggcct aaatcaactt aaaattgtct 2880
ctaaatatgt acctggatgt gtttgtactt gcagagcatg ccctcttcat gtgcctaggg 2940
ctagtaactc cctgtggcag aggcatgtaa agtattctga cttttttttt ttcaacttaa 3000
ttccatttcc aatgaaatgg atttttaaaa attttctcca gagtgtgcca tacttctcca 3060
gctattatag ttaatgtgtg tgtatccttg tgtatatgtg tgtttgtgtg tgcatatgtg 3120
ttttcctagt ggttacatgc ttactaggca attatgtaaa taagcacaga ttcataggcc 3180
agctaggcct gaggaaagaa gacattataa agggagggag tattttaaca ttagctaaag 3240
ctatcacaca aggcacccat tctgctcccc tcaacagcca cagcccactt cgtccttgtc 3300
ttaccaataa ggggaaaggc tggaggtgat atttttcaca gaaccgcaga ggttttgaac 3360
atatttgcaa cattactttg agtacacatg agcaaaaatt ctgaattaca tccaggaccc 3420
cagaagctca ttagatcaaa gagtgcgggg cccctcagag ttaccagaga ttatctgcag 3480
acttcagtgc aatcgaatga ccatggtcca ttttgatggt cagaggtagg actgaaaaac 3540
gggtagaaac aattgcttta gcgcttcctt ctgtactttg cctattaatg ttttgtcttt 3600
caaaaatata ttttctccta attgtttaat tggccaaata atggctgctt tgggagttgt 3660
ttgtatgcct tggaaggcca tggcctgcac tttaaaaata agctaagtcc attctgccca 3720
gcacgagcat taggacagag aatgcactta ttttaggatc cttaaaaatt gcttctttta 3780
tggcacactg ggttgacgac tcatctcgtg ggagccttca tggcacattg ctgctgttct 3840
gcaggtccca atacaattcc ttccccctct cagtgccacg gcccccccat tgctagctac 3900
aacaatttga tatcatattc ccttttcaac tccaaaggag atgataagaa gctatcaaat 3960
aatgctttaa aaaagcaact tgagtttctt aaaagaaagg aaatgaatac atgctgcata 4020
attacattta aaatgtaagc catgttatta taagccgcac tgagatgaag atttgttagc 4080
aaaccagttt caagcacact cacagtgaag taaaatcatg tttttagcat ctgaccattg 4140
ggtaatatta ttctttgtta tcaaaagaga aatatcaccc aagtatagta tacttagacc 4200
tcctagagga aacactccag tcctaagctt ggtgtctgaa aagaaaaaca aaaataaaga 4260
ttatggattt aggtcaggga gacagagtga tattctgaag actgtgttta ctccctcatc 4320
atcggccaac caagatggag ttctgcatcc tgcacatatc agacatttca gtccaatttc 4380
accaaagcat cagtgatgtt ctagaagcat cccagcagat ggaggatcct aatgtatttg 4440
ttctgggtat ttcccaaggc ccagcctgac tggagtgtgt gtaccaacag gatgaatcca 4500
atcaagctac gcccccattt tggtttcgga ttggccactc ttgcatgtgc tagtagattg 4560
tggaccagga ccagctgagc aaacacagtt gcagagtagc ctcctatgtt gctaagaagc 4620
tcctgctacc caggtgcttt gaacaattga gtgctccctc tggttaagta gagatggcac 4680
caccggagtt tttcttggat gtgaggctca atcctttacg gcagctatta taacaaagtg 4740
aaggttttct ccctgggaaa tgcagctttt ctctgtcttt actaattctg ccagcctgtg 4800

-continued

```
agagtaacca ccgtagctgg gcttcttctc agattaattg tcatgccagg tctccttcct   4860
ggggagctgt gatgctgctc tgaggttgat tgctgaggtt gtagtgggtt tttgtttgtt   4920
tttgtttagt ttttcttgat tgttcttctt tctcttgaat ggcaagagaa gaaacacttt   4980
ctctaaccca cggccaggaa ggaaatgggg agagagctac ttcttagttc aacctggttg   5040
ccacataaag gaatctctct ccttggactc agcccctaac tggaagcaag agccactgcc   5100
ctctgagact gagagagcag cccgaggagg agatgaatcc attctgccct ttgtttgggt   5160
ttgcttcctg tcagtgagag aatgctgagg cagttcctgt tatgtgaaac tttcattttt   5220
aaaaccagga cagtcctaaa cagactggaa tgagttggtc aatcccagtt ggtataggcc   5280
caatgatttt tgctagtaag ataggattgt cttcctcacc caaaatgcct tcaagtgccc   5340
taaaatgggt attttaaaat aagaataaat aatgtagatt tagtagaaaa cctggaaaac   5400
ataagaaaca aagatgaaac gaaaagtccc atgtaattcc accagttaga gttaaccact   5460
gatatcgttt ggatatatgg ctttctagtc ttgtggatat ccttttaatc tcttgtaata   5520
taaagtctga ccatatgtgt ccttgcattt gtttgtactg gactctgtta atatttctat   5580
agtaatggct cactttgggg agattgtgct gcacagtgtg taggaagcac attgggtgta   5640
ttattcccag ttttgtattt tgtatttcct tggagatgtg caggggttaa gagcgggggt   5700
ctggccatag ctggccacgt cagactctca tatggtaagt atcacagagc acatgaggcc   5760
tgtgttatgc gctggaaaga ctcaggaaat gagaggctct cttgttctga caaggcaggc   5820
tgagagctct catttagggt catcactcca gataactcca aatgcagttt attgctcaac   5880
tgaagcagat gatcactttt tgcctccaag ttcttcaccc tagctagctc ctttcaaaga   5940
gccgagtatg ctggatctta aagggccaaa ctagttacat ctcatacatt tcctgatgtt   6000
tagggatgcc ttcacttcca tcaaggatac cttggctgtg caaggacctc tgatagctgg   6060
agtctccttt tggtcactcc cagctttgct taaacttgat ggagtttgct gtccagtgat   6120
ccccggatct ttcatcatga aagccttcct tcctctcctg atgtctcagg cctctagacc   6180
tagactgggg ttctggcaag gaggcctcta tcaatagtat gacatccaat aatatgttag   6240
tgttgatatt ttgcacagta atattaagtt taagagatta taaaaatgag ttcaaatgaa   6300
taagttcctg tgatgtaaga gattagatat gtgtgatttc agaaccaaag gcaggggga    6360
atcccagaaa gaaaacaata atataatcct agtttctata tattattttt attcattact   6420
gtatatgggt agagatcaat attctttctt atgctgttac tattaattaa cacatttttt   6480
aaccatgcca ttgaactttt gggtgcatta aagtggaacc caagctcctc attagataat   6540
aatggcattt ggactgagtg ccatattcct aaatttccaa taaagtggtt gatatagaga   6600
ggacaggata aagccctata gtgtgcagtt atatcaaaac agctagtctc cactttaggg   6660
aatgccttta ctagagatta catgaaatgt ctgcttataa aataagcaga gatggcacca   6720
ctaagcagcc acctgaattg ttttcctaca ggaatgatta cttttcagat ccatttatgt   6780
tttcatgctc aatacttact ccccttccct gcaacaccca aagagtttac ttttgcaagt   6840
catttggtct tcagtctact actgaggaat agagaggcac taactgcttt acccaggatc   6900
agaactcatg ttcttacctt ctattaatag agtacttgag ccagatggac taactggtct   6960
cacattttct ctatcttggt tttacttcca taaacatcaa tatctttacc cacatgattt   7020
ttccatcctc ccattttttt ccatatgtat tagggttcag gaactatgat gctaatgatc   7080
acatttcttc ctagttccta atttcattag tgccatttcc tgatatctac agaaacaatt   7140
atcaatacat gtagctgctt gagccttatt tagaaggcta gcctttcttt tccaagtgct   7200
```

-continued

```
gtcagaatgt atacatttag tctgtctttt tcccttttag gagtctttgt tctgggttga   7260

tggcaaaatt cctcttttta catgtgagat ttttgatttc actgaattct acctagattt   7320

ttatggacat tggattttaa agaggaaaac actcattttc ttagtaagat attggtgata   7380

catagctatg ccattgattt ccatactcct gagctttggg gagggagaca gtggccaagt   7440

agcaggcaga ataagatcat cactcatgtc ctgaatcaat cacactttcc ttctcggatt   7500

gtgtatatgc tctgccactt cctacatatt acatcctgag tttttaagta aagtggatct   7560

tagccagatt tgagtctaat ggctgattca tcggcatagt tcttggcgtt aacatctcag   7620

tgtcctcttt agttctcttt gaggattcat gtcattgagg gcctttgtgc ctccacttgt   7680

ctcagtatga ggaagaactt tggtgtgagg gcggagctat gtgaagggtt gctgggttgg   7740

gggattagtt catatggtcc ccatgccatc tatttacttt tggagagagg ggactttgag   7800

tgggtgggta tggatagatg ttcctcaagg aaaccctgct ggctaatggg cactacatct   7860

gtgtattact gtgattctct ctgtaagctc cccatgtggc caaggacccc cctcctacca   7920

gggcacttcc tgccacctca ttgcactggt ctcaaccatt cagcctgctg ctgctgcacc   7980

atgttgggct gcggtaggat agggaagggg ttctgttgat tgctaaatgt tgcctaactt   8040

tatttccctc tcccacattt catgcaaggg agcggaccta acacatgact tgcattctct   8100

tcctatgttc agaaactcca gggcttgccc acgtgtatgt atgagtgacc aatggagctt   8160

ggaattcttt atctatatga tctgtccgaa aatgagatct tttgtactgg aatttgtgat   8220

gtagttgatc attcagagcc aaacgcatat accaataaag acaagactgt catataaaaa   8280

aaaaaaaaaa aa                                                       8292
```

<210> SEQ ID NO 8
<211> LENGTH: 549
<212> TYPE: DNA
<213> ORGANISM: Homo sapiens

<400> SEQUENCE: 8

```
acctccgcca ggaactgcag gcccacctgt ctgcaaccca gctgaggcca tgccctcccc     60

agggaccgtc tgcagcctcc tgctcctcgg catgctctgg ctggacttgg ccatggcagg    120

ctccagcttc ctgagccctg aacaccagag agtccagaga aaggagtcga agaagccacc    180

agccaagctg cagccccgag ctctagcagg ctggctccgc ccggaagatg gaggtcaagc    240

agaaggggca gaggatgaac tggaagtccg gttcaacgcc ccctttgatg ttggaatcaa    300

gctgtcaggg gttcagtacc agcagcacag ccaggccctg ggaagtttc ttcaggacat    360

cctctgggaa gaggccaaag aggccccagc cgacaagtga tcgcccacaa gccttactca    420

cctctctcta agtttagaag cgctcatctg gcttttcgct tgcttctgca gcaactccca    480

cgactgttgt acaagctcag gaggcgaata aatgttcaaa ctgtaaaaaa aaaaaaaaaa    540

aaaaaaaaa                                                            549
```

<210> SEQ ID NO 9
<211> LENGTH: 501
<212> TYPE: DNA
<213> ORGANISM: Homo sapiens

<400> SEQUENCE: 9

```
agttccccaa agataacaca gctttgcaca gtggatgttt acttgctggt ggtcttatct     60

aagatcaaca ttggcagctg tgcccggaga ggcctccagg gtccagcaga gaaaggagtc    120
```

```
gaagaagcca ccagccaagc tgcagccccg agctctagca ggctggctcc gcccggaaga    180

tggaggtcaa gcagaagggg cagaggatga actggaagtc cggttcaacg ccccctttga    240

tgttggaatc aagctgtcag gggttcagta ccagcagcac agccaggccc tggggaagtt    300

tcttcaggac atcctctggg aagaggccaa agaggcccca gccgacaagt gatcgcccac    360

aagccttact cacctctctc taagtttaga agcgctcatc tggcttttcg cttgcttctg    420

cagcaactcc cacgactgtt gtacaagctc aggaggcgaa taaatgttca aactgtaaaa    480

aaaaaaaaaa aaaaaaaaaa a                                              501
```

<210> SEQ ID NO 10
<211> LENGTH: 498
<212> TYPE: DNA
<213> ORGANISM: Homo sapiens

<400> SEQUENCE: 10

```
agttccccaa agataacaca gctttgcaca gtggatgttt acttgctggt ggtcttatct     60

aagatcaaca ttggcagctg tgcccggaga ggcctccagg gtccagagaa aggagtcgaa    120

gaagccacca gccaagctgc agccccgagc tctagcaggc tggctccgcc cggaagatgg    180

aggtcaagca gaaggggcag aggatgaact ggaagtccgg ttcaacgccc cctttgatgt    240

tggaatcaag ctgtcagggg ttcagtacca gcagcacagc caggccctgg ggaagtttct    300

tcaggacatc ctctgggaag aggccaaaga ggccccagcc gacaagtgat cgcccacaag    360

ccttactcac ctctctctaa gtttagaagc gctcatctgg cttttcgctt gcttctgcag    420

caactcccac gactgttgta caagctcagg aggcgaataa atgttcaaac tgtaaaaaaa    480

aaaaaaaaaa aaaaaaaa                                                  498
```

<210> SEQ ID NO 11
<211> LENGTH: 384
<212> TYPE: DNA
<213> ORGANISM: Homo sapiens

<400> SEQUENCE: 11

```
agttccccaa agataacaca gctttgcaca gtggatgttt acttgctggt ggtcttatct     60

aagatcaaca ttggcagctg tgcccggaga ggcctccagg gtccagttca acgccccctt    120

tgatgttgga atcaagctgt caggggttca gtaccagcag cacagccagg ccctggggaa    180

gtttcttcag gacatcctct gggaagaggc caaagaggcc ccagccgaca agtgatcgcc    240

cacaagcctt actcacctct ctctaagttt agaagcgctc atctggcttt tcgcttgctt    300

ctgcagcaac tcccacgact gttgtacaag ctcaggaggc gaataaatgt tcaaactgta    360

aaaaaaaaaa aaaaaaaaaa aaaa                                           384
```

<210> SEQ ID NO 12
<211> LENGTH: 1939
<212> TYPE: DNA
<213> ORGANISM: Homo sapiens

<400> SEQUENCE: 12

```
agtttggacg gctgcttccc accagcaaag accacgactg gagagccgag ccggaggcag     60

ctgggaaaca tgaagagcgt cttgctgctg accacgctcc tcgtgcctgc acacctggtg    120

gccgcctgga gcaataatta tgcggtggac tgccctcaac actgtgacag cagtgagtgc    180

aaaagcagcc cgcgctgcaa gaggacagtg ctcgacgact gtggctgctg ccgagtgtgc    240

gctgcagggc ggggagaaac ttgctaccgc acagtctcag gcatggatgg catgaagtgt    300
```

-continued ggcccggggc tgaggtgtca gccttctaat ggggaggatc cttttggtga agagtttggt 360
atctgcaaag agcatgacat ggcatctgga gatggcaata ttgtgagaga agaagttgtg 420
aaagagaatg ctgccgggtc tcccgtaatg aggaaatggt taaatccacg ctgatcccgg 480
ctgtgatttc tgagagaagg ctctattttc gtgattgttc aacacacagc caacatttta 540
ggaactttct agattatagc ataaggacat gtaatttttg aagaccaaat gtgatgcatg 600
gtggatccag aaaacaaaaa gtaggatact tacaatccat aacatccata tgactgaaca 660
cttgtatgtg tttgttaaat attcgaatgc atgtagattt gttaaatgtg tgtgtatagt 720
aacactgaag aactaaaaat gcaatttagg taatcttacg tggagacagg tcaaccaaag 780
agggagctag gcaaagctga agaccgcagt gagtcaaatt agttctttga ctttgatgta 840
cattaatgtt gggatatgga atgaagactt aagagcagga gaagatgggg agggggtggg 900
agtgggaaat aaaatattta gcccttcctt ggtaggtagc ttctctagaa tttaattgtg 960
cttttttttt ttttttggc tttgggaaaa gtcaaaataa aacaaccaga aaacccctga 1020
aggaagtaag atgtttgaag cttatggaaa tttgagtaac aaacagcttt gaactgagag 1080
caatttcaaa aggctgctga tgtagttccc gggttacctg tatctgaagg acggttctgg 1140
ggcataggaa acacatacac ttccataaat agctttaacg tatgccacct cagagataaa 1200
tctaagaagt attttaccca ctggtggttt gtgtgtgtat gaaggtaaat atttatatat 1260
ttttataaat aaatgtgtta gtgcaagtca tcttccctac ccatatttat catcctcttg 1320
aggaaagaaa tctagtatta tttgttgaaa atggttagaa taaaactatg actctataag 1380
gttttcaaac atctgaggca tgataaattt attatccata attatagtaa taataacctt 1440
aataagcata agaaaaacag agtcactctg gatttcaaaa atgtcaaaaa atgagcaaca 1500
gagggtcctt atttaaacat aagtgctgtg acttaggtga attttcaatt taaggtagaa 1560
aataagtttt taggaggttt gtaaaagaag aatcaatttt cagcagaaaa catgtcaact 1620
ttaaaatata gtttattttc atattttttt cttttaaact tggttgataa gtggaattag 1680
gagtatattt gaaagaatct tagcacaaac aggactgttg tactagatgt tcttaggaaa 1740
tatctcagaa gtattttatt tgaagtgaag aacttattta agaattattt cagtatttac 1800
ctgtatttta ttcttgaagt tggccaacag agttgtgaat gtgtgtggga aggcctttga 1860
atgtaaagct gcataagctg ttaggttttg ttttaaaagg acatgtttat tattgttcaa 1920
taaaaaagaa caagataca 1939

<210> SEQ ID NO 13
<211> LENGTH: 882
<212> TYPE: DNA
<213> ORGANISM: Homo sapiens

<400> SEQUENCE: 13
caccctttcc agatacacac ccgtttagtg cgagaaatgg agcggttggg gagaggatct 60
cccgaggggg ctggattgag aatgggtacc atttgagatc tcctaggagg ccggccatcg 120
ggcaatgtct gatggagtcc agccggtgga ggagactgaa aggaaacagc ctgcttcctg 180
caggtccgcg ggagggaggt ctttaagtgc gtttgtgcag ccgatttcaa ggctaagaga 240
gaaagactgc ctctgatccc tgaaggaaga aaaaaaaaaa aaaaacagga aaaaaactca 300
acatggaaaa tgtccccaag gaaaacaaag ttgtggagaa ggccccagtg cagaatgaag 360
cccccgcttt aggaggtggt gaataccagg agcctggagg aaatgttaaa ggggtttggg 420

-continued

```
ctccacctgc cccgggtttt ggagaggatg tgcccaatag gcttgtcgat aacattgata    480

tgatagatgg agatggagat gatatggaac ggttcatgga ggagatgaga gagctaagga    540

ggaaaattag ggaacttcag ttgaggtaca gtctgcgcat tcttataggg gaccctcctc    600

accatgatca tcatgatgag ttttgcctta tgccttgaat cttgaggtta ataatcataa    660

aatccctgct ttctaaattc gcatttttcc tggtgtacct ttaatgtgaa ccttttggca    720

ttcttctgca attttctgat tggagattgc attttgacct agtctgtaag tttttctgtc    780

agaagaggac tttcatcaac tttcatggaa agatgtttat tgcatactgt aaagttaata    840

aagcaattta aaagcagtct aaaaaaaaaa aaaaaaaaaa aa                        882
```

```
<210> SEQ ID NO 14
<211> LENGTH: 1278
<212> TYPE: DNA
<213> ORGANISM: Homo sapiens

<400> SEQUENCE: 14

ccattggcct gtagattcac ctcccctggg cagggcccca ggacccagga taatatctgt     60

gcctcctgcc cagaaccctc caagcagaca caatggtaag aatggtgcct gtcctgctgt    120

ctctgctgct gcttctgggt cctgctgtcc cccaggagaa ccaagatggt cgttactctc    180

tgacctatat ctacactggg ctgtccaagc atgttgaaga cgtccccgcg tttcaggccc    240

ttggctcact caatgacctc cagttcttta gatacaacag taaagacagg aagtctcagc    300

ccatgggact ctggagacag gtggaaggaa tggaggattg gaagcaggac agccaacttc    360

agaaggccag ggaggacatc tttatggaga ccctgaaaga catcgtggag tattacaacg    420

acagtaacgg gtctcacgta ttgcagggaa ggtttggttg tgagatcgag aataacagaa    480

gcagcggagc attctggaaa tattactatg atggaaagga ctacattgaa ttcaacaaag    540

aaatcccagc ctgggtcccc ttcgacccag cagcccagat aaccaagcag aagtgggagg    600

cagaaccagt ctacgtgcag cgggccaagg cttacctgga ggaggagtgc cctgcgactc    660

tgcggaaata cctgaaatac agcaaaaata tcctggaccg gcaagatcct ccctctgtgg    720

tggtcaccag ccaccaggcc ccaggagaaa agaagaaact gaagtgcctg gcctacgact    780

tctacccagg gaaaattgat gtgcactgga ctcgggccgg cgaggtgcag gagcctgagt    840

tacggggaga tgttcttcac aatggaaatg gcacttacca gtcctgggtg gtggtggcag    900

tgcccccgca ggacacagcc ccctactcct gccacgtgca gcacagcagc ctggcccagc    960

ccctcgtggt gccctgggag gccagctagg aagcaagggt tggaggcaat gtgggatctc   1020

agacccagta gctgcccttc ctgcctgatg tgggagctga accacagaaa tcacagtcaa   1080

tggatccaca aggcctgagg agcagtgtgg ggggacagac aggaggtgga tttggagacc   1140

gaagactggg atgcctgtct tgagtagact tggacccaaa aaatcatctc accttgagcc   1200

cacccccacc ccattgtcta atctgtagaa gctaataaat aatcatccct ccttgcctag   1260

cataaaaaaa aaaaaaaa                                                  1278
```

```
<210> SEQ ID NO 15
<211> LENGTH: 1801
<212> TYPE: DNA
<213> ORGANISM: Homo sapiens

<400> SEQUENCE: 15

gggttatatg atctctttgg ctttagggaa ttactccata ccagctctga gatttccagc     60

tcagcgatgc ccccaggtcc ctgggagagc tgcttctggg tgggggcct catttgtgg    120
```

ctcagcgttg gaagttcagg ggatgcacct cctaccccac agccaaagtg cgctgacttc 180
cagagcgcca accttttga aggcaccgat ctcaaagtcc agtttctcct ctttgtccct 240
tcgaatccta gctgtgggca gctagtagaa ggaagcagtg acctccaaaa ctctgggttc 300
aatgccactc tgggaaccaa actaattatc catggattca gggttttagg aacaaagcct 360
tcctggattg acacatttat tagaaccctt ctgcgtgcaa cgaatgctaa tgtgattgcc 420
gtggactgga tttatgggtc tacaggagtc tacttctcag ctgtgaaaaa tgtgctgggt 480
gtgtcggaat cctcaatcca catcattggt gttagcctgg gggcccacgt tgggggcatg 540
gtgggacagc tcttcggagg ccagctggga cagatcacag gcctggaccc cgctggacct 600
gagtacacca gggccagtgt ggaagagcgc ttggatgctg gagatgccct cttcgtggaa 660
gccatccaca cagacaccga caatttgggt attcggattc ccgttggaca tgtggactac 720
ttcgtcaacg gaggccaaga ccaacctggc tgccccacct tcttttacgc aggttatagt 780
tatctgatct gtgatcacat gagggctgtg cacctctaca tcagcgccct ggagaattcc 840
tgtccactga tggcctttcc ctgtgccagc tacaaggcct tccttgctgg acgctgtctg 900
gattgcttta accctttct gctttcctgc ccaaggatag gactggtgga acaaggtggt 960
gtcaagatag agccgctccc caaggaagtg aaagtctacc tcctgactac ttccagtgct 1020
ccgtactgca tgcatcacag cctcgtggag tttcacttga aggaactgag aaacaaggac 1080
accaacatcg aggttacctt ccttagcagt aacatcacct cttcatctaa gatcaccata 1140
cctaagcagc aacgctatgg gaaaggaatc atagcccatg ccaccccaca atgccagata 1200
aaccaagtga aattcaagtt tcagtcttcc aaccgagttt ggaaaaaaga ccggactacc 1260
attattggga agttctgcac tgccctttttg cctgtcaatg acagagaaaa gatggtctgc 1320
ttacctgaac cagtgaactt acaagcaagt gtgactgttt cctgtgacct gaagatagcc 1380
tgtgtgtagt ttaacctggg caggacacat ctccctgcat tttttttttt tttttgagag 1440
agaggtgtga tgagggatgt gtgtgtgcag cttattgtag accattacta ctaaggagaa 1500
aagcaaagct ctttcttatt ttcctcataa tcagctaccc tggaggggag ggagaactca 1560
ttttacagaa cttggtttcc tttgccgatc ttatgtacat acccatttta gctttcccat 1620
gcatacttaa ctgcacttgc tttatctcct tgggcattcg tacttaggat tcaatagaaa 1680
catgtacagg gtaaacaatt ttttaaaaat aaaacttcat ggagtatctg aaaaaaaaaa 1740
aaaaaaaaaa aaaaaaaaaa aaaaaaaaaa aaaaaaaaaa aaaaaaaaaa aaaaaaaaaa 1800
a 1801

<210> SEQ ID NO 16
<211> LENGTH: 1647
<212> TYPE: DNA
<213> ORGANISM: Homo sapiens

<400> SEQUENCE: 16
gggttatatg atctctttgg ctttagggaa ttactccata ccagctctga gatttccagc 60
tcagcgatgc ccccaggtcc ctgggagagc tgcttctggg tggggggcct cattttgtgg 120
ctcagcgttg gaagttcagg gttttaggaa caaagccttc ctggattgac acatttatta 180
gaacccttct gcgtgcaacg aatgctaatg tgattgccgt ggactggatt tatgggtcta 240
caggagtcta cttctcagct gtgaaaaatg tgattaagtt gagcctcgag atctcccttt 300
tcctcaataa actcctggtg ctgggtgtgt cggaatcctc aatccacatc attggtgtta 360

-continued

```
gcctgggggc ccacgttggg ggcatggtgg gacagctctt cggaggccag ctgggacaga    420
tcacaggcct ggaccccgct ggacctgagt acaccagggc cagtgtggaa gagcgcttgg    480
atgctggaga tgccctcttc gtggaagcca tccacacaga caccgacaat ttgggtattc    540
ggattcccgt tggacatgtg gactacttcg tcaacggagg ccaagaccaa cctggctgcc    600
ccaccttctt ttacgcaggt tatagttatc tgatctgtga tcacatgagg gctgtgcacc    660
tctacatcag cgccctggag aattcctgtc cactgatggc ctttccctgt gccagctaca    720
aggccttcct tgctggacgc tgtctggatt gctttaaccc ttttctgctt tcctgcccaa    780
ggataggact ggtggaacaa ggtggtgtca agatagagcc gctccccaag gaagtgaaag    840
tctacctcct gactacttcc agtgctccgt actgcatgca tcacagcctc gtggagtttc    900
acttgaagga actgagaaac aaggacacca acatcgaggt taccttcctt agcagtaaca    960
tcacctcttc atctaagatc accataccta agcagcaacg ctatgggaaa ggaatcatag   1020
cccatgccac cccacaatgc cagataaacc aagtgaaatt caagtttcag tcttccaacc   1080
gagtttggaa aaaagaccgg actaccatta ttgggaagtt ctgcactgcc cttttgcctg   1140
tcaatgacag agaaaagatg gtctgcttac ctgaaccagt gaacttacaa gcaagtgtga   1200
ctgtttcctg tgacctgaag atagcctgtg tgtagtttaa cctgggcagg acacatctcc   1260
ctgcattttt tttttttttt tgagagagag gtgtgatgag ggatgtgtgt gtgcagctta   1320
ttgtagacca ttactactaa ggagaaaagc aaagctcttt cttattttcc tcataatcag   1380
ctaccctgga ggggagggag aactcatttt acagaacttg gtttcctttg ccgatcttat   1440
gtacataccc attttagctt tcccatgcat acttaactgc acttgcttta tctccttggg   1500
cattcgtact taggattcaa tagaaacatg tacagggtaa acaatttttt aaaaataaaa   1560
cttcatggag tatctgaaaa aaaaaaaaaa aaaaaaaaaa aaaaaaaaaa aaaaaaaaaa   1620
aaaaaaaaaa aaaaaaaaaa aaaaaaa                                       1647
```

<210> SEQ ID NO 17
<211> LENGTH: 5622
<212> TYPE: DNA
<213> ORGANISM: Homo sapiens

<400> SEQUENCE: 17

```
ggcacgtgga ctccctttaa tccagtgact gtcaggtcga tcatatgccg aggacgatga     60
tcccgccggg ggagtgcacg tacgcgggcc ggaagcggag gaggcccctg cagaaacaga    120
ggcccgccgt gggggcagag aagtccaacc cctccaagcg acaccgggac cgcctcaacg    180
ccgagttgga ccacctggcc agcctgctgc cgttcccgcc tgacatcatc tccaagctgg    240
acaagctttc tgtcctgcgc ctcagtgtca gttacctccg ggtgaagagc ttcttccaag    300
tcgtgcagga gcagagctca cggcagcctg cggccggcgc cccctcgccc ggagacagct    360
gtcctcttgc agggtctgcc gtgctggagg gaaggctgct gttggagtct cttaatggct    420
ttgctctggt cgtgagtgca gaagggacga tattttatgc atcagcaacg atcgtggact    480
atctgggctt ccatcagacg gatgtaatgc accagaacat ttatgactac atccacgtgg    540
acgaccgcca ggacttctgc cggcagctcc actgggccat ggaccctccc caggtggtgt    600
ttgggcagcc cccgcccttg gagacaggag atgatgctat cctggggagg ctgctcaggg    660
cccaggagtg ggcacaggc acgcccaccg agtactcggc cttcctgacc cgctgcttca    720
tctgccgtgt gcgctgcctg ctggacagca cctcgggctt cctgacgatg cagtttcaag    780
gaaaactaaa attcctgttt ggacagaaga agaaggcgcc gtcaggagcc atgctcccgc    840
```

```
cgcggctgtc gctgttctgc attgcggcac ccgttctcct cccctccgca gcggagatga    900
aaatgaggag cgcgctcctg agggcaaaac ccagagcaga caccgcagcc accgcggatg    960
caaaagtaaa agccaccacc agtctgtgcg aatcggaact gcatggaaaa cccaattact   1020
cagcaggaag gagcagcaga gagagcggcg ttttggtgct cagggaacag actgacgctg   1080
gccgatgggc acaggttccc gccagggccc catgcctgtg cctccggggt ggccctgacc   1140
ttgtccttga ccccaagggg ggctcagggg acagggagga ggagcagcac aggatgctga   1200
gcagggcctc tggagtgaca gggcggaggg agactccagg acccacaaag cccctgccct   1260
ggacagcggg aaagcacagt gaggatggtg ccaggccgag gctgcagccc agcaagaatg   1320
acccgccctc cctgcgcccc atgccccgcg gctcctgcct gccctgcccg tgtgtccagg   1380
gcactttcag gaactcgccc atctctcacc cgccgagccc gtcccccagt gcctactcca   1440
gccggaccag cagacccatg cgggatgtcg gtgaggacca ggtgcaccct cccctctgcc   1500
actttcccca gaggagcctg cagcaccagc tccctcagcc tggagctcag cgttttgcca   1560
cgaggggcta tcccatggag gacatgaagc tgcaaggtgt accgatgcct ccgggggacc   1620
tgtgtggtcc gacgctgctg ctagatgtgt ccatcaagat ggagaaggac tctgggtgtg   1680
agggtgctgc agacggctgt gtgcccagcc aggtgtggct gggggccagt gacaggagcc   1740
acccagccac cttccctacc aggatgcacc tgaaaacaga gccagactct cggcaacagg   1800
tgtacatctc gcacctgggg cacggcgtgc ggggggctca gccccatggg agggccactg   1860
ctgggcgcag cagggagctg accccctttcc accctgcaca ctgtgcctgc ctggagccca   1920
cagacggcct tccccagtcg gagcctcccc accagctctg tgcacggggc cgaggtgaac   1980
agtcctgcac ctgcagagct gctgaggccg cccctgtggt caagcgggag cccttggact   2040
caccccagtg ggctactcac agccagggaa tggtgcccgg gatgttgccc aaaagtgcct   2100
tggccacgct ggtcccgccc caagcttcgg ggtgcacatt cctgccatag cgcagtgacc   2160
accatccaag ctcagatctg tgtgtctacg ctcagatgcg tcggtggctg ggctgccctg   2220
ctcctggtca ggccggagcc cgtcctaaga cacacgcttt gcagagctgt gcatgcgcag   2280
tctgctagtg tgtgtgtgca gcatacgcag gagcctatcc tgaattttgt aaaatatccc   2340
aacagttctt aaatgaaaac tggccttaag tctattcaag catgacagca tttctctttg   2400
aggaattaaa atctttagga aagtgatcat ggctggacag cttcatgccc cagaggcagc   2460
gagcacccgt cccatggctg ccaagtccac agtcggggat gaagcagtcg ggtgatgctc   2520
ccaagtccgc agtcggggat gaagcggtcg ggtgatgctc ccaagtccgc agtcggggat   2580
gaagcggtcg ggtgacacac ctagctcagc cctcccaggc cacctgcagc tcccagcctg   2640
tgctgtgcag gcagggtcag cccatcgcca cagtgcactg tagaggccag cacacggcaa   2700
attagaaata caacacgcgg agaaaggggt ccgtgagccc actcatagag gaatctagaa   2760
cgttccaggc agcagaggct ggcagcgtgg gtcccacact gccccacacc gtgcggcagg   2820
tgctccatgg cgccatgaca gagtctgagg ccagacctgg actggaattg acagcataac   2880
ccctgttcct tctggacatc tcccgagttc tcagtgggtc tctgcggacg gttcttccta   2940
atctgcctct tggtacatca cgtaatacag agttcacaga ctccgggttt ggaagtacag   3000
agaaacacac aacgtagaga gaagacacag gaaactgcgc tgcctgtggg ggtttctctc   3060
tggctggctg tacagttcac tcaaatgagg gttcccattg ccatcctagg agaataatta   3120
gggacaagac agacaagtat taatagcatt aaaacagttg taaaggcgat attttctgag   3180
```

-continued

```
agtaggaaat ttggatacaa aagcataagt cagaaagtga aggtcaccaa tccaccaacc   3240
cgagaaccta cagctgatgg tgcatttcag gcttcttcca cggtctggcc tggaacccca   3300
cccggctggt gcaggcatca gatcagggtg tagaagtcac cccaagcaag aggaagccag   3360
gcagtgaggc cctggggtgt ggctgcagct gggcccacct gtgcgggggt gggaaggccc   3420
catcctcagg gagagggcat cggcgccctg acgtcagctc cactgggagt ggcaggagct   3480
gtgggagccc atgggtgagg gacccaccac cccgctgcac tgtgcattgt gcctcccgtg   3540
tggacgccct ctctgttgtt ggcccgcggg tgagggaccc accaccccta gggacccacc   3600
accccgccgc actgtgcatt ctgcctcctg tgtggacgcc ctctctgttg tcagtggctt   3660
tgaggtgtca gtgcttactt agatgctggt ttaatgctgg acccatttgt taaacgcacc   3720
ttcactttgt caaaacccag gtttggttgg caggactggg tcttctgccc aatgccaggt   3780
gcctgcgcct ctcagtggcc tggttcttgg acagtttgcc cccatgtggc agggataggg   3840
ataaggatct cctctcagta ctggaagaga acagccaacc atctgagccc agagtcacag   3900
atccatcgtg gccccctatg acccccaagc cctaccgagg gggcactcac tctctgctta   3960
gccagggggc gtctttcaaa aggtgacctc catgctgtgc tgtcgtgggt gtgagacgtg   4020
ctcatggcct tccactgcca tctctccctt atctgatgcc taaagtcacg atggggacag   4080
agctacccag gggccagcca tggggtgacc agccacctga gggtcagtca cctgtggaga   4140
gcaggcacct gtgaagacca ggcacctgag gactggcgcc tacttcccac tttggcccta   4200
cactggcaca gagcccctct ttattcattt ctcatgctga gcatggcaca cttctggcct   4260
ctgggcattt atggatttaa gaccaggatg gtatttcaga agcttcccac ttccttccta   4320
ttctaaccga gtgcccagct cctttgctga tcatggaaag acccttaata attaggcctg   4380
caggccaggc gcagtggctc atgcctataa tcccagcact ttaggaggtc aaggtaggag   4440
gatcgcttaa gcccaggagt tcaagaccag cctgggcaac acaggaagaa tgtgtctcta   4500
caaaaaataa ttaaaaatca gatctgctgt atccctgaaa aagtctcaat caacatgcat   4560
gttccactct tggagttccc tgttctgagg gccagccacg tcctgtgtcc tggagcttag   4620
ccctcagcag ctcccttcag cctgggcgcc gcctgggtcc caaacgtggc agctgctctt   4680
ccagtctcgg ggccgaggag ggcagggagc tcagtgactg agagtcttgt gtatcacatg   4740
tcttgagtgt cctggagcca acggctgtca ctgggaaaaa caccaggccc caaagatcga   4800
atcagagacg tggctgcgtg tttgcgattg tagccaggcc cttcagtgtc atcaaaggag   4860
cactggggcc tccttaagca cagacggcag cccctgccca ggaggcttct tcaccacgtc   4920
ctgccctgca gcctcccaga cctttagatg cgcccctgcc caaggccctc ctggtgacag   4980
gtgccagatt gagtggtggg ttgctgccag gcaggccacg ctgtgttgac gctgcactca   5040
gcacgtgggt gttggctctg ccggttttgt ggtgtgggga ccctacagga ggctgcggcc   5100
ctgagagcct gggatcagcg aggtgtccga catcccttcc tcaacggcaa caaaaactcc   5160
ccaagtcagc actttggtta ttttatagcc acaaccctct tggaaaacag tggggaagac   5220
tatggaacat agaaagtgtg gatgtatcac ttctctctaa aatgtcattg ttagcactaa   5280
ttacaggttc atgtttttct gtgtatgtag cttttcccta tatagctgaa aaagtattaa   5340
agtcaaatat aaggtgggaa tgggatggaa gggaggagat caatacaact tatatttttg   5400
cagtttctac tggaagaaaa aagttttcaa tacctagacc aacttgttga atttttaaaa   5460
cttatgcact ataaatgcaa ctttctctac tgctttctca gtgcctttag gaagctttca   5520
aatttttttg tactgtggtt tgtattaaat ttgcaatatt gatgtaaaat acatgacatg   5580
```

ctagtacatg tttaacaaaa atttaaaaaa aaaaaaaaaa aa 5622

<210> SEQ ID NO 18
<211> LENGTH: 2039
<212> TYPE: DNA
<213> ORGANISM: Homo sapiens

<400> SEQUENCE: 18
gtaggtgtca cttatatcac aaggctacag gtgtctttat ttccactgca cgctggtgct 60
gggagcgcct gccttctctt gccttgaaag cctcctcttt ggacctagcc accgctgccc 120
tcacggtaat gttggactcg gtgacacaca gcaccttcct gcctaatgca tccttctgcg 180
atcccctgat gtcgtggact gatctgttca gcaatgaaga gtactaccct gcctttgagc 240
atcagacaga tgctgattcc aactgcttga aaacaagtgg catcaaaagt caagactgtc 300
acagtcatag tagaacaagc ctccaaagtt ctcatctatg ggaatttgta cgagacctgc 360
ttctatctcc tgaagaaaac tgtggcattc tggaatggga agatagggaa caaggaattt 420
ttcgggtggt taaatcggaa gccctggcaa agatgtgggg acaaaggaag aaaaatgaca 480
gaatgacata tgaaaagttg agcagagccc tgagatacta ctataaaaca ggaattttgg 540
agcgggttga ccgaaggtta gtgtacaaat ttggaaaaaa tgcacacggg tggcaggaag 600
acaagctatg atctgctcca ggcatcaagc tcattttatg gatttctgtc ttttaaaaca 660
atcagattgc aatagacatt cgaaaggctt cattttcttc tctttttttt taacctgcaa 720
acatgctgat aaaatttctc cacatctcag cttacatttg gattcagagt tgttgtctac 780
ggagggtgag agcagaaact cttaagaaat cctttcttct ccctaagggg atgaggggat 840
gatcttttgt ggtgtcttga tcaaacttta ttttcctaga gttgtggaat gacaacagcc 900
catgccattg atgctgatca gagaaaaact attcaattct gccattagag acacatccaa 960
tgctcccatc ccaaaggttc aaaagttttc aaataactgt ggcagctcac caaaggtggg 1020
ggaaagcatg attagtttgc aggttatggt aggagagggt gagatataag acatacatac 1080
tttagatttt aaattattaa agtcaaaaat ccatagaaaa gtatcccttt tttttttttt 1140
gagacgggtt ctcactatgt tgcccagggc tggtcttgaa ctcctatgct caagtgatcc 1200
tcccacctcg gcctcccaaa gtactgtgat tacaagcgtg agccacggca cctgggcaga 1260
aaagtatctt aattaatgaa agagctaagc catcaagctg ggacttaatt ggatttaaca 1320
taggttcaca gaaagtttcc taaccagagc atctttttga ccactcagca aaacttccac 1380
agacatcctt ctggacttaa acacttaaca ttaaccacat tattaattgt tgctgagttt 1440
attccccctt ctaactgatg gctggcatct gatatgcaga gttagtcaac agacactggc 1500
atcaattaca aaatcactgc tgtttctgtg attcaagctg tcaacacaat aaaatcgaaa 1560
ttcattgatt ccatctctgg tccagatgtt aaacgtttat aaaaccggaa atgtcctaac 1620
aactctgtaa tggcaaatta aattgtgtgt ctttttttgtt ttgtctttct acctgatgtg 1680
tattcaagcg ctataacacg tatttccttg acaaaaatag tgacagtgaa ttcacactaa 1740
taaatgttca taggttaaag tctgcactga cattttctca tcaatcactg gtatgtaagt 1800
tatcagtgac tgacagctag gtggactgcc cctaggactt ctgtttcacc agagcaggaa 1860
tcaagtggtg aggcactgaa tcgctgtaca ggctgaagac ctccttatta gagttgaact 1920
tcaaagtaac ttgttttaaa aaatgtgaat tactgtaaaa taatctattt tggattcatg 1980
tgttttccag gtggatatag tttgtaaaca atgtgaataa agtatttaac atgtaaaaa 2039

<210> SEQ ID NO 19
<211> LENGTH: 2222
<212> TYPE: DNA
<213> ORGANISM: Homo sapiens

<400> SEQUENCE: 19
ggctgagtgg tttgctcctt cccctctctc tgggaggctg agcaggggtg ccgggttgct 60
caggccatgg gagccacacc tgttattgct gcctctgatt tgtgtgacac tgagaagccc 120
acaggcctgt ccctccaact cggtggaccc tctctgtgtg catttggtgt gtgagccagc 180
tctgagaagg gttcagaagc cactggaggc atctggggac ctcagcttcc atgccatctc 240
tgcctcactc ccacagggta atgttggact cggtgacaca cagcaccttc ctgcctaatg 300
catccttctg cgatcccctg atgtcgtgga ctgatctgtt cagcaatgaa gagtactacc 360
ctgcctttga gcatcagaca ggttactcct tttttaatga cgctgaagaa agcaaggcca 420
ccatcaaaga ctatgctgat tccaactgct tgaaaaacaag tggcatcaaa agtcaagact 480
gtcacagtca tagtagaaca agcctccaaa gttctcatct atgggaattt gtacgagacc 540
tgcttctatc tcctgaagaa aactgtggca ttctggaatg ggaagatagg gaacaaggaa 600
tttttcgggt ggttaaatcg gaagccctgg caaagatgtg gggacaaagg aagaaaaatg 660
acagaatgac atatgaaaag ttgagcagag ccctgagata ctactataaa acaggaattt 720
tggagcgggt tgaccgaagg ttagtgtaca aatttggaaa aaatgcacac gggtggcagg 780
aagacaagct atgatctgct ccaggcatca agctcatttt atggatttct gtcttttaaa 840
acaatcagat tgcaatagac attcgaaagg cttcattttc ttctcttttt ttttaacctg 900
caaacatgct gataaaattt ctccacatct cagcttacat ttggattcag agttgttgtc 960
tacggagggt gagagcagaa actcttaaga aatcctttct tctccctaag ggatgagggg 1020
gatgatcttt tgtggtgtct tgatcaaact ttattttcct agagttgtgg aatgacaaca 1080
gcccatgcca ttgatgctga tcagagaaaa actattcaat tctgccatta gagacacatc 1140
caatgctccc atcccaaagg ttcaaaagtt ttcaaataac tgtggcagct caccaaaggt 1200
gggggaaagc atgattagtt tgcaggttat ggtaggagag ggtgagatat aagacataca 1260
tactttagat tttaaattat taaagtcaaa aatccataga aaagtatccc ttttttttt 1320 tttgagacgg gttctcacta tgttgcccag ggctggtctt gaactcctat gctcaagtga 1380
tcctcccacc tcggcctccc aaagtactgt gattacaagc gtgagccacg gcacctgggc 1440
agaaaagtat cttaattaat gaaagagcta agccatcaag ctgggactta attggattta 1500
acataggttc acagaaagtt tcctaaccag agcatctttt tgaccactca gcaaaacttc 1560
cacagacatc cttctggact taaacactta acattaacca cattattaat tgttgctgag 1620
tttattcccc cttctaactg atggctggca tctgatatgc agagttagtc aacagacact 1680
ggcatcaatt acaaaatcac tgctgtttct gtgattcaag ctgtcaacac aataaaatcg 1740
aaattcattg attccatctc tggtccagat gttaaacgtt tataaaaccg gaaatgtcct 1800
aacaactctg taatggcaaa ttaaattgtg tgtctttttt gttttgtctt tctacctgat 1860
gtgtattcaa gcgctataac acgtatttcc ttgacaaaaa tagtgacagt gaattcacac 1920
taataaatgt tcataggtta aagtctgcac tgacattttc tcatcaatca ctggtatgta 1980
agttatcagt gactgacagc taggtggact gcccctagga cttctgtttc accagagcag 2040
gaatcaagtg gtgaggcact gaatcgctgt acaggctgaa gacctcctta ttagagttga 2100
acttcaaagt aacttgtttt aaaaaatgtg aattactgta aaataatcta ttttggattc 2160
atgtgttttc caggtggata tagtttgtaa acaatgtgaa taaagtattt aacatgtaaa 2220
aa 2222

<210> SEQ ID NO 20
<211> LENGTH: 1214
<212> TYPE: DNA
<213> ORGANISM: Homo sapiens

<400> SEQUENCE: 20
agaaggttta aggccggaaa gggaaatgaa ggggcccggc gctaaccctc taaggacctg 60
ttttgcttct gtttaaacca aatgggcagt ctgtcattac acacaccctg ggtcttcata 120
tgtggccgcc aggtaggagc atcacagtca agctacggga gaaaacagtt tccaggaaac 180
tggaaatgaa cggcccgagt gctttccagg ggctcatctg tgggaagtat aatggaatgt 240
gcttacaagg gccagcagga gtgcctggtc gagacgggag ccctggggcc aatggcattc 300
cgggtacacc tgggatccca ggtcgggatg gattcaaagg agaaaagggg gaatgtctga 360
gggaaagctt tgaggagtcc tggacaccca actacaagca gtgttcatgg agttcattga 420
attatggcat agatcttggg aaaattgcgg agtgtacatt tacaaagatg cgttcaaata 480
gtgctctaag agttttgttc agtggctcac ttcggctaaa atgcagaaat gcatgctgtc 540
agcgttggta tttcacattc aatggagctg aatgttcagg acctcttccc attgaagcta 600
taatttattt ggaccaagga agccctgaaa tgaattcaac aattaatatt catcgcactt 660
cttctgtgga aggactttgt gaaggaattg gtgctggatt agtggatgtt gctatctggg 720
ttggtacttg ttcagattac ccaaaaggag atgcttctac tggatggaat tcagtttctc 780
gcatcattat tgaagaacta ccaaaataaa tgctttaatt ttcatttgct acctcttttt 840
ttattatgcc ttggaatggt tcacttaaat gacattttaa ataagtttat gtatacatct 900
gaatgaaaag caaagctaaa tatgtttaca gaccaaagtg tgatttcaca ctgtttttaa 960
atctagcatt attcattttg cttcaatcaa aagtggtttc aatatttttt ttagttggtt 1020
agaatacttt cttcatagtc acattctctc aacctataat ttggaatatt gttgtggtct 1080
tttgtttttt ctcttagtat agcattttta aaaaaatata aaagctacca atctttgtac 1140
aatttgtaaa tgttaagaat ttttttata tctgttaaat aaaaattatt tccaacaacc 1200
ttaatatctt taaa 1214

<210> SEQ ID NO 21
<211> LENGTH: 618
<212> TYPE: DNA
<213> ORGANISM: Homo sapiens

<400> SEQUENCE: 21
gcggccgcaa gctcggcact cacggctctg agggctccga cggcactgac ggccatggcg 60
cgttcgaacc tcccgctggc gctgggcctg gccctggtcg cattctgcct cctggcgctg 120
ccacgcgacg cccgggcccg gccgcaggag cgcatggtcg gagaactccg ggacctgtcg 180
cccgacgacc cgcaggtgca gaaggcggcg caggcggccg tggccagcta caacatgggc 240
agcaacagca tctactactt ccgagacacg cacatcatca aggcgcagag ccagctggtg 300
gccggcatca agtacttcct gacgatggag atggggagca cagactgccg caagaccagg 360
gtcactggag accacgtcga cctcaccact tgcccccctgg cagcaggggc gcagcaggag 420
aagctgcgct gtgactttga ggtccttgtg gttccctggc agaactcctc tcagctccta 480

```
aagcacaact gtgtgcagat gtgataagtc cccgagggcg aaggccattg ggtttggggc    540

catggtggag ggcacttcag gtccgtgggc cgtatctgtc acaataaatg gccagtgctg    600

cttcttgcaa aaaaaaaa                                                  618


<210> SEQ ID NO 22
<211> LENGTH: 2324
<212> TYPE: DNA
<213> ORGANISM: Homo sapiens

<400> SEQUENCE: 22

gtaggtgtca cttatatcac aaggctacag gtgtctttat ttccactgca cgctggtgct     60

gggagcgcct gccttctctt gccttgaaag cctcctcttt ggacctagcc accgctgccc    120

tcacggtaat gttggactcg gtgacacaca gcaccttcct gcctaatgca tccttctgcg    180

atcccctgat gtcgtggact gatctgttca gcaatgaaga gtactaccct gcctttgagc    240

atcagacagc ctgtgactca tactggacat cagtccaccc tgaatactgg actaagcgcc    300

atgtgtggga gtggctccag ttctgctgcg accagtacaa gttggacacc aattgcatct    360

ccttctgcaa cttcaacatc agtggcctgc agctgtgcag catgacacag gaggagttcg    420

tcgaggcagc tggcctctgc ggcgagtacc tgtacttcat cctccagaac atccgcacac    480

aaggttactc ctttttaat gacgctgaag aaagcaaggc caccatcaaa gactatgctg     540

attccaactg cttgaaaaca agtggcatca aaagtcaaga ctgtcacagt catagtagaa    600

caagcctcca aagttctcat ctatgggaat ttgtacgaga cctgcttcta tctcctgaag    660

aaaactgtgg cattctggaa tgggaagata gggaacaagg aatttttcgg gtggttaaat    720

cggaagccct ggcaaagatg tggggacaaa ggaagaaaaa tgacagaatg acatatgaaa    780

agttgagcag agccctgaga tactactata aaacaggaat tttggagcgg gttgaccgaa    840

ggttagtgta caaatttgga aaaaatgcac acgggtggca ggaagacaag ctatgatctg    900

ctccaggcat caagctcatt ttatggattt ctgtctttta aaacaatcag attgcaatag    960

acattcgaaa ggcttcattt tcttctcttt ttttttaacc tgcaaacatg ctgataaaat   1020

ttctccacat ctcagcttac atttggattc agagttgttg tctacggagg gtgagagcag   1080

aaactcttaa gaaatccttt cttctcccta aggggatgag ggatgatct tttgtggtgt    1140

cttgatcaaa ctttattttc ctagagttgt ggaatgacaa cagcccatgc cattgatgct   1200

gatcagagaa aaactattca attctgccat tagagacaca tccaatgctc ccatcccaaa   1260

ggttcaaaag ttttcaaata actgtggcag ctcaccaaag gtgggggaaa gcatgattag   1320

tttgcaggtt atggtaggag agggtgagat ataagacata catactttag attttaaatt   1380

attaaagtca aaaatccata gaaaagtatc ccttttttt tttttgagac gggttctcac    1440

tatgttgccc agggctggtc ttgaactcct atgctcaagt gatcctccca cctcggcctc   1500

ccaaagtact gtgattacaa gcgtgagcca cggcacctgg gcagaaaagt atcttaatta   1560

atgaaagagc taagccatca agctgggact taattggatt taacataggt tcacagaaag   1620

tttcctaacc agagcatctt tttgaccact cagcaaaact tccacagaca tccttctgga   1680

cttaaacact taacattaac cacattatta attgttgctg agtttattcc cccttctaac   1740

tgatggctgg catctgatat gcagagttag tcaacagaca ctggcatcaa ttacaaaatc   1800

actgctgttt ctgtgattca agctgtcaac acaataaaat cgaaattcat tgattccatc   1860

tctggtccag atgttaaacg tttataaaac cggaaatgtc ctaacaactc tgtaatggca   1920

aattaaattg tgtgtctttt ttgttttgtc tttctacctg atgtgtattc aagcgctata   1980
```

```
acacgtattt ccttgacaaa aatagtgaca gtgaattcac actaataaat gttcataggt   2040

taaagtctgc actgacattt tctcatcaat cactggtatg taagttatca gtgactgaca   2100

gctaggtgga ctgcccctag gacttctgtt tcaccagagc aggaatcaag tggtgaggca   2160

ctgaatcgct gtacaggctg aagacctcct tattagagtt gaacttcaaa gtaacttgtt   2220

ttaaaaaatg tgaattactg taaaataatc tattttggat tcatgtgttt tccaggtgga   2280

tatagtttgt aaacaatgtg aataaagtat ttaacatgta aaaa                    2324


<210> SEQ ID NO 23
<211> LENGTH: 1166
<212> TYPE: DNA
<213> ORGANISM: Homo sapiens

<400> SEQUENCE: 23

gctccgggaa tttccctggc ccggccgctc cgggctttcc agtctcaacc atgcataaaa     60

agggttcgcc gatcttgggg agccacacag cccgggtcgc aggcacctcc ccgccagctc    120

tcccgcttct cgcacagctt cccgacgcgt ctgctgagcc ccatggccca cgccacgctc    180

tccgccgccc ccagcaatcc ccggctcctg cgggtggcgc tgctgctcct gctcctggtg    240

gccgccagcc ggcgcgcagc aggagcgtcc gtggtcactg aactgcgctg ccagtgcttg    300

cagacactgc agggaattca cctcaagaac atccaaagtg tgaatgtaag gtcccccgga    360

ccccactgcg cccaaaccga agtcatagcc acactcaaga atgggaagaa agcttgtctc    420

aaccccgcat cccccatggt tcagaaaatc atcgaaaaga tactgaacaa ggggagcacc    480

aactgacagg agagaagtaa gaagcttatc agcgtatcat tgacacttcc tgcagggtgg    540

tccctgccct taccagagct gaaaatgaaa aagagaacag cagctttcta gggacagctg    600

gaaaggactt aatgtgtttg actatttctt acgagggttc tacttattta tgtatttatt    660

tttgaaagct tgtattttaa tattttacat gctgttattt aaagatgtga gtgtgtttca    720

tcaaacatag ctcagtcctg attatttaat tggaatatga tgggttttaa atgtgtcatt    780

aaactaatat ttagtgggag accataatgt gtcagccacc ttgataaatg acagggtggg    840

gaactggagg gtggggggat tgaaatgcaa gcaattagtg gatcactgtt agggtaaggg    900

aatgtatgta cacatctatt ttttatactt tttttttaaa aaaagaatgt cagttgttat    960

ttattcaaat tatctcacat tatgtgttca acatttttat gctgaagttt cccttagaca   1020

ttttatgtct tgcttgtagg gcataatgcc ttgtttaatg tccattctgc agcgtttctc   1080

tttcccttgg aaaagagaat ttatcattac tgttacattt gtacaaatga catgataata   1140

aaagttttat gaaaaaaaaa aaaaaa                                        1166


<210> SEQ ID NO 24
<211> LENGTH: 5189
<212> TYPE: DNA
<213> ORGANISM: Homo sapiens

<400> SEQUENCE: 24

gggaaagtga agaaaacaga aaaggagagg gacagaggcc agaggacttc tcatactgga     60

cagaaaccga tcaggcatgg aactcccctt cgtcactcac ctgttcttgc ccctggtgtt    120

cctgacaggt ctctgctccc cctttaacct ggatgaacat cacccacgcc tattcccagg    180

gccaccagaa gctgaatttg gatacagtgt cttacaacat gttgggggtg gacagcgatg    240

gatgctggtg ggcgcccccct gggatgggcc ttcaggcgac cggagggggg acgtttatcg    300
```

-continued

```
ctgccctgta ggggggcccc acaatgcccc atgtgccaag ggccacttag gtgactacca    360
actgggaaat tcatctcatc ctgctgtgaa tatgcacctg gggatgtctc tgttagagac    420
agatggtgat gggggattca tggcctgtgc ccctctctgg tctcgtgctt gtggcagctc    480
tgtcttcagt tctgggatat gtgcccgtgt ggatgcttca ttccagcctc agggaagcct    540
ggcacccact gcccaacgct gcccaacata catggatgtt gtcattgtct tggatggctc    600
caacagcatc taccctggt ctgaagttca gaccttccta cgaagactgg tagggaaact    660
gtttattgac ccagaacaga tacaggtggg actggtacag tatggggaga gccctgtaca    720
tgagtggtcc ctgggagatt tccgaacgaa ggaagaagtg gtgagagcag caaagaacct    780
cagtcggcgg gagggacgag aaacaaagac tgcccaagca ataatggtgg cctgcacaga    840
agggttcagt cagtcccatg gggccgacc cgaggctgcc aggctactgg tggttgtcac    900
tgatggagag tcccatgatg gagaggagct tcctgcagca ctaaaggcct gtgaggctgg    960
aagagtgaca cgctatggga ttgcagtcct tggtcactac ctccggcggc agcgagatcc   1020
cagctctttc ctgagagaaa ttagaactat tgccagtgat ccagatgagc gattcttctt   1080
caatgtcaca gatgaggctg ctctgactga cattgtggat gcactaggag atcggatttt   1140
tggccttgaa gggtcccatg cagaaaacga aagctccttt gggctggaaa tgtctcagat   1200
tggtttctcc actcatcggc taaaggatgg gattcttttt gggatggtgg gggcctatga   1260
ctggggaggc tctgtgctat ggcttgaagg aggccaccgc cttttccccc cacgaatggc   1320
actggaagac gagttccccc ctgcactgca gaaccatgca gcctacctgg gttactctgt   1380
ttcttccatg cttttgcggg gtggacgccg cctgtttctc tctggggctc ctcgatttag   1440
acatcgagga aaagtcatcg ccttccagct taagaaagat ggggctgtga gggttgccca   1500
gagcctccag ggggagcaga ttggttcata ctttggcagt gagctctgcc cattggatac   1560
agatagggat ggaacaactg atgtcttact tgtggctgcc cccatgttcc tgggacccca   1620
gaacaaggaa acaggacgtg tttatgtgta tctggtaggc cagcagtcct tgctgaccct   1680
ccaaggaaca cttcagccag aacccccca ggatgctcgg tttggctttg ccatgggagc   1740
tcttcctgat ctgaaccaag atggttttgc tgatgtggct gtgggggcgc ctctggaaga   1800
tgggcaccag ggagcactgt acctgtacca tggaacccag agtggagtca ggccccatcc   1860
tgcccagagg attgctgctg cctccatgcc acatgccctc agctactttg gccgaagtgt   1920
ggatggtcgg ctagatctgg atggagatga tctggtcgat gtggctgtgg gtgcccaggg   1980
ggcagccatc ctgctcagct cccggcccat tgtccatctg accccatcac tggaggtgac   2040
cccacaggcc atcagtgtgg ttcagaggga ctgtaggcgg cgaggccaag aggcagtctg   2100
tctgactgca gccctttgct tccaagtgac ctcccgtact cctggtcgct gggatcacca   2160
attctacatg aggttcaccg catcactgga tgaatggact gctggggcac gtgcagcatt   2220
tgatggctct ggccagaggt tgtcccctcg gaggctccgg ctcagtgtgg ggaatgtcac   2280
ttgtgagcag ctacacttcc atgtgctgga tacatcagat tacctccggc cagtggcctt   2340
gactgtgacc tttgccttgg acaatactac aaagccaggg cctgtgctga atgagggctc   2400
acccacctct atacaaaagc tggtcccctt ctcaaaggat tgtggccctg acaatgaatg   2460
tgtcacagac ctggtgcttc aagtgaatat ggacatcaga ggctccagga aggccccatt   2520
tgtggttcga ggtggccggc ggaaagtgct ggtatctaca actctggaga acagaaagga   2580
aaatgcttac aatacgagcc tgagtctcat cttctctaga aacctccacc tggccagtct   2640
cactcctcag agagagagcc caataaaggt ggaatgtgcc gccccttctg ctcatgcccg   2700
```

-continued

```
gctctgcagt gtggggcatc ctgtcttcca gactggagcc aaggtgacct ttctgctaga   2760
gtttgagttt agctgctcct ctctcctgag ccaggtcttc gtgaagctga ctgccagcag   2820
tgacagcctg gagagaaatg ggacccttca agataacaca gcccagacct cagcctacat   2880
ccaatatgag ccccacctcc tgttctctag tgagtctacc ctgcaccgct atgaggttca   2940
cccatatggg accctcccag tgggtcctgg cccagaattc aaaaccactc tcagggttca   3000
gaacctaggc tgctatgtgg tcagtggcct catcatctca gccctccttc cagctgtggc   3060
ccatgggggc aattacttcc tatcactgtc tcaagtcatc actaacaatg caagctgcat   3120
agtgcagaac ctgactgaac ccccaggccc acctgtgcat ccagaggagc ttcaacacac   3180
aaacagactg aatgggagca atactcagtg tcaggtggtg aggtgccacc ttgggcagct   3240
ggcaaagggg actgaggtct ctgttggact attgaggctg gttcacaatg aatttttccg   3300
aagagccaag ttcaagtccc tgacggtggt cagcaccttt gagctgggaa ccgaagaggg   3360
cagtgtccta cagctgactg aagcctcccg ttggagtgag agcctcttgg aggtggttca   3420
gacccggcct atcctcatct ccctgtggat cctcataggc agtgtcctgg gagggttgct   3480
cctgcttgct ctccttgtct tctgcctgtg gaagcttggc ttctttgccc ataagaaaat   3540
ccctgaggaa gaaaaaagag aagagaagtt ggagcaatga atgtagaata agggtctaga   3600
aagtcctccc tggcagcttc ttcaagagac ttgcataaaa gcagaggttt gggggctcag   3660
atgggacaag aagccgcctc tggactatct ccccagacca gcagcctgac ttgacttttg   3720
agtcctaggg atgctgctgg ctagagatga ggctttacct cagacaagaa gagctggcac   3780
caaaactagc catgctccca ccctctgctt ccctcctcct cgtgatcctg gttccatagc   3840
caacactggg gcttttgttt ggggtccttt tatccccagg aatcaataat ttttttgcct   3900
aggtgcctga ctcctttcag attccctctt tatcttccct cacagtttgg aaaggatgag   3960
ggttatcttc ctcgattctt ccaccctctc actttcctgc ctgttcccca ctccacagga   4020
gggagctgac gttggcttga aaggagtaaa gtcaacatct gctgctttcc tgtggactct   4080
ggtgattcat agagccggat ggggagagtc aacaggaaaa aaggagggag gaggaaaagc   4140
cacaagagac attctgtaca attccaagga acagagaagc ctttagacag gcaactgcca   4200
tccccccctga aacctgagac ctgtagtgca ctcgaccgcc ctcaggtgtt ggtgaaacag   4260
agctgccccc aggctcgctg ggcataggct tcctgattcc aagccttttc tgggagcaaa   4320
gccagggcct ggtgcctgat tttctgaagc caggagccct caggtggctg gagctggaat   4380
agcagggagg actgggtgta cctaggcagt attttctcta cttctctcaa gtcttatact   4440
cactcttgag ccctccttgg ggcctgctta gaaagcagac aggagagaga gtactgctac   4500
ttgatgatgg gaaatgcttt cactttacca gctttgggaa gcagcagccc catgggatct   4560
aaaagtgtgg agtctgcatt aagaaaccta catgggtggc atggggctct ggggagcaag   4620
cccttacttg ctcagcactg gttatgtagc acaaatagct cctaggaaaa tgtttctggg   4680
gcaaccctag aaccctggtc atattttgca gggtttctct ggtggaatca gtttgccagc   4740
ccttgcttga tgcttactgg aaatctccag gttaatttct atctctgatc cctccccaac   4800
ccactccata tttgggtcat ggacagtaaa ggcagttgga ttctcataga caactgggta   4860
acttatattt ctttgtaatc aagacttgag atatcgaagt cagttattgg tctccagagt   4920
gcagctctgg gagccttttg aagaatcagc actcattaag agctgagaag agagaagacc   4980
tgattgggtg gttgactagc agtcacagaa cctgtcctcc caggctgttc ctgaggcctg   5040
```

-continued accacagtat ttattttggc atgtctctgg ccttctgcag aggcccaccc tcatgggcat 5100
tgtctctgtt tcccagtggg gtggacagta tatcagatgg tcagaacaaa taaagttcag 5160
tgtcaaatga aaaaaaaaaa aaaaaaaaa 5189

<210> SEQ ID NO 25
<211> LENGTH: 2005
<212> TYPE: DNA
<213> ORGANISM: Homo sapiens

<400> SEQUENCE: 25
tttcctctca gggggcagca ggaagtgagg agaaagggct gggatgggag gcgggagcgg 60
atgggaggga atggggttta tcaagtcctc ggcgagctgc ccaacgggca gcagctggcg 120
caagtagcct agctggagag gctcacccca ggaaggaggg aggccaccga cctactgggc 180
cgacggactc ccacacagtt cctgagctgg tgccaggcag gtgacacctc ctgcagcccc 240
cagcatgcgg gcaggcccag gccccaccgt tacattggcc ctggtgctgg cggtgtcatg 300
ggccatggag ctcaagccca cagcaccacc catcttcact ggccggccct ttgtggtagc 360
gtgggacgtg cccacacagg actgtggccc acgcctcaag gtgccactgg acctgaatgc 420
ctttgatgtg caggcctcac ctaatgaggg ttttgtgaac cagaatatta ccatcttcta 480
ccgcgaccgt ctaggcctgt atccacgctt cgattctgcc ggaaggtctg tgcatggtgg 540
tgtgccacag aatgtcagcc tttgggcaca ccggaagatg ctgcagaaac gtgtggagca 600
ctacattcgg acacaggagt ctgcggggct ggcggtcatc gactgggagg actggcgacc 660
tgtgtgggtg cgcaactggc aggacaaaga tgtgtatcgc cggttatcac gccagctagt 720
ggccagtcgt caccctgact ggcctccaga ccgcatagtc aaacaggcac aatatgagtt 780
tgagttcgca gcacagcagt tcatgctgga gacactgcgt tatgtcaagg cagtgcggcc 840
ccggcacctc tggggcttct acctctttcc tgactgctac aatcatgatt atgtgcagaa 900
ctgggagagc tacacaggcc gctgccctga tgttgaggtg gcccgcaatg accagctggc 960
ctggctgtgg gctgagagca cggccctctt cccgtctgtc tacctggacg agacacttgc 1020
ttcctcccgc catggccgca actttgtgag cttccgtgtt caggaggccc ttcgtgtggc 1080
tcgcacccac catgccaacc atgcactccc agtctacgtc ttcacacgac ccacctacag 1140
ccgcaggctc acggggctta gtgagatgga cctcatctct accattggcg agagtgcggc 1200
cctgggcgca gctggtgtca tcctctgggg tgacgcgggg tacaccacaa gcacggagac 1260
ctgccagtac ctcaaagatt acctgacacg gctgctggtc ccctacgtgg tcaatgtgtc 1320
ctgggccacc caatattgca gccgggccca gtgccatggc catgggcgct gtgtgcgccg 1380
caaccccagt gccagtacct tcctgcatct cagcaccaac agtttccgcc tagtgcctgg 1440
ccatgcacct ggtgaacccc agctgcgacc tgtgggggag ctcagttggg ccgacattga 1500
ccacctgcag acacacttcc gctgccagtg ctacttgggc tggagtggtg agcaatgcca 1560
gtgggaccat aggcaggcag ctggaggtgc cagcgaggcc tgggctgggt cccacctcac 1620
cagtctgctg gctctggcag ccctggcctt tacctggacc ttgtaggggt ctcctgccta 1680
gctgcctagc aagctggcct ctaccacaag ggctctctta ggcatgtagg accctgcagg 1740
gggtggacaa actggagtct ggagtgggca gagcccccag gaagcccagg agggcatcca 1800
taccagctcg caccccccctg ttctaagggg gaggggaagt ccctgggagg ccccttctct 1860
ccctgccaga ggggaaggag ggtacagctg ggctggggag gacctgaccc tactcccttg 1920
ccctagatag tttattatta ttattatttt ggggtctctt ttgtaaatta aacataaaac 1980
aattgcttct ctgcttggat tttgt 2005

<210> SEQ ID NO 26
<211> LENGTH: 5802
<212> TYPE: DNA
<213> ORGANISM: Homo sapiens

<400> SEQUENCE: 26
tttatagcag cagtagaaat ataccaccct agaggacaca cctcctttta gctaggtacc 60
tataaatgtc caggattttc tattcaattg agaagaaccc agcaaaatgg ggatctccac 120
agtcatcctt gaaatgtgtc ttttatgggg acaagttcta tctacaggtg ggtggatccc 180
aaggactaca gactacgctt cactgattcc ctcggaggtg cccttggatc caactgtagc 240
agaaggttct ccatttccct cggagtcgac cctggagtca actgtagcag aaggttctcc 300
gatttccttg gagtcaaccc tggagtcaac cgtagcagaa ggttctctga ttccctcaga 360
gtcaaccctg gagtcaactg tagcagaagg atctgattct ggtttggccc tgaggctggt 420
gaatggagat ggcaggtgtc agggccgagt ggagatccta taccgaggct cctggggcac 480
cgtgtgtgat gacagctggg acaccaatga tgccaacgtg gtctgtaggc agctgggttg 540
tggctgggcc atgtcagctc caggaaatgc ctggtttggc cagggctcag gacccattgc 600
cctggatgat gtgcgctgct caggacacga atcctacctg tggagctgcc cccacaatgg 660
ctggctctcc cataactgtg gccatggtga agatgctggt gttatctgct cagctgccca 720
gcctcagtca acactcaggc cagaaagttg gcctgtcagg atatcaccac ctgtacccac 780
agaaggatct gaatccagtt tggccctgag gctggtgaat ggaggcgaca ggtgtcgagg 840
ccgagtggag gtcctatacc gaggctcctg gggcaccgtg tgtgatgact actgggacac 900
caatgatgcc aatgtggtct gcaggcagct gggctgtggc tgggccatgt cagccccagg 960
aaatgcccag tttggccagg gctcaggacc cattgtcctg gatgatgtgc gctgctcagg 1020
acatgagtcc tacctgtgga gctgccccca caatggctgg ctcacccaca actgtggcca 1080
tagtgaagac gctggtgtca tctgctcagc tccccagtcc cggccgacac ccagcccaga 1140
tacttggccg acctcacatg catcaacagc aggacctgaa tccagtttgg ccctgaggct 1200
ggtgaatgga ggtgacaggt gtcagggccg agtggaggtc ctataccgag gctcctgggg 1260
caccgtgtgt gatgatagct gggacaccag tgacgccaat gtggtctgcc ggcagctggg 1320
ctgtggctgg gccacgtcag ccccaggaaa tgcccggttt ggccagggtt caggacccat 1380
tgtcctggat gacgtgcgct gctcaggcta tgagtcctac ctgtggagct gcccccacaa 1440
tggctggctc tcccataact gtcagcacag tgaagacgct ggtgtcatct gctcagctgc 1500
ccactcctgg tcgacgccca gtccagacac attgccgacc atcaccttgc ctgcatcgac 1560
agtaggatct gaatccagtt tggccctgag gctggtgaat ggaggtgaca ggtgtcaggg 1620
ccgagtggag gtcctatacc aaggctcctg gggcaccgtg tgcgatgaca gctgggacac 1680
caatgatgcc aatgtcgtct gcaggcaact gggctgtggc tgggccatgt cagccccagg 1740
aaatgcccgg tttggtcagg gctcaggacc cattgtcctg gatgatgtgc gctgctcagg 1800
acacgagtct tacctgtgga gctgccccca caatggctgg ctctcccaca actgtggcca 1860
tagtgaagac gctggtgtca tctgctcagc ttcccagtcc cggccaacac ctagtccaga 1920
cacttggcca acctcacatg catcaacagc aggatctgaa tccagtttgg ccctgaggct 1980
ggtgaatgga ggtgacaggt gtcagggccg agtggaggtc ctataccgag gctcctgggg 2040

-continued

```
caccgtgtgt gatgactact gggacaccaa tgatgccaat gtggtttgca ggcagctggg   2100
ctgtggctgg gccatgtcag ccccaggaaa tgcccggttt ggccagggtt caggacccat   2160
tgtcctggat gatgtgcgct gctcaggaca tgagtcctat ctgtggagct gcccccacaa   2220
tggctggctc tcccacaact gtggccatca tgaagacgct ggtgtcatct gctcagcttc   2280
ccagtcccag ccgacaccca gcccagacac ttggccaacc tcacatgcat caacagcagg   2340
atctgaatcc agtttggccc tgaggctggt gaatggaggt gacaggtgtc agggccgagt   2400
ggaggtccta taccgaggct cctggggcac cgtgtgtgat gactactggg acaccaatga   2460
tgccaatgtg gtttgcaggc agctgggctg tggctgggcc acgtcagccc caggaaatgc   2520
ccggtttggc cagggttcag gacccattgt cctggatgat gtgcgctgct caggacatga   2580
gtcctatctg tggagctgcc cccacaatgg ctggctctcc cacaactgtg gccatcatga   2640
agacgctggt gtcatctgct cagcttccca gtcccagccg acacccagcc cagacacttg   2700
gccaacctct cgtgcatcaa cagcaggatc tgaatccact ttggccctga gactggtgaa   2760
tggaggtgac aggtgtcgag gccgagtgga ggtcctatac caaggctcct ggggcaccgt   2820
gtgtgatgac tactgggaca ccaatgatgc caacgtggtc tgcaggcagc tgggctgtgg   2880
ctgggccatg tcagccccag gaaatgccca gtttggccag ggctcaggac ccattgtcct   2940
ggatgatgtg cgctgctcag gacacgagtc ttacctgtgg agctgccccc acaatggctg   3000
gctctcccac aactgtggcc atcatgaaga tgctggtgtc atctgctcag ctgctcagtc   3060
ccagtcaacg cccaggccag atacttggct gaccaccaac ttaccggcat tgacagtagg   3120
atctgaatcc agtttggctc tgaggctggt gaatggaggt gacaggtgtc gaggccgagt   3180
ggaggtcctg tatcgaggct cctggggaac cgtgtgtgat gacagctggg acaccaatga   3240
tgccaatgtg gtctgcaggc agctgggctg tggctgggcc atgtcggccc caggaaatgc   3300
ccggtttggc cagggctcag gacccattgt cctggatgat gtgcgctgct cagggaatga   3360
gtcctacctg tggagctgcc cccacaaagg ctggctcacc cacaactgtg gccatcacga   3420
agacgctggt gtcatctgct cagccaccca aataaattct actacgacag attggtggca   3480
tccaacaact acaaccactg caagaccctc ttcaaattgt ggtggcttct tattctatgc   3540
cagtgggaca ttctccagcc catcctaccc tgcatactac cccaacaatg ctaagtgtgt   3600
ttgggaaata gaagtgaatt ctggttatcg cataaacctg ggcttcagta atctgaaatt   3660
ggaggcacac cataactgca gttttgatta tgttgaaatc tttgatggat cattgaatag   3720
cagtctcctg ctggggaaaa tctgtaatga taccaggcaa atatttacat cttcttacaa   3780
ccgaatgacc attcactttc gaagtgacat cagtttccaa aacactggct ttttggcttg   3840
gtataactcc ttcccaagcg atgccacctt gaggttggtc aatttaaatt catcctatgg   3900
tctatgtgcc gggcgtgtag aaatttacca tggtggcacc tgggggacag tttgtgatga   3960
ctcctggacc attcaggaag ctgaggtggt ctgcagacag ctagggtgtg gacgtgcagt   4020
ttcagccctt ggaaatgcat attttggctc tggctctggc cccatcaccc tggacgatgt   4080
agagtgctca gggacggaat ccactctctg gcagtgccgg aaccgaggct ggttctccca   4140
caactgtaat catcgtgaag atgctggtgt catctgctca ggaaaccatc tatcgacacc   4200
tgctcctttt ctcaacatca cccgtccaaa cacagattat tcctgcggag gcttcctatc   4260
ccaaccatca ggggactttt ccagcccatt ctatcccggg aactatccaa acaatgccaa   4320
gtgtgtgtgg gacattgagg tgcaaaacaa ctaccgtgtg actgtgatct tcagagatgt   4380
ccagcttgaa ggtggctgca actatgatta tattgaagtt ttcgatggcc cctaccgcag   4440
```

```
ttcccctctc attgctcgag tttgtgatgg ggccagaggc tccttcactt cttcctccaa   4500
cttcatgtcc attcgcttca tcagtgacca cagcatcaca aggagagggt tccgggctga   4560
gtactactcc agtccctcca atgacagcac caacctgctc tgtctgccaa atcacatgca   4620
agccagtgtg agcaggagct atctccaatc cttgggcttt tctgccagtg accttgtcat   4680
ttccacctgg aatggatact acgagtgtcg gccccagata acgccgaacc tggtgatatt   4740
cacaattccc tactcaggct gcggcacctt caagcaggca gacaatgaca ccatcgacta   4800
ttccaacttc ctcacagcag ctgtctcagg tggcatcatc aagaggagga cagacctccg   4860
tattcacgtc agctgcagaa tgcttcagaa cacctgggtc gacaccatgt acattgctaa   4920
tgacaccatc cacgttgcta ataacaccat ccaggtcgag gaagtccagt atggcaattt   4980
tgacgtgaac atttcctttt atacttcctc atctttcttg tatcctgtga ccagccgccc   5040
ttactacgtg gacctgaacc aggacttgta cgttcaggct gaaatcctcc attctgatgc   5100
tgtactgacc ttgtttgtgg acacctgcgt ggcatcacca tactccaatg acttcacgtc   5160
tttgacttat gatctaatcc ggagtggatg cgtgagggat gacacctacg gaccctactc   5220
ctcgccatct cttcgcattg cccgcttccg gttcagggcc ttccacttcc tgaaccgctt   5280
cccctccgtg tacctgcgtt gtaaaatggt ggtgtgcaga gcgtatgacc cctcttcccg   5340
ctgctaccga ggctgtgtgt tgaggtcgaa gagggatgtg ggctcctacc aggaaaaggt   5400
ggacgtcgtc ctgggtccca tccagctgca gacccccccca cgccgagaag aggagcctcg   5460
gtaggtggtc gctctcagac cccactgtcc accggggcgc agacccctga ctcggggact   5520
tgggatgttc ctcttggtgt catattccaa ctcagattga gccctacatt gtgctgcacc   5580
tggtcatacg gagttgaatc agacctggtt cccgcctccc ccaaggctca tggtccttgg   5640
aggacccgtt gcagggtgag gtcaagagag ttctgacctg gatggcccat agacctgacg   5700
tcccagaatc catgcttctc atctgcaaaa tgaaaatgtc aatacttact tcttagcact   5760
gttgagaggg ttacttacat aaaggaattt tggtgaaact gc                      5802
```

<210> SEQ ID NO 27
<211> LENGTH: 1220
<212> TYPE: DNA
<213> ORGANISM: Homo sapiens

<400> SEQUENCE: 27

```
agtcccagct cagagccgca acctgcacag ccatgcccgg gcaagaactc aggacggtga     60
atggctctca gatgctcctg gtgttgctgg tgctctcgtg gctgccgcat gggggcgccc    120
tgtctctggc cgaggcgagc cgcgcaagtt tcccgggacc ctcagagttg cactccgaag    180
actccagatt ccgagagttg cggaaacgct acgaggacct gctaaccagg ctgcgggcca    240
accagagctg ggaagattcg aacaccgacc tcgtcccggc ccctgcagtc cggatactca    300
cgccagaagt gcggctggga tccggcggcc acctgcacct gcgtatctct cgggccgccc    360
ttcccgaggg gctccccgag gcctcccgcc ttcaccgggc tctgttccgg ctgtccccga    420
cggcgtcaag gtcgtgggac gtgacacgac cgctgcggcg tcagctcagc cttgcaagac    480
cccaggcgcc cgcgctgcac ctgcgactgt cgccgccgcc gtcgcagtcg gaccaactgc    540
tggcagaatc ttcgtccgca cggccccagc tggagttgca cttgcggccg caagccgcca    600
gggggcgccg cagagcgcgt gcgcgcaacg gggaccactg tccgctcggg cccgggcgtt    660
gctgccgtct gcacacggtc cgcgcgtcgc tggaagacct gggctgggcc gattgggtgc    720
```

```
tgtcgccacg ggaggtgcaa gtgaccatgt gcatcggcgc gtgcccgagc cagttccggg    780
cggcaaacat gcacgcgcag atcaagacga gcctgcaccg cctgaagccc gacacggtgc    840
cagcgccctg ctgcgtgccc gccagctaca atcccatggt gctcattcaa aagaccgaca    900
ccggggtgtc gctccagacc tatgatgact tgttagccaa agactgccac tgcatatgag    960
cagtcctggt ccttccactg tgcacctgcg cggaggacgc gacctcagtt gtcctgccct   1020
gtggaatggg ctcaaggttc ctgagacacc cgattcctgc ccaaacagct gtatttatat   1080
aagtctgtta tttattatta atttattggg gtgaccttct tggggactcg gggctggtc    1140
tgatggaact gtgtatttat ttaaaactct ggtgataaaa ataaagctgt ctgaactgtt   1200
aaaaaaaaaa aaaaaaaaaa                                               1220
```

```
<210> SEQ ID NO 28
<211> LENGTH: 1882
<212> TYPE: DNA
<213> ORGANISM: Homo sapiens

<400> SEQUENCE: 28

agcgctccta taaagggagc caccagcgct ggaggccgct gctcgctgcg ccaccgcctc     60
ccgccacccc tgcccgcccg acagcgccgc cgcctgcccc gccatgggtc gacagaagga    120
gctggtgtcc cgctgcgggg agatgctcca catccgctac cggctgctcc gacaggcgct    180
ggccgagtgc ctggggaccc tcatcctggt gatgtttggc tgtggctccg tggcccaggt    240
tgtgctcagc cggggcaccc acggtggttt cctcaccatc aacctggcct ttggctttgc    300
tgtcactctg ggcatcctca tcgctggcca ggtctctggg gcccacctga accctgccgt    360
gacctttgcc atgtgcttcc tggctcgtga gccctggatc aagctgccca tctacaccct    420
ggcacagacg ctgggagcct tcttgggtgc tggaatagtt tttgggctgt attatgatgc    480
aatctggcac ttcgccgaca accagctttt tgtttcgggc cccaatggca cagccggcat    540
ctttgctacc taccccctctg gacacttgga tatgatcaat ggcttctttg accagttcat    600
aggcacagcc tcccttatcg tgtgtgtgct ggccattgtt gaccccctaca acaaccccgt    660
cccccgaggc ctggaggcct tcaccgtggg cctggtggtc ctggtcattg gcacctccat    720
gggcttcaac tccggctatg ccgtcaaccc tgcccgggac tttggccccc gcctttttac    780
agcccttgcg ggctggggct ctgcagtctt cacgaccggc cagcattggt ggtgggtgcc    840
catcgtgtcc ccactcctgg gctccattgc gggtgtcttc gtgtaccagc tgatgatcgg    900
ctgccacctg gagcagcccc caccctccaa cgaggaagag aatgtgaagc tggcccatgt    960
gaagcacaag gagcagatct gagtgggcag gggccatctc cccactccgc tgccctggcc   1020
ttgagcatcc actgactgtc caagggccac tcccaagaag ccccccttcac gatccaccct   1080
ttcaggctaa ggagctccct atctaccctc accccacgag acagcccctt caggatttcc   1140
actggacctt gcccaaatag caccttaggc cactgcccct aagctggggt ggaaccggaa   1200
tttgggtcaa tacatccttt tgtctcccaa gggaagagaa tgggcagcag gtatgtgtgt   1260
gtgtgcatgt gtgtgcatgt gtgtgcatgt gtgtgcaggg gtgtgtgtgt gtggggggggg   1320
ttcccagata ttcagggcaa gggaccagtc ggaagggatt ctggctattg gggagcccca   1380
gagacagggg aaggcagcct gtccatctgt gcataaggag aggaaagttc cagggtgtgt   1440
atgtttcagg ggcttcacat ggaggagctg cagatagata tgtgtttctg tgtatgtgta   1500
tgtctgcctt tttttctaag tgggggcttc tacaggcttt tgggaagtag ggtggatgtg   1560
ggtagggctg ggaggagggg gccacagctt aggtttggag ctctggatgt acatacataa   1620
```

gtaggagcag tgggacgtgt ttctgtcata atgcaggcat gaagggtgga gtgaagtcag 1680
gtcataagtt tcatgtttgc ttttgttttg ttttgttttt aatgtatgta gcagatgtta 1740
cagtcttagg gatccgggat gggagacccc actttagaaa gggtcgtcac tcctttaatc 1800
ctctactcaa caatgtactc ttttactttt atattaaaaa aaataaaata aatatgtgcc 1860
taaaacctcc aaaaaaaaaa aa 1882

<210> SEQ ID NO 29
<211> LENGTH: 1336
<212> TYPE: DNA
<213> ORGANISM: Homo sapiens

<400> SEQUENCE: 29
gagagacaca gagtccggca ttggtcccag gcagcagtta gcccgccgcc cgcctgtgtg 60
tccccagagc catggagaga gccagtctga tccagaaggc caagctggca gagcaggccg 120
aacgctatga ggacatggca gccttcatga aggcgccgt ggagaagggc gaggagctct 180
cctgcgaaga gcgaaacctg ctctcagtag cctataagaa cgtggtgggc ggccagaggg 240
ctgcctggag ggtgctgtcc agtattgagc agaaaagcaa cgaggagggc tcggaggaga 300
aggggcccga ggtgcgtgag taccgggaga aggtggagac tgagctccag ggcgtgtgcg 360
acaccgtgct gggcctgctg gacagccacc tcatcaagga ggccggggac gccgagagcc 420
gggtcttcta cctgaagatg aagggtgact actaccgcta cctggccgag gtggccaccg 480
gtgacgacaa gaagcgcatc attgactcag cccggtcagc ctaccaggag gccatggaca 540
tcagcaagaa ggagatgccg cccaccaacc ccatccgcct gggcctggcc ctgaactttt 600
ccgtcttcca ctacgagatc gccaacagcc ccgaggaggc catctctctg gccaagacca 660
ctttcgacga ggccatggct gatctgcaca ccctcagcga ggactcctac aaagacagca 720
ccctcatcat gcagctgctg cgagacaacc tgacactgtg gacggccgac aacgccgggg 780
aagagggggg cgaggctccc caggagcccc agagctgagt gttgcccgcc accgccccgc 840 cctgcccccct ccagtccccc accctgccga gaggactagt atggggtggg aggccccacc 900
cttctcccct aggcgctgtt cttgctccaa agggctccgt ggagagggac tggcagagct 960
gaggccacct ggggctgggg atcccactct tcttgcagct gttgagcgca cctaaccact 1020
ggtcatgccc ccacccctgc tctccgcacc cgcttcctcc cgaccccagg accaggctac 1080
ttctcccctc ctcttgcctc cctcctgccc ctgctgcctc tgatcgtagg aattgaggag 1140
tgtcccgcct tgtggctgag aactggacag tggcaggggc tggagatggg tgtgtgtgtg 1200
tgtgtgtgtg tgtgtgtgtg tgtgcgcgcg cgccagtgca agaccgagat tgagggaaag 1260
catgtctgct gggtgtgacc atgtttcctc tcaataaagt tcccctgtga cactcaaaaa 1320
aaaaaaaaaa aaaaaa 1336

<210> SEQ ID NO 30
<211> LENGTH: 8171
<212> TYPE: DNA
<213> ORGANISM: Homo sapiens

<400> SEQUENCE: 30
gaggcagggg tgagaccggc ggccacccgt gagccctccg cacccgcacc atgcagaaga 60
gcgtgcgcta caacgagggg cacgccctgt acctggcctt tctggcgcgc aaggagggca 120
ccaagcgcgg cttcctgagt aagaagacgg ccgaggcgag ccgctggcac gagaagtggt 180

```
tcgccctcta ccagaatgtg ctcttctact tcgagggcga gcagagctgc cgcccggcgg    240
gcatgtacct cctggagggc tgcagctgcg aacgaacgcc cgcgccaccc agggccggcg    300
ccgggcaggg aggcgtccga gacgcgctgg acaagcagta ttactttact gttctttttg    360
gccatgaagg tcagaagcca ctggagctgc gctgtgagga ggagcaggat ggtaaagagt    420
ggatggaggc cattcaccaa gccagttatg cagacatttt gattgagagg gaagtattaa    480
tgcagaagta cattcatcta gttcagatcg tagagacaga aaaaattgca gctaaccaac    540
tccgacatca acttgaagat caagacacag aaatcgaaag gcttaaatca gagattattg    600
ctcttaataa aaccaaagaa cgaatgcgac cttaccaaag caaccaagaa gacgaagatc    660
cagacatcaa gaagattaaa aaggttcaga gcttcatgcg aggatggttg tgcagaagga    720
aatggaagac catcgtgcag gattacattt gttctcctca tgctgaaagt atgaggaaga    780
gaaaccagat tgtgttcacc atggtggagg cagagtcaga gtacgttcac cagctctaca    840
tcctggtcaa tggctttctc cggcccctgc gtatggccgc cagctccaag aagcccccca    900
tcagccacga cgacgtcagc agtatttttc ttaacagtga aacaatcatg tttcttcatg    960
aaatatttca tcaaggacta aaggcaagga tagcaaactg gcccacttta attttagctg   1020
atctgtttga tattttgctc cccatgctga acatttatca agaatttgtg cgtaatcacc   1080
agtacagcct gcaagttctc gccaattgta agcaaaacag agattttgac aaactcttaa   1140
aacagtatga agccaatcca gcctgtgagg ggaggatgct ggagacattc ttgacctatc   1200
ccatgtttca gatccccaga tatatcatca cactccatga gctccttgct cacacacccc   1260
atgagcatgt ggaaaggaaa agcctggagt ttgccaaatc aaagctagag gaactatcca   1320
gagtaatgca cgatgaagtc agcgacactg aaaacataag gaaaaacctt gccatcgaaa   1380
gaatgatcgt ggagggctgt gacatcttgc tggacaccag ccaaacgttc atccgccaag   1440
gttctcttat tcaagtacct tccgttgaga gggggaaact tagtaaagtt cgcctgggtt   1500
cgttgtcttt gaaaaaggaa ggagagagac aatgcttctt atttacaaaa cactttttaa   1560
tatgtacaag aagttcagga gggaagcttc atctgctcaa gacaggtggg gttctgtctc   1620
taatagactg cacattgatt gaggagccag atgcaagcga tgatgactct aaaggttctg   1680
ggcaagtgtt tgggcacctg gattttaaaa tagtggtgga gcctcctgac gctgccgcct   1740
tcactgttgt cttgttagca ccctcacgcc aggagaaagc tgcctggatg agtgacatca   1800
gtcagtgtgt ggacaatata cgatgtaatg gtttaatgac tatagtgttt gaagagaatt   1860
ccaaagtcac tgtgccacat atgattaagt ctgatgcccg tcttcataaa gacgacactg   1920
acatttgctt cagtaaaaca ctcaactcct gcaaagtgcc ccagatccgt tatgccagcg   1980
tggagcgcct cttggaacga ctgacagact tgcggtttct tagtattgat ttcctcaaca   2040
cctttctgca cacctatcgt attttcacta ctgccgctgt ggtgctgggg aaactctccg   2100
acatatacaa gaggcctttc acctccatcc ctgtcaggtc attggaattg ttttttgcta   2160
ccagccagaa caacagaggt gaacatttgg tggatggcaa atccccacgt ctgtgtcgca   2220
aattctcttc cccgccacca ctggctgtgt ccagaacatc ttccccagtg agggccagaa   2280
agctgtcttt gacttctccc ttgaactcaa agataggagc attggacctg acaacttcca   2340
gcagtcccac caccaccacc cagagtcccg ctgcgtctcc accaccacac actggtcaga   2400
taccactgga tctcagcaga ggcctctctt ctccagagca aagcccggga acggtagaag   2460
agaatgtcga taacccacgc gtggatctgt gtaacaagct aaaacgaagt attcaaaaag   2520
cagtcctaga gtctgcacca gcggaccgag caggagtgga aagctcccct gcagcggaca   2580
```

-continued

```
ccacagaact ttcaccttgc agatccccct caactcctcg gcacctccgc tatcgacagc   2640
ctggaggaca gacggcggac aatgcccact gctctgtttc accggcttct gcttttgcaa   2700
tagccacagc tgcagcagga catgggagtc caccaggctt taacaacacc gagagaacat   2760
gtgataaaga gtttattata cggagaacgg ctaccaatcg agttctgaac gtcctccgtc   2820
actgggtctc aaagcacgca caggatttcg aactcaacaa tgaactaaag atgaatgtcc   2880
taaatttgct agaagaagtt ttgcgagacc cagaccttct tccccaagaa aggaaagccg   2940
ccgcgaatat cctcagggcc ctttcacaag atgaccaaga tgacatccac ctaaaattag   3000
aggatataat tcaaatgact gactgcatga aggccgaatg ctttgagtcc ttgtcggcca   3060
tggagctggc agaacagatc accctcctgg accatgtcat tttcagaagc attccctacg   3120
aggagtttct tgggcagggg tggatgaagc tggataaaaa cgaaagaact ccttacatta   3180
tgaaaaccag ccaacacttc aatgacatga gtaacctggt ggcctcccag ataatgaact   3240
atgctgatgt cagctcccgt gccaacgcca tcgagaaatg ggtggcagtg gcggacatct   3300
gccgatgcct gcacaactac aacggcgtgc tggagatcac ctcggcctta aacagaagtg   3360
ccatctacag gctgaagaaa acctgggcca aggtctctaa gcagacaaaa gctctaatgg   3420
acaaacttca aaagactgtt tcctctgaag gaagatttaa aaatcttaga gaaaccctta   3480
aaaattgtaa ccctcctgca gttccttatc ttgggatgta cttgacagac ctggcattta   3540
ttgaagaagg aacaccaaac tttactgagg aaggccttgt caatttctcc aaaatgagaa   3600
tgatatcaca catcatcaga gagatacgcc agttccagca gacttcctac agaatagatc   3660
atcagccaaa ggtcgcacag tacttgcttg acaaagacct tatcatagat gaagatacgc   3720
tatatgagct gtcactaaaa attgaacctc gactccctgc ttgaagatct ggccttgccc   3780
ctgagtccac gggatgttca tggaaagcag gacagacaga attgtgtatg ccttgcctat   3840
cacggtacag cacgaagcca ggctcctttc tccaccaaag aagatggaac cagactggaa   3900
ttctgtctcc agagagaaac ccagctgttt gggtcaaaga cagatgcttc agacttgggt   3960
gggaaggtga aagatggcta tttagaaagc tggtggcacg ttttacataa gggaatgtca   4020
gatgggagat gctagttgcc attttaacaa agcaggtaaa tcggtaaatt ttaaactctg   4080
tccatgttct gttagaactc agggacaagg atccatgaaa aagacctgtg atgtttctct   4140
ggcgctttac tggcctgggc acacctacca atcttctagg atttgactgg ttccattaca   4200
tttcctttttg gtataagctt cacagaaaag ctgacacttc ctctacagag atggaccaaa   4260
acataagcaa tttcagtcta cagcatgtgc atggttgtca gtgcattcta aatatttcta   4320
tgtgaggaat ggtaccttct gaaactgcct ttccagtctt taggcaatgg gataggaaag   4380
aaagaatgaa acacaaatgg atttgtatgt aacatttcct taattaaatg cagtaggctg   4440
tgccccagag gattccagac agtggctggc tgaggtgggt ggggagcttt tccttgagac   4500
tgttggtcct aagaagccag ccctttttgga gaggcagctg caaaaaggtg cacgcccatc   4560
tcaccgacaa aactgtggaa cagaaggcca ccaagtgctg tggggaatca tgggtttcag   4620
tgctgagtga aaatctatac ctaaaaatca tctctgcacc ttgctttgtt tgttttcttt   4680
ccccactcat agtactgcag gaatctattc tcatttacac agaccttttt ttaggcttac   4740
tatgaacatt ggctgtattt tttttaaaca gtttagtgaa attttctttt caaaacccac   4800
acttccatat gctgttcgta gatctctttc tttaaaaact gatgttgaga gatctctgag   4860
aatattataa gtgcatggga aatgggccca accaccgaac agctcttaca ttacaaaacc   4920
```

-continued

```
aaatgcaagg gttagtcctg ctacctgagg ctggggaagt gaccttcctt ttcccaagat   4980
tgtcagttgt tgaagaaata gggctatctc attgtttacc tccctcttct cttctcaggg   5040
agactgctgc tttaaaagaa ggaagagaaa aaatatagtt ctatttccct gaacctgttg   5100
cacctgacat tttctcttag cagcatgaaa cttattgatg ctgacaatga aaaatggatc   5160
tgtctggctg ctttccctct ttccttgcac tttaattatg ttgctagagc taacagacta   5220
ataaattcca cctgctggct cttaagactc agtgaaagag ctagcattgg taatgcacca   5280
tagaggtaga gaatgtacac tttctgcacg gtaagtgcca tctctgtatg taactatata   5340
gtgaaatatc aactaagtaa aagaaaatat aatatttgaa gaccattccc aaaatatttt   5400
caatagttca tattagccaa cagtgtagca ctcaacccaa ggagggttcc ttatggatgc   5460
tttctttttc ttttttaaag ttgcttgttt gttctcttta gtttcaaata agaggttgac   5520
gcatcttgat gcatgatgag aagcatgggc tgtttggatc ctaacaacgc ataacttgtg   5580
atttatttct cagtgctcca gaaactgagg gtttgaaata atatgtatca gttgcaccaa   5640
acacctcaag gtcttgcaga agaaaagtaa aggttagctt tcatggctca aaagcatagt   5700
cctgaagggt gaactaaaac cgggacaaat ctgtgagagg accacacaca tactagtttc   5760
gggccaaaca acacgtggaa aggtgcatgc attctactct gccttggagt tgccagagtc   5820
cttcagaggg aaagggatgg ttctgtgtgc actttttctg gaagttcgga ctcatttctt   5880
tgacccaaat gttccagaga cactgcagcc attcttatta acaaaaaata agacaggagt   5940
ttccaaatgc tccttccctt ttggatcgca gcttttcttc aactagtgac aaagcttttg   6000
cgcctatttc ctgcaggatg ttggaactgc cccgcactgg tcatattagg cactgtcaat   6060
tgctatgctg actttttaggg ggtttttgtt tgtttgaaaa acagggtctc accatgttgc  6120
ccaggctggt ctcgaactcc tggactcaag caatcttcct gcctcagcct ctcaagcagc   6180
tgggactgca ggggtgtgcc actcactagc ctttcgcatt tttgtttgag aattacacca   6240
ctttctggag tctgcagcct tcctggagct gcaagagggc aagagagaga gctccacctc   6300
tgagggagtg tctgttgatg acctgcacta ttcgtgtgcc agctgggaga ggaatgcaca   6360
ttttaaaatc ccttcaattt ggtcaaatta aaaatcccca agagcaattt gcagtgtttt   6420
ttctggtcgt taaagtaccc atcctcttct gcctacacac aaagcatgca ttcccagctg   6480
catctgcctc tagtccatta tggagaccca tttctaagag gagatgggag gtcaacctct   6540
aacagccaag tagcgaacat gtatactgta aaattaacct agaaaatcag aagaaaaatc   6600
caatttcatg ctttcgaatg aatgcccaca ttttgtactg tcaacgaaat tatcttggag   6660
cttttagggg atgccttttc gttattaact gagacatcta gttttgctac agggacaaat   6720
ctcttaccta atccaatata ttatttgaca gattcaggca tgaagtaaaa cgtcgtcact   6780
tttccttagt gcttttctga aggaatttaa agacggaatt ttaaacggcc attgcaatat   6840
tttcaagtgg ctctcatacc aagtcccatt actgtttgtt aaatttcagt acgtcttaaa   6900
gtactactta taaacaaatg aaactcagag aaactgaatc acctggaaga gaaaaatcca   6960
ttatggtccc atgtggagtg aataatgatg gatcagcacc ctttctctca tgttattgta   7020
taagacgaga cttttgggcc agcagcgatt gggcagcttt taaattctta actgaaaaga   7080
gtaatgcaat acagggatta ttcccaataa aattaacttt tatttaaaag caagagattt   7140
tacttagctt tttttttca aagtttgatt ttatcccctt gaaaaaaaat ctcttcactt    7200
taaagtataa aggtttttaa aaatccaatt gcaaaatgta ttattttttac aactatcgaa  7260
aaggcataaa agagaacata ctatttatgg ctgaagggta tagccaggct aatgtgcaca   7320
```

-continued

```
gagggaatca ataaataaaa ctctttttca tttcagtaag aaatcagatt gtaagtttaa   7380

tggctccatt atagatacca ccgtgtaata gaagacttaa gtcaatgaaa tctaatcagt   7440

gtgtcatttc tcagcggcca ttggtgactt aaaattaaga tgaggcagag ccaaaatgga   7500

aaacagtcat tttgttgtag gtataaacac atgaacgatt cagaaaatta ttcatctcag   7560

ctgccatgca gcatgacatt aacattagga ttgatagcac tagtctgatc tgctcaagga   7620

aaataatagt tctattatac ttaatgatgt tggtttttac acagctcatt tcatttttca   7680

ctagaaagcc agttatgaaa gagagctggc ctaggcatcc cggccctgag tcctaggccc   7740

agtctccaac tggaaaacct taggctggtg tttacacatc cctgagcctc agtttcctca   7800

tctgcaaaac ggtgtgaata gtaatccctg tgctgcttat ctcacagggc tattgtgagg   7860

accaaatgga ttagactgta aactgcaaag tgctgtccgc acatgaggtc atctgattac   7920

tgtcctcaga tctcttttgt agaggatttc aatgtatttc tttatcattt gagtgtgtgt   7980

gtgatggacg aatatgtgtg tgagtttgag aagcatatcg ttcgtgtcca gttactttgc   8040

aaatttgtgg acatttgtga ttggacagag gggtttgtgc tgtggcctaa cacttgccaa   8100

gtgaggtgta ggttatgcct atatgcaaat taaacttcac ctttcttgaa tattcaaaaa   8160

aaaaaaaaaa a                                                        8171
```

<210> SEQ ID NO 31
<211> LENGTH: 2089
<212> TYPE: DNA
<213> ORGANISM: Homo sapiens

<400> SEQUENCE: 31

```
agtttggacg gctgcttccc accagcaaag accacgactg gagagccgag ccggaggcag     60

ctgggaaaca tgaagagcgt cttgctgctg accacgctcc tcgtgcctgc acacctggtg    120

gccgcctgga gcaataatta tgcggtggac tgccctcaac actgtgacag cagtgagtgc    180

aaaagcagcc cgcgctgcaa gaggacagtg ctcgacgact gtggctgctg ccgagtgtgc    240

gctgcagggc ggggagaaac ttgctaccgc acagtctcag gcatggatgg catgaagtgt    300

ggcccggggc tgaggtgtca gccttctaat ggggaggatc cttttggtga agagtttggt    360

atctgcaaag actgtcccta cggcaccttc gggatggatt gcagagagac ctgcaactgc    420

cagtcaggca tctgtgacag ggggacggga aaatgcctga aattcccctt cttccaatat    480

tcagtaacca agtcttccaa cagatttgtt tctctcacgg agcatgacat ggcatctgga    540

gatggcaata ttgtgagaga agaagttgtg aaagagaatg ctgccgggtc tcccgtaatg    600

aggaaatggt taaatccacg ctgatcccgg ctgtgatttc tgagagaagg ctctattttc    660

gtgattgttc aacacacagc caacatttta ggaactttct agattatagc ataaggacat    720

gtaatttttg aagaccaaat gtgatgcatg gtggatccag aaaacaaaaa gtaggatact    780

tacaatccat aacatccata tgactgaaca cttgtatgtg tttgttaaat attcgaatgc    840

atgtagattt gttaaatgtg tgtgtatagt aacactgaag aactaaaaat gcaatttagg    900

taatcttacg tggagacagg tcaaccaaag agggagctag gcaaagctga agaccgcagt    960

gagtcaaatt agttctttga ctttgatgta cattaatgtt gggatatgga atgaagactt   1020

aagagcagga gaagatgggg agggggtggg agtgggaaat aaaatattta gcccttcctt   1080

ggtaggtagc ttctctagaa tttaattgtg cttttttttt tttttttggc tttgggaaaa   1140

gtcaaaataa aacaaccaga aaacccctga aggaagtaag atgtttgaag cttatggaaa   1200
```

-continued

```
tttgagtaac aaacagcttt gaactgagag caatttcaaa aggctgctga tgtagttccc   1260

gggttacctg tatctgaagg acggttctgg ggcataggaa acacatacac ttccataaat   1320

agctttaacg tatgccacct cagagataaa tctaagaagt attttaccca ctggtggttt   1380

gtgtgtgtat gaaggtaaat atttatatat ttttataaat aaatgtgtta gtgcaagtca   1440

tcttccctac ccatatttat catcctcttg aggaaagaaa tctagtatta tttgttgaaa   1500

atggttagaa taaaactatg actctataag gttttcaaac atctgaggca tgataaattt   1560

attatccata attatagtaa taataacctt aataagcata agaaaaacag agtcactctg   1620

gatttcaaaa atgtcaaaaa atgagcaaca gagggtcctt atttaaacat aagtgctgtg   1680

acttaggtga attttcaatt taaggtagaa aataagtttt taggaggttt gtaaaagaag   1740

aatcaatttt cagcagaaaa catgtcaact ttaaaatata gtttattttc atattttttt   1800

cttttaaact tggttgataa gtggaattag gagtatattt gaaagaatct tagcacaaac   1860

aggactgttg tactagatgt tcttaggaaa tatctcagaa gtattttatt tgaagtgaag   1920

aacttattta agaattattt cagtatttac ctgtatttta ttcttgaagt tggccaacag   1980

agttgtgaat gtgtgtggga aggcctttga atgtaaagct gcataagctg ttaggttttg   2040

ttttaaaagg acatgtttat tattgttcaa taaaaaagaa caagataca               2089
```

<210> SEQ ID NO 32
<211> LENGTH: 7686
<212> TYPE: DNA
<213> ORGANISM: Homo sapiens

<400> SEQUENCE: 32

```
tttatagcag cagtagaaat ataccaccct agaggacaca cctcctttta gctaggtacc     60

tataaatgtc caggattttc tattcaattg agaagaaccc agcaaaatgg ggatctccac    120

agtcatcctt gaaatgtgtc ttttatgggg acaagttcta tctacaggtg ggtggatccc    180

aaggactaca gactacgctt cactgattcc ctcggaggtg cccttggatc caactgtagc    240

agaaggttct ccatttccct cggagtcgac cctggagtca actgtagcag aaggttctcc    300

gatttccttg gagtcaaccc tggagtcaac cgtagcagaa ggttctctga ttccctcaga    360

gtcaaccctg gagtcaactg tagcagaagg atctgattct ggtttggccc tgaggctggt    420

gaatggagat ggcaggtgtc agggccgagt ggagatccta taccgaggct cctggggcac    480

cgtgtgtgat gacagctggg acaccaatga tgccaacgtg gtctgtaggc agctgggttg    540

tggctgggcc atgtcagctc caggaaatgc ctggtttggc cagggctcag gacccattgc    600

cctggatgat gtgcgctgct caggacacga atcctacctg tggagctgcc cccacaatgg    660

ctggctctcc cataactgtg gccatggtga agatgctggt gttatctgct cagctgccca    720

gcctcagtca acactcaggc cagaaagttg gcctgtcagg atatcaccac ctgtacccac    780

agaaggatct gaatccagtt tggccctgag gctggtgaat ggaggcgaca ggtgtcgagg    840

ccgagtggag gtcctatacc gaggctcctg gggcaccgtg tgtgatgact actgggacac    900

caatgatgcc aatgtggtct gcaggcagct gggctgtggc tgggccatgt cagccccagg    960

aaatgcccag tttggccagg gctcaggacc cattgtcctg gatgatgtgc gctgctcagg   1020

acatgagtcc tacctgtgga gctgccccca caatggctgg ctcacccaca actgtggcca   1080

tagtgaagac gctggtgtca tctgctcagc tccccagtcc cggccgacac ccagcccaga   1140

tacttggccg acctcacatg catcaacagc aggacctgaa tccagtttgg ccctgaggct   1200

ggtgaatgga ggtgacaggt gtcagggccg agtggaggtc ctataccgag gctcctgggg   1260
```

caccgtgtgt gatgatagct gggacaccag tgacgccaat gtggtctgcc ggcagctggg 1320
ctgtggctgg gccacgtcag ccccaggaaa tgcccggttt ggccagggtt caggacccat 1380
tgtcctggat gacgtgcgct gctcaggcta tgagtcctac ctgtggagct gcccccacaa 1440
tggctggctc tcccataact gtcagcacag tgaagacgct ggtgtcatct gctcagctgc 1500
ccactcctgg tcgacgccca gtccagacac gttgccgacc atcaccttac ctgcatcgac 1560
agtaggatct gaatccagtt tggccctgag gctggtgaat ggaggtgaca ggtgtcaggg 1620
ccgagtggag gtcctatacc gaggctcctg gggcaccgtg tgtgatgaca gctgggacac 1680
caatgatgcc aatgtggtct gcaggcagct gggctgtggc tgggccatgt tggccccagg 1740
aaatgcccgg tttggtcagg gctcaggacc cattgtcctg gatgacgtgc gctgctcagg 1800
gaatgagtcc tacttgtgga gctgccccca caatggctgg ctctcccata actgtggcca 1860
tagtgaagac gctggtgtca tctgctcagg acctgaatcc agtttggccc tgaggctggt 1920
gaatggaggt gacaggtgtc agggccgagt ggaggtccta taccgaggct cttggggcac 1980
cgtgtgtgat gacagctggg acaccaatga tgccaatgtg gtctgcaggc agctgggctg 2040
tggctgggcc acgtcagccc caggaaatgc ccggtttggt cagggctcag gacccattgt 2100
cctggatgat gtgcgctgct caggacatga gtcctacctg tggagctgcc ccaacaatgg 2160
ctggctctcc cacaactgtg gccatcatga agatgctggt gtcatctgct cagctgccca 2220
gtcccggtcg acgcccaggc cagacacgtt gtcgaccatc acgttacctc catcgacagt 2280
aggatctgaa tccagtttga ccctgaggct ggtgaatgga agtgacaggt gtcagggccg 2340
agtagaggtc ctataccgag gctcctgggg caccgtgtgt gatgacagct gggataccaa 2400
tgatgccaat gtggtctgca ggcagctggg ctgtggctgg gccacgtcgg ccccaggaaa 2460
tgcccggttt ggccagggct caggacccat tgttctggat gatgtgcgct gctcaggaca 2520
cgagtcctac ctgtggagct gcccccacaa tggctggctc tcccacaact gtggccatca 2580
tgaagatgct ggtgtcatct gctcagtttc ccagtcccgg ccgacaccca gtccagatac 2640
ttggccgacc tcacatgcat caacagcagg acctgaatcc agtttggccc tgaggctggt 2700
gaatggaggt gacaggtgtc agggccgagt ggaggtccta taccgaggct cctggggcac 2760
cgtgtgtgat gatagctggg acaccagtga cgccaatgtg gtctgccggc agctgggctg 2820
tggctgggcc acgtcagccc caggaaatgc ccggtttggc cagggttcag gacccattgt 2880
cctggatgac gtgcgctgct caggctatga gtcctacctg tggagctgcc cccacaatgg 2940
ctggctctcc cataactgtc agcacagtga agacgctggt gtcatctgct cagctgccca 3000
ctcctggtcg acgcccagtc cagacacatt gccgaccatc accttgcctg catcgacagt 3060
aggatctgaa tccagtttgg ccctgaggct ggtgaatgga ggtgacaggt gtcagggccg 3120
agtggaggtc ctataccaag gctcctgggg caccgtgtgc gatgacagct gggacaccaa 3180
tgatgccaat gtcgtctgca ggcaactggg ctgtggctgg gccatgtcag ccccaggaaa 3240
tgcccggttt ggtcagggct caggacccat tgtcctggat gatgtgcgct gctcaggaca 3300
cgagtcttac ctgtggagct gcccccacaa tggctggctc tcccacaact gtggccatag 3360
tgaagacgct ggtgtcatct gctcagcttc ccagtcccgg ccaacaccta gtccagacac 3420
ttggccaacc tcacatgcat caacagcagg atctgaatcc agtttggccc tgaggctggt 3480
gaatggaggt gacaggtgtc agggccgagt ggaggtccta taccgaggct cctggggcac 3540
cgtgtgtgat gactactggg acaccaatga tgccaatgtg gtttgcaggc agctgggctg 3600

-continued

```
tggctgggcc atgtcagccc caggaaatgc ccggtttggc cagggttcag gacccattgt   3660
cctggatgat gtgcgctgct caggacatga gtcctatctg tggagctgcc cccacaatgg   3720
ctggctctcc cacaactgtg gccatcatga agacgctggt gtcatctgct cagcttccca   3780
gtcccagccg acacccagcc cagacacttg gccaacctca catgcatcaa cagcaggatc   3840
tgaatccagt ttggccctga ggctggtgaa tggaggtgac aggtgtcagg gccgagtgga   3900
ggtcctatac cgaggctcct ggggcaccgt gtgtgatgac tactgggaca ccaatgatgc   3960
caatgtggtt tgcaggcagc tgggctgtgg ctgggccacg tcagccccag gaaatgcccg   4020
gtttggccag ggttcaggac ccattgtcct ggatgatgtg cgctgctcag gacatgagtc   4080
ctatctgtgg agctgccccc acaatggctg gctctcccac aactgtggcc atcatgaaga   4140
cgctggtgtc atctgctcag cttcccagtc ccagccgaca cccagcccag acacttggcc   4200
aacctcacat gcatcaacag caggatctga atccagtttg gccctgaggc tggtgaatgg   4260
aggtgacagg tgtcagggcc gagtggaggt cctataccga ggctcctggg gcaccgtgtg   4320
tgatgactac tgggacacca atgatgccaa tgtggtttgc aggcagctgg gctgtggctg   4380
ggccacgtca gccccaggaa atgcccggtt tggccagggt tcaggaccca ttgtcctgga   4440
tgatgtgcgc tgctcaggac atgagtccta tctgtggagc tgcccccaca atggctggct   4500
ctcccacaac tgtggccatc atgaagacgc tggtgtcatc tgctcagctt cccagtccca   4560
gccgacaccc agcccagaca cttggccaac ctctcgtgca tcaacagcag gatctgaatc   4620
cactttggcc ctgagactgg tgaatggagg tgacaggtgt cgaggccgag tggaggtcct   4680
ataccaaggc tcctggggca ccgtgtgtga tgactactgg gacaccaatg atgccaacgt   4740
ggtctgcagg cagctgggct gtggctgggc catgtcagcc ccaggaaatg cccagtttgg   4800
ccagggctca ggacccattg tcctggatga tgtgcgctgc tcaggacacg agtcttacct   4860
gtggagctgc ccccacaatg gctggctctc ccacaactgt ggccatcatg aagatgctgg   4920
tgtcatctgc tcagctgctc agtcccagtc aacgcccagg ccagatactt ggctgaccac   4980
caacttaccg gcattgacag taggatctga atccagtttg gctctgaggc tggtgaatgg   5040
aggtgacagg tgtcgaggcc gagtggaggt cctgtatcga ggctcctggg gaaccgtgtg   5100
tgatgacagc tgggacacca atgatgccaa tgtggtctgc aggcagctgg gctgtggctg   5160
ggccatgtcg gccccaggaa atgcccggtt tggccagggc tcaggaccca ttgtcctgga   5220
tgatgtgcgc tgctcaggga atgagtccta cctgtggagc tgcccccaca aaggctggct   5280
cacccacaac tgtggccatc acgaagacgc tggtgtcatc tgctcagcca cccaaataaa   5340
ttctactacg acagattggt ggcatccaac aactacaacc actgcaagac cctcttcaaa   5400
ttgtggtggc ttcttattct atgccagtgg gacattctcc agcccatcct accctgcata   5460
ctaccccaac aatgctaagt gtgtttggga aatagaagtg aattctggtt atcgcataaa   5520
cctgggcttc agtaatctga aattggaggc acaccataac tgcagttttg attatgttga   5580
aatctttgat ggatcattga atagcagtct cctgctgggg aaaatctgta atgataccag   5640
gcaaatattt acatcttctt acaaccgaat gaccattcac tttcgaagtg acatcagttt   5700
ccaaaacact ggctttttgg cttggtataa ctccttccca agcgatgcca ccttgaggtt   5760
ggtcaattta aattcatcct atggtctatg tgccgggcgt gtagaaattt accatggtgg   5820
cacctggggg acagtttgtg atgactcctg gaccattcag gaagctgagg tggtctgcag   5880
acagctaggg tgtggacgtg cagtttcagc ccttggaaat gcatattttg gctctggctc   5940
tggccccatc accctggacg atgtagagtg ctcagggacg gaatccactc tctggcagtg   6000
```

```
ccggaaccga ggctggttct cccacaactg taatcatcgt gaagatgctg gtgtcatctg   6060
ctcaggaaac catctatcga cacctgctcc ttttctcaac atcacccgtc caaacacaga   6120
ttattcctgc ggaggcttcc tatcccaacc atcaggggac ttttccagcc cattctatcc   6180
cgggaactat ccaaacaatg ccaagtgtgt gtgggacatt gaggtgcaaa acaactaccg   6240
tgtgactgtg atcttcagag atgtccagct tgaaggtggc tgcaactatg attatattga   6300
agttttcgat ggcccctacc gcagttcccc tctcattgct cgagtttgtg atggggccag   6360
aggctccttc acttcttcct ccaacttcat gtccattcgc ttcatcagtg accacagcat   6420
cacaaggaga gggttccggg ctgagtacta ctccagtccc tccaatgaca gcaccaacct   6480
gctctgtctg ccaaatcaca tgcaagccag tgtgagcagg agctatctcc aatccttggg   6540
cttttctgcc agtgaccttg tcatttccac ctggaatgga tactacgagt gtcggcccca   6600
gataacgccg aacctggtga tattcacaat tccctactca ggctgcggca ccttcaagca   6660
ggcagacaat gacaccatcg actattccaa cttcctcaca gcagctgtct caggtggcat   6720
catcaagagg aggacagacc tccgtattca cgtcagctgc agaatgcttc agaacacctg   6780
ggtcgacacc atgtacattg ctaatgacac catccacgtt gctaataaca ccatccaggt   6840
cgaggaagtc cagtatggca attttgacgt gaacatttcc ttttatactt cctcatcttt   6900
cttgtatcct gtgaccagcc gcccttacta cgtggacctg aaccaggact tgtacgttca   6960
ggctgaaatc ctccattctg atgctgtact gaccttgttt gtggacacct gcgtggcatc   7020
accatactcc aatgacttca cgtctttgac ttatgatcta atccggagtg gatgcgtgag   7080
ggatgacacc tacggaccct actcctcgcc atctcttcgc attgcccgct tccggttcag   7140
ggccttccac ttcctgaacc gcttcccctc cgtgtacctg cgttgtaaaa tggtggtgtg   7200
cagagcgtat gacccctctt cccgctgcta ccgaggctgt gtgttgaggt cgaagaggga   7260
tgtgggctcc taccaggaaa aggtggacgt cgtcctgggt cccatccagc tgcagacccc   7320
cccacgccga gaagaggagc ctcggtaggt ggtcgctctc agaccccact gtccaccggg   7380
gcgcagaccc ctgactcggg gacttgggat gttcctcttg gtgtcatatt ccaactcaga   7440
ttgagcccta cattgtgctg cacctggtca tacggagttg aatcagacct ggttcccgcc   7500
tcccccaagg ctcatggtcc ttggaggacc cgttgcaggg tgaggtcaag agagttctga   7560
cctggatggc ccatagacct gacgtcccag aatccatgct tctcatctgc aaaatgaaaa   7620
tgtcaatact tacttcttag cactgttgag agggttactt acataaagga attttggtga   7680
aactgc                                                              7686
```

<210> SEQ ID NO 33
<211> LENGTH: 1665
<212> TYPE: DNA
<213> ORGANISM: Homo sapiens

<400> SEQUENCE: 33

```
agttggaggg aggcagggaa tctggcttga ttggcgtgct gagacgcacc tggcgcaacc     60
ctcccttctg aatcgaagtt caagtcccgc ggacactgca accatgaagg agagacgggc    120
cccccagcca gtcgtggcca gatgtaagct cgttctggtc ggggacgtgc agtgtgggaa    180
gaccgcgatg ttgcaagtgt tagcgaagga ttgctatcca gagacctatg tgcccaccgt    240
gttcgaaaat tacacagcct gtttggagac agaggaacag agggtggagc ttagtctctg    300
ggatacctca ggatctccct actacgataa tgtccgtcca ctctgctaca gcgactcgga    360
```

```
tgcagtatta ctatgttttg acatcagccg tccagagaca gtggacagcg cactcaagaa    420
gtggaggaca gaaatcctag attattgtcc cagcacccgc gttttgctca ttggctgcaa    480
gacagacctg cgaacagacc tgagtactct gatggagctg tcccaccaga agcaggcgcc    540
catctcctat gagcagggtt gtgcaatagc aaagcagctg ggtgcagaaa tctacctgga    600
aggctcagct ttcacctcag aaaagagcat ccacagcatc tttcggacgg catccatgct    660
gtgtctgaac aagcctagcc cactgcccca gaagagccct gtccgaagcc tctccaaacg    720
actgctccac ctccccagtc gctctgaact catctcttct accttcaaga aggaaaaggc    780
caaaagctgt tccattatgt gaagtggaaa ttggaggggg gagacaaccc cctacttcct    840
cccttggggt gcagaggcac ggggagaggg aggatgagac aatttaggac actggacatg    900
agtttttcag atggccacgg tgagggcttg gaaggagaca ggaatggggc gaggaaggag    960
ccaggcccgg catgaggacc tgacgctgag agagaaccat cataccccaa gccaggcact   1020
agattttgga gggggcgact accccagtgc cccccccgct ccagaggaag gaaagctgtg   1080
ggggacgggg ggcatgctgg cctcatgggc ttgggggcct acagcagcct caccttcagc   1140
ttcatgcctc ttccacacag cgtttccatg caggtcaggg gatgggaggg gtccctgagc   1200
ccttcccttc ccctctaagg aggcagcaac ggagagtggg gaagtggagc ggcagctccc   1260
ttgggggctt agcccaggtg cttcgtaact gcaatcggaa gtgcaggagc tggtcagagc   1320
caatgagaag gaaacctcat ctttgcatag cccatgcctc atggagaggt gacatcatac   1380
attcacatgc ttctcaccta agtccccagg gtccaaggga gaagccccag accccccttct   1440
cttgcagagt gtgggggtgg tggtgctgca ggggcagggc tgggtggggg tcaccagact   1500
ttttctgccc ttagggtagt acagctggca tttgttttat agactcttgt ctttggaatt   1560
ggggggaggg ggggagtgtt tcaatctgtt atatgttctg tgtttaatga agaaaaccta   1620
tttattaatg aaaaatataa tacatataaa gaatttggct ccgta                   1665
```

<210> SEQ ID NO 34
<211> LENGTH: 1849
<212> TYPE: DNA
<213> ORGANISM: Homo sapiens

<400> SEQUENCE: 34

```
gggttatatg atctctttgg ctttagggaa ttactccata ccagctctga gatttccagc     60
tcagcgatgc ccccaggtcc ctgggagagc tgcttctggg tggggggcct cattttgtgg    120
ctcagcgttg gaagttcagg ggatgcacct cctaccccac agccaaagtg cgctgacttc    180
cagagcgcca acctttttga aggcaccgat ctcaaagtcc agtttctcct ctttgtccct    240
tcgaatccta gctgtgggca gctagtagaa ggaagcagtg acctccaaaa ctctgggttc    300
aatgccactc tgggaaccaa actaattatc catggattca gggttttagg aacaaagcct    360
tcctggattg acacatttat tagaaccctt ctgcgtgcaa cgaatgctaa tgtgattgcc    420
gtggactgga tttatgggtc tacaggagtc tacttctcag ctgtgaaaaa tgtgattaag    480
ttgagcctcg agatctccct tttcctcaat aaactcctgg tgctgggtgt gtcggaatcc    540
tcaatccaca tcattggtgt tagcctgggg gcccacgttg ggggcatggt gggacagctc    600
ttcggaggcc agctgggaca gatcacaggc ctggaccccg ctggacctga gtacaccagg    660
gccagtgtgg aagagcgctt ggatgctgga gatgccctct tcgtggaagc catccacaca    720
gacaccgaca atttgggtat tcggattccc gttggacatg tggactactt cgtcaacgga    780
ggccaagacc aacctggctg ccccaccttc ttttacgcag gttatagtta tctgatctgt    840
```

```
gatcacatga gggctgtgca cctctacatc agcgccctgg agaattcctg tccactgatg    900
gcctttccct gtgccagcta caaggccttc cttgctggac gctgtctgga ttgctttaac    960
ccttttctgc tttcctgccc aaggatagga ctggtggaac aaggtggtgt caagatagag   1020
ccgctcccca aggaagtgaa agtctacctc ctgactactt ccagtgctcc gtactgcatg   1080
catcacagcc tcgtggagtt tcacttgaag gaactgagaa acaaggacac caacatcgag   1140
gttaccttcc ttagcagtaa catcacctct tcatctaaga tcaccatacc taagcagcaa   1200
cgctatggga aaggaatcat agcccatgcc accccacaat gccagataaa ccaagtgaaa   1260
ttcaagtttc agtcttccaa ccgagtttgg aaaaaagacc ggactaccat tattgggaag   1320
ttctgcactg ccctttttgcc tgtcaatgac agagaaaaga tggtctgctt acctgaacca   1380
gtgaacttac aagcaagtgt gactgtttcc tgtgacctga agatagcctg tgtgtagttt   1440
aacctgggca ggacacatct ccctgcattt tttttttttt tttgagagag aggtgtgatg   1500
agggatgtgt gtgtgcagct tattgtagac cattactact aaggagaaaa gcaaagctct   1560
ttcttatttt cctcataatc agctaccctg gaggggaggg agaactcatt ttacagaact   1620
tggtttcctt tgccgatctt atgtacatac ccattttagc tttcccatgc atacttaact   1680
gcacttgctt tatctccttg ggcattcgta cttaggattc aatagaaaca tgtacagggt   1740
aaacaatttt ttaaaaataa aacttcatgg agtatctgaa aaaaaaaaaa aaaaaaaaaa   1800
aaaaaaaaaa aaaaaaaaaa aaaaaaaaaa aaaaaaaaaa aaaaaaaaa               1849

<210> SEQ ID NO 35
<211> LENGTH: 7656
<212> TYPE: DNA
<213> ORGANISM: Homo sapiens

<400> SEQUENCE: 35

tttatagcag cagtagaaat ataccaccct agaggacaca cctcctttta gctaggtacc     60
tataaatgtc caggattttc tattcaattg agaagaaccc agcaaaatgg ggatctccac    120
agtcatcctt gaaatgtgtc ttttatgggg acaagttcta tctacaggtg ggtggatccc    180
aaggactaca gactacgctt cactgattcc ctcggaggtg cccttggatc caactgtagc    240
agaaggttct ccatttccct cggagtcgac cctggagtca actgtagcag aaggttctcc    300
gatttccttg gagtcaaccc tggagtcaac cgtagcagaa ggttctctga ttccctcaga    360
gtcaaccctg gagtcaactg tagcagaagg atctgattct ggtttggccc tgaggctggt    420
gaatggagat ggcaggtgtc agggccgagt ggagatccta taccgaggct cctggggcac    480
cgtgtgtgat gacagctggg acaccaatga tgccaacgtg gtctgtaggc agctgggttg    540
tggctgggcc atgtcagctc caggaaatgc ctggtttggc cagggctcag gacccattgc    600
cctggatgat gtgcgctgct caggacacga atcctacctg tggagctgcc cccacaatgg    660
ctggctctcc cataactgtg gccatggtga agatgctggt gttatctgct cagctgccca    720
gcctcagtca acactcaggc cagaaagttg gcctgtcagg atatcaccac ctgtacccac    780
agaaggatct gaatccagtt tggccctgag gctggtgaat ggaggcgaca ggtgtcgagg    840
ccgagtggag gtcctatacc gaggctcctg gggcaccgtg tgtgatgact actgggacac    900
caatgatgcc aatgtggtct gcaggcagct gggctgtggc tgggccatgt cagccccagg    960
aaatgcccag tttggccagg gctcaggacc cattgtcctg gatgatgtgc gctgctcagg   1020
acatgagtcc tacctgtgga gctgccccca caatggctgg ctcacccaca actgtggcca   1080
```

-continued

```
tagtgaagac gctggtgtca tctgctcagc tccccagtcc cggccgacac ccagcccaga   1140

tacttggccg acctcacatg catcaacagc aggacctgaa tccagtttgg ccctgaggct   1200

ggtgaatgga ggtgacaggt gtcagggccg agtggaggtc ctataccgag gctcctgggg   1260

caccgtgtgt gatgatagct gggacaccag tgacgccaat gtggtctgcc ggcagctggg   1320

ctgtggctgg gccacgtcag ccccaggaaa tgcccggttt ggccagggtt caggacccat   1380

tgtcctggat gacgtgcgct gctcaggcta tgagtcctac ctgtggagct gcccccacaa   1440

tggctggctc tcccataact gtcagcacag tgaagacgct ggtgtcatct gctcagacac   1500

gttgccgacc atcaccttac ctgcatcgac agtaggatct gaatccagtt tggccctgag   1560

gctggtgaat ggaggtgaca ggtgtcaggg ccgagtggag gtcctatacc gaggctcctg   1620

gggcaccgtg tgtgatgaca gctgggacac caatgatgcc aatgtggtct gcaggcagct   1680

gggctgtggc tgggccatgt tggccccagg aaatgcccgg tttggtcagg gctcaggacc   1740

cattgtcctg gatgacgtgc gctgctcagg gaatgagtcc tacttgtgga gctgccccca   1800

caatggctgg ctctcccata actgtggcca tagtgaagac gctggtgtca tctgctcagg   1860

acctgaatcc agtttggccc tgaggctggt gaatggaggt gacaggtgtc agggccgagt   1920

ggaggtccta taccgaggct cttggggcac cgtgtgtgat gacagctggg acaccaatga   1980

tgccaatgtg gtctgcaggc agctgggctg tggctgggcc acgtcagccc caggaaatgc   2040

ccggtttggt cagggctcag gacccattgt cctggatgat gtgcgctgct caggacatga   2100

gtcctacctg tggagctgcc ccaacaatgg ctggctctcc cacaactgtg gccatcatga   2160

agatgctggt gtcatctgct cagctgccca gtcccggtcg acgcccaggc cagacacgtt   2220

gtcgaccatc acgttacctc catcgacagt aggatctgaa tccagtttga ccctgaggct   2280

ggtgaatgga agtgacaggt gtcagggccg agtagaggtc ctataccgag gctcctgggg   2340

caccgtgtgt gatgacagct gggataccaa tgatgccaat gtggtctgca ggcagctggg   2400

ctgtggctgg gccacgtcgg ccccaggaaa tgcccggttt ggccagggct caggacccat   2460

tgttctggat gatgtgcgct gctcaggaca cgagtcctac ctgtggagct gcccccacaa   2520

tggctggctc tcccacaact gtggccatca tgaagatgct ggtgtcatct gctcagtttc   2580

ccagtcccgg ccgacaccca gtccagatac ttggccgacc tcacatgcat caacagcagg   2640

acctgaatcc agtttggccc tgaggctggt gaatggaggt gacaggtgtc agggccgagt   2700

ggaggtccta taccgaggct cctggggcac cgtgtgtgat gatagctggg acaccagtga   2760

cgccaatgtg gtctgccggc agctgggctg tggctgggcc acgtcagccc caggaaatgc   2820

ccggtttggc cagggttcag gacccattgt cctggatgac gtgcgctgct caggctatga   2880

gtcctacctg tggagctgcc cccacaatgg ctggctctcc cataactgtc agcacagtga   2940

agacgctggt gtcatctgct cagctgccca ctcctggtcg acgcccagtc cagacacatt   3000

gccgaccatc accttgcctg catcgacagt aggatctgaa tccagtttgg ccctgaggct   3060

ggtgaatgga ggtgacaggt gtcagggccg agtggaggtc ctataccaag gctcctgggg   3120

caccgtgtgc gatgacagct gggacaccaa tgatgccaat gtcgtctgca ggcaactggg   3180

ctgtggctgg gccatgtcag ccccaggaaa tgcccggttt ggtcagggct caggacccat   3240

tgtcctggat gatgtgcgct gctcaggaca cgagtcttac ctgtggagct gcccccacaa   3300

tggctggctc tcccacaact gtggccatag tgaagacgct ggtgtcatct gctcagcttc   3360

ccagtcccgg ccaacaccta gtccagacac ttggccaacc tcacatgcat caacagcagg   3420

atctgaatcc agtttggccc tgaggctggt gaatggaggt gacaggtgtc agggccgagt   3480
```

```
ggaggtccta taccgaggct cctggggcac cgtgtgtgat gactactggg acaccaatga   3540
tgccaatgtg gtttgcaggc agctgggctg tggctgggcc atgtcagccc caggaaatgc   3600
ccggtttggc cagggttcag gacccattgt cctggatgat gtgcgctgct caggacatga   3660
gtcctatctg tggagctgcc cccacaatgg ctggctctcc cacaactgtg gccatcatga   3720
agacgctggt gtcatctgct cagcttccca gtcccagccg acacccagcc cagacacttg   3780
gccaacctca catgcatcaa cagcaggatc tgaatccagt ttggccctga ggctggtgaa   3840
tggaggtgac aggtgtcagg gccgagtgga ggtcctatac cgaggctcct ggggcaccgt   3900
gtgtgatgac tactgggaca ccaatgatgc caatgtggtt tgcaggcagc tgggctgtgg   3960
ctgggccacg tcagccccag gaaatgcccg gtttggccag ggttcaggac ccattgtcct   4020
ggatgatgtg cgctgctcag gacatgagtc ctatctgtgg agctgccccc acaatggctg   4080
gctctcccac aactgtggcc atcatgaaga cgctggtgtc atctgctcag cttcccagtc   4140
ccagccgaca cccagcccag acacttggcc aacctcacat gcatcaacag caggatctga   4200
atccagtttg gccctgaggc tggtgaatgg aggtgacagg tgtcagggcc gagtggaggt   4260
cctataccga ggctcctggg gcaccgtgtg tgatgactac tgggacacca atgatgccaa   4320
tgtggtttgc aggcagctgg gctgtggctg ggccacgtca gccccaggaa atgcccggtt   4380
tggccagggt tcaggaccca ttgtcctgga tgatgtgcgc tgctcaggac atgagtccta   4440
tctgtggagc tgcccccaca atggctggct ctcccacaac tgtggccatc atgaagacgc   4500
tggtgtcatc tgctcagctt cccagtccca gccgacaccc agcccagaca cttggccaac   4560
ctctcgtgca tcaacagcag gatctgaatc cactttggcc ctgagactgg tgaatggagg   4620
tgacaggtgt cgaggccgag tggaggtcct ataccaaggc tcctggggca ccgtgtgtga   4680
tgactactgg gacaccaatg atgccaacgt ggtctgcagg cagctgggct gtggctgggc   4740
catgtcagcc ccaggaaatg cccagtttgg ccagggctca ggacccattg tcctggatga   4800
tgtgcgctgc tcaggacacg agtcttacct gtggagctgc ccccacaatg gctggctctc   4860
ccacaactgt ggccatcatg aagatgctgg tgtcatctgc tcagctgctc agtcccagtc   4920
aacgcccagg ccagatactt ggctgaccac caacttaccg gcattgacag taggatctga   4980
atccagtttg gctctgaggc tggtgaatgg aggtgacagg tgtcgaggcc gagtggaggt   5040
cctgtatcga ggctcctggg gaaccgtgtg tgatgacagc tgggacacca atgatgccaa   5100
tgtggtctgc aggcagctgg gctgtggctg ggccatgtcg gccccaggaa atgcccggtt   5160
tggccagggc tcaggaccca ttgtcctgga tgatgtgcgc tgctcaggga atgagtccta   5220
cctgtggagc tgcccccaca aaggctggct cacccacaac tgtggccatc acgaagacgc   5280
tggtgtcatc tgctcagcca cccaaataaa ttctactacg acagattggt ggcatccaac   5340
aactacaacc actgcaagac cctcttcaaa ttgtggtggc ttcttattct atgccagtgg   5400
gacattctcc agcccatcct accctgcata ctaccccaac aatgctaagt gtgtttggga   5460
aatagaagtg aattctggtt atcgcataaa cctgggcttc agtaatctga aattggaggc   5520
acaccataac tgcagttttg attatgttga aatctttgat ggatcattga atagcagtct   5580
cctgctgggg aaaatctgta atgataccag gcaaatattt acatcttctt acaaccgaat   5640
gaccattcac tttcgaagtg acatcagttt ccaaaacact ggctttttgg cttggtataa   5700
ctccttccca agcgatgcca ccttgaggtt ggtcaattta aattcatcct atggtctatg   5760
tgccgggcgt gtagaaattt accatggtgg cacctggggg acagtttgtg atgactcctg   5820
```

```
gaccattcag gaagctgagg tggtctgcag acagctaggg tgtggacgtg cagtttcagc   5880

ccttggaaat gcatattttg gctctggctc tggccccatc accctggacg atgtagagtg   5940

ctcagggacg gaatccactc tctggcagtg ccggaaccga ggctggttct cccacaactg   6000

taatcatcgt gaagatgctg gtgtcatctg ctcaggaaac catctatcga cacctgctcc   6060

ttttctcaac atcacccgtc caaacacaga ttattcctgc ggaggcttcc tatcccaacc   6120

atcaggggac ttttccagcc cattctatcc cgggaactat ccaaacaatg ccaagtgtgt   6180

gtgggacatt gaggtgcaaa acaactaccg tgtgactgtg atcttcagag atgtccagct   6240

tgaaggtggc tgcaactatg attatattga agttttcgat ggcccctacc gcagttcccc   6300

tctcattgct cgagtttgtg atggggccag aggctccttc acttcttcct ccaacttcat   6360

gtccattcgc ttcatcagtg accacagcat cacaaggaga gggttccggg ctgagtacta   6420

ctccagtccc tccaatgaca gcaccaacct gctctgtctg ccaaatcaca tgcaagccag   6480

tgtgagcagg agctatctcc aatccttggg cttttctgcc agtgaccttg tcatttccac   6540

ctggaatgga tactacgagt gtcggcccca gataacgccg aacctggtga tattcacaat   6600

tccctactca ggctgcggca ccttcaagca ggcagacaat gacaccatcg actattccaa   6660

cttcctcaca gcagctgtct caggtggcat catcaagagg aggacagacc tccgtattca   6720

cgtcagctgc agaatgcttc agaacacctg ggtcgacacc atgtacattg ctaatgacac   6780

catccacgtt gctaataaca ccatccaggt cgaggaagtc cagtatggca attttgacgt   6840

gaacatttcc ttttatactt cctcatcttt cttgtatcct gtgaccagcc gcccttacta   6900

cgtggacctg aaccaggact tgtacgttca ggctgaaatc ctccattctg atgctgtact   6960

gaccttgttt gtggacacct gcgtggcatc accatactcc aatgacttca cgtctttgac   7020

ttatgatcta atccggagtg gatgcgtgag ggatgacacc tacggaccct actcctcgcc   7080

atctcttcgc attgcccgct tccggttcag ggccttccac ttcctgaacc gcttcccctc   7140

cgtgtacctg cgttgtaaaa tggtggtgtg cagagcgtat gacccctctt cccgctgcta   7200

ccgaggctgt gtgttgaggt cgaagaggga tgtgggctcc taccaggaaa aggtggacgt   7260

cgtcctgggt cccatccagc tgcagacccc cccacgccga gaagaggagc ctcggtaggt   7320

ggtcgctctc agaccccact gtccaccggg gcgcagaccc ctgactcggg gacttgggat   7380

gttcctcttg gtgtcatatt ccaactcaga ttgagcccta cattgtgctg cacctggtca   7440

tacggagttg aatcagacct ggttcccgcc tcccccaagg ctcatggtcc ttggaggacc   7500

cgttgcaggg tgaggtcaag agagttctga cctggatggc ccatagacct gacgtcccag   7560

aatccatgct tctcatctgc aaaatgaaaa tgtcaatact tacttcttag cactgttgag   7620

agggttactt acataaagga attttggtga aactgc                            7656
```

<210> SEQ ID NO 36
<211> LENGTH: 2413
<212> TYPE: DNA
<213> ORGANISM: Homo sapiens

<400> SEQUENCE: 36

```
cccgggctcg cgggcagacg gaggcgcctc tctttccccg cccctcgcct cggccctttc     60

tcttcccagc acctcggctg ttccccggcg gcggcagcgg cagcggcggc ccacacagca    120

gcgagaggcg agaggaggct gcctcgagga ggctgcctcg aggatgaagt gcaaacccaa    180

ccagacgcgg acctacgacc ccgaggggtt caagaagcgg gcggcgtgcc tgtgcttccg    240

gagcgaacgc gaggacgagg tcctgttagt gagtagcagc cggtacccgg accgctggat    300
```

```
cgtgccgggc gggggcatgg agcccgagga ggagccgggc ggtgcggcgg tccgagaggt    360

gtacgaagaa gcgggagtca aggggaagtt aggccggctc ctgggcgtct tcgaacagaa    420

ccaggatcgc aagcacagaa cgtacgtgta tgtactgact gtcacggagc tgctggagga    480

ttgggaagat tcggttagca ttgggaggaa gcgagagtgg ttcaaagtcg aagatgccat    540

caaggttctc cagtgccaca agcccgtgca cgccgaatat ctggagaaac taaagctggg    600

cggttcccca accaatggaa actccatggc cccatcctcg ccagatagcg atccctaatg    660

aacagcaaag atgttcagta ttgtgctgaa agaaacattg atgtgaaccc agtgatcagt    720

ggaattgtca agtacaggtg agcacttctg tgttcccaag aagacagctc atctggtttc    780

ttcctgcatc ttgggacact ccttccctgt ctataccact gactcttgct ctggttgttg    840

tactcttata cgtgaataga ctcttaattc agcacctata gccttttgtt gtgctttttt    900

gatgtgtctg ccttcattag actatgatgt ctttgagagc aaagactatt tttccttact    960

ctttgcatat tctgcatctg agacactact tgaaatatgg ttggcatcac tgaaggttct   1020

ttgattcaat taatattttg taatcaccgt gtggcaaaac attccccttc caatctggtg   1080

ctagtagagt atatgctatc taggcaccat gtgtgtggct tttgtgtatc aggtgtttca   1140

gaaatatttc aagacagttg taagatgttt gaggacaaga attattactc ctatttctat   1200

gtcataccac acagtagctg cacagtttta agattatgcc atcacctagg gtaatgtttt   1260

gtagaatcag tccttcgtgt aacaactcta gtgtttttgt actgttgatg atttgcttaa   1320

attttattca aaaactatca cttgctataa aggtaattgt aaaaataaat acagtggacg   1380

caaaataatg ttgtgagttt ttataaaaat aaattttaaa atgatatata agacattttt   1440

ttgcaatgcc tgccctaacc acttcttaca tgtcatctta acatctcttt gaggaaacac   1500

tgtttcctca ttttacagat ttaacatact gtattatttg atgccagagc caacaggcta   1560

tatcataggc agtttccaaa cttaattatg ccatttagtt tgtctagatt tcttttgcct   1620

ctctcactga tccatttggc tgtagttttc atccctttc cagtacacac agctagctcc    1680

tcatcctacc tggtttctgc atatgagaat gcagagggct gagagagggc aaaattgttg   1740

tcatttagaa aaggcattta ggaaagaggc tgctattaga ggggaacaca aagtgaaggt   1800

tttttaaaa aagaggactt gcatcagctg cctccagaac aattttaaga aaataacaaa    1860

gatgtttaga agaaatctta cggagtttgc catgggatgt gtgatatcag cagtcttcag   1920

ctccttacaa attaccaaaa gtggttctaa tatgctagtt tgtttgattt tttcttttat   1980

attataaagc aattgcatcg ataaaagctt ggactccatt ttagtgtgac actcttcctc   2040

atgataccag tgaaatgtat tgattgtgtc cccagttgtt acataatttg aaataaaaat   2100

ataacttctt gatttattgt tttttaagat gtgatatggt actgtggtta tgttgtttta   2160

aaaaatgatt atcttttaga gaagtatact gaaaaatgta caggtgaaat gatatgttac   2220

tggtattcgc ttcaaaatca tctgagtgtg gggtaattga gtacatagat gaaacaagat   2280

tggccataaa ttggtaattg ctgaagctgt gtgatggatg tttgagagtt cattatacta   2340

ttctctatac ttttgtatat gtttgaaatt ttccataata aaaattgaaa aaagtaaaaa   2400

aaaaaaaaaa aaa                                                        2413
```

<210> SEQ ID NO 37
<211> LENGTH: 862
<212> TYPE: DNA
<213> ORGANISM: Homo sapiens

<400> SEQUENCE: 37

```
cttggcggtg acgcacggcc ctcacgtgac cgggagctgc agagctacgc agccttcggt     60
gcagtcgtca ctcgtgtctc gctaccagct ccccgctgcc ctgcgctcgg cgggctggca    120
tccggcccgg gggaaagcgg accagccctt ctgcaggtct gcggggccaa gtgtcccggc    180
ggcgcacctc gtggcgagaa tcgggagaag gaggagacta caaggatagg cccaggagta    240
atggagtcca aagagaaacg agcagtaaac agtctcagca tggaaaatgc caaccaagaa    300
aatgaagaaa aggagcaagt tgctaataaa ggggagccct tggccctccc tttggatgct    360
ggtgaatact gtgtgcctag aggaaatcgt aggcggttcc gcgttaggca gcccatcctg    420
cagtatagat gggatatgat gcataggctt ggagaaccac aggcaaggat gagagaagag    480
aatatggaaa ggattgggga ggaggtgaga cagctgatgg aaaagctgag ggaaaagcag    540
ttgagtcata gtctgcgggc agtcagcact gacccccctc accatgacca tcatgatgag    600
ttttgcctta tgccctgaat cctgatggtt tccctaaagt tattacggaa acagacccct    660
gctttcgaat ttacatgttc atgatgtgcc cttgttgtaa acctttacct gtcacttgtt    720
tacgtgggtc tcctattacc agcttctaat tgaatattgt gtttttgaac cagtctgtaa    780
gatttttgtt agcagaagaa ttttacctat tgcatggaaa gatgctcatt atagtgaagt    840
taataaagca cctttaaaaa gc                                             862
```

<210> SEQ ID NO 38
<211> LENGTH: 7080
<212> TYPE: DNA
<213> ORGANISM: Homo sapiens

<400> SEQUENCE: 38

```
gagctagcgc tcaagcagag cccagcgcgg tgctatcgga cagagcctgg cgagcgcaag     60
cggcgcgggg agccagcggg gctgagcgcg gccagggtct gaacccagat ttcccagact    120
agctaccact ccgcttgccc acgccccggg agctcgcggc gcctggcggt cagcgaccag    180
acgtccgggg ccgctgcgct cctggcccgc gaggcgtgac actgtctcgg ctacagaccc    240
agagggagca cactgccagg atgggagctg ctgggaggca ggacttcctc ttcaaggcca    300
tgctgaccat cagctggctc actctgacct gcttccctgg ggccacatcc acagtggctg    360
ctgggtgccc tgaccagagc cctgagttgc aaccctggaa ccctggccat gaccaagacc    420
accatgtgca tatcggccag ggcaagacac tgctgctcac ctcttctgcc acggtctatt    480
ccatccacat ctcagaggga ggcaagctgg tcattaaaga ccacgacgag ccgattgttt    540
tgcgaacccg gcacatcctg attgacaacg gaggagagct gcatgctggg agtgccctct    600
gccctttcca gggcaatttc accatcattt tgtatggaag ggctgatgaa ggtattcagc    660
cggatcctta ctatggtctg aagtacattg ggttggtaa aggaggcgct cttgagttgc     720
atggacagaa aaagctctcc tggacatttc tgaacaagac ccttcaccca ggtggcatgg    780
cagaaggagg ctattttttt gaaaggagct ggggccaccg tggagttatt gttcatgtca    840
tcgaccccaa atcaggcaca gtcatccatt ctgaccggtt tgacacctat agatccaaga    900
aagagagtga acgtctggtc cagtatttga acgcggtgcc cgatggcagg atcctttctg    960
ttgcagtgaa tgatgaaggt tctcgaaatc tggatgacat ggccaggaag gcgatgacca   1020
aattgggaag caaacacttc ctgcaccttg gatttagaca ccccttggagt tttctaactg   1080
tgaaaggaaa tccatcatct tcagtggaag accatattga atatcatgga catcgaggct   1140
ctgctgctgc ccgggtattc aaattgttcc agacagagca tggcgaatat ttcaatgttt   1200
```

ctttgtccag tgagtgggtt caagacgtgg agtggacgga gtggttcgat catgataaag 1260
tatctcagac taaaggtggg gagaaaattt cagacctctg gaaagctcac ccaggaaaaa 1320
tatgcaatcg tcccattgat atacaggcca ctacaatgga tggagttaac ctcagcaccg 1380
aggttgtcta caaaaaaggc caggattata ggtttgcttg ctacgaccgg ggcagagcct 1440
gccggagcta ccgtgtacgg ttcctctgtg ggaagcctgt gaggcccaaa ctcacagtca 1500
ccattgacac caatgtgaac agcaccattc tgaacttgga ggataatgta cagtcatgga 1560
aacctggaga taccctggtc attgccagta ctgattactc catgtaccag gcagaagagt 1620
tccaggtgct tccctgcaga tcctgcgccc ccaaccaggt caaagtggca gggaaaccaa 1680
tgtacctgca catcggggag gagatagacg gcgtggacat gcgggcggag gttgggcttc 1740
tgagccggaa catcatagtg atgggggaga tggaggacaa atgctacccc tacagaaacc 1800
acatctgcaa tttctttgac ttcgatacct ttggggccca catcaagttt gctctgggat 1860
ttaaggcagc acacttggag ggcacggagc tgaagcatat gggacagcag ctggtgggtc 1920
agtacccgat tcacttccac ctggccggtg atgtagacga aaggggaggt tatgacccac 1980
ccacatacat cagggacctc tccatccatc atacattctc tcgctgcgtc acagtccatg 2040
gctccaatgg cttgttgatc aaggacgttg tgggctataa ctctttgggc cactgcttct 2100
tcacggaaga tgggccggag gaacgcaaca cttttgacca ctgtcttggc ctccttgtca 2160
agtctggaac cctcctcccc tcggaccgtg acagcaagat gtgcaagatg atcacagagg 2220
actcctaccc ggggtacatc cccaagccca ggcaagactg caatgctgtg tccaccttct 2280
ggatggccaa tcccaacaac aacctcatca actgtgccgc tgcaggatct gaggaaactg 2340
gattttggtt tatttttcac cacgtaccaa cgggcccctc cgtgggaatg tactccccag 2400
gttattcaga gcacattcca ctgggaaaat tctataacaa ccgagcacat tccaactacc 2460
gggctggcat gatcatagac aacggagtca aaaccaccga ggcctctgcc aaggacaagc 2520
ggccgttcct ctcaatcatc tctgccagat acagccctca ccaggacgcc gacccgctga 2580
agccccggga gccggccatc atcagacact tcattgccta caagaaccag gaccacgggg 2640
cctggctgcg cggcggggat gtgtggctgg acagctgccg gtttgctgac aatggcattg 2700
gcctgaccct ggccagtggt ggaaccttcc cgtatgacga cggctccaag caagagataa 2760
agaacagctt gtttgttggc gagagtggca acgtggggac ggaaatgatg gacaatagga 2820
tctggggccc tggcggcttg gaccatagcg gaaggaccct ccctataggc cagaattttc 2880
caattagagg aattcagtta tatgatggcc ccatcaacat ccaaaactgc actttccgaa 2940
agtttgtggc cctggagggc cggcacacca gcgccctggc cttccgcctg aataatgcct 3000
ggcagagctg cccccataac aacgtgaccg gcattgcctt tgaggacgtt ccgattactt 3060
ccagagtgtt cttcggagag cctgggccct ggttcaacca gctggacatg gatggggata 3120
agacatctgt gttccatgac gtcgacggct ccgtgtccga gtaccctggc tcctacctca 3180
cgaagaatga caactggctg gtccggcacc cagactgcat caatgttccc gactggagag 3240
gggccatttg cagtgggtgc tatgcacaga tgtacattca agcctacaag accagtaacc 3300
tgcgaatgaa gatcatcaag aatgacttcc ccagccaccc tctttacctg gagggggcgc 3360
tcaccaggag cacccattac cagcaatacc aaccggttgt caccctgcag aagggctaca 3420
ccatccactg ggaccagacg gcccccgccg aactcgccat ctggctcatc aacttcaaca 3480
agggcgactg gatccgagtg gggctctgct acccgcgagg caccacattc tccatcctct 3540

-continued

```
cggatgttca caatcgcctg ctgaagcaaa cgtccaagac gggcgtcttc gtgaggacct   3600
tgcagatgga caaagtggag cagagctacc ctggcaggag ccactactac tgggacgagg   3660
actcagggct gttgttcctg aagctgaaag ctcagaacga gagagagaag tttgctttct   3720
gctccatgaa aggctgtgag aggataaaga ttaaagctct gattccaaag aacgcaggcg   3780
tcagtgactg cacagccaca gcttacccca agttcaccga gagggctgtc gtagacgtgc   3840
cgatgcccaa gaagctcttt ggttctcagc tgaaaacaaa ggaccatttc ttggaggtga   3900
agatggagag ttccaagcag cacttcttcc acctctggaa cgacttcgct tacattgaag   3960
tggatgggaa gaagtacccc agttcggagg atggcatcca ggtggtggtg attgacggga   4020
accaagggcg cgtggtgagc cacacgagct tcaggaactc cattctgcaa ggcataccat   4080
ggcagctttt caactatgtg gcgaccatcc ctgacaattc catagtgctt atggcatcaa   4140
agggaagata cgtctccaga ggcccatgga ccagagtgct ggaaaagctt ggggcagaca   4200
ggggtctcaa gttgaaagag caaatggcat tcgttggctt caaaggcagc ttccggccca   4260
tctgggtgac actggacact gaggatcaca aagccaaaat cttccaagtt gtgcccatcc   4320
ctgtggtgaa gaagaagaag ttgtgaggac agctgccgcc cggtgccacc tcgtggtaga   4380
ctatgacggt gactcttggc agcagaccag tgggggatgg ctgggtcccc cagcccctgc   4440
cagcagctgc ctgggaaggc cgtgtttcag ccctgatggg ccaagggaag gctatcagag   4500
accctggtgc tgccacctgc ccctactcaa gtgtctacct ggagcccctg gggcggtgct   4560
ggccaatgct ggaaacattc actttcctgc agcctcttgg gtgcttctct cctatctgtg   4620
cctcttcagt gggggtttgg ggaccatatc aggagacctg ggttgtgctg acagcaaaga   4680
tccactttgg caggagccct gacccagcta ggaggtagtc tggagggctg gtcattcaca   4740
gatccccatg gtcttcagca gacaagtgag ggtggtaaat gtaggagaaa gagccttggc   4800
cttaaggaaa tctttactcc tgtaagcaag agccaacctc acaggattag gagctggggt   4860
agaactggct atccttgggg aagaggcaag ccctgcctct ggccgtgtcc acctttcagg   4920
agactttgag tggcaggttt ggacttggac tagatgactc tcaaaggccc ttttagttct   4980
gagattccag aaatctgctg catttcacat ggtacctgga acccaacagt tcatggatat   5040
ccactgatat ccatgatgct gggtgcccca gcgcacacgg gatggagagg tgagaactaa   5100
tgcctagctt gaggggtctg cagtccagta gggcaggcag tcaggtccat gtgcactgca   5160
atgccaggtg gagaaatcac agagaggtaa aatggaggcc agtgccattt cagaggggag   5220
gctcaggaag gcttcttgct tacaggaatg aaggctgggg gcattttgct ggggggagat   5280
gaggcagcct ctggaatggc tcagggattc agccctccct gccgctgcct gctgaagctg   5340
gtgactacgg ggtcgccctt tgctcacgtc tctctggccc actcatgatg gagaagtgtg   5400
gtcagagggg agcaatgggc tttgctgctt atgagcacag aggaattcag tccccaggca   5460
gccctgcctc tgactccaag agggtgaagt ccacagaagt gagctcctgc cttagggcct   5520
catttgctct tcatccaggg aactgagcac agggggcctc caggagaccc tagatgtgct   5580
cgtactccct cggcctggga tttcagagct ggaaatatag aaaatatcta gcccaaagcc   5640
ttcattttaa cagatgggga aagtgagccc ccaagatggg aaagaaccac acagctaagg   5700
gagggcctgg ggagccccac cctagccctt gctgccacac cacattgcct caacaaccgg   5760
ccccagagtg cccaggcact cctgaggtag cttctggaaa tggggacaag tcccctcgaa   5820
ggaaaggaaa tgactagagt agaatgacag ctagcagatc tcttccctcc tgctcccagc   5880
gcacacaaac ccgccctccc cttggtgttg gcggtccctg tggccttcac tttgttcact   5940
```

acctgtcagc ccagcctggg tgcacagtag ctgcaactcc ccattggtgc tacctggctc 6000
tcctgtctct gcagctctac aggtgaggcc cagcagaggg agtagggctc gccatgtttc 6060
tggtgagcca atttggctga tcttgggtgt ctgaacagct attgggtcca ccccagtccc 6120
tttcagctgc tgcttaatgc cctgctctct ccctggccca ccttatagag agcccaaaga 6180
gctcctgtaa gagggagaac tctatctgtg gtttataatc ttgcacgagg caccagagtc 6240
tccctgggtc ttgtgatgaa ctacatttat ccccttttcct gccccaacca caaactcttt 6300
ccttcaaaga gggcctgcct ggctccctcc acccaactgc acccatgaga ctcggtccaa 6360
gagtccattc cccaggtggg agccaactgt cagggaggtc tttcccacca aacatctttc 6420
agctgctggg aggtgaccat agggctctgc ttttaaagat atggctgctt caaaggccag 6480
agtcacagga aggacttctt ccagggagat tagtggtgat ggagaggaga gttaaaatga 6540
cctcatgtcc ttcttgtcca cggttttgtt gagttttcac tcttctaatg caagggtctc 6600
acactgtgaa ccacttagga tgtgatcact ttcaggtggc caggaatgtt gaatgtcttt 6660
ggctcagttc atttaaaaaa gatatctatt tgaaagttct cagagttgta catatgtttc 6720
acagtacagg atctgtacat aaaagtttct ttcctaaacc attcaccaag agccaatatc 6780
taggcatttt cttggtagca caaattttct tattgcttag aaaattgtcc tccttgttat 6840
ttctgtttgt aagacttaag tgagttaggt ctttaaggaa agcaacgctc ctctgaaatg 6900
cttgtctttt ttctgttgcc gaaatagctg gtccttttttc gggagttaga tgtatagagt 6960
gtttgtatgt aaacatttct tgtaggcatc accatgaaca aagatatatt ttctatttat 7020
ttattatatg tgcacttcaa gaagtcactg tcagagaaat aaagaattgt cttaaatgtc 7080

<210> SEQ ID NO 39
<211> LENGTH: 5676
<212> TYPE: DNA
<213> ORGANISM: Homo sapiens

<400> SEQUENCE: 39
ggcacgtgga ctccctttaa tccagtgact gtcaggtcga tcatatgccg aggacgatga 60
tcccgccggg ggagtgcacg tacgcgggcc ggaagcggag gaggcccctg cagaaacaga 120
ggcccgccgt gggggcagag aagtccaacc cctccaagcg acaccgggac cgcctcaacg 180
ccgagttgga ccacctggcc agcctgctgc cgttcccgcc tgacatcatc tccaagctgg 240
acaagctttc tgtcctgcgc ctcagtgtca gttacctccg ggtgaagagc ttcttccaag 300
tcgtgcagga gcagagctca cggcagcctg cggccggcgc cccctcgccc ggagacagct 360
gtcctcttgc agggtctgcc gtgctggagg gaaggctgct gttggagtct cttaatggct 420
ttgctctggt cgtgagtgca gaagggacga tattttatgc atcagcaacg atcgtggact 480
atctgggctt ccatcagacg gatgtaatgc accagaacat ttatgactac atccacgtgg 540
acgaccgcca ggacttctgc cggcagctcc actgggccat ggaccctccc caggtggtgt 600
ttgggcagcc cccgcccttg gagacaggag atgatgctat cctggggagg ctgctcaggg 660
cccaggagtg gggcacaggc acgcccaccg agtactcggc cttcctgacc cgctgcttca 720
tctgccgtgt gcgctgcctg ctggacagca cctcgggctt cctggcccgg gggtcacagg 780
cttggcagct gcggctctgc tgtcccgagc cactcatgac gatgcagttt caaggaaaac 840
taaaattcct gtttggacag aagaagaagg cgccgtcagg agccatgctc ccgccgcggc 900
tgtcgctgtt ctgcattgcg gcacccgttc tcctcccctc cgcagcggag atgaaaatga 960

-continued

```
ggagcgcgct cctgagggca aaacccagag cagacaccgc agccaccgcg gatgcaaaag   1020
taaaagccac caccagtctg tgcgaatcgg aactgcatgg aaaacccaat tactcagcag   1080
gaaggagcag cagagagagc ggcgttttgg tgctcaggga acagactgac gctggccgat   1140
gggcacaggt tcccgccagg gccccatgcc tgtgcctccg ggtggccct gaccttgtcc   1200
ttgaccccaa ggggggctca ggggacaggg aggaggagca gcacaggatg ctgagcaggg   1260
cctctggagt gacagggcgg agggagactc caggacccac aaagcccctg ccctggacag   1320
cgggaaagca cagtgaggat ggtgccaggc cgaggctgca gcccagcaag aatgacccgc   1380
cctccctgcg ccccatgccc cgcggctcct gcctgccctg cccgtgtgtc cagggcactt   1440
tcaggaactc gcccatctct cacccgccga gcccgtcccc cagtgcctac tccagccgga   1500
ccagcagacc catgcgggat gtcggtgagg accaggtgca ccctccccctc tgccactttc   1560
cccagaggag cctgcagcac cagctccctc agcctggagc tcagcgtttt gccacgaggg   1620
gctatcccat ggaggacatg aagctgcaag gtgtaccgat gcctccgggg gacctgtgtg   1680
gtccgacgct gctgctagat gtgtccatca agatggagaa ggactctggg tgtgagggtg   1740
ctgcagacgg ctgtgtgccc agccaggtgt ggctgggggc cagtgacagg agccacccag   1800
ccaccttccc taccaggatg cacctgaaaa cagagccaga ctctcggcaa caggtgtaca   1860
tctcgcacct ggggcacggc gtgcgggggg ctcagcccca tgggagggcc actgctgggc   1920
gcagcaggga gctgacccct ttccaccctg cacactgtgc ctgcctggag cccacagacg   1980
gccttcccca gtcggagcct ccccaccagc tctgtgcacg gggccgaggt gaacagtcct   2040
gcacctgcag agctgctgag gccgcccctg tggtcaagcg ggagcccttg gactcacccc   2100
agtgggctac tcacagccag ggaatggtgc ccgggatgtt gcccaaaagt gccttggcca   2160
cgctggtccc gccccaagct tcggggtgca cattcctgcc atagcgcagt gaccaccatc   2220
caagctcaga tctgtgtgtc tacgctcaga tgcgtcggtg gctgggctgc cctgctcctg   2280
gtcaggccgg agcccgtcct aagacacacg ctttgcagag ctgtgcatgc gcagtctgct   2340
agtgtgtgtg tgcagcatac gcaggagcct atcctgaatt ttgtaaaata tcccaacagt   2400
tcttaaatga aaactggcct taagtctatt caagcatgac agcatttctc tttgaggaat   2460
taaaatcttt aggaaagtga tcatggctgg acagcttcat gccccagagg cagcgagcac   2520
ccgtcccatg gctgccaagt ccacagtcgg ggatgaagca gtcgggtgat gctcccaagt   2580
ccgcagtcgg ggatgaagcg gtcgggtgat gctcccaagt ccgcagtcgg ggatgaagcg   2640
gtcgggtgac acacctagct cagccctccc aggccacctg cagctcccag cctgtgctgt   2700
gcaggcaggg tcagcccatc gccacagtgc actgtagagg ccagcacacg gcaaattaga   2760
aatacaacac gcggagaaag gggtccgtga gcccactcat agaggaatct agaacgttcc   2820
aggcagcaga ggctggcagc gtgggtccca cactgcccca caccgtgcgg caggtgctcc   2880
atggcgccat gacagagtct gaggccagac ctggactgga attgacagca taacccctgt   2940
tccttctgga catctcccga gttctcagtg ggtctctgcg gacggttctt cctaatctgc   3000
ctcttggtac atcacgtaat acagagttca cagactccgg gtttggaagt acagagaaac   3060
acacaacgta gagagaagac acaggaaact gcgctgcctg tgggggtttc tctctggctg   3120
gctgtacagt tcactcaaat gagggttccc attgccatcc taggagaata attagggaca   3180
agacagacaa gtattaatag cattaaaaca gttgtaaagg cgatattttc tgagagtagg   3240
aaatttggat acaaaagcat aagtcagaaa gtgaaggtca ccaatccacc aacccgagaa   3300
cctacagctg atggtgcatt tcaggcttct tccacggtct ggcctggaac cccacccggc   3360
```

-continued

```
tggtgcaggc atcagatcag ggtgtagaag tcaccccaag caagaggaag ccaggcagtg   3420
aggccctggg gtgtggctgc agctgggccc acctgtgcgg gggtgggaag gccccatcct   3480
cagggagagg gcatcggcgc cctgacgtca gctccactgg gagtggcagg agctgtggga   3540
gcccatgggt gagggaccca ccaccccgct gcactgtgca ttgtgcctcc cgtgtggacg   3600
ccctctctgt tgttggcccg cgggtgaggg acccaccacc cctagggacc caccaccccg   3660
ccgcactgtg cattctgcct cctgtgtgga cgccctctct gttgtcagtg gctttgaggt   3720
gtcagtgctt acttagatgc tggtttaatg ctggacccat ttgttaaacg caccttcact   3780
ttgtcaaaac ccaggtttgg ttggcaggac tgggtcttct gcccaatgcc aggtgcctgc   3840
gcctctcagt ggcctggttc ttggacagtt tgcccccatg tggcagggat agggataagg   3900
atctcctctc agtactggaa gagaacagcc aaccatctga gcccagagtc acagatccat   3960
cgtggccccc tatgaccccc aagccctacc gagggggcac tcactctctg cttagccagg   4020
gggcgtcttt caaaaggtga cctccatgct gtgctgtcgt gggtgtgaga cgtgctcatg   4080
gccttccact gccatctctc ccttatctga tgcctaaagt cacgatgggg acagagctac   4140
ccaggggcca gccatggggt gaccagccac ctgagggtca gtcacctgtg gagagcaggc   4200
acctgtgaag accaggcacc tgaggactgg cgcctacttc ccactttggc cctacactgg   4260
cacagagccc ctctttattc atttctcatg ctgagcatgg cacacttctg gcctctgggc   4320
atttatggat ttaagaccag gatggtattt cagaagcttc ccacttcctt cctattctaa   4380
ccgagtgccc agctcctttg ctgatcatgg aaagaccctt aataattagg cctgcaggcc   4440
aggcgcagtg gctcatgcct ataatcccag cactttagga ggtcaaggta ggaggatcgc   4500
ttaagcccag gagttcaaga ccagcctggg caacacagga agaatgtgtc tctacaaaaa   4560
ataattaaaa atcagatctg ctgtatccct gaaaaagtct caatcaacat gcatgttcca   4620
ctcttggagt tccctgttct gagggccagc cacgtcctgt gtcctggagc ttagccctca   4680
gcagctccct tcagcctggg cgccgcctgg gtcccaaacg tggcagctgc tcttccagtc   4740
tcggggccga ggagggcagg gagctcagtg actgagagtc ttgtgtatca catgtcttga   4800
gtgtcctgga gccaacggct gtcactggga aaaacaccag gccccaaaga tcgaatcaga   4860
gacgtggctg cgtgtttgcg attgtagcca ggcccttcag tgtcatcaaa ggagcactgg   4920
ggcctcctta agcacagacg gcagcccctg cccaggaggc ttcttcacca cgtcctgccc   4980
tgcagcctcc cagaccttta gatgcgcccc tgcccaaggc cctcctggtg acaggtgcca   5040
gattgagtgg tgggttgctg ccaggcaggc cacgctgtgt tgacgctgca ctcagcacgt   5100
gggtgttggc tctgccggtt ttgtggtgtg gggaccctac aggaggctgc ggccctgaga   5160
gcctgggatc agcgaggtgt ccgacatccc ttcctcaacg gcaacaaaaa ctccccaagt   5220
cagcactttg gttattttat agccacaacc ctcttggaaa acagtgggga agactatgga   5280
acatagaaag tgtggatgta tcacttctct ctaaaatgtc attgttagca ctaattacag   5340
gttcatgttt ttctgtgtat gtagcttttc cctatatagc tgaaaaagta ttaaagtcaa   5400
atataaggtg ggaatgggat ggaagggagg agatcaatac aacttatatt tttgcagttt   5460
ctactggaag aaaaaagttt tcaataccta gaccaacttg ttgaattttt aaaacttatg   5520
cactataaat gcaactttct ctactgcttt ctcagtgcct ttaggaagct ttcaaatttt   5580
tttgtactgt ggtttgtatt aaatttgcaa tattgatgta aaatacatga catgctagta   5640
catgtttaac aaaaatttaa aaaaaaaaaa aaaaaa                             5676
```

<210> SEQ ID NO 40
<211> LENGTH: 1763
<212> TYPE: DNA
<213> ORGANISM: Homo sapiens

<400> SEQUENCE: 40
cttctggtaa ggaggccccg tgatcagctc cagccatttg cagtcctggc tatcccagga 60
gcttacataa agggacaatt ggagcctgag aggtgacagt gctgacacta caaggctcgg 120
agctccgggc actcagacat catgagttgg tccttgcacc cccggaattt aattctctac 180
ttctatgctc ttttatttct ctcttcaaca tgtgtagcat atgttgctac cagagacaac 240
tgctgcatct tagatgaaag attcggtagt tattgtccaa ctacctgtgg cattgcagat 300
ttcctgtcta cttatcaaac caaagtagac aaggatctac agtctttgga agacatctta 360
catcaagttg aaaacaaaac atcagaagtc aaacagctga taaaagcaat ccaactcact 420
tataatcctg atgaatcatc aaaaccaaat atgatagacg ctgctacttt gaagtccagg 480
aaaatgttag aagaaattat gaaatatgaa gcatcgattt taacacatga ctcaagtatt 540
cgatatttgc aggaaatata taattcaaat aatcaaaaga ttgttaacct gaaagagaag 600
gtagcccagc ttgaagcaca gtgccaggaa ccttgcaaag acacggtgca aatccatgat 660
atcactggga aagattgtca agacattgcc aataagggag ctaaacagag cgggctttac 720
tttattaaac ctctgaaagc taaccagcaa ttcttagtct actgtgaaat cgatgggtct 780
ggaaatggat ggactgtgtt tcagaagaga cttgatggca gtgtagattt caagaaaaac 840
tggattcaat ataaagaagg atttggacat ctgtctccta ctggcacaac agaattttgg 900
ctgggaaatg agaagattca tttgataagc acacagtctg ccatcccata tgcattaaga 960
gtggaactgg aagactggaa tggcagaacc agtactgcag actatgccat gttcaaggtg 1020
ggacctgaag ctgacaagta ccgcctaaca tatgcctact tcgctggtgg ggatgctgga 1080
gatgcctttg atggctttga ttttggcgat gatcctagtg acaagttttt cacatcccat 1140
aatggcatgc agttcagtac ctgggacaat gacaatgata agtttgaagg caactgtgct 1200
gaacaggatg gatctggttg gtggatgaac aagtgtcacg ctggccatct caatggagtt 1260
tattaccaag gtggcactta ctcaaaagca tctactccta atggttatga taatggcatt 1320
atttgggcca cttggaaaac ccggtggtat tccatgaaga aaaccactat gaagataatc 1380
ccattcaaca gactcacaat tggagaagga cagcaacacc acctgggggg agccaaacag 1440
gtcagaccag agcaccctgc ggaaacagaa tatgactcac tttaccctga ggatgatttg 1500
tagaaaatta actgctaact tctattgacc cacaaagttt cagaaattct ctgaaagttt 1560
cttccttttt tctcttacta tatttattga tttcaagtct tctattaagg acatttagcc 1620
ttcaatggaa attaaaactc atttaggact gtatttccaa attactgata tcagagttat 1680
ttaaaaattg tttatttgag gagataacat ttcaactttg ttcctaaata tataataata 1740
aaatgattga ctttatttgc aaa 1763

<210> SEQ ID NO 41
<211> LENGTH: 666
<212> TYPE: DNA
<213> ORGANISM: Homo sapiens

<400> SEQUENCE: 41
gggtggctta gcactgcagg gctctgcgcg ggaacgctaa cctggtccgg agcgagtctg 60
ggtctcagcc ccgcgaacag cctttcacga gtcttcaagc tttcaggcta tcttctagtc 120
aagatgagtg ataagccaga cttgtcggaa gtggagaagt ttgacaggtc aaaactgaag 180
aaaactaata ctgaagaaaa aaatactctt ccctcaaagg aaactatcca gcaagagaaa 240
gagtgtgttc aaacatcata aaatggggat cgcctcccaa cagcagattt cgacattacc 300
tgagagtctt gattttaggc ttgttttttg taaacccatg tgtttgtaga gattttaggc 360
gtcttcggat atcttctcac ctatgttccc tggctaagaa gtcagaggta gccaatgttt 420
ccttaaattc atttttaaac ttaccattgg tgcatatgtt ccagatggca gatgctgtca 480
ataatctcac cattgatgac ctttgtgtat gtagttcttg catcctatac tggataagcc 540
tgttttaacc tgctatgatg ggtgcttcca ttgcttcata atcttcatga agttgcatgc 600
ttttgcagct tttcacagtt tatttgcatt tctaatgtag taataaagta accaatataa 660
tcatta 666

<210> SEQ ID NO 42
<211> LENGTH: 1437
<212> TYPE: DNA
<213> ORGANISM: Homo sapiens

<400> SEQUENCE: 42
attgctgatg gatcagtgag cctgtgttca tgccagtgag ctgctgtggc tcagatactg 60
atactttctt tccaaacagc ataagaagtg attgagccac aagtatactg aaggaagggc 120
tccctcgagt tctggtgtga agagataaat caccagtcac agactatgca cccgactgct 180
gctgttcagt ccagggaaaa tgaaagttgg agtgctgtgg ctcatttctt tcttcacctt 240
cactgacggc cacggtggct tcctggggaa aaatgatggc atcaaaacaa aaaaagaact 300
cattgtgaat aagaaaaaac atctaggccc agtcgaagaa tatcagctgc tgcttcaggt 360
gacctataga gattccaagg agaaaagaga tttgagaaat tttctgaagc tcttgaagcc 420
tccattatta tggtcacatg ggctaattag aattatcaga gcaaaggcta ccacagactg 480
caacagcctg aatggagtcc tgcagtgtac ctgtgaagac agctacacct ggtttcctcc 540
ctcatgcctt gatccccaga actgctacct tcacacggct ggagcactcc caagctgtga 600
atgtcatctc aacaacctca gccagagtgt caatttctgt gagagaacaa agatttgggg 660
cactttcaaa attaatgaaa ggtttacaaa tgaccttttg aattcatctt ctgctatata 720
ctccaaatat gcaaatggaa ttgaaattca acttaaaaaa gcatatgaaa gaattcaagg 780
ttttgagtcg gttcaggtca cccaatttcg aatgtcactc ttgtcgccca agttggagtg 840
caatggcaca atctaggctc actgcaaccc tgcaacctct gcctaccggg ttcaagagat 900
tcccctgcct cagcctccca agtagctgga attacaggca cctgccacca catccagcta 960
actttttttg tatttttact agagacaggg tttcaccatg ttggccacac tggtctcaaa 1020
ctcctgacct caggtgatcc gcctgcctcg gcccccaaag tgctgggatt acaggcatga 1080
gccaccacat ctggcctagg accttaaata ttggaaagca tcctcaaaac tgtgggtcag 1140
tgagtagaac tacaaaacaa tagcagtagg gcagaaactt gaaagaaggc aggagatcat 1200
ggtgacagtg gatgggaaaa agtgagggtt ggggataagg gttgcgggtt gtcgaagggt 1260
ggattttctc cttcagcaac tacaggagat atgatgcctc ataattcgga gccagaagtg 1320
gggctttggg tgagatatct ttgcacagat aacatgtata catcatagtt caaaacccag 1380
tagtcattgt ttacagcaaa taaagaaata tttagtaaat taaaaaaaaa aaaaaaa 1437

<210> SEQ ID NO 43

<211> LENGTH: 2413
<212> TYPE: DNA
<213> ORGANISM: Homo sapiens

<400> SEQUENCE: 43

```
tttcctctca gggggcagca ggaagtgagg agaaagggct gggatgggag gcgggagcgg      60
atgggaggga atggggttta tcaagtcctc ggcgagctgc ccaacgggca gcagctggcg     120
caagtagcct agctggagag gctcacccca ggaaggaggg aggccaccga cctactgggc     180
cgacggactc ccacacaggg ctggcggcgc cgcggagctg ggaggactga accaccggcc     240
tcgggctgca ggggaaacat ttcaggctga ctggcgctcg tggctgagac tcccatagaa     300
agcccggctc agaggggcat tagggtccta aatgggcggc cacgtccctc tgcagaggac     360
ctggggctct tcgagcccga aacgaggcac cggcaccgag aaaggtggac cacaccttcc     420
cgccccgtcc gcaagtccaa tcccgggccc acctccgcac tggagtctta aagggccagc     480
gtgcctgggg gcggagccag cagaggcgct gagccgggcc gcgcctgggc gaacggccgg     540
agcgggctgg gctgggcccg ggatggcggt ggccctggcg ccggtcccgg tggcgccccg     600
cgcgagttcc tgagctggtg ccaggcaggt gacacctcct gcagcccccca gcatgcgggc     660
aggcccaggc cccaccgtta cattggccct ggtgctggcg gtgtcatggg ccatggagct     720
caagcccaca gcaccaccca tcttcactgg ccggcccttt gtggtagcgt gggacgtgcc     780
cacacaggac tgtggcccac gcctcaaggt gccactggac ctgaatgcct ttgatgtgca     840
ggcctcacct aatgagggtt ttgtgaacca gaatattacc atcttctacc gcgaccgtct     900
aggcctgtat ccacgcttcg attctgccgg aaggtctgtg catggtggtg tgccacagaa     960
tgtcagcctt tgggcacacc ggaagatgct gcagaaacgt gtggagcact acattcggac    1020
acaggagtct gcggggctgg cggtcatcga ctgggaggac tggcgacctg tgtgggtgcg    1080
caactggcag gacaaagatg tgtatcgccg gttatcacgc cagctagtgg ccagtcgtca    1140
ccctgactgg cctccagacc gcatagtcaa acaggcacaa tatgagtttg agttcgcagc    1200
acagcagttc atgctggaga cactgcgtta tgtcaaggca gtgcggcccc ggcacctctg    1260
gggcttctac ctctttcctg actgctacaa tcatgattat gtgcagaact gggagagcta    1320
cacaggccgc tgccctgatg ttgaggtggc ccgcaatgac cagctggcct ggctgtgggc    1380
tgagagcacg gccctcttcc cgtctgtcta cctggacgag acacttgctt cctcccgcca    1440
tggccgcaac tttgtgagct tccgtgttca ggaggccctt cgtgtggctc gcacccacca    1500
tgccaaccat gcactcccag tctacgtctt cacacgaccc acctacagcc gcaggctcac    1560
ggggcttagt gagatggacc tcatctctac cattggcgag agtgcggccc tgggcgcagc    1620
tggtgtcatc ctctggggtg acgcggggta caccacaagc acggagacct gccagtacct    1680
caaagattac ctgacacggc tgctggtccc ctacgtggtc aatgtgtcct gggccaccca    1740
atattgcagc cgggcccagt gccatggcca tgggcgctgt gtgcgccgca accccagtgc    1800
cagtaccttc ctgcatctca gcaccaacag tttccgccta gtgcctggcc atgcacctgg    1860
tgaaccccag ctgcgacctg tgggggagct cagttgggcc gacattgacc acctgcagac    1920
acacttccgc tgccagtgct acttgggctg gagtggtgag caatgccagt gggaccatag    1980
gcaggcagct ggaggtgcca gcgaggcctg ggctgggtcc cacctcacca gtctgctggc    2040
tctggcagcc ctggccttta cctggacctt gtaggggtct cctgcctagc tgcctagcaa    2100
gctggcctct accacaaggg ctctcttagg catgtaggac cctgcagggg gtggacaaac    2160
tggagtctgg agtgggcaga gcccccagga agcccaggag ggcatccata ccagctcgca    2220
```

```
ccccccctgtt ctaaggggga ggggaagtcc ctgggaggcc ccttctctcc ctgccagagg   2280

ggaaggaggg tacagctggg ctggggagga cctgacccta ctcccttgcc ctagatagtt   2340

tattattatt attattttgg ggtctctttt gtaaattaaa cataaaacaa ttgcttctct   2400

gcttggattt tgt                                                       2413
```

<210> SEQ ID NO 44
<211> LENGTH: 1279
<212> TYPE: DNA
<213> ORGANISM: Homo sapiens

<400> SEQUENCE: 44

```
gggagggaga gaggcgcgcg ggtgaaaggc gcattgatgc agcctgcggc ggcctcggag     60

cgcggcggag ccagacgctg accacgttcc tctcctcggt ctcctccgcc tccagctccg    120

cgctgcccgg cagccgggag ccatgcgacc ccagggcccc gccgcctccc cgcagcggct    180

ccgcggcctc ctgctgctcc tgctgctgca gctgcccgcg ccgtcgagcg cctctgagat    240

ccccaagggg aagcaaaagg cgcagctccg gcagagggag gtggtggacc tgtataatgg    300

aatgtgctta caagggccag caggagtgcc tggtcgagac gggagccctg ggccaatgg    360

cattccgggt acacctggga tcccaggtcg ggatggattc aaaggagaaa agggggaatg    420

tctgagggaa agctttgagg agtcctggac acccaactac aagcagtgtt catggagttc    480

attgaattat ggcatagatc ttgggaaaat tgcggagtgt acatttacaa agatgcgttc    540

aaatagtgct ctaagagttt tgttcagtgg ctcacttcgg ctaaaatgca gaaatgcatg    600

ctgtcagcgt tggtatttca cattcaatgg agctgaatgt tcaggacctc ttcccattga    660

agctataatt tatttggacc aaggaagccc tgaaatgaat tcaacaatta atattcatcg    720

cacttcttct gtggaaggac tttgtgaagg aattggtgct ggattagtgg atgttgctat    780

ctgggttggt acttgttcag attacccaaa aggagatgct tctactggat ggaattcagt    840

ttctcgcatc attattgaag aactaccaaa ataaatgctt taattttcat ttgctacctc    900

ttttttttatt atgccttgga atggttcact taaatgacat tttaaataag tttatgtata    960

catctgaatg aaaagcaaag ctaaatatgt ttacagacca aagtgtgatt tcacactgtt   1020

tttaaatcta gcattattca ttttgcttca atcaaaagtg gtttcaatat ttttttttagt   1080

tggttagaat actttcttca tagtcacatt ctctcaacct ataatttgga atattgttgt   1140

ggtcttttgt tttttctctt agtatagcat ttttaaaaaa atataaaagc taccaatctt   1200

tgtacaattt gtaaatgtta agaatttttt ttatatctgt taaataaaaa ttatttccaa   1260

caaccttaat atctttaaa                                                 1279
```

<210> SEQ ID NO 45
<211> LENGTH: 4571
<212> TYPE: DNA
<213> ORGANISM: Homo sapiens

<400> SEQUENCE: 45

```
gcagtcagag ctgcctctcg ccctcgctag ctgggctcgc agcctcttcc tccctccctg     60

gctcctggct ttttgtttaa agcaacaccc accctccatc caggcttttt ttctttcttt    120

ctttattggt agcggccaaa aagagttgat tgctattggg atccgctgag taaagacacg    180

ggcaggggtg cgcggaggtg agaaaactga agacctggaa gattttttttt tccttcaaaa    240

acccgtttcc atccagtctt cagccagtcc agtctacttt aatcctcacc aggacaatgg    300
```

-continued

```
attaagtttc tcttccctgg accagaagtc gggttcggac ttggggcaaa atgaaggaaa    360
aggccatgat caagaccgct aagatgcagg ggaacgtgat ggagctggtg gggagtaacc    420
ctccgcagag gaattggaaa ggaatagcaa ttgcactgct tgtcattctg gtcatctgct    480
ccttgatcgt cacctcggtc atacttctga caccagcgga agataatagt ctgtctcaaa    540
agaagaaggt cactgtagaa gatctcttca gtgaagactt caaaattcat gaccccgagg    600
ctaagtggat aagtgataca gaattcatct acagagaaca gaaaggaaca gtgagactgt    660
ggaatgttga aacaaatact tctactgtct taatagaagg caaaaaaatt gaatcattaa    720
gagccatcag atatgaaata tctccagata gagagtatgc actttttttca tacaatgtgg    780
aacccatata tcaacactcg tatactggat attacgtcct gagcaaaatt cctcatgggg    840
atcctcaaag tctggaccca ccagaagtca gcaatgcaaa acttcagtat gcaggatggg    900
gccctaaagg ccaacagctg atatttattt ttgaaaacaa tatctactac tgtgcacatg    960
tcgggaaaca ggccatccgt gtggtctcca ctggcaagga aggtgtgatt tacaatggcc   1020
tcagtgactg gctgtatgaa gaggagattt tgaagacaca catcgcacac tggtggtctc   1080
cggatggcac gagactcgcc tacgccgcca tcaatgattc ccgtgtcccc atcatggagc   1140
tcccaactta caccggctcc atctacccca ccgtgaagcc ctaccactat cccaaggctg   1200
gaagtgagaa ccccagcatt tccctacacg ttattggctt aaatggaccc acccatgatc   1260
tggagatgat gccgcctgat gatccacgga tgagggagta ctacatcacc atggtgaagt   1320
gggccaccag caccaaggtc gccgtgacct ggctgaaccg ggcgcagaac gtgtccatcc   1380
tcaccctctg cgacgccacc acgggggtct gcacgaagaa acacgaggat gaaagtgagg   1440
cctggctcca cagacagaat gaagaacctg tgttctccaa ggatggccga aagttttttct   1500
tcatcagagc catcccccag ggaggacgag ggaaattcta tcacatcacg gtgtcctcgt   1560
cccagcccaa cagcagcaac gacaacatcc agtccatcac ctccggggac tgggacgtga   1620
ccaagatcct agcctacgat gagaagggga ataagatcta cttcctgagc acggaggacc   1680
tgcctcggag acgacaactc tacagtgcca acacggtggg caacttcaac aggcagtgcc   1740
tctcctgtga cctggttgag aactgcacct acttcagcgc ttccttcagc catagcatgg   1800
acttcttcct gctcaagtgc gaaggtcctg gtgttcctat ggtgacggtg cacaacacaa   1860
cagataagaa aaaaatgttt gacctagaaa caaatgaaca tgtcaagaag gccataaatg   1920
accgacagat gcctaaagtg gaatacaggg acattgagat tgatgattac aacctgccca   1980
tgcagatact gaagccagca accttcaccg acaccaccca ctaccctctg ctcctggtgg   2040
tggatggcac ccccaggcagc cagagtgtgg ctgagaagtt cgaggtgagc tgggagacgg   2100
tgatggtgag cagccacggc gcggtggtgg taaagtgtga cggccgtggc agcggcttcc   2160
aagggaccaa gctcctgcac gaagtgaggc ggcggctggg cttgctggag gagaaggacc   2220
agatggaggc cgtgcggacg atgctgaagg agcagtacat tgacaggacg cgcgtggccg   2280
tgtttgggaa ggattacggt ggctacctga gcacctacat cctcccagca aagggagaaa   2340
atcaaggcca gacattcacc tgcggctctg ctctctctcc aataacagac ttcaaactct   2400
atgcctctgc gttttccgag aggtacttgg gcctccatgg acttgacaac agagcatacg   2460
agatgaccaa ggtagcccat cgagtctccg cgctggaaga acagcagttc ctgatcattc   2520
atcccactgc cgatgaaaaa attcatttcc agcacacagc agaactcatt acacaactaa   2580
ttaggggaaa ggctaattac agcttacaga tttacccgga cgaaagccat tactttacca   2640
gctccagcct caaacagcat ctgtaccggt ccatcatcaa cttcttcgtg gaatgcttca   2700
```

-continued

```
ggatccagga caaactgctg acagtcacag cgaaagagga cgaggaggag gactaagctc   2760

aggtcgctct aagcacaaac gtggctcttt ctacaaccag atgcaaccga gggatttccc   2820

tgccctccct cttccctcgg aggggcgggg cggggcgggg ccgggtgttc catagcatgt   2880

gtgtctcgga tgcggaaggc agttttgctt gggaaacaag ctccttcccc ggggtcatca   2940

ctcacggcct ccatggcacc agggacaacg ctgtccccgc agcagcgcct cctcccggcg   3000

cccgagagac cggcacgcca cggcccctcc cccaaggaac agagcaaagg atggtggccg   3060

caggccccac gcgagcccac aggacaccgg cccctagatt ccagccacca agcggaagca   3120

tgagacccgc ccacactagc ctctgtgttc ccgttaggga catcacaccc tgtctcacgt   3180

cgcagtgcca tggacgcagc agttacagca ccattgtttt agcagtgcgt gttcatatat   3240

gggcttgcta cttcctgtaa tgaggacgtt caacatggtg aggggctaca agaaaacgct   3300

tttctgtaca gagtcttact gtagctacgc taatggttaa cctgatagaa ttaactcgta   3360

tttttctatg gttttaacct gatgctccac tgtctccgtc atggggttgt tttgctgttt   3420

ggggttgggc cttgtttccc tttcctttct ccagtccacg tgtagacttt gcgcttgatg   3480

aagaagcaga tcggaagtaa ctgctccctc ctcaaggttg tcttcagacg tcttggggac   3540

gttcctaaac actgaggggg aagacagcca atagcaccca ttaaaagaaa tacctaaata   3600

aaacctctct cccactcagc tatgctaggg cttggctgta ggtgtgcact gtctatttac   3660

atccgtcctt acaaccatcc ttgtcctcct tggtaccgta tcaagctctt tcccatgaca   3720

tttggtttaa aaaaaaaaaa aaaaaaaaaa aaaaaaacaga aaaaagacaa agcgtcaact   3780

ccacccacag gcccgctgtg tgtgctcggg ccacgggagt cctgagggtt ctgtgggcct   3840

gcgcgcatcc ctctcccatc gtgggggtgg ctccgtgacc ttcctgccac gagcaggagg   3900

ttgatgatgt gctacgttag ccttgtaaga tacaccccca ccaaatgtgc agccggtgtt   3960

cccagtgtat atttcattct cttgtatata aaggaagcaa tgtgtgtcag gcctctgtgc   4020

agtcaaccca gcctcctccc gccagtgcta accccgtgtt gagcctgcat gctgacactg   4080

tggccgatct ggactctaga agtgctagtt tgaaatatat ccattactgt catttccttt   4140

tgagcttgtg gacaagctga atgtcaggac tgacttcgcc agctcccagc cctgcggggg   4200

tgtccttggc atcccatcag cagaggagat gcgtccctgt tgcattttgg cgtttggggc   4260

tttgggttta tccacatgag ctctgaacgt ccgttatagt tagggtgatt ggaaggtctc   4320

catcactggg tgttttaaag gtgattcacc accatttgtg aaaggaccaa cgtgctgata   4380

aacaggaccg atccgagtgc tacatgactg tgcgtttgct atttcaatgg gcctgaacga   4440

ctacaaagcc agctaggtct ggaaggggaa gccagctctg gccacgacat ctggtcggag   4500

ggaagtgggg atgtggcatg gtagcgtctg ttcatccatg gaataaaaca ttattttacc   4560

aaaaaaaaaa a                                                        4571
```

<210> SEQ ID NO 46
<211> LENGTH: 4460
<212> TYPE: DNA
<213> ORGANISM: Homo sapiens

<400> SEQUENCE: 46

```
actaagcagc ggcagcttcc tgcttcggat cctctctctg ctgcttgcat ttaaagagca     60

aactcgtctt gtctacccac cctccctccc ccatcctccc caaaatagcc ttgtgatttc    120

ggaagtatgg actaaaatca cactcctcct taccttaccg cttggactct ggtggctccc    180
```

-continued

```
aactcgccgt cagaccccac ctgccccggt ggtgggaagc gcctggacag accatgacca    240
cagccaagga gccaagcgct tcggggaaat ccgtgcagca gcaggaacag gagctggtgg    300
ggagtaaccc tccgcagagg aattggaaag gaatagcaat tgcactgctt gtcattctgg    360
tcatctgctc cttgatcgtc acctcggtca tacttctgac accagcggaa gataatagtc    420
tgtctcaaaa gaagaaggtc actgtagaag atctcttcag tgaagacttc aaaattcatg    480
accccgaggc taagtggata agtgatacag aattcatcta cagagaacag aaaggaacag    540
tgagactgtg gaatgttgaa acaaatactt ctactgtctt aatagaaggc aaaaaaattg    600
aatcattaag agccatcaga tatgaaatat ctccagatag agagtatgca ctttttttcat    660
acaatgtgga acccatatat caacactcgt atactggata ttacgtcctg agcaaaattc    720
ctcatgggga tcctcaaagt ctggacccac cagaagtcag caatgcaaaa cttcagtatg    780
caggatgggg ccctaaaggc caacagctga tatttatttt tgaaaacaat atctactact    840
gtgcacatgt cgggaaacag gccatccgtg tggtctccac tggcaaggaa ggtgtgattt    900
acaatggcct cagtgactgg ctgtatgaag aggagatttt gaagacacac atcgcacact    960
ggtggtctcc ggatggcacg agactcgcct acgccgccat caatgattcc cgtgtcccca   1020
tcatggagct cccaacttac accggctcca tctaccccac cgtgaagccc taccactatc   1080
ccaaggctgg aagtgagaac cccagcattt ccctacacgt tattggctta aatggaccca   1140
cccatgatct ggagatgatg ccgcctgatg atccacggat gagggagtac tacatcacca   1200
tggtgaagtg ggccaccagc accaaggtcg ccgtgacctg gctgaaccgg gcgcagaacg   1260
tgtccatcct caccctctgc gacgccacca cgggggtctg cacgaagaaa cacgaggatg   1320
aaagtgaggc ctggctccac agacagaatg aagaacctgt gttctccaag gatggccgaa   1380
agtttttctt catcagagcc atcccccagg gaggacgagg gaaattctat cacatcacgg   1440
tgtcctcgtc ccagcccaac agcagcaacg acaacatcca gtccatcacc tccggggact   1500
gggacgtgac caagatccta gcctacgatg agaaggggaa taagatctac ttcctgagca   1560
cggaggacct gcctcggaga cgacaactct acagtgccaa cacggtgggc aacttcaaca   1620
ggcagtgcct ctcctgtgac ctggttgaga actgcaccta cttcagcgct tccttcagcc   1680
atagcatgga cttcttcctg ctcaagtgcg aaggtcctgg tgttcctatg gtgacggtgc   1740
acaacacaac agataagaaa aaaatgtttg acctagaaac aaatgaacat gtcaagaagg   1800
ccataaatga ccgacagatg cctaaagtgg aatacaggga cattgagatt gatgattaca   1860
acctgcccat gcagatactg aagccagcaa ccttcaccga caccacccac taccctctgc   1920
tcctggtggt ggatggcacc ccaggcagcc agagtgtggc tgagaagttc gaggtgagct   1980
gggagacggt gatggtgagc agccacggcg cggtggtggt aaagtgtgac ggccgtggca   2040
gcggcttcca agggaccaag ctcctgcacg aagtgaggcg gcggctgggc ttgctggagg   2100
agaaggacca gatggaggcc gtgcggacga tgctgaagga gcagtacatt gacaggacgc   2160
gcgtggccgt gtttgggaag gattacggtg gctacctgag cacctacatc ctcccagcaa   2220
agggagaaaa tcaaggccag acattcacct gcggctctgc tctctctcca ataacagact   2280
tcaaactcta tgcctctgcg ttttccgaga ggtacttggg cctccatgga cttgacaaca   2340
gagcatacga gatgaccaag gtagcccatc gagtctccgc gctggaagaa cagcagttcc   2400
tgatcattca tcccactgcc gatgaaaaaa ttcatttcca gcacacagca gaactcatta   2460
cacaactaat taggggaaag gctaattaca gcttacagat ttacccggac gaaagccatt   2520
actttaccag ctccagcctc aaacagcatc tgtaccggtc catcatcaac ttcttcgtgg   2580
```

-continued

```
aatgcttcag gatccaggac aaactgctga cagtcacagc gaaagaggac gaggaggagg   2640

actaagctca ggtcgctcta agcacaaacg tggctctttc tacaaccaga tgcaaccgag   2700

ggatttccct gccctccctc ttccctcgga ggggcggggc ggggcggggc cgggtgttcc   2760

atagcatgtg tgtctcggat gcggaaggca gttttgcttg ggaaacaagc tccttccccg   2820

gggtcatcac tcacggcctc catggcacca gggacaacgc tgtccccgca gcagcgcctc   2880

ctcccggcgc ccgagagacc ggcacgccac ggcccctccc ccaaggaaca gagcaaagga   2940

tggtggccgc aggccccacg cgagcccaca ggacaccggc ccctagattc cagccaccaa   3000

gcggaagcat gagacccgcc cacactagcc tctgtgttcc cgttagggac atcacaccct   3060

gtctcacgtc gcagtgccat ggacgcagca gttacagcac cattgtttta gcagtgcgtg   3120

ttcatatatg ggcttgctac ttcctgtaat gaggacgttc aacatggtga ggggctacaa   3180

gaaaacgctt ttctgtacag agtcttactg tagctacgct aatggttaac ctgatagaat   3240

taactcgtat ttttctatgg ttttaacctg atgctccact gtctccgtca tggggttgtt   3300

ttgctgtttg gggttgggcc ttgtttccct ttcctttctc cagtccacgt gtagactttg   3360

cgcttgatga agaagcagat cggaagtaac tgctccctcc tcaaggttgt cttcagacgt   3420

cttggggacg ttcctaaaca ctgaggggga agacagccaa tagcacccat taaaagaaat   3480

acctaaataa aacctctctc ccactcagct atgctagggc ttggctgtag gtgtgcactg   3540

tctatttaca tccgtcctta caaccatcct tgtcctcctt ggtaccgtat caagctcttt   3600

cccatgacat ttggtttaaa aaaaaaaaaa aaaaaaaaaa aaaaacagaa aaaagacaaa   3660

gcgtcaactc cacccacagg cccgctgtgt gtgctcgggc cacgggagtc ctgagggttc   3720

tgtgggcctg cgcgcatccc tctcccatcg tgggggtggc tccgtgacct tcctgccacg   3780

agcaggaggt tgatgatgtg ctacgttagc cttgtaagat acaccccccac caaatgtgca   3840

gccggtgttc ccagtgtata tttcattctc ttgtatataa aggaagcaat gtgtgtcagg   3900

cctctgtgca gtcaacccag cctcctcccg ccagtgctaa ccccgtgttg agcctgcatg   3960

ctgacactgt ggccgatctg gactctagaa gtgctagttt gaaatatatc cattactgtc   4020

atttcctttt gagcttgtgg acaagctgaa tgtcaggact gacttcgcca gctcccagcc   4080

ctgcgggggt gtccttggca tcccatcagc agaggagatg cgtccctgtt gcattttggc   4140

gtttggggct ttgggtttat ccacatgagc tctgaacgtc cgttatagtt agggtgattg   4200

gaaggtctcc atcactgggt gttttaaagg tgattcacca ccatttgtga aaggaccaac   4260

gtgctgataa acaggaccga tccgagtgct acatgactgt gcgtttgcta tttcaatggg   4320

cctgaacgac tacaaagcca gctaggtctg gaaggggaag ccagctctgg ccacgacatc   4380

tggtcggagg gaagtgggga tgtggcatgg tagcgtctgt tcatccatgg aataaaacat   4440

tattttacca aaaaaaaaaa                                               4460


<210> SEQ ID NO 47
<211> LENGTH: 4542
<212> TYPE: DNA
<213> ORGANISM: Homo sapiens

<400> SEQUENCE: 47

gctgctgctg ctgctgcctc cccaccgcct tttttttttt ttaatctgga gcggggtggg     60

gagtgggaac cggagagaaa gcaaaatatt aaaaagcccc aaagacagcc agcaggagcg    120

cggtgcccga tggcttcgct gtaccagagg ttcactggca agatcaacac ctcgaggtcc    180
```

-continued

```
ttccccgcgc ccccggaggc gagtcacctc ctgggcggcc aggggcccga ggaggacggc    240
ggcgcaggag ccaagcccct cggcccgcgg gcgcaggcgg cggcgccccg ggagcgcggc    300
ggcggcggcg gcggcgcggg tggccggccc cggttccagt accaggcgcg gagcgatggt    360
gacgaggagg acgagctggt ggggagtaac cctccgcaga ggaattggaa aggaatagca    420
attgcactgc ttgtcattct ggtcatctgc tccttgatcg tcacctcggt catacttctg    480
acaccagcgg aagataatag tctgtctcaa aagaagaagg tcactgtaga agatctcttc    540
agtgaagact tcaaaattca tgaccccgag gctaagtgga taagtgatac agaattcatc    600
tacagagaac agaaaggaac agtgagactg tggaatgttg aaacaaatac ttctactgtc    660
ttaatagaag gcaaaaaaat tgaatcatta agagccatca gatatgaaat atctccagat    720
agagagtatg cactttttttc atacaatgtg gaacccatat atcaacactc gtatactgga    780
tattacgtcc tgagcaaaat tcctcatggg gatcctcaaa gtctggaccc accagaagtc    840
agcaatgcaa aacttcagta tgcaggatgg ggccctaaag gccaacagct gatatttatt    900
tttgaaaaca atatctacta ctgtgcacat gtcgggaaac aggccatccg tgtggtctcc    960
actggcaagg aaggtgtgat ttacaatggc ctcagtgact ggctgtatga agaggagatt   1020
ttgaagacac acatcgcaca ctggtggtct ccggatggca cgagactcgc ctacgccgcc   1080
atcaatgatt cccgtgtccc catcatggag ctcccaactt acaccggctc catctacccc   1140
accgtgaagc cctaccacta tcccaaggct ggaagtgaga accccagcat ttccctacac   1200
gttattggct taaatggacc cacccatgat ctggagatga tgccgcctga tgatccacgg   1260
atgagggagt actacatcac catggtgaag tgggccacca gcaccaaggt cgccgtgacc   1320
tggctgaacc gggcgcagaa cgtgtccatc ctcaccctct gcgacgccac cacgggggtc   1380
tgcacgaaga aacacgagga tgaaagtgag gcctggctcc acagacagaa tgaagaacct   1440
gtgttctcca aggatggccg aaagtttttc ttcatcagag ccatccccca gggaggacga   1500
gggaaattct atcacatcac ggtgtcctcg tcccagccca acagcagcaa cgacaacatc   1560
cagtccatca cctccgggga ctgggacgtg accaagatcc tagcctacga tgagaagggg   1620
aataagatct acttcctgag cacggaggac ctgcctcgga gacgacaact ctacagtgcc   1680
aacacggtgg gcaacttcaa caggcagtgc ctctcctgtg acctggttga gaactgcacc   1740
tacttcagcg cttccttcag ccatagcatg gacttcttcc tgctcaagtg cgaaggtcct   1800
ggtgttccta tggtgacggt gcacaacaca acagataaga aaaaaatgtt tgacctagaa   1860
acaaatgaac atgtcaagaa ggccataaat gaccgacaga tgcctaaagt ggaatacagg   1920
gacattgaga ttgatgatta caacctgccc atgcagatac tgaagccagc aaccttcacc   1980
gacaccaccc actaccctct gctcctggtg gtggatggca ccccaggcag ccagagtgtg   2040
gctgagaagt tcgaggtgag ctgggagacg gtgatggtga gcagccacgg cgcggtggtg   2100
gtaaagtgtg acggccgtgg cagcggcttc caagggacca agctcctgca cgaagtgagg   2160
cggcggctgg gcttgctgga ggagaaggac cagatggagg ccgtgcggac gatgctgaag   2220
gagcagtaca ttgacaggac gcgcgtggcc gtgtttggga aggattacgg tggctacctg   2280
agcacctaca tcctcccagc aaagggagaa aatcaaggcc agacattcac ctgcggctct   2340
gctctctctc caataacaga cttcaaactc tatgcctctg cgttttccga gaggtacttg   2400
ggcctccatg gacttgacaa cagagcatac gagatgacca aggtagccca tcgagtctcc   2460
gcgctggaag aacagcagtt cctgatcatt catcccactg ccgatgaaaa aattcatttc   2520
cagcacacag cagaactcat tacacaacta attaggggaa aggctaatta cagcttacag   2580
```

-continued

```
atttacccgg acgaaagcca ttactttacc agctccagcc tcaaacagca tctgtaccgg   2640

tccatcatca acttcttcgt ggaatgcttc aggatccagg acaaactgct gacagtcaca   2700

gcgaaagagg acgaggagga ggactaagct caggtcgctc taagcacaaa cgtggctctt   2760

tctacaacca gatgcaaccg agggatttcc ctgccctccc tcttccctcg gaggggcggg   2820

gcggggcggg gccgggtgtt ccatagcatg tgtgtctcgg atgcggaagg cagttttgct   2880

tgggaaacaa gctccttccc cggggtcatc actcacggcc tccatggcac cagggacaac   2940

gctgtccccg cagcagcgcc tcctcccggc gcccgagaga ccggcacgcc acggcccctc   3000

ccccaaggaa cagagcaaag gatggtggcc gcaggcccca cgcgagccca caggacaccg   3060

gcccctagat tccagccacc aagcggaagc atgagacccg cccacactag cctctgtgtt   3120

cccgttaggg acatcacacc ctgtctcacg tcgcagtgcc atggacgcag cagttacagc   3180

accattgttt tagcagtgcg tgttcatata tgggcttgct acttcctgta atgaggacgt   3240

tcaacatggt gaggggctac aagaaaacgc ttttctgtac agagtcttac tgtagctacg   3300

ctaatggtta acctgataga attaactcgt atttttctat ggttttaacc tgatgctcca   3360

ctgtctccgt catggggttg ttttgctgtt tggggttggg ccttgtttcc ctttcctttc   3420

tccagtccac gtgtagactt tgcgcttgat gaagaagcag atcggaagta actgctccct   3480

cctcaaggtt gtcttcagac gtcttgggga cgttcctaaa cactgagggg gaagacagcc   3540

aatagcaccc attaaaagaa atacctaaat aaaacctctc tcccactcag ctatgctagg   3600

gcttggctgt aggtgtgcac tgtctattta catccgtcct tacaaccatc cttgtcctcc   3660

ttggtaccgt atcaagctct ttcccatgac atttggttta aaaaaaaaaa aaaaaaaaaa   3720

aaaaaaacag aaaaaagaca aagcgtcaac tccacccaca ggcccgctgt gtgtgctcgg   3780

gccacgggag tcctgagggt tctgtgggcc tgcgcgcatc cctctcccat cgtgggggtg   3840

gctccgtgac cttcctgcca cgagcaggag gttgatgatg tgctacgtta gccttgtaag   3900

atacaccccc accaaatgtg cagccggtgt tcccagtgta tatttcattc tcttgtatat   3960

aaaggaagca atgtgtgtca ggcctctgtg cagtcaaccc agcctcctcc cgccagtgct   4020

aaccccgtgt tgagcctgca tgctgacact gtggccgatc tggactctag aagtgctagt   4080

ttgaaatata tccattactg tcatttcctt ttgagcttgt ggacaagctg aatgtcagga   4140

ctgacttcgc cagctcccag ccctgcgggg gtgtccttgg catcccatca gcagaggaga   4200

tgcgtccctg ttgcattttg gcgtttgggg ctttgggttt atccacatga gctctgaacg   4260

tccgttatag ttagggtgat tggaaggtct ccatcactgg gtgttttaaa ggtgattcac   4320

caccatttgt gaaaggacca acgtgctgat aaacaggacc gatccgagtg ctacatgact   4380

gtgcgtttgc tatttcaatg ggcctgaacg actacaaagc cagctaggtc tggaagggga   4440

agccagctct ggccacgaca tctggtcgga gggaagtggg gatgtggcat ggtagcgtct   4500

gttcatccat ggaataaaac attattttac caaaaaaaaa aa                      4542
```

<210> SEQ ID NO 48
<211> LENGTH: 940
<212> TYPE: DNA
<213> ORGANISM: Homo sapiens

<400> SEQUENCE: 48

```
cctgggcgtg tgctaaggcc agagctacca gatgggtcca gctgccgcag gctctccagg     60

cactgtcccc taagtgacag ctgttactgc ctgggagagc tcaagtgcaa agactatcct    120
```

```
gttctcccat aaagaggagg aaaaggaaga tacagaaatc ggtgctgctc ccaacagcag    180

atcaaggcag tcgtcaggaa ctcaggatcc ggggggtctt cacggcttct ctgcccaggg    240

gccagaaccg aggaggccag gagggctgct ggggctaagg ggtctaagga cctcgttgca    300

cacgctacca ggagcagggg catggagcac agtgaggggg ctcccggaga cccagccggt    360

actgtggtac cccaggagct gctggaagag atgctttggt tttttcgtgt ggaagatgca    420

tctccctgga atcattccat ccttgccctg gcagctgtgg tggtcattat aagcatggtc    480

ctcctgggaa gaagcatcca ggcaagcaga aaagaaaaga tgcagccacc agaaaaagaa    540

actccagaag tcctgcattt ggatgaggcc aaggatcaca acagcctaaa caacctaaga    600

gaaactttgc tctcagaaaa gccaaacttg gcccaggtgg aacttgagtt aaaagagaga    660

gatgtgctgt cagttttcct tccggatgta ccagaaactg agagctagtg agggttcaga    720

gaagccccat cctaagccag acacatgatg tgggctcagc tcagtggcct gaaacctctc    780

aggttttaga gtctctccca agaagccgct tttttctttt tctttctttc ttttttttt    840

tcttagcaga tacaatgaat gaactgcaag caaactaaaa ttctgttatt aaaaaaaatc    900

ttttattaaa atgctcctgg aagggagcag gtggtattgc                         940
```

<210> SEQ ID NO 49
<211> LENGTH: 5018
<212> TYPE: DNA
<213> ORGANISM: Homo sapiens

<400> SEQUENCE: 49

```
gcccgggact atcccttcgc ggtgtagcgg cagccggaga cctggctgag gaggcaaccg     60

cgtagacacc tccctgctta gaaaacaaac actgaaccag accgatccca gttggagggt    120

tcgaaaatgt tccagacagc ctgtcgggag gggttgttgt tgctgttgga ctaaatagct    180

attcctgatt ggtcatgtat agggtttttt aaggcgggtg gggggaggag ggggtagagg    240

aaaggctcca aacacctgca ggttgggggc ggaaagctgt ttgcgattcc ctggactggt    300

tggtcgggga caggaggtaa ttcccagcca ttgaccccca tttctctctc tccctccctc    360

ttgccctgcc tctttctctc cacccctatc tttcctggaa actcgctttg ggcgcggcag    420

atcgcccagg accacaccgc agcgtaactg caggcctctc agcgaaaaag ggggaaagca    480

aagacccggg tgtgcatcct cttcctcggc ttccgcccct ttccggcgga gtggagatcc    540

tattcagagg ggccggtctc tctaaatatg ccccaggatg accgagcggc cgcccgagcga    600

ggcggctcgc agtgaccccc agctagaggg acgggacgcg gccgaggcca gcatggcccc    660

cccgcacctg gtcctgctga acggcgtcgc caaggagacg agccgcgcgg ccgcagcgga    720

gcccccagtc atcgaactgg gcgcgcgcgg aggcccgggg ggcggccctg ccggtggggg    780

cggcgccgcg agagacttaa agggccgcga cgcggcgacg gccgaagcgc gccatcgggt    840

gcccaccacc gagctgtgca gacctcccgg gcccgccccg gcccccgcgc ccgcctcggt    900

tacagcggag ctgcccggcg acggccgcat ggtgcagctg agtcctcccg cgctggctgc    960

ccccgccgcc cccggccgcg cgctgctcta cagcctcagc cagccgctgg cctctctcgg   1020

cagcgggttc tttggggagc cggatgcctt ccctatgttc accaccaaca atcgagtgaa   1080

gaggagacct tccccctatg agatggagat tactgatggt ccccacacca aagttgtgcg   1140

gcgtatcttc accaacagcc gggagcgatg gcggcagcag aatgtgaacg gggcctttgc   1200

cgagctccgc aagctgatcc ccacacatcc cccggacaag aagctcagca agaatgagat   1260

cctccgcctg gccatgaagt atatcaactt cttggccaag ctgctcaatg accaggagga   1320
```

ggagggcacc cagcgggcca agactggcaa ggaccctgtg gtgggggctg gtgggggtgg 1380
aggtggggga gggggcggcg cgcccccaga tgacctcctg caagacgtgc tttcccccaa 1440
ctccagctgc ggcagctccc tggatggggc agccagcccg gacagctaca cggaggagcc 1500
cgcgcccaaa cacacggccc gcagcctcca tcctgccatg ctgcctgccg ccgatggagc 1560
cggccctcgg tgatgggtct gggccaccag gatcagccag gagggcgttc ttaggctgct 1620
gggatggtgg gcttcagggc aggtggggtg agaattgggc ggctctgaag caaggcggtg 1680
gacttgaact ttcctggatg tctgaacttt gggaagcctt tactgaccct ggggctggct 1740
tttctgtttc ctgtaccagt aggagatcag aaaaatggag caaagtggta ggtacttttt 1800
gtgaagacgg cacggtcttc cctcttccct cagtcccaaa tccttcccaa gtaagaggct 1860
ggagttgtca ctgcttttgg cctggagttt gggatccctg tctttcctaa gacctggggt 1920
tgtcagctct catctgaggc atccagcagt ctctgccttg cctttagccc ctcccaagct 1980
ggctggggtg gcctgtgtgg ccacttctgt ccatatttat aggtacccaa tagctgccca 2040
tttcgtgagc cccatcttca cccaggccta tgttgatcca tccagcttgc cagatgctgc 2100
agagtcacaa gcctcgaggt gccttcttca gggcctggtt gaagaagatg atcagtggac 2160
agtctgctct agatgagctg ggccggaggg tcaggaaacc cagtcgccct tacttcttgc 2220
cctggggatc aaagttctgc tttctcccca atgagacttg ccttcctaag cctgtggctg 2280
tggagacaat gtctgcagcc ctgagaaagc cctgtcgggc tttgtgtgaa ggcagagaaa 2340
gggacaatga tagtagagtg atatggagca agagatattt tgggcatgtg ggcttcaact 2400
cctcgacatc actgttcatg ctggcgagtg aatgccagtg tgctgatggg cgtacgctgg 2460
tgctgagtag atgcgcagcc ccatctgtgc attctcctgg atgcttagag ggatttcttt 2520
gctgtaagat gtctgtttgc tgatggtctg gtctatgttc cgaattgagc acaaaacctg 2580
tcctatgaat gctttgcatt tggaattttt gcttgacttc agttattggt ggaatcttta 2640
gcgctcaata ggaccaggat ccagcctcac ttctagggta tgggaaatcc aatcagagac 2700
caggccctgg ctaagaccca aacatatgca cattcactta gcagaacctt aaacacccct 2760
cagttgtgca gcttttggtc atcaagggtg cgtctgggag gttggtttaa tgcaatagaa 2820
gtgctcccct ctgaaagttg tacatgaaat ttttgtaaat cacatcctta tccttcatct 2880
tttaaagaaa taaccactgc aagtcctttt gtaaagtgaa gaatcctttt gtagaatgaa 2940
ccactgcccc ttcattgatt tcctgtgtca atccagatgg tgggatgtgg ttttcttaag 3000
gtgaggcctg tctgtgacct gcatctaagc ccatgggaca aattgcacag aagtcctgta 3060
tgtctgtcat tgtaccctta agtcacccta gccctctccc tctaggctct gccttcgagg 3120
tcagaggaga gatagcctgt ggccctgtcc tgccatgcaa gaactcatca ctgtggctgt 3180
ctggaaagcc ccccttata gtttgggctt cagcctagtg gcttgtcctc accatgatgg 3240
ggccctaatt cagccatgta cagacagaga atatgtctgc tcctttcccc ttcctttttaa 3300
gtaaggtcca attctcgagc ttggggcaac attgttcacc tttgtagcac tcaggctctc 3360
cattcaattt caggctcccc agatcatgtt ttggtgaaaa ttagggttgg ttcctttcca 3420
acgtttggaa gatcctgtga ggagccccat ctgtctaaag atagagtcat tgctgtagga 3480
tctaaggctg tttgcttcac cgtggattcg cttgagttag gaatgagaag tagccacagt 3540
atggatgggt ggatgggttt tatgagatgg atcacatatt ttattaagaa ctcaaacttc 3600
tggctccctc ttctttcaga cttgccatgt gactctggct tggcctatct cctagggcta 3660
tggtgtggac tgaatgggat catgaaagta gacagttttg agaacgtaaa gaactttttc 3720
ttttccctca atctcaatcc tgcagtgggg tttcgcagcc tgagtccacg acctaggcag 3780
taggccggtg tgcctgactg cccagcattt gggtaattta gattgtaaac cgctttggcc 3840
tgagttattg agattgtcct catttctcca gattatctat ttgtgtgtgt gtgtgtgtgt 3900
gtgtgagaga cggtgtcttg ttctgtcact caggctggag tacagtggtg ccatcattgc 3960
tgtctgcagc cttgaactct gggctcaagc aatcctctca cctcagcctc ccgagtaggg 4020
aggaccacag gtgtgagcca ccacacctgg ctaattttta cttttttttt tttttggtag 4080
agatggagtc ttgctatatt gcccaggctg gtcttgaagt cctggcttca ggcaattctc 4140
ctgcctttgc ctccagaagc actgggatca caggtgtcag ccattgcacc cagcccagat 4200
tgtcttaatt tctatcttgt tccaaggcca gggacagtaa taagaatgga aaagagatat 4260
gggaacactg gcagactgtg taaaatgtaa tgcaactacc caaaacaagc ctggtaggaa 4320
agggcaagtc tttaggtctt tgtaagaact aaagaagatc tgtaattttt attttcaccc 4380
tctgtacccc atgaccttat ccttcctctc cttccttgtt acccatgaaa aactggcaac 4440
attccaagaa tagcatctgt acaaagggga aagaacataa aggtaaaaca aaacaaaaca 4500
acattttgag aacaaagatg accataacca ctgaagggaa tcacatcttt taagacaaat 4560
tcatattctt ttatttgtta tggcagatga caagatggta caacctttat tcttttccaa 4620
aataaaacaa agggcacagc atctgtagtc agccgacaac tatttcggcc ttttgggggt 4680
gggtctggcc gtacttgtga tttcgatggt acgtgaccct ctgctgaaga cttgcccccct 4740 gcccgtgtac atagtgcatt gtttctgtgg gcgggcccag cactttccgt caacgttgta 4800
ctgtatgtga tgaattgcgt tggtctctgc atttttctgc agaagaggag taaccgctcc 4860
aggtaccttg acctttgtac agcccagagg ccaacactgt gggtgtgtga ctctttagca 4920
aaaaaaaccc atgtggtgat gatgtgtata tatatgtgag gatgtatcgg gaagatttct 4980
aaataaaagt tttacaaagg ggaaaaaaaa aaaaaaaa 5018

<210> SEQ ID NO 50
<211> LENGTH: 3024
<212> TYPE: DNA
<213> ORGANISM: Homo sapiens

<400> SEQUENCE: 50
aggatatctt tagccaaagg aaaagctccg cattcccacc cagtccagaa attgaaatac 60
tatcaggggg caagagcctt tctctccagc tacacactcc atctcccggg agcaagggga 120
aactccgaga ggagggcaac agagccagca tcttgccagg gccccggagg aggggttccc 180
cgctacgcct gtgccggagg agttccagtc accgagcgag gggcgcaagg gtgggtgcat 240
cctgcgctgc ggcgggcgcg ctacccagac gctggtgtgc agagccacat gaagcctgct 300
ggggactggg ggccagggag cagcaagcca gctgggactg aggcggacgc tgtctcaggg 360
agacgctgac tcgcaaagac actcccttcc ttgtgcctgg gtaaaaagtc tcctcctggg 420
gtccctggcc atcctgaata tccagaatgg tgtttctgaa gttcttctgc atgagtttct 480
tctgccacct gtgtcaaggc tacttcgatg gccccctcta cccagagatg tccaatggga 540
ctctgcacca ctacttcgtg cccgatgggg actatgagga gaacgatgac cccgagaagt 600
gccagctgct cttcagggtg agtgaccaca ggcgctgctc ccagggggag gggagccagg 660
ttggcagcct gctgagcctc accctgcggg aggagttcac cgtgctgggc cgccaggtgg 720
aggatgctgg gcgcgtgctg gagggcatca gcaaaagcat ctcctacgac ctagacgggg 780

```
aagagagcta tggcaagtac ctgcggcggg agtcccacca gatcggggat gcctactcca    840
actcggacaa atccctcact gagctggaga gcaagttcaa gcagggccag gaacaggaca    900
gccggcagga gagcaggctc aacgaggact ttctgggaat gctggtccac accaggtccc    960
tgctgaagga gacactggac atctctgtgg ggctcaggga caaatacgag ctgctggccc   1020
tcaccattag gagccatggg acccgactag gtcggctgaa aaatgattat cttaaagtat   1080
aggtggaagg atacaaatgc tagaaagagg gaatcaaatc agccccgttt tggagggtgg   1140
gggacagaag atggggctac atttccccca tacctactat ttttttatat cccgatttgc   1200
actttgagaa tacatctaag gtcatctttc aaaagagaaa aattggacac ttgagtgact   1260
ttgtttttag ttttgttttt gtacattatt tatgtgattg ttatggaatt gtcacctgga   1320
aagaacaatt ttaagcaatg tcatttctag atgggtttct aattctgcag agacacccgt   1380
ttcagccaca tctaaaagag cacagtttat gtggtgcgga attaaacttc cccatcctgc   1440
agattatgtg gaaataccca aagataatag tgcatagctc ctttcagcct ctagccttca   1500
ctcctgggct ccaaaagcta tcccagttgc ctgtttttca aatgaggttc aaggtgctgc   1560
tttgcatgcc tgccaaccca tggaagttgt ttcttacttc ttttctctct tatttattaa   1620
ccatggtctg agagttgttt ttgttctatg taacagtatt gccacaaaac tataggcaaa   1680
tcgtgtttgc agggagattt ctgatgcctc tgtgggtgtg tgtaagttaa agtggccaca   1740
tttaagaagg ccaagctttg tagtggttgc acagtcacac tgatatgctg atttgctctt   1800
tctcattgta tgtctatgct ttgtcatcag tgctatagta aattacaaag aaataggtag   1860
attgtatgaa catacccaca aatgcctatg atttaggtta ccaatgtatt ctttctcatt   1920
tggggttttg cttctgtctg tctgtttatt ggaaacttgt acttcaagta gggggaatcc   1980
taattctaat aactccttag ctaagtttta ttattcaggc aataaacatg ttttcatgta   2040
atactggctt actttgtaat ttacatctgt aactttcata tttctaaaag gggccaatgc   2100
aaaaggagag agaaggactg gatttaagcc agtttactta gagtatatga taaagaaggc   2160
agaggaatag ctacatattt ggcaattctc ctctctgtag tcaccctgac atcctcacaa   2220
gaaaacaaat ctagccattg cccaaacttt aaatttgatc tctataggtc tgcttaaaga   2280
ctcaaatttt ctccagtttc tctcataaat tcaattgcaa aagtttctga caaggctcat   2340
accctgtacc cttatgcaga gcaagcattc catcctaagt tataaactac agtgatgttt   2400
aattttgaag ccaggtctac attatttaat taatggcttc aaaaggtgga gatgcacttt   2460
atttaatgtc tttccctagc taattcttac tctcacctta aatatgcttt cttgttgcat   2520
atatgcacag atacacacac acacacacac gaaaataaat aaatgttcat attcttctgt   2580
tcaacagaca tttattttct cctctccctt gaataagaaa ataagttttc cattcctatg   2640
aactgtctaa tatctttcta ttacagaagg ggaaactgag gctgggaaag gctaaatgac   2700
ttatcctcca tcagttataa cagcccctgg tcttcttaaa tttaaacacg ggacttcccg   2760
aactaatttt tttaaggata ctgaaaaatg agagagagtg gtcgaatgcc tgaaattttg   2820
cttaacttac tgtacttaaa atcaattata acttcttttt gttactcagg gccccacttt   2880
ttgttgcttt ctagacttgt gtgtagaaag aagattaatg atcacttaaa gtagtttcct   2940
tctttattct gaaaaaatga ggaaaaaata acaacagtgg caaataaaat catatttggt   3000
actaaaaaaa aaaaaaaaaa aaaa                                          3024
```

<210> SEQ ID NO 51

<211> LENGTH: 7111
<212> TYPE: DNA
<213> ORGANISM: Homo sapiens

<400> SEQUENCE: 51
gcgtcagccc tcacgtcact tcgccagcag tagcagaggc ggcggcggcg gctcccggaa 60
ttgggttgga gcaggagcct cgctggctgc ttcgctcgcg ctctacgcgc tcagtccccg 120
gcggtagcag gagcctggac ccaggcgccg ccggcgggcg tgaggcgccg gagcccggcc 180
tcgaggtgca taccggaccc ccattcgcat ctaacaagga atctgcgccc cagagagtcc 240
cgggagcgcc gccggtcggt gcccggcgcg ccgggccatg cagcgacggc cgccgcggag 300
ctccgagcag cggtagcgcc cccctgtaaa gcggttcgct atgccggggc cactgtgaac 360
cctgccgcct gccggaacac tcttcgctcc ggaccagctc agcctctgat aagctggact 420
cggcacgccc gcaacaagca ccgaggagtt aagagagccg caagcgcagg gaaggcctcc 480
ccgcacgggt gggggaaagc ggccggtgca gcgcggggac aggcactcgg gctggcactg 540
gctgctaggg atgtcgtcct ggataaggtg gcatggaccc gccatggcgc ggctctgggg 600
cttctgctgg ctggttgtgg gcttctggag ggccgctttc gcctgtccca cgtcctgcaa 660
atgcagtgcc tctcggatct ggtgcagcga cccttctcct ggcatcgtgg catttccgag 720
attggagcct aacagtgtag atcctgagaa catcaccgaa attttcatcg caaaccagaa 780
aaggttagaa atcatcaacg aagatgatgt tgaagcttat gtgggactga gaaatctgac 840
aattgtggat tctggattaa aatttgtggc tcataaagca tttctgaaaa acagcaacct 900
gcagcacatc aattttaccc gaaacaaact gacgagtttg tctaggaaac atttccgtca 960
ccttgacttg tctgaactga tcctggtggg caatccattt acatgctcct gtgacattat 1020
gtggatcaag actctccaag aggctaaatc cagtccagac actcaggatt tgtactgcct 1080
gaatgaaagc agcaagaata ttcccctggc aaacctgcag atacccaatt gtggtttgcc 1140
atctgcaaat ctggccgcac ctaacctcac tgtggaggaa ggaaagtcta tcacattatc 1200
ctgtagtgtg gcaggtgatc cggttcctaa tatgtattgg gatgttggta acctggtttc 1260
caaacatatg aatgaaacaa gccacacaca gggctcctta aggataacta acatttcatc 1320
cgatgacagt gggaagcaga tctcttgtgt ggcggaaaat cttgtaggag aagatcaaga 1380
ttctgtcaac ctcactgtgc attttgcacc aactatcaca tttctcgaat ctccaacctc 1440
agaccaccac tggtgcattc cattcactgt gaaaggcaac cccaaaccag cgcttcagtg 1500
gttctataac ggggcaatat tgaatgagtc caaatacatc tgtactaaaa tacatgttac 1560
caatcacacg gagtaccacg gctgcctcca gctggataat ccccactcaca tgaacaatgg 1620 ggactacact ctaatagcca agaatgagta tgggaaggat gagaaacaga tttctgctca 1680
cttcatgggc tggcctggaa ttgacgatgg tgcaaaccca aattatcctg atgtaattta 1740
tgaagattat ggaactgcag cgaatgacat cggggacacc acgaacagaa gtaatgaaat 1800
cccttccaca gacgtcactg ataaaaccgg tcgggaacat ctctcggtct atgctgtggt 1860
ggtgattgcg tctgtggtgg gattttgcct tttggtaatg ctgtttctgc ttaagttggc 1920
aagacactcc aagtttggca tgaaaggttt tgttttgttt cataagatcc cactggatgg 1980
gtagctgaaa taaaggaaaa gacagagaaa ggggctgtgg tgcttgttgg ttgatgctgc 2040
catgtaagct ggactcctgg gactgctgtt ggcttatccc gggaagtgct gcttatctgg 2100
ggttttctgg tagatgtggg cggtgtttgg aggctgtact atatgaagcc tgcatatact 2160
gtgagctgtg attggggaac accaatgcag aggtaactct caggcagcta agcagcacct 2220

-continued caagaaaaca tgttaaatta atgcttctct tcttacagta gttcaaatac aaaactgaaa 2280
tgaaatccca ttggattgta cttctcttct gaaaagtgtg ctttttgacc ctactggaca 2340
tttattgact taattgcttc tgtttattaa aattgacctg caaagttaaa aaaaaattaa 2400
agttgagaac aggtataagt gcacactgaa tagtctaatc tacatgtaac acatatttta 2460
gtgtgatttt ctatactcta atcagcactg aattcagagg gtttgacttt ttcatctata 2520
acacagtgac taaaagagtt aagggtatat ataccatcac tttgggactt ggtagtatta 2580
ttaaaaggtt atttccttca ctgtcaataa aagtccaaat gtttagctta ggtctgagag 2640
tcaaacaatg ttaaggattg tcttaaagtt ccttagccag caaaacaaaa caaaacaaaa 2700
caaacaaatg aaaaacgttt aaaaagaaga agaagaaaaa aaacaagaac aagcagcaac 2760
agctgttttg ttggggctat agatttaagt taggcatagt caatttcaga ataactaaga 2820
gtggaatata tgcatatggt gaaattataa ccttgccctt ttttatttgc cctctgcgat 2880
ccacctgctt tttagaagtc tgccgagtga gaaggccaca gtatctcatg ctgtttgcat 2940
tacagaactg cagcttttct actctgaaaa ggcctgggag cagaatggct ggcctgctgt 3000
gagcaggaga ggagattcta agaaggatag tccccctac aacatactgt catactgctg 3060
ggttttcatg ggtaggaaag cttgtcctga ccccagcagc aaagaggtgg caggtcgcta 3120
atgaatatat gctttataat gtccttcttc attgctgaga gggcagcctt agagctgtgg 3180
atttctgcat cccccctgag tctgacccat ggacacctgt ttcattcact ttagcatcac 3240
agtgaccttt gtatgctctg ttcagtctgt gtcaggcagt atgcttgtcc tgaagagagg 3300
tttggctatc cccaccccac cccaccccac cctgttcctt ttttatcagg aggacttcag 3360
agccaggcct gcagcatttt gtttgaaaac acaatcagct ctgacagtta gacatgcaca 3420
cagacgccat agctggattg gaaacattga tgttttaaaa atttattttt tttggaaata 3480
gttgcacaaa tgctgcaatt tagctttaag gttctataga tttttaacta gtccaacaca 3540
gtcagaaaca ttgttttgaa tcctctgtaa accaaggcat taatcttaat aaaccaggat 3600
ccatttaggt accacttgat ataaaaagga tatccataat gaatatttta tactgcatcc 3660
tttacattag ccactaaata cgttattgct tgatgaagac ctttcacaga atcctatgga 3720
ttgcagcatt tcacttggct acttcatacc catgccttaa agaggggcag tttctcaaaa 3780
gcagaaacat gccgccagtt ctcaagtttt cctcctaact ccatttgaat gtaagggcag 3840
ctggccccca atgtggggag gtccgaacat tttctgaatt cccattttct tgttcgcggc 3900
taaatgacag tttctgtcat tacttagatt ccgatctttc ccaaaggtgt tgatttacaa 3960
agaggccagc taatagcaga aatcatgacc ctgaaagaga gatgaaattc aagctgtgag 4020
ccaggcagga gctcagtatg gcaaaggttc ttgagaatca gccatttggt acaaaaaaga 4080
tttttaaagc ttttatgtta taccatggag ccatagaaag gctatggatt gtttaagaac 4140
tattttaaag tgttccagac ccaaaaagga aaaataaaaa aaaaggaata tttgtaccca 4200
acagctagaa ggattgcaag gtagattttt gttttaaaat ggagagaagt ggacagataa 4260
ggccatttaa tatatcaaag atcagttgac atctcctagg gaatgatgaa aacagcaggc 4320
tattagaaaa ttatttcata tagttctcgt gttcttttct tttttttaat ccctgaaggg 4380
atgatcagta acatagcttc tcttttctgt actctagacc accccttttc atcattttgc 4440
tttttatgtc tcccataaga aatgtgcttt ttagagcttc ctaatgcatg tgttgcatta 4500
ttgcagcatt agaaaaggag aggtagcatt tttgctgaaa tcgggcctgt cactctccaa 4560

-continued

```
taaaggttct ggcacttcaa tgccaggcag gtctcctaaa tgaacagaat gatctgtgtg   4620
agccgatgcc tgcccttcca gaggggccac tgtccccagc cgcagccaac tgtgtcccac   4680
aggaatggga gcctaggttt ccaaatcttg tgattcttta ggagaaacat gaaacctgga   4740
tttcgtgtga aatgtcccga ttgttaaaaa gttggctcaa ttatttttaa aacattttgt   4800
aagccaacaa aagtctgtgg gctgccagtt tattactttt gtcttaaaac atgatcattg   4860
ttctctcacg gtatccttct gtcttcccgt tgcaaattca cttttctttc ttcctgacat   4920
tgccattgag ggctttgtta ccacaagcta agaaactgag tttaacagcc cagttatctg   4980
caacatgtca attacctttg ctcctctcct gtgattccca ccatgctgtg accctcagct   5040
gtctcccttt gctgggaatt ctgcaccaat gtctcccctc aacccattcc ctggttggtc   5100
ctactcccgt gtggccagag acatcctagc aaatccttcc tcctattata tctgacacta   5160
atttcttttc aacagcgctc atgtctcttg gcccagtcag gtgctgccag gtttagatag   5220
gaaagtacat gtcccatttt catgggtgcc cttaatgtgg tccacgtcct atatcttatt   5280
atatttactc atggctcaat gggggcctcc agagaccctc tcaggctgct gagctagact   5340
aaggaatgca tccaccgtca tcacatgaga cactgactct gtgacgacaa aagtacaaac   5400
agtctgaggc taagaaaggt tcatctcaca acaggaaaaa caaatctcaa cacacattag   5460
agataattga ttcaggggtt ttctctccca gtctcccagc agggactgat ttcatttctg   5520
acccactagg ttttctttcc agaaataggt agcaaggaca agaactaaac aatcccagcc   5580
ccacccagca acacagaaca caggagtttg cttttggctt ctcactctcc aagtaaccct   5640
gaattaggcc cagaatggct gaggcttgga gcatctcctc agacagagca gaggcgacac   5700
ctcttcaggg gtgtgtggag taaatagctc gaagagctga agacagaaaa ccagtttcac   5760
gccaggtgcg agagagagca taatggaggg aagcccgctt tctctctcct cttcttttct   5820
ctttatttct ttagagcact tgactttttt ttctctctct ctctagtatt ctaaactgac   5880
cccatgacca actgagaatt tatttttgtt tcattggttg tttcacagaa ttagaacaca   5940
cacgactttt tattcctcca ttgcaaaatg gaatcaagat actacacaag acctgtgctt   6000
tcttcctttg catgatttac acctccgcct gttttggtgc tagctgtcta gaacttctct   6060
cttggtttga atctgattcc ttcacactac actagaagtt tatttcatct tgttttgtct   6120
agactccaga tacagaggga cagctggact gaggacaagc aattccatct agcatagggt   6180
ctctcagggt tggtgcatcc agccacatgg gcagggccag tcacatctag tctatgtccc   6240
cagagccctt ggagttgcgc agcttagctg acttgactcc aaggaaatta gtacagaagt   6300
aaccactcta ttaagtgtgt tctgctatgt tcacatgcct gtagtacctg caaaccatgc   6360
caggttcatc taaagacata ggggaagatt aaggactctt ttggacagac catgaattga   6420
atttgctgcc aggtgctgcc agactgaatt tggctgacag aactcccagc ccaggaaagt   6480
tccatgacaa tgactgtcgc agaaggaaat ttcccactaa agtcagtcca ttttcaagtt   6540
ttggtcttca gagacaaaag aacgtcccag ccacctgatt ttgatggtga ggtaactcta   6600
agttgaattc aggctagtgt tgcagtatag ctttggcatg ttcatgagtg agcacccaga   6660
atgtgttgaa ccaaccccca cccctaacta ctgactatga ctgcagtggg tttttatggg   6720
gaaaaaaagt gtgaaaagca aaaagaaagg aacagagatt ttttatcacc tttattgtaa   6780
gacagtccat ttatgaattg agtataaaca catacaaagt aacaagagat tcctaagaaa   6840
cgcaaatcct tgagtttcac gcacttcatg ttcaaccatt tgctgtaatc cagaggcagc   6900
ctgtgaatca ttctcatgcc ctgttttttt ttttttttc ctataatgtt ctgggtttaa   6960
```

-continued aagccatctt ttccacattt tctgtaaata atggataatc attttaaaaa tttttatttt 7020
tagtgctgtt ttaacaatgt agatagatca taaatgtact tgctgaattc aatcattttt 7080
aacaagccaa taaagtttga taattcatct c 7111

<210> SEQ ID NO 52
<211> LENGTH: 5560
<212> TYPE: DNA
<213> ORGANISM: Homo sapiens

<400> SEQUENCE: 52
aagacggatt ctcagacaag gcttgcaaat gccccgcagc catcatttaa ctgcacccgc 60
agaatagtta cggtttgtca cccgaccctc ccggatcgcc taatttgtcc ctagtgagac 120
cccgaggctc tgcccgcgcc tggcttcttc gtagctggat gcatatcgtg ctccgggcag 180
cgcgggcgca gggcacgcgt tcgcgcacac cctagcacac atgaacacgc gcaagagctg 240
aaccaagcac ggtttccatt tcaaaaaggg agacagcctc taccgcgatt gtagaagaga 300
ctgtggtgtg aattagggac cgggaggcgt cgaacggagg aacggttcat cttagagact 360
aattttctgg agtttctgcc cctgctctgc gtcagccctc acgtcacttc gccagcagta 420
gcagaggcgg cggcggcggc tcccggaatt gggttggagc aggagcctcg ctggctgctt 480
cgctcgcgct ctacgcgctc agtccccggc ggtagcagga gcctggaccc aggcgccgcc 540
ggcgggcgtg aggcgccgga gcccggcctc gaggtgcata ccggaccccc attcgcatct 600
aacaaggaat ctgcgcccca gagagtcccg ggagcgccgc cggtcggtgc ccggcgcgcc 660
gggccatgca gcgacggccg ccgcggagct ccgagcagcg gtagcgcccc cctgtaaagc 720
ggttcgctat gccggggcca ctgtgaaccc tgccgcctgc cggaacactc ttcgctccgg 780
accagctcag cctctgataa gctggactcg gcacgcccgc aacaagcacc gaggagttaa 840
gagagccgca agcgcaggga aggcctcccc gcacgggtgg gggaaagcgg ccggtgcagc 900
gcggggacag gcactcgggc tggcactggc tgctagggat gtcgtcctgg ataaggtggc 960
atggacccgc catggcgcgg ctctggggct tctgctggct ggttgtgggc ttctggaggg 1020
ccgctttcgc ctgtcccacg tcctgcaaat gcagtgcctc tcggatctgg tgcagcgacc 1080
cttctcctgg catcgtggca tttccgagat tggagcctaa cagtgtagat cctgagaaca 1140
tcaccgaaat tttcatcgca aaccagaaaa ggttagaaat catcaacgaa gatgatgttg 1200
aagcttatgt gggactgaga aatctgacaa ttgtggattc tggattaaaa tttgtggctc 1260
ataaagcatt tctgaaaaac agcaacctgc agcacatcaa ttttacccga aacaaactga 1320
cgagtttgtc taggaaacat ttccgtcacc ttgacttgtc tgaactgatc ctggtgggca 1380
atccatttac atgctcctgt gacattatgt ggatcaagac tctccaagag gctaaatcca 1440
gtccagacac tcaggatttg tactgcctga atgaaagcag caagaatatt cccctggcaa 1500
acctgcagat acccaattgt ggtttgccat ctgcaaatct ggccgcacct aacctcactg 1560
tggaggaagg aaagtctatc acattatcct gtagtgtggc aggtgatccg gttcctaata 1620
tgtattggga tgttggtaac ctggtttcca aacatatgaa tgaaacaagc cacacacagg 1680
gctccttaag gataactaac atttcatccg atgacagtgg gaagcagatc tcttgtgtgg 1740
cggaaaatct tgtaggagaa gatcaagatt ctgtcaacct cactgtgcat tttgcaccaa 1800
ctatcacatt tctcgaatct ccaacctcag accaccactg gtgcattcca ttcactgtga 1860
aaggcaaccc caaaccagcg cttcagtggt tctataacgg ggcaatattg aatgagtcca 1920

-continued

```
aatacatctg tactaaaata catgttacca atcacacgga gtaccacggc tgcctccagc   1980
tggataatcc cactcacatg aacaatgggg actacactct aatagccaag aatgagtatg   2040
ggaaggatga gaaacagatt tctgctcact tcatgggctg gcctggaatt gacgatggtg   2100
caaacccaaa ttatcctgat gtaatttatg aagattatgg aactgcagcg aatgacatcg   2160
gggacaccac gaacagaagt aatgaaatcc cttccacaga cgtcactgat aaaaccggtc   2220
gggaacatct ctcggtctat gctgtggtgg tgattgcgtc tgtggtggga ttttgccttt   2280
tggtaatgct gtttctgctt aagttggcaa gacactccaa gtttggcatg aaaggcccag   2340
cctccgttat cagcaatgat gatgactctg ccagcccact ccatcacatc tccaatggga   2400
gtaacactcc atcttcttcg gaaggtggcc cagatgctgt cattattgga atgaccaaga   2460
tccctgtcat tgaaaatccc cagtactttg gcatcaccaa cagtcagctc aagccagaca   2520
catttgttca gcacatcaag cgacataaca ttgttctgaa aagggagcta ggcgaaggag   2580
cctttggaaa agtgttccta gctgaatgct ataacctctg tcctgagcag gacaagatct   2640
tggtggcagt gaagaccctg aaggatgcca gtgacaatgc acgcaaggac ttccaccgtg   2700
aggccgagct cctgaccaac ctccagcatg agcacatcgt caagttctat ggcgtctgcg   2760
tggagggcga ccccctcatc atggtctttg agtacatgaa gcatggggac ctcaacaagt   2820
tcctcagggc acacggccct gatgccgtgc tgatggctga gggcaacccg cccacggaac   2880
tgacgcagtc gcagatgctg catatagccc agcagatcgc cgcgggcatg gtctacctgg   2940
cgtcccagca cttcgtgcac cgcgatttgg ccaccaggaa ctgcctggtc ggggagaact   3000
tgctggtgaa aatcggggac tttgggatgt cccgggacgt gtacagcact gactactaca   3060
gggtcggtgg ccacacaatg ctgcccattc gctggatgcc tccagagagc atcatgtaca   3120
ggaaattcac gacggaaagc gacgtctgga gcctgggggt cgtgttgtgg gagattttca   3180
cctatggcaa acagccctgg taccagctgt caaacaatga ggtgatagag tgtatcactc   3240
agggccgagt cctgcagcga ccccgcacgt gcccccagga ggtgtatgag ctgatgctgg   3300
ggtgctggca gcgagagccc cacatgagga agaacatcaa gggcatccat accctccttc   3360
agaacttggc caaggcatct ccggtctacc tggacattct aggctagggc ccttttcccc   3420
agaccgatcc ttcccaacgt actcctcaga cgggctgaga ggatgaacat cttttaactg   3480
ccgctggagg ccaccaagct gctctccttc actctgacag tattaacatc aaagactccg   3540
agaagctctc gagggaagca gtgtgtactt cttcatccat agacacagta ttgacttctt   3600
tttggcatta tctctttctc tctttccatc tcccttggtt gttccttttt cttttttttaa   3660
attttctttt tcttttttttt ttcgtcttcc ctgcttcacg attcttaccc tttcttttga   3720
atcaatctgg cttctgcatt actattaact ctgcatagac aaaggcctta acaaacgtaa   3780
tttgttatat cagcagacac tccagtttgc ccaccacaac taacaatgcc ttgttgtatt   3840
cctgcctttg atgtggatga aaaaaaggga aaacaaatat ttcacttaaa ctttgtcact   3900
tctgctgtac agatatcgag agtttctatg gattcacttc tatttattta ttattattac   3960
tgttcttatt gtttttggat ggcttaagcc tgtgtataaa aaagaaaact tgtgttcaat   4020
ctgtgaagcc tttatctatg ggagattaaa accagagaga aagaagattt attatgaacc   4080
gcaatatggg aggaacaaag acaaccactg ggatcagctg gtgtcagtcc ctacttagga   4140
aatactcagc aactgttagc tgggaagaat gtattcggca ccttcccctg aggacctttc   4200
tgaggagtaa aaagactact ggcctctgtg ccatggatga ttcttttccc atcaccagaa   4260
atgatagcgt gcagtagaga gcaaagatgg cttccgtgag acacaagatg gcgcatagtg   4320
```

```
tgctcggaca cagttttgtc ttcgtaggtt gtgatgatag cactggtttg tttctcaagc   4380

gctatccaca gaacctttgt caacttcagt tgaaaagagg tggattcatg tccagagctc   4440

atttcggggt caggtgggaa agccaagaac ttggaaaaga taagacaagc tataaattcg   4500

gaggcaagtt tcttttacaa tgaacttttc agatctcact tccctccgac ccctaacttc   4560

catgcccacc cgtcctttta actgtgcaag caaaattgtg catggtcttc gtcgattaat   4620

accttgtgtg cagacactac tgctccagac gtcgtttccc tgataggtag agcagatcca   4680

taaaaaggta tgacttatac aattagggga agctaatgga gtttattagc tgagtatcaa   4740

tgtctctgcg ttgtacggtg gtgatgggtt ttaatgaata tggaccctga agcctggaaa   4800

tcctcatcca cgtcgaaccc acaggactgt gggaagggca gaatcaatcc ctaagggaaa   4860

ggaaacctca ccctgagggc atcacatgca ctcatgttca gtgtacacag gtcaagtccc   4920

ttgctctggg ctctagttgg gagagtggtt tcattccaag tgtactccat tgtcagtatg   4980

ctgtttttgt ttccttcact ccattcaaaa agtcaaaata caaaatttgg cacagcatgc   5040

caacgggagg ctgtgcccag accaagcact ggaagtgtgc ttctaggcat agtcattggt   5100

tttgcaaaaa gagggctcaa atttaaatag aaatttacag ctatttgaat ggtcagatat   5160

accaagaaag aaaaatattt ctgttcctca agaaaacttg ctaccctctg tgaggggaat   5220

tttgctaaac ttgacatctt tataacatga gccagattga aagggagtga ttttcattca   5280

tcttaggtca tgttatttca tatttgtttc tgaaggtgcg atagctctgt tttaggtttt   5340

gcttgcgcct gttaattact ggaacacctt atttttcatt aaaggctttg aaagccaatt   5400

ctcaaaaatt caaaagtgca aattaacaga acaaaaggaa atccagtagc aactgcagtc   5460

aagcgaggga gttgacaaga taaaccttac gtccattcaa gttatatgct ggcctatgag   5520

agatgagagt tgggtcgttt gttctctttg ttgatgattt                         5560
```

<210> SEQ ID NO 53
<211> LENGTH: 5608
<212> TYPE: DNA
<213> ORGANISM: Homo sapiens

<400> SEQUENCE: 53

```
aagacggatt ctcagacaag gcttgcaaat gccccgcagc catcatttaa ctgcacccgc     60

agaatagtta cggtttgtca cccgaccctc ccggatcgcc taatttgtcc ctagtgagac    120

cccgaggctc tgcccgcgcc tggcttcttc gtagctggat gcatatcgtg ctccgggcag    180

cgcgggcgca gggcacgcgt tcgcgcacac cctagcacac atgaacacgc gcaagagctg    240

aaccaagcac ggtttccatt tcaaaaaggg agacagcctc taccgcgatt gtagaagaga    300

ctgtggtgtg aattagggac cgggaggcgt cgaacggagg aacggttcat cttagagact    360

aattttctgg agtttctgcc cctgctctgc gtcagccctc acgtcacttc gccagcagta    420

gcagaggcgg cggcggcggc tcccggaatt gggttggagc aggagcctcg ctggctgctt    480

cgctcgcgct ctacgcgctc agtccccggc ggtagcagga gcctggaccc aggcgccgcc    540

ggcgggcgtg aggcgccgga gcccggcctc gaggtgcata ccggaccccc attcgcatct    600

aacaaggaat ctgcgcccca gagagtcccg ggagcgccgc cggtcggtgc ccggcgcgcc    660

gggccatgca gcgacggccg ccgcggagct ccgagcagcg gtagcgcccc cctgtaaagc    720

ggttcgctat gccggggcca ctgtgaaccc tgccgcctgc cggaacactc ttcgctccgg    780

accagctcag cctctgataa gctggactcg gcacgcccgc aacaagcacc gaggagttaa    840
```

-continued

```
gagagccgca agcgcaggga aggcctcccc gcacgggtgg gggaaagcgg ccggtgcagc    900
gcggggacag gcactcgggc tggcactggc tgctagggat gtcgtcctgg ataaggtggc    960
atggacccgc catggcgcgg ctctggggct tctgctggct ggttgtgggc ttctggaggg   1020
ccgctttcgc ctgtcccacg tcctgcaaat gcagtgcctc tcggatctgg tgcagcgacc   1080
cttctcctgg catcgtggca tttccgagat tggagcctaa cagtgtagat cctgagaaca   1140
tcaccgaaat tttcatcgca aaccagaaaa ggttagaaat catcaacgaa gatgatgttg   1200
aagcttatgt gggactgaga aatctgacaa ttgtggattc tggattaaaa tttgtggctc   1260
ataaagcatt tctgaaaaac agcaacctgc agcacatcaa ttttacccga aacaaactga   1320
cgagtttgtc taggaaacat ttccgtcacc ttgacttgtc tgaactgatc ctggtgggca   1380
atccatttac atgctcctgt gacattatgt ggatcaagac tctccaagag gctaaatcca   1440
gtccagacac tcaggatttg tactgcctga atgaaagcag caagaatatt cccctggcaa   1500
acctgcagat acccaattgt ggtttgccat ctgcaaatct ggccgcacct aacctcactg   1560
tggaggaagg aaagtctatc acattatcct gtagtgtggc aggtgatccg gttcctaata   1620
tgtattggga tgttggtaac ctggtttcca aacatatgaa tgaaacaagc cacacacagg   1680
gctccttaag gataactaac atttcatccg atgacagtgg gaagcagatc tcttgtgtgg   1740
cggaaaatct tgtaggagaa gatcaagatt ctgtcaacct cactgtgcat tttgcaccaa   1800
ctatcacatt tctcgaatct ccaacctcag accaccactg gtgcattcca ttcactgtga   1860
aaggcaaccc caaaccagcg cttcagtggt tctataacgg ggcaatattg aatgagtcca   1920
aatacatctg tactaaaata catgttacca atcacacgga gtaccacggc tgcctccagc   1980
tggataatcc cactcacatg aacaatgggg actacactct aatagccaag aatgagtatg   2040
ggaaggatga gaaacagatt tctgctcact tcatgggctg gcctggaatt gacgatggtg   2100
caaacccaaa ttatcctgat gtaatttatg aagattatgg aactgcagcg aatgacatcg   2160
gggacaccac gaacagaagt aatgaaatcc cttccacaga cgtcactgat aaaaccggtc   2220
gggaacatct ctcggtctat gctgtggtgg tgattgcgtc tgtggtggga ttttgccttt   2280
tggtaatgct gtttctgctt aagttggcaa gacactccaa gtttggcatg aaagatttct   2340
catggtttgg atttgggaaa gtaaaatcaa gacaaggtgt tggcccagcc tccgttatca   2400
gcaatgatga tgactctgcc agcccactcc atcacatctc caatgggagt aacactccat   2460
cttcttcgga aggtggccca gatgctgtca ttattggaat gaccaagatc cctgtcattg   2520
aaaatcccca gtactttggc atcaccaaca gtcagctcaa gccagacaca tttgttcagc   2580
acatcaagcg acataacatt gttctgaaaa gggagctagg cgaaggagcc tttggaaaag   2640
tgttcctagc tgaatgctat aacctctgtc ctgagcagga caagatcttg gtggcagtga   2700
agaccctgaa ggatgccagt gacaatgcac gcaaggactt ccaccgtgag gccgagctcc   2760
tgaccaacct ccagcatgag cacatcgtca agttctatgg cgtctgcgtg gagggcgacc   2820
ccctcatcat ggtctttgag tacatgaagc atggggacct caacaagttc ctcagggcac   2880
acggccctga tgccgtgctg atggctgagg gcaacccgcc cacggaactg acgcagtcgc   2940
agatgctgca tatagcccag cagatcgccg cgggcatggt ctacctggcg tcccagcact   3000
tcgtgcaccg cgatttggcc accaggaact gcctggtcgg ggagaacttg ctggtgaaaa   3060
tcggggactt tgggatgtcc cgggacgtgt acagcactga ctactacagg gtcggtggcc   3120
acacaatgct gcccattcgc tggatgcctc cagagagcat catgtacagg aaattcacga   3180
cggaaagcga cgtctggagc ctgggggtcg tgttgtggga gattttcacc tatggcaaac   3240
```

-continued

```
agccctggta ccagctgtca aacaatgagg tgatagagtg tatcactcag ggccgagtcc   3300
tgcagcgacc ccgcacgtgc ccccaggagg tgtatgagct gatgctgggg tgctggcagc   3360
gagagcccca catgaggaag aacatcaagg gcatccatac cctccttcag aacttggcca   3420
aggcatctcc ggtctacctg gacattctag gctagggccc ttttccccag accgatcctt   3480
cccaacgtac tcctcagacg ggctgagagg atgaacatct tttaactgcc gctggaggcc   3540
accaagctgc tctccttcac tctgacagta ttaacatcaa agactccgag aagctctcga   3600
gggaagcagt gtgtacttct tcatccatag acacagtatt gacttctttt tggcattatc   3660
tctttctctc tttccatctc ccttggttgt tccttttct ttttttaaat tttcttttc   3720
ttttttttt cgtcttccct gcttcacgat tcttaccctt tcttttgaat caatctggct   3780
tctgcattac tattaactct gcatagacaa aggccttaac aaacgtaatt tgttatatca   3840
gcagacactc cagtttgccc accacaacta acaatgcctt gttgtattcc tgcctttgat   3900
gtggatgaaa aaaagggaaa acaaatattt cacttaaact ttgtcacttc tgctgtacag   3960
atatcgagag tttctatgga ttcacttcta tttatttatt attattactg ttcttattgt   4020
ttttggatgg cttaagcctg tgtataaaaa agaaaacttg tgttcaatct gtgaagcctt   4080
tatctatggg agattaaaac cagagagaaa gaagatttat tatgaaccgc aatatgggag   4140
gaacaaagac aaccactggg atcagctggt gtcagtccct acttaggaaa tactcagcaa   4200
ctgttagctg ggaagaatgt attcggcacc ttcccctgag gacctttctg aggagtaaaa   4260
agactactgg cctctgtgcc atggatgatt cttttcccat caccagaaat gatagcgtgc   4320
agtagagagc aaagatggct tccgtgagac acaagatggc gcatagtgtg ctcggacaca   4380
gttttgtctt cgtaggttgt gatgatagca ctggtttgtt tctcaagcgc tatccacaga   4440
acctttgtca acttcagttg aaaagaggtg gattcatgtc cagagctcat ttcggggtca   4500
ggtgggaaag ccaagaactt ggaaaagata agacaagcta taaattcgga ggcaagtttc   4560
ttttacaatg aacttttcag atctcacttc cctccgaccc ctaacttcca tgcccacccg   4620
tcctttaac tgtgcaagca aaattgtgca tggtcttcgt cgattaatac cttgtgtgca   4680
gacactactg ctccagacgt cgtttccctg ataggtagag cagatccata aaaaggtatg   4740
acttatacaa ttaggggaag ctaatggagt ttattagctg agtatcaatg tctctgcgtt   4800
gtacggtggt gatgggtttt aatgaatatg gaccctgaag cctggaaatc ctcatccacg   4860
tcgaacccac aggactgtgg gaagggcaga atcaatccct aagggaaagg aaacctcacc   4920
ctgagggcat cacatgcact catgttcagt gtacacaggt caagtccctt gctctgggct   4980
ctagttggga gagtggtttc attccaagtg tactccattg tcagtatgct gtttttgttt   5040
ccttcactcc attcaaaaag tcaaaataca aaatttggca cagcatgcca acgggaggct   5100
gtgcccagac caagcactgg aagtgtgctt ctaggcatag tcattggttt tgcaaaaaga   5160
gggctcaaat ttaaatagaa atttacagct atttgaatgg tcagatatac caagaaagaa   5220
aaatatttct gttcctcaag aaaacttgct accctctgtg aggggaattt tgctaaactt   5280
gacatcttta taacatgagc cagattgaaa gggagtgatt ttcattcatc ttaggtcatg   5340
ttatttcata tttgtttctg aaggtgcgat agctctgttt taggttttgc ttgcgcctgt   5400
taattactgg aacaccttat ttttcattaa aggctttgaa agccaattct caaaaattca   5460
aaagtgcaaa ttaacagaac aaaaggaaat ccagtagcaa ctgcagtcaa gcgagggagt   5520
tgacaagata aaccttacgt ccattcaagt tatatgctgg cctatgagag atgagagttg   5580
```

ggtcgtttgt tctctttgtt gatgattt 5608

<210> SEQ ID NO 54
<211> LENGTH: 3600
<212> TYPE: DNA
<213> ORGANISM: Homo sapiens

<400> SEQUENCE: 54
gaagagactc agggcagagg gaggaaggac agcagaccag acagtcacag cagccttgac 60
aaaacgttcc tggaactcaa gctcttctcc acagaggagg acagagcaga cagcagagac 120
catggagtct ccctcggccc ctccccacag atggtgcatc cctggcagag gctcctgct 180 cacagcctca cttctaacct tctggaaccc gcccaccact gccaagctca ctattgaatc 240
cacgccgttc aatgtcgcag aggggaagga ggtgcttcta cttgtccaca atctgcccca 300
gcatcttttt ggctacagct ggtacaaagg tgaaagagtg gatggcaacc gtcaaattat 360
aggatatgta ataggaactc aacaagctac cccagggccc gcatacagtg gtcgagagat 420
aatatacccc aatgcatccc tgctgatcca gaacatcatc cagaatgaca caggattcta 480
caccctacac gtcataaagt cagatcttgt gaatgaagaa gcaactggcc agttccgggt 540
atacccggag ctgcccaagc cctccatctc cagcaacaac tccaaacccg tggaggacaa 600
ggatgctgtg gccttcacct gtgaacctga gactcaggac gcaacctacc tgtggtgggt 660
aaacaatcag agcctcccgg tcagtcccag gctgcagctg tccaatggca acaggaccct 720
cactctattc aatgtcacaa gaaatgacac agcaagctac aaatgtgaaa cccagaaccc 780
agtgagtgcc aggcgcagtg attcagtcat cctgaatgtc ctctatggcc cggatgcccc 840
caccatttcc cctctaaaca catcttacag atcaggggaa aatctgaacc tctcctgcca 900
cgcagcctct aacccacctg cacagtactc ttggtttgtc aatgggactt tccagcaatc 960
cacccaagag ctctttatcc ccaacatcac tgtgaataat agtggatcct atacgtgcca 1020
agcccataac tcagacactg gcctcaatag gaccacagtc acgacgatca cagtctatgc 1080
agagccaccc aaacccttca tcaccagcaa caactccaac cccgtggagg atgaggatgc 1140
tgtagcctta acctgtgaac ctgagattca gaacacaacc tacctgtggt gggtaaataa 1200
tcagagcctc ccggtcagtc ccaggctgca gctgtccaat gacaacagga ccctcactct 1260
actcagtgtc acaaggaatg atgtaggacc ctatgagtgt ggaatccaga acaaattaag 1320
tgttgaccac agcgacccag tcatcctgaa tgtcctctat ggcccagacg accccaccat 1380
ttccccctca tacacctatt accgtccagg ggtgaacctc agcctctcct gccatgcagc 1440
ctctaaccca cctgcacagt attcttggct gattgatggg aacatccagc aacacacaca 1500
agagctcttt atctccaaca tcactgagaa gaacagcgga ctctatacct gccaggccaa 1560
taactcagcc agtggccaca gcaggactac agtcaagaca atcacagtct ctgcggagct 1620
gcccaagccc tccatctcca gcaacaactc caaacccgtg gaggacaagg atgctgtggc 1680
cttcacctgt gaacctgagg ctcagaacac aacctacctg tggtgggtaa atggtcagag 1740
cctcccagtc agtcccaggc tgcagctgtc caatggcaac aggaccctca ctctattcaa 1800
tgtcacaaga aatgacgcaa gagcctatgt atgtggaatc cagaactcag tgagtgcaaa 1860
ccgcagtgac ccagtcaccc tggatgtcct ctatgggccg gacaccccca tcatttcccc 1920
cccagactcg tcttaccttt cgggagcgaa cctcaacctc tcctgccact cggcctctaa 1980
cccatccccg cagtattctt ggcgtatcaa tgggataccg cagcaacaca cacaagttct 2040
ctttatcgcc aaaatcacgc caaataataa cgggacctat gcctgttttg tctctaactt 2100

```
ggctactggc cgcaataatt ccatagtcaa gagcatcaca gtctctgcat ctggaacttc   2160

tcctggtctc tcagctgggg ccactgtcgg catcatgatt ggagtgctgg ttggggttgc   2220

tctgatatag cagccctggt gtagtttctt catttcagga agactgacag ttgttttgct   2280

tcttccttaa agcatttgca acagctacag tctaaaattg cttctttacc aaggatattt   2340

acagaaaaga ctctgaccag agatcgagac catcctagcc aacatcgtga aaccccatct   2400

ctactaaaaa tacaaaaatg agctgggctt ggtggcgcgc acctgtagtc ccagttactc   2460

gggaggctga ggcaggagaa tcgcttgaac ccgggaggtg gagattgcag tgagcccaga   2520

tcgcaccact gcactccagt ctggcaacag agcaagactc catctcaaaa agaaaagaaa   2580

agaagactct gacctgtact cttgaataca agtttctgat accactgcac tgtctgagaa   2640

tttccaaaac tttaatgaac taactgacag cttcatgaaa ctgtccacca agatcaagca   2700

gagaaaataa ttaatttcat gggactaaat gaactaatga ggataatatt ttcataattt   2760

tttatttgaa attttgctga ttctttaaat gtcttgtttc ccagatttca ggaaactttt   2820

tttcttttaa gctatccaca gcttacagca atttgataaa atatactttt gtgaacaaaa   2880

attgagacat ttacattttc tccctatgtg gtcgctccag acttgggaaa ctattcatga   2940

atatttatat tgtatggtaa tatagttatt gcacaagttc aataaaaatc tgctctttgt   3000

atgacagaat acatttgaaa acattggtta tattaccaag actttgacta gaatgtcgta   3060

tttgaggata taaacccata ggtaataaac ccacaggtac tacaaacaaa gtctgaagtc   3120

agccttggtt tggcttccta gtgtcaatta aacttctaaa agtttaatct gagattcctt   3180

ataaaaactt ccagcaaagc aactttaaaa aagtctgtgt gggccgggcg cggtggctca   3240

cgcctgtaat cccagcactt tgatccgccg aggcgggcgg atcacgaggt caggagatcc   3300

agaccatcct ggctaacaca gtgaaacccc gtctctacta aaaatacaaa aaaagttagc   3360

cgggcgtggt ggtgggggcc tgtagtccca gctactcagg aggctgaggc aggagaacgg   3420

catgaacccg ggaggcaggg cttgcagtga gccaagatca tgccgctgca ctccagcctg   3480

ggagacaaag tgagactccg tcaaaaaaaa aaaaaagtct atgtggtcag tcactactct   3540

tgctgcagtt atgaaaagaa tgaggccaag tctgatgaaa ataaacttat tttgaaaaca   3600
```

<210> SEQ ID NO 55
<211> LENGTH: 3095
<212> TYPE: DNA
<213> ORGANISM: Homo sapiens

<400> SEQUENCE: 55

```
attgctgatg gatcagtgag cctgtgttca tgccagtgag ctgctgtggc tcagatactg     60

atactttctt tccaaacagc ataagaagtg attgagccac aagtatactg aaggaagggc    120

tccctcgagt tctggtgtga agagataaat caccagtcac agactatgca cccgactgct    180

gctgttcagt ccagggaaaa tgaaagttgg agtgctgtgg ctcatttctt tcttcacctt    240

cactgacggc cacggtggct tcctggggaa aaatgatggc atcaaaacaa aaaaagaact    300

cattgtgaat aagaaaaaac atctaggccc agtcgaagaa tatcagctgc tgcttcaggt    360

gacctataga gattccaagg agaaaagaga tttgagaaat tttctgaagc tcttgaagcc    420

tccattatta tggtcacatg ggctaattag aattatcaga gcaaaggcta ccacagactg    480

caacagcctg aatggagtcc tgcagtgtac ctgtgaagac agctacacct ggtttcctcc    540

ctcatgcctt gatccccaga actgctacct tcacacggct ggagcactcc caagctgtga    600
```

-continued

```
atgtcatctc aacaacctca gccagagtgt caatttctgt gagagaacaa agatttgggg    660
cactttcaaa attaatgaaa ggtttacaaa tgaccttttg aattcatctt ctgctatata    720
ctccaaatat gcaaatggaa ttgaaattca acttaaaaaa gcatatgaaa gaattcaagg    780
ttttgagtcg gttcaggtca cccaatttcg aaatggaagc atcgttgctg ggtatgaagt    840
tgttggctcc agcagtgcat ctgaactgct gtcagccatt gaacatgttg ccgagaaggc    900
taagacagcc cttcacaagc tgtttccatt agaagacggc tctttcagag tgttcggaaa    960
agcccagtgt aatgacattg tctttggatt tgggtccaag gatgatgaat ataccctgcc   1020
ctgcagcagt ggctacaggg gaaacatcac agccaagtgt gagtcctctg ggtggcaggt   1080
catcagggag acttgtgtgc tctctctgct tgaagaactg aacaagaatt tcagtatgat   1140
tgtaggcaat gccactgagg cagctgtgtc atccttcgtg caaaatcttt ctgtcatcat   1200
tcggcaaaac ccatcaacca cagtggggaa tctggcttcg gtggtgtcga ttctgagcaa   1260
tatttcatct ctgtcactgg ccagccattt cagggtgtcc aattcaacaa tggaggatgt   1320
catcagtata gctgacaata tccttaattc agcctcagta accaactgga cagtcttact   1380
gcgggaagaa aagtatgcca gctcacggtt actagagaca ttagaaaaca tcagcactct   1440
ggtgcctccg acagctcttc ctctgaattt ttctcggaaa ttcattgact ggaaagggat   1500
tccagtgaac aaaagccaac tcaaaagggg ttacagctat cagattaaaa tgtgtcccca   1560
aaatacatct attcccatca gaggccgtgt gttaattggg tcagaccaat tccagagatc   1620
ccttccagaa actattatca gcatggcctc gttgactctg gggaacattc tacccgtttc   1680
caaaaatgga aatgctcagg tcaatggacc tgtgatatcc acggttattc aaaactattc   1740
cataaatgaa gttttcctat ttttttccaa gatagagtca aacctgagcc agcctcattg   1800
tgtgttttgg gatttcagtc atttgcagtg gaacgatgca ggctgccacc tagtgaatga   1860
aactcaagac atcgtgacgt gccaatgtac tcacttgacc tccttctcca tattgatgtc   1920
accttttgtc ccctctacaa tcttccccgt tgtaaaatgg atcacctatg tgggactggg   1980
tatctccatt ggaagtctca ttttatgcct gatcatcgag gctttgtttt ggaagcagat   2040
taaaaaaagc caaacctctc acacacgtcg tatttgcatg gtgaacatag ccctgtccct   2100
cttgattgct gatgtctggt ttattgttgg tgccacagtg gacaccacgg tgaacccttc   2160
tggagtctgc acagctgctg tgttctttac acacttcttc tacctctctt tgttcttctg   2220
gatgctcatg cttggcatcc tgctggctta ccggatcatc ctcgtgttcc atcacatggc   2280
ccagcatttg atgatggctg ttggattttg cctgggttat gggtgccctc tcattatatc   2340
tgtcattacc attgctgtca cgcaacctag caatacctac aaaaggaaag atgtgtgttg   2400
gcttaactgg tccaatggaa gcaaaccact cctggctttt gttgtccctg cactggctat   2460
tgtggctgtg aacttcgttg tggtgctgct agttctcaca aagctctgga ggccgactgt   2520
tggggaaaga ctgagtcggg atgacaaggc caccatcatc cgcgtgggga agagcctcct   2580
cattctgacc cctctgctag ggctcacctg gggctttgga ataggaacaa tagtggacag   2640
ccagaatctg gcttggcatg ttatttttgc tttactcaat gcattccagg gatttttat    2700
cttatgcttt ggaatactct tggacagtaa gctgcgacaa cttctgttca acaagttgtc   2760
tgccttaagt tcttggaagc aaacagaaaa gcaaaactca tcagatttat ctgccaaacc   2820
caaattctca aagcctttca acccactgca aaacaaaggc cattatgcat tttctcatac   2880
tggagattcc tccgacaaca tcatgctaac tcagtttgtc tcaaatgaat aaggcaagga   2940
atcataaaat caagaaaaaa tttccagaac aacttgacat ttagagacaa atgtcaatga   3000
```

agaaattatg ctcagtattc gatcgggttt tctgatttag gggtctggga ataaaacaag 3060
aatgtctcag tggcttcaaa aaaaaaaaaa aaaaa 3095

<210> SEQ ID NO 56
<211> LENGTH: 4071
<212> TYPE: DNA
<213> ORGANISM: Homo sapiens

<400> SEQUENCE: 56
tgattcgagc gggaagaggg gggtgggtgg gatcggtggg ggagaccatg acctccagct 60
acgggcacgt tctggagcgg caaccggcgc tgggcggccg cttggacagc ccgggcaacc 120
tcgacaccct gcaggcgaaa aagaacttct ccgtcagtca cctgctagac ctggaggaag 180
ccggggacat ggtggcggca caggcggatg agaacgtggg cgaggctggc cggagcctgc 240
tggagtcgcc gggactcacc agcggcagcg acaccccgca gcaggacaat gaccagctga 300
actcagaaga aaaaaagaag agaaagcagc gaaggaatag gacaaccttc aatagcagcc 360
agctgcaggc tttggagcgt gtctttgagc ggacacacta tcctgatgct tttgtgcgag 420
aagaccttgc ccgccgggtg aacctcaccg aggcgagagt gcaggtgtgg tttcagaacc 480
gaagagccaa gttccgcagg aatgagagag ccatgctagc caataaaaac gcttccctcc 540
tcaaatccta ctcaggagac gtgactgctg tggagcagcc catcgtacct cgtcctgctc 600
cgagacccac cgattatctc tcctgggga cagcgtctcc gtacagatcc tcgtccctcc 660
caagatgttg tttacacgag gggcttcata acggattcta acggaagaca ctgaaaagcg 720
ccatggctac ttattctgcc acatgtgcca acaatagccc tgcacagggc atcaacatgg 780
ccaacagcat tgccaacctg agactgaagg ccaaggaata tagtttacag aggaaccagg 840
tgccaacagt caactgagga aaaaaaataa ttaaacaggc ctaagaagaa atcaaaaacc 900
ataagacacc tatcctgctc tgttatttct tcatctgctg gggggaaaaa gtaaattaca 960
aacaaacaaa caaagcagaa ctaaaatatt gggaccatgg cagagaaaag caggagagga 1020
gcaaaatgaa aattagttaa caaatgttcc tcctccctct gggataccac caccacttgt 1080
ttctgtgtgt gtttattttg tttttctttc attcatgctt tgcttaatgt actccaggct 1140
tcttcagata ggttcagccc acccaccccc atgattgtat gaagttttaa aaaaaactac 1200
agcagccaaa gaaactatat atatatatat atatatatat atccagaatg attgcctcta 1260
ctgtcctcat tgacttgttt gaaccttagt gccttaccct gtcctcttcc cagttctctt 1320
tatagaagct ctaggagctt tcgaaaagcc aaagtctttc tgaagaatct gtgctggaca 1380
gacataattc cctttctcat tgtctccatc tttgttggtc atggtaaggt ttttccatca 1440
gcctctgaaa aaatagttgt gcacaacatc tgctcactgg actgtctgat ccaatgtaat 1500
tggctgcgtc tggctaattc taagcactaa agtctacatc taagctatag atttaagctt 1560
gaagctacag attatatcac tatcaccacc acccctcacc ctatgcaatc aatcaatcaa 1620
tcatcttaag ttaaagatat ttgttgtctt tgaatgattt gctgtcacag actatttggt 1680
agaagaaata tttttcacct gagagaggaa gagaaatttc tctagtaaca caaagagtga 1740
gttctaaaag gcatgcccac atctctttcg tgccttaagg atagtgagat gcacacttat 1800
atatatactg tatatattta tatatttata tatatatttc atatatatat ataatattgc 1860
aagcttaagt ttgcaatttc ccaaacaata caaaaagcaa attacacacc ctcaccactg 1920
ttcttatctc tatagtgatg aaacattaat tagggatctt gctgcttttc tttttctaca 1980

```
cgaagttttc attaaagcca cagaataatt gatagggcag ctgtttgaga acaggtccca   2040
ttttcacatt agggctttaa atgaattaga aactatttga ggctataaaa atgtccttga   2100
gtttggagcc tgagctctgg tgaaatgctg atacatctga tctatcatgg gaattgcagt   2160
tagagagagt aaggaatacc atttagtcat ctatccgttc ttcacttagc aggaatatga   2220
aagaaaggca catgtttaag aggaatacct aaaggttttt ctaaattcca acatttaaaa   2280
ggcaattgtg ggctattttt atttttttaat attttgaaat aaagtttagt gtctagggct   2340
gggagccagg actgatcttc catttctttt tctttgttcc cagccatgct tttgtaactt   2400
gccaggtgga cttgaccaac tacattacca tgctgtgcct cagtttaccc atttgtaaaa   2460
tgggattaat aatacttacc tacctcacag gggtgttgtg aggctctatt catttgctcc   2520
tttattcttt cctgtattct ctgtatgtcc agcactttgt agccatggga ggaaagggac   2580
tataaaagtg tacaatgtta atggaatgat acggtacctg aaagccttgt tttctagtaa   2640
gaaaatgcta ccttgctgta catacttata accttgtatt tggaaatgag aaataggttt   2700
atattttcag atctctcaaa aatcacatca tttgaccaaa gaataattta agacacatag   2760
aacagatttt tttaatttat attttcatcc tgaccagctt agttctaata atttttagtt   2820
gtgagtgatt aaaaaacttt ggatcaattt tggtcaaaca tgccaacttt gtagtctgag   2880
tgacaggcaa ggatttttgg gtttaagatg cacttttagc acacatttgt atttcccttg   2940
gcatatcaga ttgagctaat ggtgatgtta tttcaatcta acagccacca atctgaaatt   3000
gtatttcaaa tgttgattct gtagttcttt aaataataat gaagctcatc ttatacattt   3060
tgctttcacc aattgattcc ttcttctttt agcccactat taaaacattt cttactgaat   3120
ggttcatgta ggcttgctga acagcacgca ttacttgctt cctgaagagt tcccccattc   3180
atccatttgt cccattagtt gctgtggatt atcaagtttt gaaggaactg tacatcccaa   3240
cagactgaaa cattctaagt gaaatgagta taatccaagt aactggtgaa ctttggaggt   3300
ttggagcttg aagagaatgg ctaagaagat ttgaattata gggagggaac agaaatcata   3360
catgaaaagg ttttactgag aaggggaaaa ccttagatag agggacatgt gaaacaaaat   3420
catttgaaat tttgattcag acatccattt ccagtggcaa acagcaaagc ctgaacccat   3480
aaacccaaat gataggtgaa gttgggtggt tttatccaat gtctcaagca agcaatgtct   3540
gggaatatca tagagtaaca agtgctggtc agccaaagaa acattcactg ctggtgaacc   3600
aataccataa gcatgtatta tctaagcact tgatcaagaa atatacatgt tgtacaagct   3660
ctcaattttg ttcatttatt atcaaatttt taaaatacaa gtttggtatg tgatttggaa   3720
aagatgcctt ctggatctta agccagttgt cagtggaggt cctcagggct gcaaatgtca   3780
agacataacc ctgttcctca ccatcatgat accagataca ggtgaataca taggaactat   3840
ctgcctgtgt cctcaatctc ccttcaaaca agatgctgat ttgtagggta cttggcaggt   3900
taaattaaac cagaagaggt gacttaataa aaaagggaat gacatttagg gtataaagat   3960
ctcataagaa atgtaatatg taaattatat cttgctttat gttgtaaaat atacattgtt   4020
tgcgctagaa tagaaatgat ttcttttcaa taaaaagaaa gaaggactct a            4071
```

<210> SEQ ID NO 57
<211> LENGTH: 3999
<212> TYPE: DNA
<213> ORGANISM: Homo sapiens

<400> SEQUENCE: 57

```
tgattcgagc gggaagaggg gggtgggtgg gatcggtggg ggagaccatg acctccagct     60
```

```
acgggcacgt tctggagcgg caaccggcgc tgggcggccg cttggacagc ccgggcaacc    120
tcgacaccct gcaggcgaaa aagaacttct ccgtcagtca cctgctagac ctggaggaag    180
ccggggacat ggtggcggca caggcggatg agaacgtggg cgaggctggc cggagcctgc    240
tggagtcgcc gggactcacc agcggcagcg acaccccgca gcaggacaat gaccagctga    300
actcagaaga aaaaaagaag agaaagcagc gaaggaatag gacaaccttc aatagcagcc    360
agctgcaggc tttggagcgt gtctttgagc ggacacacta tcctgatgct tttgtgcgag    420
aagaccttgc ccgccgggtg aacctcaccg aggcgagagt gcaggtgtgg tttcagaacc    480
gaagagccaa gttccgcagg aatgagagag ccatgctagc caataaaaac gcttccctcc    540
tcaaatccta ctcaggagac gtgactgctg tggagcagcc catcgtacct cgtcctgctc    600
cgagacccac cgattatctc tcctggggga cagcgtctcc gtacagcgcc atggctactt    660
attctgccac atgtgccaac aatagccctg cacagggcat caacatggcc aacagcattg    720
ccaacctgag actgaaggcc aaggaatata gtttacagag gaaccaggtg ccaacagtca    780
actgaggaaa aaaaataatt aaacaggcct aagaagaaat caaaaaccat aagacaccta    840
tcctgctctg ttatttcttc atctgctggg gggaaaaagt aaattacaaa caaacaaaca    900
aagcagaact aaaatattgg gaccatggca gagaaaagca ggagaggagc aaaatgaaaa    960
ttagttaaca aatgttcctc ctccctctgg gataccacca ccacttgttt ctgtgtgtgt   1020
ttattttgtt tttctttcat tcatgctttg cttaatgtac tccaggcttc ttcagatagg   1080
ttcagcccac ccacccccat gattgtatga agttttaaaa aaaactacag cagccaaaga   1140
aactatatat atatatatat atatatatat ccagaatgat tgcctctact gtcctcattg   1200
acttgtttga accttagtgc cttaccctgt cctcttccca gttctcttta tagaagctct   1260
aggagctttc gaaaagccaa agtctttctg aagaatctgt gctggacaga cataattccc   1320
tttctcattg tctccatctt tgttggtcat ggtaaggttt ttccatcagc ctctgaaaaa   1380
atagttgtgc acaacatctg ctcactggac tgtctgatcc aatgtaattg gctgcgtctg   1440
gctaattcta agcactaaag tctacatcta agctatagat ttaagcttga agctacagat   1500
tatatcacta tcaccaccac ccctcaccct atgcaatcaa tcaatcaatc atcttaagtt   1560
aaagatattt gttgtctttg aatgatttgc tgtcacagac tatttggtag aagaaatatt   1620
tttcacctga gagaggaaga gaaatttctc tagtaacaca aagagtgagt tctaaaaggc   1680
atgcccacat ctctttcgtg ccttaaggat agtgagatgc acacttatat atatactgta   1740
tatatttata tatttatata tatatttcat atatatatat aatattgcaa gcttaagttt   1800
gcaatttccc aaacaataca aaaagcaaat tacacaccct caccactgtt cttatctcta   1860
tagtgatgaa acattaatta gggatcttgc tgcttttctt tttctacacg aagttttcat   1920
taaagccaca gaataattga tagggcagct gtttgagaac aggtcccatt ttcacattag   1980
ggctttaaat gaattagaaa ctatttgagg ctataaaaat gtccttgagt ttggagcctg   2040
agctctggtg aaatgctgat acatctgatc tatcatggga attgcagtta gagagagtaa   2100
ggaataccat ttagtcatct atccgttctt cacttagcag gaatatgaaa gaaaggcaca   2160
tgtttaagag gaatacctaa aggtttttct aaattccaac atttaaaagg caattgtggg   2220
ctatttttat tttttaatat tttgaaataa agtttagtgt ctagggctgg gagccaggac   2280
tgatcttcca tttctttttc tttgttccca gccatgcttt tgtaacttgc caggtggact   2340
tgaccaacta cattaccatg ctgtgcctca gtttacccat ttgtaaaatg ggattaataa   2400
```

```
tacttaccta cctcacaggg gtgttgtgag gctctattca tttgctcctt tattctttcc   2460
tgtattctct gtatgtccag cactttgtag ccatgggagg aaagggacta taaaagtgta   2520
caatgttaat ggaatgatac ggtacctgaa agccttgttt tctagtaaga aaatgctacc   2580
ttgctgtaca tacttataac cttgtatttg gaaatgagaa ataggtttat attttcagat   2640
ctctcaaaaa tcacatcatt tgaccaaaga ataatttaag acacatagaa cagatttttt   2700
taatttatat tttcatcctg accagcttag ttctaataat tttagttgt gagtgattaa   2760
aaaactttgg atcaattttg gtcaaacatg ccaactttgt agtctgagtg acaggcaagg   2820
atttttgggt ttaagatgca cttttagcac acatttgtat ttcccttggc atatcagatt   2880
gagctaatgg tgatgttatt tcaatctaac agccaccaat ctgaaattgt atttcaaatg   2940
ttgattctgt agttctttaa ataataatga agctcatctt atacattttg ctttcaccaa   3000
ttgattcctt cttcttttag cccactatta aaacatttct tactgaatgg ttcatgtagg   3060
cttgctgaac agcacgcatt acttgcttcc tgaagagttc ccccattcat ccatttgtcc   3120
cattagttgc tgtggattat caagttttga aggaactgta catcccaaca gactgaaaca   3180
ttctaagtga aatgagtata atccaagtaa ctggtgaact ttggaggttt ggagcttgaa   3240
gagaatggct aagaagattt gaattatagg gagggaacag aaatcataca tgaaaaggtt   3300
ttactgagaa ggggaaaacc ttagatagag ggacatgtga aacaaaatca tttgaaattt   3360
tgattcagac atccatttcc agtggcaaac agcaaagcct gaacccataa acccaaatga   3420
taggtgaagt tgggtggttt tatccaatgt ctcaagcaag caatgtctgg gaatatcata   3480
gagtaacaag tgctggtcag ccaaagaaac attcactgct ggtgaaccaa taccataagc   3540
atgtattatc taagcacttg atcaagaaat atacatgttg tacaagctct caattttgtt   3600
catttattat caaattttta aaatacaagt ttggtatgtg atttggaaaa gatgccttct   3660
ggatcttaag ccagttgtca gtggaggtcc tcagggctgc aaatgtcaag acataaccct   3720
gttcctcacc atcatgatac cagatacagg tgaatacata ggaactatct gcctgtgtcc   3780
tcaatctccc ttcaaacaag atgctgattt gtagggtact tggcaggtta aattaaacca   3840
gaagaggtga cttaataaaa aagggaatga catttagggt ataaagatct cataagaaat   3900
gtaatatgta aattatatct tgctttatgt tgtaaaatat acattgtttg cgctagaata   3960
gaaatgattt cttttcaata aaaagaaaga aggactcta                          3999
```

<210> SEQ ID NO 58
<211> LENGTH: 2466
<212> TYPE: DNA
<213> ORGANISM: Homo sapiens

<400> SEQUENCE: 58

```
ggctgagtgg tttgctcctt cccctctctc tgggaggctg agcaggggtg ccgggttgct     60
caggccatgg gagccacacc tgttattgct gcctctgatt tgtgtgacac tgagaagccc    120
acaggcctgt ccctccaact cggtggaccc tctctgtgtg catttggtgt gtgagccagc    180
tctgagaagg gttcagaagc cactggaggc atctggggac ctcagcttcc atgccatctc    240
tgcctcactc ccacagggta atgttggact cggtgacaca cagcaccttc ctgcctaatg    300
catccttctg cgatcccctg atgtcgtgga ctgatctgtt cagcaatgaa gagtactacc    360
ctgcctttga gcatcagaca gcctgtgact catactggac atcagtccac cctgaatact    420
ggactaagcg ccatgtgtgg gagtggctcc agttctgctg cgaccagtac aagttggaca    480
ccaattgcat ctccttctgc aacttcaaca tcagtggcct gcagctgtgc agcatgacac    540
```

-continued

```
aggaggagtt cgtcgaggca gctggcctct gcggcgagta cctgtacttc atcctccaga    600
acatccgcac acaaggttac tcctttttta atgacgctga agaaagcaag gccaccatca    660
aagactatgc tgattccaac tgcttgaaaa caagtggcat caaaagtcaa gactgtcaca    720
gtcatagtag aacaagcctc caaagttctc atctatggga atttgtacga gacctgcttc    780
tatctcctga agaaaactgt ggcattctgg aatgggaaga tagggaacaa ggaatttttc    840
gggtggttaa atcggaagcc ctggcaaaga tgtggggaca aaggaagaaa aatgacagaa    900
tgacatatga aaagttgagc agagccctga gatactacta taaaacagga attttggagc    960
gggttgaccg aaggttagtg tacaaatttg gaaaaaatgc acacgggtgg caggaagaca   1020
agctatgatc tgctccaggc atcaagctca ttttatggat ttctgtcttt taaaacaatc   1080
agattgcaat agacattcga aaggcttcat ttttcttctct tttttttttaa cctgcaaaca   1140
tgctgataaa atttctccac atctcagctt acatttggat tcagagttgt tgtctacgga   1200
gggtgagagc agaaactctt aagaaatcct ttcttctccc taaggggatg aggggatgat   1260
cttttgtggt gtcttgatca aactttattt tcctagagtt gtggaatgac aacagcccat   1320
gccattgatg ctgatcagag aaaaactatt caattctgcc attagagaca catccaatgc   1380
tcccatccca aaggttcaaa agttttcaaa taactgtggc agctcaccaa aggtggggga   1440
aagcatgatt agtttgcagg ttatggtagg agagggtgag atataagaca tacatacttt   1500
agattttaaa ttattaaagt caaaaatcca tagaaaagta tcccttttttt tttttttgag   1560
acgggttctc actatgttgc ccagggctgg tcttgaactc ctatgctcaa gtgatcctcc   1620
cacctcggcc tcccaaagta ctgtgattac aagcgtgagc cacggcacct gggcagaaaa   1680
gtatcttaat taatgaaaga gctaagccat caagctggga cttaattgga tttaacatag   1740
gttcacagaa agtttcctaa ccagagcatc tttttgacca ctcagcaaaa cttccacaga   1800
catccttctg gacttaaaca cttaacatta accacattat taattgttgc tgagtttatt   1860
ccccctcta actgatggct ggcatctgat atgcagagtt agtcaacaga cactggcatc   1920
aattacaaaa tcactgctgt ttctgtgatt caagctgtca acacaataaa atcgaaattc   1980
attgattcca tctctggtcc agatgttaaa cgtttataaa accggaaatg tcctaacaac   2040
tctgtaatgg caaattaaat tgtgtgtctt ttttgttttg tctttctacc tgatgtgtat   2100
tcaagcgcta taacacgtat ttccttgaca aaaatagtga cagtgaattc acactaataa   2160
atgttcatag gttaaagtct gcactgacat tttctcatca atcactggta tgtaagttat   2220
cagtgactga cagctaggtg gactgcccct aggacttctg tttcaccaga gcaggaatca   2280
agtggtgagg cactgaatcg ctgtacaggc tgaagacctc cttattagag ttgaacttca   2340
aagtaacttg ttttaaaaaa tgtgaattac tgtaaaataa tctattttgg attcatgtgt   2400
tttccaggtg gatatagttt gtaaacaatg tgaataaagt atttaacatg taaaaaaaaa   2460
aaaaaa                                                              2466
```

<210> SEQ ID NO 59
<211> LENGTH: 3127
<212> TYPE: DNA
<213> ORGANISM: Homo sapiens

<400> SEQUENCE: 59

```
gaagctccac accagccatt acaaccctgc caatctcaag cacctgcctc tacagttggt     60
acagatggca ttgtcccagt ctgttccctt ctcggccaca gagcttctcc tggcctctgc    120
```

-continued

```
catcttctgc ctggtattct gggtgctcaa gggtttgagg cctcgggtcc ccaaaggcct    180
gaaaagtcca ccagagccat ggggctggcc cttgctcggg catgtgctga ccctggggaa    240
gaacccgcac ctggcactgt caaggatgag ccagcgctac ggggacgtcc tgcagatccg    300
cattggctcc acgcccgtgc tggtgctgag ccgcctggac accatccggc aggccctggt    360
gcggcagggc gacgatttca agggccggcc tgacctctac acctccaccc tcatcactga    420
tggccagagc ttgaccttca gcacagactc tggaccggtg tgggctgccc gccggcgcct    480
ggcccagaat gccctcaaca ccttctccat cgcctctgac ccagcttcct catcctcctg    540
ctacctggag gagcatgtga gcaaggaggc taaggccctg atcagcaggt tgcaggagct    600
gatggcaggg cctgggcact tcgaccctta caatcaggtg gtggtgtcag tggccaacgt    660
cattggtgcc atgtgcttcg gacagcactt ccctgagagt agcgatgaga tgctcagcct    720
cgtgaagaac actcatgagt tcgtggagac tgcctcctcc gggaaccccc tggacttctt    780
ccccatcctt cgctacctgc ctaaccctgc cctgcagagg ttcaaggcct tcaaccagag    840
gttcctgtgg ttcctgcaga aaacagtcca ggagcactat caggactttg acaagaacag    900
tgtccgggac atcacgggtg ccctgttcaa gcacagcaag aaggggccta gagccagcgg    960
caacctcatc ccacaggaga agattgtcaa ccttgtcaat gacatctttg gagcaggatt   1020
tgacacagtc accacagcca tctcctggag cctcatgtac cttgtgacca agcctgagat   1080
acagaggaag atccagaagg agctggacac tgtgattggc agggagcggc ggccccggct   1140
ctctgacaga ccccagctgc cctacttgga ggccttcatc ctggagacct tccgacactc   1200
ctccttcttg cccttcacca tcccccacag cacaacaagg gacacaacgc tgaatggctt   1260
ctacatcccc aagaaatgct gtgtcttcgt aaaccagtgg caggtcaacc atgacccaga   1320
gctgtgggag gacccctctg agttccggcc tgagcggttc ctcaccgccg atggcactgc   1380
cattaacaag cccttgagtg agaagatgat gctgtttggc atgggcaagc gccggtgtat   1440
cggggaagtc ctggccaagt gggagatctt cctcttcctg gccatcctgc tacagcaact   1500
ggagttcagc gtgccgccgg gcgtgaaagt cgacctgacc cccatctacg ggctgaccat   1560
gaagcacgcc cgctgtgaac atgtccaggc gcggctgcgc ttctccatca attgaagaag   1620
acaccaccat tctgaggcca gggagcgagt gggggccagc cacggggact cagcccttgt   1680
ttctcttcct ttcttttttt aaaaaatagc agctttagcc aagtgcaggg cctgtaatcc   1740
cagcatttta ggaggccaag gttggaggat catttgagcc caggaattgg aaagcagcct   1800
ggccaacata gtgggaccct gtctctacaa aaaaaaaatt tgccaagagc ctgagtgaca   1860
gagcaagacc ccatctcaaa aaaaaaaaca aacaaacaaa aaaaaaacca tatatataca   1920
tatatatata gcagctttat ggagatataa ttcttatgcc atataattca ccttcttttt   1980
tttttttgt ctgagacaga atctcagtct gtcacccagg ttggagtgca gtggcgtgat   2040
ctcagctcac tgcaacctcc acctcgcagg ttcaagcaat cctcccactt cagcctccca   2100
agcacctggg attacaagca tgagtcacta cgcctggctg atttttgtag ttttagtgga   2160
gatggggttt caccatgttg gccaggcttg tctcgaactc ctgaccccaa gttatccacc   2220
tgccttggct tcccaaagtc ctgggattac aggtgtgagc caccacatcc agcctaactt   2280
acattcttaa agtgtcgaat gacttctagt gtagaattgt gcaaccatca ccagaattaa   2340
ttttattatt cttattattt ttgagacaga gtcttactct gttgccaggc tggagtgcag   2400
tggcgcgatc tcagctcact acaacctccg cctcccatgt tcaagcgatt ctcctgcctc   2460
agcctcccga gtagctggga ctataggcat gcgccaccat ggccagctaa tttttgtatt   2520
```

```
tttagtagag acgaggtttc actgtgttgg ccaggatggt ctccatctct tgacctcgtg    2580

atccacccgc ctcagcctcc caaagtgctg ggattaacag gtatgaacca ccgcgcccag    2640

cctttttgtt tttttttttt ttgagacaga gtcttcctct gtctcctaag ctggagtgca    2700

gtggcatcat ctcagctcac tgcaacctct gcctcccagg ttcaagtgct tctccagcct    2760

cagcctccca agtagctgag actacaggca cacaccacca cgcctggcta atttttgtat    2820

ttttagtaga gacgggtttc accatgttgg ctagactagt ctcaaactcc tgacctcaag    2880

tgatctgccc gcctcgacct ctctcaaagt gctggcatta caggtgtgag ccacggtgcc    2940

cggcccacaa ttaattttag aacattttca tcaccoctaa aagaaaccct gcacccatta    3000

gcagtccctc cacatttccc cctagcctgc ctcccctgcc tcaccagccc tggcaactgc    3060

taatctactt tctgtgtcta tggatttgcc ttctctaaac atttcatata aatggaatta    3120

cacaatg                                                             3127
```

METHODS OF DIAGNOSING CHRONIC OBSTRUCTIVE PULMONARY DISEASE (COPD) USING NOVEL MOLECULAR BIOMARKERS

This application is a divisional of U.S. application Ser. No. 15/316,105, filed Dec. 2, 2016, which is a national phase application under 35 U.S.C. § 371 of International Application No. PCT/EP2015/062431, filed Jun. 3, 2015, which claims benefit of European Application No. 14171388.3, filed Jun. 5, 2014, the entire contents of each of which are hereby incorporated by reference.

The present invention relates to in vitro methods for the diagnosis of chronic obstructive pulmonary disease (COPD), wherein the expression of the marker gene DMBT1 is determined. In particular, the invention relates to an in vitro diagnostic method of assessing the susceptibility of a subject to develop progressive COPD involving the appearance of irreversible lung damage, wherein the expression of the marker gene DMBT1 and optionally one or more further marker genes selected from KIAA1199, TMSB15A, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL is determined. The invention also relates to an in vitro method of diagnosing stable COPD or assessing the susceptibility of a subject to develop stable COPD, wherein the expression of DMBT1 and optionally one or more further marker genes selected from KIAA1199, TMSB15A, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL is determined. Furthermore, the invention relates to the use of primers for transcripts of the aforementioned marker genes, the use of nucleic acid probes to transcripts of these marker genes, the use of microarrays comprising nucleic acid probes to transcripts of these marker genes, and the use of antibodies against the proteins expressed from these marker genes in corresponding in vitro methods. In vitro methods of monitoring the progression of COPD are also provided, in which the expression of marker genes according to the invention is determined.

COPD represents one of the leading pathologies of the world's elderly population. Triggered by long-term exposure to combustion products, climatic conditions and repeated infections, COPD has become the fourth-leading cause of mortality in aged individuals. During the last decades, the worldwide prevalence of COPD has risen by more than 10%, particularly in active smokers beyond the age of 55 (Murray et al., 1997). Given the increasing number of elderly people in the world's population and the world-wide increase of inhalative hazards, both occupational and personal, COPD must be regarded as one of the most challenging threats to the world's health systems (Halbert et al., 2006; US Burden of Disease Collaborators, 2013). However, although the impact of COPD on health conditions is increasingly understood, the mechanisms that cause and maintain the progression of the disease are largely unknown. Based on clinical experience and results of controlled studies, COPD is regarded as a largely inflammatory disease. However, while long-term anti-inflammatory treatment may improve the outcome in COPD, its impact on the overall pathology of the disease is less clear. The TORCH (TOwards a Revolution in COPD Health) study has clearly shown that this unilateral view upon the pathophysiology of COPD is not entirely correct as patients who were under continuous treatment with inhaled corticosteroids did not have a better outcome than those without. In line with this, several well-defined clinical trials have tried to stratify patients according to relevant clinical phenotypes, the ECLIPSE (Evaluation of COPD Longitudinally to Identify Predictive Surrogate Endpoints) study being the latest and most important attempt thus far (Vestbo et al., 2011). While these attempts have proven the remarkable heterogeneity of the clinical manifestations of COPD, they unfortunately failed to improve the understanding of the disease's central driving forces, their mediators, and their hierarchy in evoking the clinical phenotypes of COPD.

Until recently, COPD has been largely defined by the limitation of the maximum volume of air exhaled in one second during forced expiration ($FEV_1$), as well as by the total amount of air exhaled (forced [expiratory] vital capacity, FVC), and their respective relationship (Wedzicha J A, 2000). However, the variability of the clinical presentation of COPD regardless of any individual degree of airflow limitation suggested that the disease comprises different mechanisms related to bronchial and peribronchial pathologies (Hurst et al., 2010; Han et al., 2010). As a consequence, further clinical measures have been added to the diagnostic process in COPD, such as the intensity of bronchial inflammation, the frequency of disease exacerbations or the presence of comorbidities (Vestbo et al., 2013).

Not surprisingly, $FEV_1$ does not correlate well with symptom development. However, many studies have clearly demonstrated that $FEV_1$ is a strong predictor of mortality and morbidity in COPD, suggesting a relevant correlation between the (morphologically fixed) obstruction of the peripheral airways and the pathophysiology of the disease. Given the probability that the morphology of the small airways is going to reflect the pathologic net result of all metabolic events within this lung compartment, including chronic inflammatory and regenerative activities, this is more than plausible. Based on these facts, it still seems appropriate to apply the symptoms of the most established clinical manifestations of COPD, i.e. fixed bronchial obstruction and intensity of bronchitis as the main clinical indicators for a first attempt to delineate mechanisms and mediators capable of driving the pathology of COPD. In view of the well-documented long-term history of COPD often covering periods of more than two decades, any attempt to delineate the pathology of the disease ought to a) cover the earliest phase of pathologic development, the establishment of chronic bronchitis (COPD "at risk" according to the GOLD (Global Initiative on Obstructive Lung Disease) criteria) likely to precede the first manifestation of "irreversible" bronchial obstruction, b) to include both long-term development of the disease preceding the controlled phase of clinical assessment and c) to span a period long enough to allow for the identification of important short-range effects on COPD pathology. Lastly, as the pathology of COPD is focused in the small airways (Hogg J C, et al., 2004 (a)), the initial biological assessment ought to be performed in this compartment, regardless of the fact that some characteristic symptoms, such as the production of phlegm as a sign of intensified bronchitis, will also reflect the metabolic activity of the more central airways.

COPD progressively debilitates patients, resulting in an increasing disability and worsening impact of exacerbations. In particular, the development of irreversible damage to the lungs commences and then gradually worsens when a patient suffering from COPD advances from the stable early disease stage into the progressive stage of COPD. Unfortunately, many patients with COPD remain undiagnosed and potentially unknown to healthcare providers until the more advanced stages of the disease. In such cases, the delayed diagnosis of COPD results in patients suffering from symptoms and limitations that could otherwise be alleviated by treatment (Price et al., 2011). It would therefore be highly desirable to be able to diagnose COPD at an early disease stage and, in particular, to identify patients who are at risk of developing progressive COPD in order to be able to prevent these patients from suffering significant irreversible damage.

It is therefore an object of the present invention to provide novel and/or improved methods that allow to diagnose COPD at an early disease stage or to assess the risk or susceptibility of a subject to develop COPD. It is furthermore an object of the invention to provide novel and/or improved methods that allow to assess the susceptibility of a subject to develop progressive COPD.

The present invention is based on the unexpected finding that the gene DMBT1 as well as the genes KIAA1199, TMSB15A, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL are differentially expressed in samples from subjects suffering from progressive COPD or subjects at risk/prone to develop progressive COPD on the one hand, and in control samples from healthy subjects on the other hand. In particular, and as also described in Example 1, it has been found that the expression of the genes DMBT1, KIAA1199, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and COMP is upregulated in samples from patients suffering from progressive COPD or at risk of developing progressive COPD, while the expression of the genes TMSB15A, DPP6, SLC51B, NUDT11, PLA1A, HYAL2, CST6, ITGA10, CTHRC1, TAL1, FIBIN, BEX5, BEX1, ESM1 and GHRL is downregulated in samples from patients suffering from progressive COPD or at risk of developing progressive COPD, as compared to the expression of the corresponding genes in control samples from healthy patients. Therefore, in accordance with the present invention, these novel molecular biomarkers can advantageously be used for assessing the susceptibility/proneness of a subject to develop progressive COPD. It has further been surprisingly found that the genes DMBT1, KIAA1199, TMSB15A, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL are differentially expressed in samples from subjects suffering from stable COPD or subjects at risk/prone to develop stable COPD on the one hand, and in control samples from healthy subjects on the other hand. In this connection, it has particularly been found that the expression of the genes KIAA1199, TMSB15A, DPP6, SLC51B, NUDT11, PLA1A, HYAL2, CST6, ITGA10, CTHRC1, TAL1, FIBIN, BEX5, BEX1, ESM1 and GHRL is downregulated in samples from patients having stable COPD or at risk of developing stable COPD, while the expression of the genes DMBT1, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and COMP is upregulated in samples from patients having stable COPD or at risk of developing stable COPD, as compared to the expression of the corresponding genes in control samples from healthy patients. In accordance with the present invention, these novel molecular biomarkers can thus be used for diagnosing stable COPD and/or assessing the susceptibility/proneness of a subject to develop stable COPD. Moreover, the biomarkers provided herein have excellent sensitivity and/or specificity.

Accordingly, in a first aspect the present invention provides an in vitro method for the diagnosis of COPD, the method comprising determining the level of expression of the gene DMBT1 in a sample obtained from a subject.

In accordance with this first aspect, the invention also relates to the use of DMBT1 as a marker for the in vitro diagnosis of COPD.

In a second aspect, the present invention provides an in vitro diagnostic method of assessing the susceptibility of a subject to develop progressive COPD involving the appearance of irreversible lung damage, the method comprising:

- determining the level of expression of the gene DMBT1 in a sample obtained from the subject;
- comparing the level of expression of DMBT1 in the sample from the subject to a control expression level of DMBT1 in a healthy subject; and
- determining whether or not the subject is prone to develop progressive COPD involving the appearance of irreversible lung damage, wherein an increase in the level of expression of DMBT1 in the sample from the subject as compared to the control expression level of DMBT1 is indicative of a proneness to develop progressive COPD.

It is preferred that in this second aspect the method further comprises:

- determining the level of expression of one or more further genes selected from KIAA1199, TMSB15A, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL in the sample obtained from the subject;
- comparing the level of expression of the one or more further genes to a control expression level of the corresponding gene(s) in a healthy subject; and
- determining whether or not the subject is prone to develop progressive COPD involving the appearance of irreversible lung damage, wherein an increase in the level of expression of DMBT1, KIAA1199, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the sample from the subject as compared to the control expression level of the corresponding gene(s) is indicative of a proneness to develop progressive COPD, and wherein a decrease in the level of expression of TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject as compared to the control expression level of the corresponding gene(s) is indicative of a proneness to develop progressive COPD.

In a third aspect, the invention provides an in vitro method of diagnosing stable COPD in a subject or assessing the susceptibility of a subject to develop stable COPD, the method comprising:

determining the level of expression of the gene DMBT1 in a sample obtained from the subject;

comparing the level of expression of DMBT1 in the sample from the subject to a control expression level of DMBT1 in a healthy subject; and determining whether or not the subject suffers from stable COPD or is prone to suffer from stable COPD, wherein an increase in the level of expression of DMBT1 in the sample from the subject as compared to the control expression level of DMBT1 is indicative of stable COPD or a proneness to stable COPD.

The method according to this third aspect preferably further comprises:

determining the level of expression of one or more further genes selected from KIAA1199, TMSB15A, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL in the sample obtained from the subject;

comparing the level of expression of the one or more further genes to a control expression level of the corresponding gene(s) in a healthy subject; and determining whether or not the subject suffers from stable COPD or is prone to suffer from stable COPD, wherein an increase in the level of expression of DMBT1, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the sample from the subject as compared to the control expression level of the corresponding gene(s) is indicative of stable COPD or a proneness to stable COPD, and wherein a decrease in the level of expression of KIAA1199, TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject as compared to the control expression level of the corresponding gene(s) is indicative of stable COPD or a proneness to stable COPD.

In a fourth aspect, the invention relates to an in vitro diagnostic method of assessing the susceptibility of a subject suffering from stable COPD to develop progressive COPD involving the appearance of irreversible lung damage, the method comprising:

determining the level of expression of the gene DMBT1 in a sample obtained from the subject;

comparing the level of expression of DMBT1 in the sample from the subject to a control expression level of DMBT1 in a subject suffering from stable COPD; and determining whether or not the subject is prone to develop progressive COPD involving the appearance of irreversible lung damage, wherein a decrease in the level of expression of DMBT1 in the sample from the subject as compared to the control expression level of DMBT1 is indicative of a proneness to develop progressive COPD.

It is preferred that the method of this fourth aspect further comprises:

determining the level of expression of one or more further genes selected from KIAA1199, ELF5, AZGP1, PRRX1, AQP3, GPR110, GDF15, RASGRF2, RND1, FGG, CEACAM5, HYAL2, AHRR, CXCL3, CYP1A1, CYP1B1, CYP1A2, CST6, NTRK2, COMP, ITGA10, CTHRC1, TAL1, BEX1 and GHRL in the sample obtained from the subject;

comparing the level of expression of the one or more further genes to a control expression level of the corresponding gene(s) in a subject suffering from stable COPD; and determining whether or not the subject is prone to develop progressive COPD involving the appearance of irreversible lung damage, wherein an increase in the level of expression of KIAA1199, GPR110, GDF15, RASGRF2, RND1, FGG, CEACAM5, HYAL2, AHRR, CXCL3, CYP1A1, CYP1B1, CYP1A2, CST6, NTRK2 and/or TAL1 in the sample from the subject as compared to the control expression level of the corresponding gene(s) is indicative of a proneness to develop progressive COPD, and wherein a decrease in the level of expression of DMBT1, ELF5, AZGP1, PRRX1, AQP3, COMP, ITGA10, CTHRC1, BEX1 and/or GHRL in the sample from the subject as compared to the control expression level of the corresponding gene(s) is indicative of a proneness to develop progressive COPD.

In a fifth aspect, the invention relates to the use of (i) a pair of primers for a transcript of the gene DMBT1, (ii) a nucleic acid probe to a transcript of the gene DMBT1, (iii) a microarray comprising a nucleic acid probe to the transcript of DMBT1 and optionally comprising nucleic acid probes to the transcripts of one or more further genes selected from KIAA1199, TMSB15A, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL, or (iv) an antibody against the protein DMBT1, in an in vitro diagnostic method of assessing the susceptibility of a subject to develop progressive COPD involving the appearance of irreversible lung damage.

In a sixth aspect, the invention relates to a drug against COPD for use in treating COPD in a subject that has been identified in a method according to the second aspect of the invention as being prone to develop progressive COPD involving the appearance of irreversible lung damage.

The invention further relates to the use of a drug against COPD in the preparation of a pharmaceutical composition for treating COPD in a subject that has been identified in a method according to the second aspect of the invention as being prone to develop progressive COPD involving the appearance of irreversible lung damage.

Moreover, in accordance with this sixth aspect, the invention also provides a method of treating COPD, the method comprising administering a drug against COPD to a subject that has been identified in a method according to the second aspect of the invention as being prone to develop progressive COPD involving the appearance of irreversible lung damage.

In a seventh aspect, the invention relates to the use of (i) a pair of primers for a transcript of the gene DMBT1, (ii) a nucleic acid probe to a transcript of the gene DMBT1, (iii) a microarray comprising a nucleic acid probe to the transcript of DMBT1 and optionally comprising nucleic acid probes to the transcripts of one or more further genes selected from KIAA1199, TMSB15A, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL, or (iv) an antibody against the protein DMBT1, in an in vitro method of diagnosing stable COPD in a subject or assessing the susceptibility of a subject to develop stable COPD.

In an eighth aspect, the invention relates to a drug against COPD for use in treating or preventing COPD in a subject that has been identified in a method according to the third aspect of the invention as suffering from stable COPD or as being prone to suffer from stable COPD.

The invention also relates to the use of a drug against COPD in the preparation of a pharmaceutical composition for treating or preventing COPD in a subject that has been identified in a method according to the third aspect of the invention as suffering from stable COPD or as being prone to suffer from stable COPD.

In this aspect, the invention likewise relates to a method of treating or preventing COPD, the method comprising administering a drug against COPD to a subject that has been identified in a method according to the third aspect of the invention as suffering from stable COPD or as being prone to suffer from stable COPD.

In a ninth aspect, the invention relates to the use of (i) a pair of primers for a transcript of the gene DMBT1, (ii) a nucleic acid probe to a transcript of the gene DMBT1, (iii) a microarray comprising a nucleic acid probe to the transcript of DMBT1 and optionally comprising nucleic acid probes to the transcripts of one or more further genes selected from KIAA1199, ELF5, AZGP1, PRRX1, AQP3, GPR110, GDF15, RASGRF2, RND1, FGG, CEACAM5, HYAL2, AHRR, CXCL3, CYP1A1, CYP1B1, CYP1A2, CST6, NTRK2, COMP, ITGA10, CTHRC1, TAL1, BEX1 and GHRL, or (iv) an antibody against the protein DMBT1, in an in vitro diagnostic method of assessing the susceptibility of a subject suffering from stable COPD to develop progressive COPD involving the appearance of irreversible lung damage.

In a tenth aspect, the invention relates to a drug against COPD for use in treating COPD in a subject suffering from stable COPD, wherein the subject has been identified in a method according to the fourth aspect of the invention as being prone to develop progressive COPD involving the appearance of irreversible lung damage.

The invention further refers to the use of a drug against COPD in the preparation of a pharmaceutical composition for treating COPD in a subject suffering from stable COPD, wherein the subject has been identified in a method according to the fourth aspect of the invention as being prone to develop progressive COPD involving the appearance of irreversible lung damage.

The invention according to this tenth aspect also relates to a method of treating COPD, the method comprising administering a drug against COPD to a subject suffering from stable COPD, wherein the subject has been identified in a method according to the fourth aspect of the invention as being prone to develop progressive COPD involving the appearance of irreversible lung damage.

In an eleventh aspect, the present invention provides an in vitro method of monitoring the progression of COPD in a subject, the method comprising:

determining the level of expression of one or more genes selected from NTRK2 and RASGRF2 in a first sample obtained from the subject;

determining the level of expression of the one or more genes in a second sample obtained from the subject at a later point in time than the first sample;

comparing the level of expression of the one or more genes in the second sample to the level of expression of the corresponding gene(s) in the first sample; and assessing the progression of COPD in the subject, wherein a decrease in the level of expression of NTRK2 and/or RASGRF2 in the second sample as compared to the level of expression of the corresponding gene(s) in the first sample is indicative of an amelioration of COPD in the subject, and wherein an increase in the level of expression of NTRK2 and/or RASGRF2 in the second sample as compared to the level of expression of the corresponding gene(s) in the first sample is indicative of a worsening of COPD in the subject.

The following description of general and preferred features and embodiments relates to each one of the methods, uses and drugs against COPD provided in the present specification, including in particular those according to the above-described first, second, third, fourth, fifth, sixth, seventh, eighth, ninth, tenth and eleventh aspects of the invention, unless explicitly indicated otherwise.

Chronic obstructive pulmonary disease (COPD) is a lung disease characterized by persistent airflow limitation that is usually progressive and associated with an enhanced chronic inflammatory response in the airways and the lung to noxious particles or gases. COPD is typically classified into four different stages based on the extent of non-reversible pulmonary obstruction to be determined by spirometry, as specified by the Global Initiative for Obstructive Lung Disease (GOLD) (see, e.g., Vestbo et al., 2013; and Pauwels et al., 2001). COPD stage I ("mild COPD") is characterized by an $FEV_1$/FVC ratio of <70% and an $FEV_1$ of ≥80%. At stage I, the patient may not be aware that his/her lung function is abnormal. COPD stage II ("moderate COPD") is characterized by an $FEV_1$/FVC ratio of <70% and an $FEV_1$ of ≥50% and <80%. This is the stage at which patients typically seek medical attention because of chronic respiratory symptoms or an exacerbation of their disease. COPD stage III ("severe COPD") is characterized by an $FEV_1$/FVC ratio of <70% and an $FEV_1$ of ≥30% and <50%. COPD stage IV ("very severe COPD") is characterized by an $FEV_1$/FVC ratio of <70% and an $FEV_1$ of <30%, or chronic respiratory failure and an $FEV_1$ of <50%. The pathological development of COPD may be preceded by chronic respiratory symptoms (particularly chronic bronchitis) without airways obstruction ($FEV_1$/FVC ratio of 70%), which is also referred to as "stage 0" or "at risk for COPD". The terms "stage I", "stage II", stage "III", "stage IV", and "stage 0" as used in the present specification refer to the corresponding GOLD stages, i.e., the corresponding COPD stages according to the above-described GOLD criteria.

As used herein, the term "stable COPD" (used synonymously with "stable early-stage COPD") refers to the initial stages of COPD that precede the development of irreversible lung damage. In particular, "stable COPD" refers to the initial COPD stages from the earliest signs for the onset of the disease through to mild airflow limitation characterized by an $FEV_1$/FVC ratio of <70% and an $FEV_1$ of ≥80%. "Stable COPD" thus preferably refers to COPD stage 0 (i.e., the COPD "at risk" stage) and COPD stage I (according to GOLD criteria), and more preferably refers to COPD stage I.

The terms "progressive COPD" and "progressive COPD involving the appearance of irreversible lung damage" are used herein synonymously/interchangeably, and refer to the disease stage of COPD in which irreversible damage to the lungs occurs and progressively worsens. In particular, "progressive COPD" refers to the COPD disease stage characterized by moderate airflow limitation, i.e., an $FEV_1$/FVC ratio of <70% and an $FEV_1$ of ≥50% and <80%. Accordingly, it is particularly preferred that "progressive COPD" refers to COPD stage II (according to GOLD criteria).

As used herein, the terms "KIAA1199", "DMBT1", "TMSB15A", "DPP6", "SLC51B", "NUDT11", "ITGA10", "CST6", "TAL1", "FIBIN", "BEX5", "BEX1", "ESM1", "GHRL", "NTRK2", "SFN", "GPR110", "FGG", "CEACAM5", "AZGP1", "COMP", "PRRX1", "AHRR", "CYP1A1", "CYP1A2", "CYP1B1", "GDF15", "ELF5", "AQP3", "RASGRF2", "PLA1A", "HYAL2", "CTHRC1", "RND1" and "CXCL3" each refer to the respective human gene, the corresponding mRNA (including all possible transcripts/splice variants), and the corresponding protein (including all possible isoforms). These terms also refer to homologs and/or orthologs of the corresponding human genes that are found in other (non-human) species, particularly other mammalian species, as well as their corresponding mRNAs and their corresponding proteins. It is to be understood that, if the subject to be tested in the methods of the present invention is a non-human animal (particularly a non-human mammal), then the one or more marker genes (the level of expression of which is to be determined) will be the homologs/orthologs of the indicated human genes that are found in the non-human animal to be tested. Preferably, the subject is a human and, accordingly, the above-mentioned terms preferably refer to the respective human genes and the corresponding mRNAs and proteins.

The full names of the human forms of the above-mentioned marker genes, their Entrez Gene ID, and NCBI reference sequences of their mRNAs and proteins are listed in the following Table 1:

TABLE 1

Overview of the marker genes provided herein (human forms), including their full names, their Entrez Gene ID, and NCBI reference sequences of their mRNAs and their proteins (where applicable, different mRNA transcripts/splice variants and the corresponding protein isoforms are indicated; further possible mRNA variants and protein isoforms of the indicated genes may also be used to determine the corresponding levels of marker gene expression in accordance with the invention).

| Marker gene | Full name | Gene ID | mRNA (NCBI ref. seq.) | Protein (NCBI ref. seq.) |
|---|---|---|---|---|
| KIAA1199 | KIAA1199 | 57214 | NM_018689.1 (preferably as indicated in SEQ ID NO: 38) | NP_061159.1 |
| DMBT1 | deleted in malignant brain tumors 1 | 1755 | NM_004406.2 (preferably as indicated in SEQ ID NO: 26) NM_007329.2 (preferably as indicated in SEQ ID NO: 32) NM_017579.2 (preferably as indicated in SEQ ID NO: 35) | NP_004397.2 NP_015568.2 NP_060049.2 |
| TMSB15A | thymosin beta 15a | 11013 | NM_021992.2 (preferably as indicated in SEQ ID NO: 41) | NP_068832.1 |
| DPP6 | dipeptidyl-peptidase 6 | 1804 | NM_001039350.1 (preferably as indicated in SEQ ID NO: 45) NM_001936.3 (preferably as indicated in SEQ ID NO: 46) NM_130797.2 (preferably as indicated in SEQ ID NO: 47) | NP_001034439.1 NP_001927.3 NP_570629.2 |
| SLC51B | solute carrier family 51, beta subunit | 123264 | NM_178859.3 (preferably as indicated in SEQ ID NO: 48) | NP_849190.2 |
| NUDT11 | nudix (nucleoside diphosphate linked moiety X)-type motif 11 | 55190 | NM_018159.3 (preferably as indicated in SEQ ID NO: 36) | NP_060629 |
| ITGA10 | integrin, alpha 10 | 8515 | NM_003637.3 (preferably as indicated in SEQ ID NO: 24) | NP_003628.2 |
| CST6 | cystatin E/M | 1474 | NM_001323.3 (preferably as indicated in SEQ ID NO: 21) | NP_001314.1 |
| TAL1 | T-cell acute lymphocytic | 6886 | NM_003189.2 (preferably as | NP_003180.1 |

TABLE 1-continued

Overview of the marker genes provided herein (human forms), including their full names, their Entrez Gene ID, and NCBI reference sequences of their mRNAs and their proteins (where applicable, different mRNA transcripts/splice variants and the corresponding protein isoforms are indicated; further possible mRNA variants and protein isoforms of the indicated genes may also be used to determine the corresponding levels of marker gene expression in accordance with the invention).

| Marker gene | Full name | Gene ID | mRNA (NCBI ref. seq.) | Protein (NCBI ref. seq.) |
|---|---|---|---|---|
| | leukemia 1 | | indicated in SEQ ID NO: 49) | |
| FIBIN | fin bud initiation factor homolog (zebrafish) | 387758 | NM_203371.1 (preferably as indicated in SEQ ID NO: 50) | NP_976249.1 |
| BEX5 | brain expressed, X-linked 5 | 340542 | NM_001012978.2 (preferably as indicated in SEQ ID NO: 5)<br>NM_001159560.1 (preferably as indicated in SEQ ID NO: 13) | NP_001012996.1<br>NP_001153032.1 |
| BEX1 | brain expressed, X-linked 1 | 55859 | NM_018476.3 (preferably as indicated in SEQ ID NO: 37) | NP_060946.3 |
| ESM1 | endothelial cell-specific molecule 1 | 11082 | NM_001135604.1 (preferably as indicated in SEQ ID NO: 12)<br>NM_007036.4 (preferably as indicated in SEQ ID NO: 31) | NP_001129076.1<br>NP_008967.1 |
| GHRL | ghrelin/obestatin prepropeptide | 51738 | NM_001134941.1 (preferably as indicated in SEQ ID NO: 8)<br>NM_001134944.1 (preferably as indicated in SEQ ID NO: 9)<br>NM_001134945.1 (preferably as indicated in SEQ ID NO: 10)<br>NM_001134946.1 (preferably as indicated in SEQ ID NO: 11) | NP_001128413.1<br>NP_001128416.1<br>NP_001128417.1<br>NP_001128418.1<br>NP_001128418.1 |
| NTRK2 | neurotrophic tyrosine kinase, receptor, type 2 | 4915 | NM_001007097.1 (preferably as indicated in SEQ ID NO: 51)<br>NM_001018064.1 (preferably as indicated in SEQ ID NO: 52)<br>NM_001018065.2 (preferably as indicated in SEQ ID NO: 6)<br>NM_001018066.2 (preferably as indicated in SEQ ID NO: 7)<br>NM_006180.3 (preferably as indicated in SEQ ID NO: 53) | NP_001007098.1<br>NP_001018074.1<br>NP_001018075.1<br>NP_001018076.1<br>NP_006171.2 |
| SFN | stratifin | 2810 | NM_006142.3 (preferably as indicated in SEQ ID NO: 29) | NP_006133.1 |
| GPR110 | G protein-coupled receptor 110 | 266977 | NM_025048.2 (preferably as indicated in SEQ ID NO: 42) | NP_079324.2<br>NP_722582.2 |

TABLE 1-continued

Overview of the marker genes provided herein (human forms), including their full names, their Entrez Gene ID, and NCBI reference sequences of their mRNAs and their proteins (where applicable, different mRNA transcripts/splice variants and the corresponding protein isoforms are indicated; further possible mRNA variants and protein isoforms of the indicated genes may also be used to determine the corresponding levels of marker gene expression in accordance with the invention).

| Marker gene | Full name | Gene ID | mRNA (NCBI ref. seq.) | Protein (NCBI ref. seq.) |
|---|---|---|---|---|
| | | | NM_153840.2 (preferably as indicated in SEQ ID NO: 55) | |
| CYP1B1 | cytochrome P450, family 1, subfamily B, polypeptide 1 | 1545 | NM_000104.3 (preferably as indicated in SEQ ID NO: 2) | NP_000095.2 |
| FGG | fibrinogen gamma chain | 2266 | NM_000509.4 (preferably as indicated in SEQ ID NO: 4) NM_021870.2 (preferably as indicated in SEQ ID NO: 40) | NP_000500.2 NP_068656.2 |
| CEACAM5 | carcinoembryonic antigen-related cell adhesion molecule 5 | 1048 | NM_004363.2 (preferably as indicated in SEQ ID NO: 54) | NP_004354.2 |
| AZGP1 | alpha-2-glycoprotein 1, zinc-binding | 563 | NM_001185.3 (preferably as indicated in SEQ ID NO: 14) | NP_001176.1 |
| COMP | cartilage oligomeric matrix protein | 1311 | NM_000095.2 (preferably as indicated in SEQ ID NO: 1) | NP_000086.2 |
| PRRX1 | paired related homeobox 1 | 5396 | NM_006902.3 (preferably as indicated in SEQ ID NO: 56) NM_022716.2 (preferably as indicated in SEQ ID NO: 57) | NP_008833.1 NP_073207.1 |
| AHRR | aryl-hydrocarbon receptor repressor | 57491 | NM_001242412.1 (preferably as indicated in SEQ ID NO: 17) NM_020731.4 (preferably as indicated in SEQ ID NO: 39) | NP_001229341.1 NP_065782.2 |
| GDF15 | growth differentiation factor 15 | 9518 | NM_004864.2 (preferably as indicated in SEQ ID NO: 27) | NP_004855.2 |
| ELF5 | E74-like factor 5 (ets domain transcription factor) | 2001 | NM_001243080.1 (preferably as indicated in SEQ ID NO: 18) NM_001243081.1 (preferably as indicated in SEQ ID NO: 19) NM_001422.3 (preferably as indicated in SEQ ID NO: 22) NM_198381.1 (preferably as indicated in SEQ ID NO: 58) | NP_001230009.1 NP_001230010.1 NP_001413.1 NP_938195.1 |
| AQP3 | aquaporin 3 (Gill blood group) | 360 | NM_004925.4 (preferably as indicated in SEQ ID NO: 28) | NP_004916.1 |
| RASGRF2 | Ras protein-specific guanine | 5924 | NM_006909.2 (preferably as | NP_008840.1 |

TABLE 1-continued

Overview of the marker genes provided herein (human forms), including their full names, their Entrez Gene ID, and NCBI reference sequences of their mRNAs and their proteins (where applicable, different mRNA transcripts/splice variants and the corresponding protein isoforms are indicated; further possible mRNA variants and protein isoforms of the indicated genes may also be used to determine the corresponding levels of marker gene expression in accordance with the invention).

| Marker gene | Full name | Gene ID | mRNA (NCBI ref. seq.) | Protein (NCBI ref. seq.) |
|---|---|---|---|---|
| | nucleotide-releasing factor 2 | | indicated in SEQ ID NO: 30) | |
| PLA1A | phospholipase A1 member A | 51365 | NM_001206960.1 (preferably as indicated in SEQ ID NO: 15) NM_001206961.1 (preferably as indicated in SEQ ID NO: 16) NM_015900.3 (preferably as indicated in SEQ ID NO: 34) | NP_001193889.1 NP_001193890.1 NP_056984.1 |
| HYAL2 | hyalurono-glucosaminidase 2 | 8692 | NM_003773.4 (preferably as indicated in SEQ ID NO: 25) NM_033158.4 (preferably as indicated in SEQ ID NO: 43) | NP_003764.3 NP_149348.2 |
| CTHRC1 | collagen triple helix repeat containing 1 | 115908 | NM_001256099.1 (preferably as indicated in SEQ ID NO: 20) NM_138455.3 (preferably as indicated in SEQ ID NO: 44) | NP_001243028.1 NP_612464.1 |
| RND1 | Rho family GTPase 1 | 27289 | NM_014470.3 (preferably as indicated in SEQ ID NO: 33) | NP_055285.1 |
| CXCL3 | chemokine (C—X—C motif) ligand 3 | 2921 | NM_002090.2 (preferably as indicated in SEQ ID NO: 23) | NP_002081.2 |
| CYP1A1 | cytochrome P450, family 1, subfamily A, polypeptide 1 | 1543 | NM_000499.3 (preferably as indicated in SEQ ID NO: 3) | NP_000490.1 |
| CYP1A2 | cytochrome P450, family 1, subfamily A, polypeptide 2 | 1544 | NM_000761.4 (preferably as indicated in SEQ ID NO: 59) | NP_000752.2 |

In the methods according to the present invention, including in particular the methods according to the first, second, third, fourth and eleventh aspect of the invention, the level of expression of one or more genes is determined in a sample obtained from the subject to be tested.

The level of expression can be determined, e.g., by determining the level of transcription or the level of translation of the corresponding marker gene(s). Thus, the amount of mRNA of these gene(s) in the sample can be measured or the amount of the corresponding protein(s) can be measured in order to determine the level of expression of the respective genes. This can be accomplished using methods known in the art, as described, e.g., in Green et al., 2012. The level of transcription of these gene(s) can, for example, be determined using a quantitative (real-time) reverse transcriptase polymerase chain reaction ("qRT-PCR") or using a microarray (see, e.g., Ding et al., 2004). The use of a microarray can be advantageous, e.g., if the level of transcription of a number of different marker genes is to be determined. Using a microarray can also be advantageous if various different diseases/disorders or the susceptibility to various diseases/disorders is to be tested or diagnosed simultaneously. If the level of transcription is to be determined, it may further be advantageous to include one or more RNase inhibitors in the sample from the subject. The level of translation of the corresponding marker gene(s) can, for example, be determined using antibody-based assays, such as an enzyme-linked immunosorbent assay (ELISA) or a radioimmunoassay (RIA), wherein antibodies directed specifically against the protein(s) to be quantified are employed, or mass spectrometry, a gel-based or blot-based assay, or flow cytometry (e.g., FACS). If the level of translation is to be determined, it may be advantageous to include one or more protease inhibitors in the sample from the subject. Since mRNA can be isolated and quantified more easily and in a more cost-effective manner than proteins, it is preferred in the methods of the present invention that the level of expression of the one or more genes is determined by determining the level of transcription of the corresponding gene(s). The level of transcription is preferably determined using qRT-PCR or a microarray.

The subject to be tested in accordance with the present invention may be an animal and is preferably a mammal. The mammal to be tested in accordance with the invention may be, e.g., a rodent (such as, e.g., a guinea pig, a hamster, a rat or a mouse), a murine (such as, e.g., a mouse), a canine (such as, e.g., a dog), a feline (such as, e.g., a cat), a porcine (such as, e.g., a pig), an equine (such as, e.g., a horse), a primate, a simian (such as, e.g., a monkey or an ape), a monkey (such as, e.g., a marmoset or a baboon), an ape (such as, e.g., a gorilla, a chimpanzee, an orang-utan or a gibbon), or a human. It is particularly envisaged that non-human mammals are to be tested, which are economically, agronomically or scientifically important. Scientifically important mammals include, e.g., mice, rats and rabbits. Non-limiting examples of agronomically important mammals are sheep, cattle and pigs. Economically important mammals include, e.g., cats and dogs. Most preferably, the subject to be tested in accordance with the present invention is a human.

In the second and the fourth aspect of the invention, it is furthermore preferred that the subject to be tested is a subject (preferably a human) that has been diagnosed as suffering from stable COPD or is suspected of suffering from stable COPD.

In accordance with the third aspect of the invention, it is preferred that the subject to be tested is a subject (preferably a human) that is suspected to suffer from stable COPD or a subject (preferably a human) suspected to be prone to suffer from stable COPD.

The sample obtained from the subject to be tested can, in principle, be any tissue sample or serum from the subject. Preferably, the sample is a lung tissue sample. More preferably, the sample is a transbronchial lung biopsy sample or a bronchoalveolar lavage (BAL) sample.

In some of the methods provided herein, including in particular the methods according to the second and the third aspect of the invention, the level of expression of one or more specific genes is compared to a control expression level of the corresponding gene(s) in a healthy subject. Such control expression levels can be established as part of the respective methods of the invention, which may thus include a further step of determining the level of expression of the corresponding gene(s) in a sample obtained from a healthy subject (i.e., a subject that does not suffer from COPD and does not have an increased risk of developing COPD) or in a mixture of samples from several healthy subjects (e.g., about 10, about 20, about 50, about 100, or about 500 healthy subjects). It is to be understood that the healthy subject(s) will be of the same species as the subject to be tested and should preferably have the same age, gender and ethnicity as the subject to be tested. Alternatively, these control expression levels can also be derived from the medical literature or from experiments conducted before carrying out the methods of the invention. It will be understood that the conditions under which the control expression levels are or were obtained (regardless of whether they are derived from the literature or earlier experiments or whether they are determined in the course of carrying out the methods of the invention), including also the type/origin of the sample (or mixture of samples) from the healthy subject, should be identical or at least similar/comparable to the conditions used for determining the level of expression of the one or more genes in the sample obtained from the subject to be tested.

In the method according to the fourth aspect, the level of expression of one or more specific genes is compared to a control expression level of the corresponding gene(s) in a subject suffering from stable COPD. Such control expression levels can be established as part of the method according to the fourth aspect of the invention, which may thus include a further step of determining the level of expression of the corresponding gene(s) in a sample obtained from a subject suffering from stable COPD (particularly a subject that has been diagnosed as suffering from stable COPD) or in a mixture of samples from several subjects (e.g., about 10, about 20, about 50, about 100, or about 500 subjects) suffering from stable COPD. It is to be understood that these control subject(s) will be of the same species as the subject to be tested and should preferably have the same age, gender and ethnicity as the subject to be tested. Alternatively, the corresponding control expression levels can also be derived from experiments conducted before carrying out the method of the fourth aspect of the invention. It will be understood that the conditions under which the control expression levels are or were obtained (regardless of whether they are derived from earlier experiments or whether they are determined in the course of carrying out the method of the fourth aspect), including also the type/origin of the sample (or mixture of samples) from the control subject, should be identical or at least similar/comparable to the conditions used for determining the level of expression of the one or more genes in the sample obtained from the subject to be tested. The control subject suffering from stable COPD in accordance with the fourth aspect of the invention is preferably a subject suffering from stage I COPD (particularly a subject that has been diagnosed as suffering from stage I COPD).

In the methods according to the second, third and fourth aspect of the present invention, the level of expression of DMBT1 and optionally of one or more further marker genes is determined. Preferably, the level of expression of DMBT1 and at least one of the corresponding further marker genes is determined, more preferably the level of expression of DMBT1 and at least two of these further marker genes is determined, and even more preferably the level of expression of DMBT1 and at least three of the corresponding further marker genes is determined, whereby the reliability of the diagnosis or assessment can be further improved. In general, the greater the number of marker genes the expression of which is altered (as defined in the corresponding aspect of the invention), and also the more pronounced the upregulation or downregulation of the expression of each of these marker genes, the more likely it will be that the subject tested is prone to develop progressive COPD (in the methods of the second and the fourth aspect) or that the subject tested suffers from stable COPD or is prone to suffer from stable COPD (in the method of the third aspect of the invention).

Thus, both (i) the number of tested marker genes showing an altered expression level as described above and (ii) the extent of alteration of the expression level of each one of the marker genes tested can be taken into consideration when determining whether or not the subject is prone to develop progressive COPD (in accordance with the second or the fourth aspect) or whether or not the subject suffers from stable COPD or is prone to suffer from stable COPD (in accordance with the third aspect of the invention). Further factors, signs and symptoms indicative of COPD, such as, e.g., airflow limitation (as determined, e.g., by spirometry), coughing, expiratory wheezing, further respiratory symptoms, the subject's smoking history, bronchial inflammation and/or further biomarkers (including molecular biomarkers), can additionally be taken into account in order to further improve the accuracy of the determination whether or not the subject is prone to develop progressive COPD (in accordance with the second or the fourth aspect) or whether or not the subject suffers from stable COPD or is prone to suffer from stable COPD (in accordance with the third aspect).

In one embodiment of the method according to the second aspect of the invention, it is preferred that the level of expression of DMBT1 and at least one further gene selected from FGG, CYP1A1, CEACAM5, CTHRC1, NTRK2 and RASGRF2 is determined in the sample obtained from the subject. In this embodiment, it is furthermore preferred that the level of expression of at least two of the aforementioned further genes is determined. For example, the level of expression of DMBT1, FGG and CYP1A1 may be determined, or the level of expression of DMBT1, FGG and CEACAM5 may be determined, or the level of expression of DMBT1, FGG and CTHRC1 may be determined, or the level of expression of DMBT1, FGG and NTRK2 may be determined, or the level of expression of DMBT1, FGG and RASGRF2 may be determined, or the level of expression of DMBT1, CYP1A1 and CEACAM5 may be determined, or the level of expression of DMBT1, CYP1A1 and CTHRC1 may be determined, or the level of expression of DMBT1, CYP1A1 and NTRK2 may be determined, or the level of expression of DMBT1, CYP1A1 and RASGRF2 may be determined, or the level of expression of DMBT1, CEACAM5 and CTHRC1 may be determined, or the level of expression of DMBT1, CEACAM5 and NTRK2 may be determined, or the level of expression of DMBT1, CEACAM5 and RASGRF2 may be determined, or the level of expression of DMBT1, CTHRC1 and NTRK2 may be determined, or the level of expression of DMBT1, CTHRC1 and RASGRF2 may be determined, or the level of expression of DMBT1, NTRK2 and RASGRF2 may be determined. In addition thereto, the level of expression of at least one further gene selected from ELF5, AZGP1, PRRX1, AQP3, SFN, GPR110, GDF15, RASGRF2 and RND1 and/or the level of expression of at least one further gene selected from KIAA1199, TMSB15A, DPP6, SLC51B and NUDT11 (particularly KIAA1199 and/or TMSB15A) may also be determined.

In a further embodiment of the method according to the second aspect of the invention, it is preferred that the level of expression of DMBT1 and at least one further gene selected from ELF5, AZGP1, PRRX1, AQP3, SFN, GPR110, GDF15, RASGRF2 and RND1 is determined in the sample obtained from the subject. In this embodiment, it is furthermore preferred that the level of expression of at least two of the aforementioned further genes is determined. For example, the level of expression of DMBT1, ELF5 and AZGP1 may be determined, or the level of expression of DMBT1, ELF5 and PRRX1 may be determined, or the level of expression of DMBT1, ELF5 and AQP3 may be determined, or the level of expression of DMBT1, ELF5 and SFN may be determined, or the level of expression of DMBT1, ELF5 and GPR110 may be determined, or the level of expression of DMBT1, ELF5 and GDF15 may be determined, or the level of expression of DMBT1, ELF5 and RASGRF2 may be determined, or the level of expression of DMBT1, ELF5 and RND1 may be determined, or the level of expression of DMBT1, AZGP1 and PRRX1 may be determined, or the level of expression of DMBT1, AZGP1 and AQP3 may be determined, or the level of expression of DMBT1, AZGP1 and SFN may be determined, or the level of expression of DMBT1, AZGP1 and GPR110 may be determined, or the level of expression of DMBT1, AZGP1 and GDF15 may be determined, or the level of expression of DMBT1, AZGP1 and RASGRF2 may be determined, or the level of expression of DMBT1, AZGP1 and RND1 may be determined, or the level of expression of DMBT1, PRRX1 and AQP3 may be determined, or the level of expression of DMBT1, PRRX1 and SFN may be determined, or the level of expression of DMBT1, PRRX1 and GPR110 may be determined, or the level of expression of DMBT1, PRRX1 and GDF15 may be determined, or the level of expression of DMBT1, PRRX1 and RASGRF2 may be determined, or the level of expression of DMBT1, PRRX1 and RND1 may be determined, or the level of expression of DMBT1, AQP3 and SFN may be determined, or the level of expression of DMBT1, AQP3 and GPR110 may be determined, or the level of expression of DMBT1, AQP3 and GDF15 may be determined, or the level of expression of DMBT1, AQP3 and RASGRF2 may be determined, or the level of expression of DMBT1, AQP3 and RND1 may be determined, or the level of expression of DMBT1, SFN and GPR110 may be determined, or the level of expression of DMBT1, SFN and GDF15 may be determined, or the level of expression of DMBT1, SFN and RASGRF2 may be determined, or the level of expression of DMBT1, SFN and RND1 may be determined, or the level of expression of DMBT1, GPR110 and GDF15 may be determined, or the level of expression of DMBT1, GPR110 and RASGRF2 may be determined, or the level of expression of DMBT1, GPR110 and RND1 may be determined, or the level of expression of DMBT1, GDF15 and RASGRF2 may be determined, or the level of expression of DMBT1, GDF15 and RND1 may be determined, or the level of expression of DMBT1, RASGRF2 and RND1 may be determined. In addition thereto, the level of expression of at least one further gene selected from FGG, CYP1A1, CEACAM5, CTHRC1, NTRK2 and RASGRF2 and/or the level of expression of at least one further gene selected from KIAA1199, TMSB15A, DPP6, SLC51B and NUDT11 (particularly KIAA1199 and/or TMSB15A) may also be determined.

In a further embodiment of the method according to the second aspect of the invention, it is preferred that the level of expression of DMBT1 and at least one further gene selected from KIAA1199, TMSB15A, DPP6, SLC51B and NUDT11 is determined in the sample obtained from the subject. In this embodiment, it is furthermore preferred that the level of expression of at least two of the aforementioned further genes is determined. For example, the level of expression of KIAA1199, DMBT1 and TMSB15A may be determined, or the level of expression of KIAA1199, DMBT1 and DPP6 may be determined, or the level of expression of KIAA1199, DMBT1 and SLC51B may be determined, or the level of expression of KIAA1199, DMBT1 and NUDT11 may be determined, or the level of expression of DMBT1, TMSB15A and DPP6 may be determined, or the level of expression of DMBT1, TMSB15A and SLC51B may be determined, or the level of expression of DMBT1, TMSB15A and NUDT11 may be determined, or the level of expression of DMBT1, DPP6 and SLC51B may be determined, or the level of expression of DMBT1, DPP6 and NUDT11 may be determined, or the level of expression of DMBT1, SLC51B and NUDT11 may be determined. In addition thereto, the level of expression of at least one further gene selected from FGG, CYP1A1, CEACAM5, CTHRC1, NTRK2 and RASGRF2 and/or the level of expression of at least one further gene selected from ELF5, AZGP1, PRRX1, AQP3, SFN, GPR110, GDF15, RASGRF2 and RND1 may also be determined.

In the method according to the second aspect of the invention, it is particularly preferred that the level of expression of DMBT1 and at least one further gene selected from KIAA1199 and TMSB15A is determined in the sample obtained from the subject. Accordingly, it is preferred that the level of expression of DMBT1 and KIAA1199 is determined, or that the level of expression of DMBT1 and TMSB15A is determined. Most preferably, the level of expression of DMBT1, KIAA1199 and TMSB15A is determined in the sample obtained from the subject. For example, the level of expression of DMBT1, KIAA1199, TMSB15A and at least one further gene selected from FGG, CYP1A1, CEACAM5, CTHRC1, NTRK2, RASGRF2, ELF5, AZGP1, PRRX1, AQP3, SFN, GPR110, GDF15, RASGRF2, RND1, DPP6, SLC51B and NUDT11 may be determined.

In one embodiment of the method according to the third aspect of the invention, it is preferred that the level of expression of DMBT1 and at least one further gene selected from FGG, CYP1A1, CEACAM5, CTHRC1, NTRK2 and RASGRF2 is determined in the sample obtained from the subject. In this embodiment, it is furthermore preferred that the level of expression of at least two of the aforementioned further genes is determined. For example, the level of expression of DMBT1, FGG and CYP1A1 may be determined, or the level of expression of DMBT1, FGG and CEACAM5 may be determined, or the level of expression of DMBT1, FGG and CTHRC1 may be determined, or the level of expression of DMBT1, FGG and NTRK2 may be determined, or the level of expression of DMBT1, FGG and RASGRF2 may be determined, or the level of expression of DMBT1, CYP1A1 and CEACAM5 may be determined, or the level of expression of DMBT1, CYP1A1 and CTHRC1 may be determined, or the level of expression of DMBT1, CYP1A1 and NTRK2 may be determined, or the level of expression of DMBT1, CYP1A1 and RASGRF2 may be determined, or the level of expression of DMBT1, CEACAM5 and CTHRC1 may be determined, or the level of expression of DMBT1, CEACAM5 and NTRK2 may be determined, or the level of expression of DMBT1, CEACAM5 and RASGRF2 may be determined, or the level of expression of DMBT1, CTHRC1 and NTRK2 may be determined, or the level of expression of DMBT1, CTHRC1 and RASGRF2 may be determined, or the level of expression of DMBT1, NTRK2 and RASGRF2 may be determined. In addition thereto, the level of expression of at least one further gene selected from ELF5, AZGP1, PRRX1, AQP3, SFN, GPR110, GDF15, RASGRF2 and RND1 and/or the level of expression of at least one further gene selected from KIAA1199, TMSB15A, DPP6, SLC51B and NUDT11 (particularly KIAA1199 and/or TMSB15A) may also be determined.

In a further embodiment of the method according to the third aspect of the invention, it is preferred that the level of expression of DMBT1 and at least one further gene selected from ELF5, AZGP1, PRRX1, AQP3, SFN, GPR110, GDF15, RASGRF2 and RND1 is determined in the sample obtained from the subject. In this embodiment, it is furthermore preferred that the level of expression of at least two of the aforementioned further genes is determined. For example, the level of expression of DMBT1, ELF5 and AZGP1 may be determined, or the level of expression of DMBT1, ELF5 and PRRX1 may be determined, or the level of expression of DMBT1, ELF5 and AQP3 may be determined, or the level of expression of DMBT1, ELF5 and SFN may be determined, or the level of expression of DMBT1, ELF5 and GPR110 may be determined, or the level of expression of DMBT1, ELF5 and GDF15 may be determined, or the level of expression of DMBT1, ELF5 and RASGRF2 may be determined, or the level of expression of DMBT1, ELF5 and RND1 may be determined, or the level of expression of DMBT1, AZGP1 and PRRX1 may be determined, or the level of expression of DMBT1, AZGP1 and AQP3 may be determined, or the level of expression of DMBT1, AZGP1 and SFN may be determined, or the level of expression of DMBT1, AZGP1 and GPR110 may be determined, or the level of expression of DMBT1, AZGP1 and GDF15 may be determined, or the level of expression of DMBT1, AZGP1 and RASGRF2 may be determined, or the level of expression of DMBT1, AZGP1 and RND1 may be determined, or the level of expression of DMBT1, PRRX1 and AQP3 may be determined, or the level of expression of DMBT1, PRRX1 and SFN may be determined, or the level of expression of DMBT1, PRRX1 and GPR110 may be determined, or the level of expression of DMBT1, PRRX1 and GDF15 may be determined, or the level of expression of DMBT1, PRRX1 and RASGRF2 may be determined, or the level of expression of DMBT1, PRRX1 and RND1 may be determined, or the level of expression of DMBT1, AQP3 and SFN may be determined, or the level of expression of DMBT1, AQP3 and GPR110 may be determined, or the level of expression of DMBT1, AQP3 and GDF15 may be determined, or the level of expression of DMBT1, AQP3 and RASGRF2 may be determined, or the level of expression of DMBT1, AQP3 and RND1 may be determined, or the level of expression of DMBT1, SFN and GPR110 may be determined, or the level of expression of DMBT1, SFN and GDF15 may be determined, or the level of expression of DMBT1, SFN and RASGRF2 may be determined, or the level of expression of DMBT1, SFN and RND1 may be determined, or the level of expression of DMBT1, GPR110 and GDF15 may be determined, or the level of expression of DMBT1, GPR110 and RASGRF2 may be determined, or the level of expression of DMBT1, GPR110 and RND1 may be determined, or the level of expression of DMBT1, GDF15 and RASGRF2 may be determined, or the level of expression of DMBT1, GDF15 and RND1 may be determined, or the level of expression of DMBT1, RASGRF2 and RND1 may be determined. In addition thereto, the level of expression of at least one further gene selected from FGG, CYP1A1, CEACAM5, CTHRC1, NTRK2 and RASGRF2 and/or the level of expression of at least one further gene selected from KIAA1199, TMSB15A, DPP6, SLC51B and NUDT11 (particularly KIAA1199 and/or TMSB15A) may also be determined.

In a further embodiment of the method according to the third aspect of the invention, it is preferred that the level of expression of DMBT1 and at least one further gene selected from KIAA1199, TMSB15A, DPP6, SLC51B and NUDT11 is determined in the sample obtained from the subject. In this embodiment, it is furthermore preferred that the level of expression of at least two of the aforementioned further genes is determined. For example, the level of expression of KIAA1199, DMBT1 and TMSB15A may be determined, or the level of expression of KIAA1199, DMBT1 and DPP6 may be determined, or the level of expression of KIAA1199, DMBT1 and SLC51B may be determined, or the level of expression of KIAA1199, DMBT1 and NUDT11 may be determined, or the level of expression of DMBT1, TMSB15A and DPP6 may be determined, or the level of expression of DMBT1, TMSB15A and SLC51B may be determined, or the level of expression of DMBT1, TMSB15A and NUDT11 may be determined, or the level of expression of DMBT1, DPP6 and SLC51B may be determined, or the level of expression of DMBT1, DPP6 and NUDT11 may be determined, or the level of expression of DMBT1, SLC51B and NUDT11 may be determined. In addition thereto, the level of expression of at least one further gene selected from FGG, CYP1A1, CEACAM5, CTHRC1, NTRK2 and RASGRF2 and/or the level of expression of at least one further gene selected from ELF5, AZGP1, PRRX1, AQP3, SFN, GPR110, GDF15, RASGRF2 and RND1 may also be determined.

In the method according to the third aspect of the invention, it is particularly preferred that the level of expression of DMBT1 and at least one further gene selected from KIAA1199 and TMSB15A is determined in the sample obtained from the subject. Accordingly, it is preferred that the level of expression of KIAA1199 and DMBT1 is determined, or that the level of expression of DMBT1 and TMSB15A is determined. Most preferably, the level of expression of KIAA1199, DMBT1 and TMSB15A is determined in the sample obtained from the subject.

In one embodiment of the method according to the fourth aspect of the invention, it is preferred that the level of expression of DMBT1 and at least one further gene selected from FGG, CYP1A1, CEACAM5, CTHRC1, NTRK2 and RASGRF2 is determined in the sample obtained from the subject. In this embodiment, it is furthermore preferred that the level of expression of at least two of the aforementioned further genes is determined. For example, the level of expression of DMBT1, FGG and CYP1A1 may be determined, or the level of expression of DMBT1, FGG and CEACAM5 may be determined, or the level of expression of DMBT1, FGG and CTHRC1 may be determined, or the level of expression of DMBT1, FGG and NTRK2 may be determined, or the level of expression of DMBT1, FGG and RASGRF2 may be determined, or the level of expression of DMBT1, CYP1A1 and CEACAM5 may be determined, or the level of expression of DMBT1, CYP1A1 and CTHRC1 may be determined, or the level of expression of DMBT1, CYP1A1 and NTRK2 may be determined, or the level of expression of DMBT1, CYP1A1 and RASGRF2 may be determined, or the level of expression of DMBT1, CEACAM5 and CTHRC1 may be determined, or the level of expression of DMBT1, CEACAM5 and NTRK2 may be determined, or the level of expression of DMBT1, CEACAM5 and RASGRF2 may be determined, or the level of expression of DMBT1, CTHRC1 and NTRK2 may be determined, or the level of expression of DMBT1, CTHRC1 and RASGRF2 may be determined, or the level of expression of DMBT1, NTRK2 and RASGRF2 may be determined. In addition thereto, the level of expression of at least one further gene selected from ELF5, AZGP1, PRRX1, AQP3, GPR110, GDF15, RASGRF2 and RND1 and/or the level of expression of at least one further gene selected from KIAA1199 and TMSB15A may also be determined.

In a further embodiment of the method according to the fourth aspect of the invention, it is preferred that the level of expression of DMBT1 and at least one further gene selected from ELF5, AZGP1, PRRX1, AQP3, GPR110, GDF15, RASGRF2 and RND1 is determined in the sample obtained from the subject. In this embodiment, it is furthermore preferred that the level of expression of at least two of the aforementioned further genes is determined. For example, the level of expression of DMBT1, ELF5 and AZGP1 may be determined, or the level of expression of DMBT1, ELF5 and PRRX1 may be determined, or the level of expression of DMBT1, ELF5 and AQP3 may be determined, or the level of expression of DMBT1, ELF5 and GPR110 may be determined, or the level of expression of DMBT1, ELF5 and GDF15 may be determined, or the level of expression of DMBT1, ELF5 and RASGRF2 may be determined, or the level of expression of DMBT1, ELF5 and RND1 may be determined, or the level of expression of DMBT1, AZGP1 and PRRX1 may be determined, or the level of expression of DMBT1, AZGP1 and AQP3 may be determined, or the level of expression of DMBT1, AZGP1 and GPR110 may be determined, or the level of expression of DMBT1, AZGP1 and GDF15 may be determined, or the level of expression of DMBT1, AZGP1 and RASGRF2 may be determined, or the level of expression of DMBT1, AZGP1 and RND1 may be determined, or the level of expression of DMBT1, PRRX1 and AQP3 may be determined, or the level of expression of DMBT1, PRRX1 and GPR110 may be determined, or the level of expression of DMBT1, PRRX1 and GDF15 may be determined, or the level of expression of DMBT1, PRRX1 and RASGRF2 may be determined, or the level of expression of DMBT1, PRRX1 and RND1 may be determined, or the level of expression of DMBT1, AQP3 and GPR110 may be determined, or the level of expression of DMBT1, AQP3 and GDF15 may be determined, or the level of expression of DMBT1, AQP3 and RASGRF2 may be determined, or the level of expression of DMBT1, AQP3 and RND1 may be determined, or the level of expression of DMBT1, GPR110 and GDF15 may be determined, or the level of expression of DMBT1, GPR110 and RASGRF2 may be determined, or the level of expression of DMBT1, GPR110 and RND1 may be determined, or the level of expression of DMBT1, GDF15 and RASGRF2 may be determined, or the level of expression of DMBT1, GDF15 and RND1 may be determined, or the level of expression of DMBT1, RASGRF2 and RND1 may be determined. In addition thereto, the level of expression of at least one further gene selected from FGG, CYP1A1, CEACAM5, CTHRC1, NTRK2 and RASGRF2 and/or the level of expression of at least one further gene selected from KIAA1199 and TMSB15A may also be determined.

In the method according to the fourth aspect of the invention, it is particularly preferred that the level of expression of DMBT1 and at least one further gene selected from KIAA1199 and TMSB15A is determined in the sample obtained from the subject. Accordingly, it is preferred that the level of expression of KIAA1199 and DMBT1 is determined, or that the level of expression of DMBT1 and TMSB15A is determined. Most preferably, the level of expression of KIAA1199, DMBT1 and TMSB15A is determined in the sample obtained from the subject.

In the method according to the second aspect of the invention, preferably, it is determined that the subject is prone to develop progressive COPD if the level of expression of a majority of the number of genes tested (i.e., of the number of genes, the expression of which has been tested) is altered in the sense that (i) the level of expression of DMBT1, KIAA1199, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the sample from the subject is increased as compared to the control expression level of the corresponding gene(s) and (ii) the level of expression of TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject is decreased as compared to the control expression level of the corresponding gene(s). If only one marker gene (i.e., DMBT1) is tested, then the alteration of the level of expression of this marker gene is decisive for determining whether or not the subject is prone to develop progressive COPD. If two or more marker genes are tested, then a decrease or increase in the level of expression of a majority of the number of these marker genes is required for determining that the subject is prone to develop progressive COPD. The term "majority" (as in the expression "majority of the number of genes tested") means more than 50% of the number of the marker genes tested.

In accordance with the second aspect, it is furthermore preferred that an alteration in the level of expression of at least 60%, more preferably at least 70%, even more preferably at least 80%, and still more preferably at least 90% of the number of genes tested—i.e., an alteration in the sense that (i) the level of expression of DMBT1, KIAA1199, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the sample from the subject is increased as compared to the control expression level of the corresponding gene(s) and (ii) the level of expression of TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject is decreased as compared to the control expression level of the corresponding gene(s)—is required for determining that the subject is prone to develop progressive COPD.

The decrease or increase in the level of expression of the marker gene(s) tested which is required for determining that the subject is prone to develop progressive COPD in accordance with the second aspect is preferably at least a 1.5-fold decrease or increase, more preferably at least a 2-fold decrease or increase, even more preferably at least a 3-fold decrease or increase, even more preferably at least a 5-fold decrease or increase, and yet even more preferably at least a 10-fold decrease or increase.

In a preferred embodiment of the method according to the second aspect of the invention, it is determined that the subject to be tested is prone to develop progressive COPD if the level of expression of a majority of the number of genes tested is altered in the sense that (i) the level of expression of DMBT1, KIAA1199, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the sample from the subject is at least 3-fold (more preferably at least 5-fold, even more preferably at least 10-fold) increased as compared to the control expression level of the corresponding gene(s) and (ii) the level of expression of TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject is at least 3-fold (more preferably at least 5-fold, even more preferably at least 10-fold) decreased as compared to the control expression level of the corresponding gene(s).

In a further preferred embodiment of the method according to the second aspect of the invention, it is determined that the subject to be tested is prone to develop progressive COPD if the level of expression of at least 70% (more preferably at least 80%, and even more preferably at least 90%) of the number of genes tested is altered in the sense that (i) the level of expression of DMBT1, KIAA1199, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the sample from the subject is increased as compared to the control expression level of the corresponding gene(s) and (ii) the level of expression of TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject is decreased as compared to the control expression level of the corresponding gene(s).

In a further preferred embodiment of the method according to the second aspect of the invention, it is determined that the subject to be tested is prone to develop progressive COPD if the level of expression of at least 70% (more preferably at least 80%, and even more preferably at least 90%) of the number of genes tested is altered in the sense that (i) the level of expression of DMBT1, KIAA1199, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the sample from the subject is at least 3-fold (more preferably at least 5-fold, even more preferably at least 10-fold) increased as compared to the control expression level of the corresponding gene(s) and (ii) the level of expression of TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject is at least 3-fold (more preferably at least 5-fold, even more preferably at least 10-fold) decreased as compared to the control expression level of the corresponding gene(s).

In the method according to the second aspect of the invention, it is particularly preferred to determine the level of expression of DMBT1 and KIAA1199 since the disease stage of COPD is particularly well reflected by the expression patterns of these marker genes. While an initial decrease in the expression of KIAA1199 and a simultaneous increase in the expression of DMBT1 is observed when a subject develops stable COPD, the ratio between the expression levels of KIAA1199 and DMBT1 changes upon entering the progressive stage of COPD, i.e., the expression of KIAA1199 increases while the expression of DMBT1 decreases. Therefore, in a particularly preferred embodiment of the method according to the second aspect, if the difference between the expression levels of DMBT1 and KIAA1199 (i.e., the expression level of DMBT1 minus the expression level of KIAA1199) in the sample from the subject is increased as compared to the difference between the control expression levels of DMBT1 and KIAA1199 (i.e., as compared to the value obtained when subtracting the control expression level of KIAA1199 from the control expression level of DMBT1) by a factor of more than $2^{3.63}$ (i.e., by a factor of more than 12.38; preferably by a factor of more than $2^{3.8}$, i.e., more than 13.93; and more preferably by a factor of more than $2^4$, i.e., more than 16), then it is determined that the subject is prone to develop progressive COPD. This procedure allows to particularly reliably distinguish between progressive COPD and stable COPD (see also FIG. 6E) and, thus, further improves the accurateness of the method of assessing the susceptibility of a subject to develop progressive COPD in accordance with the second aspect of the invention.

In the method according to the third aspect of the invention, preferably, it is determined that the subject suffers from stable COPD or is prone to suffer from stable COPD if the level of expression of a majority (i.e., more than 50%) of the number of genes tested is altered in the sense that (i) the level of expression of DMBT1, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the sample from the subject is increased as compared to the control expression level of the corresponding gene(s) and (ii) the level of expression of KIAA1199, TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject is decreased as compared to the control expression level of the corresponding gene(s).

In accordance with the third aspect, it is furthermore preferred that an alteration in the level of expression of at least 60%, more preferably at least 70%, even more preferably at least 80%, and still more preferably at least 90% of the number of genes tested—i.e., an alteration in the sense that (i) the level of expression of DMBT1, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the sample from the subject is increased as compared to the control expression level of the corresponding gene(s) and (ii) the level of expression of KIAA1199, TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject is decreased as compared to the control expression level of the corresponding gene(s)—is required for determining that the subject suffers from stable COPD or is prone to suffer from stable COPD.

The decrease or increase in the level of expression of the marker gene(s) tested which is required for determining that the subject suffers from stable COPD or is prone to suffer from stable COPD in accordance with the third aspect is preferably at least a 1.5-fold decrease or increase, more preferably at least a 2-fold decrease or increase, even more preferably at least a 3-fold decrease or increase, even more preferably at least a 5-fold decrease or increase, and yet even more preferably at least a 10-fold decrease or increase.

In a preferred embodiment of the method according to the third aspect of the invention, it is determined that the subject to be tested suffers from stable COPD or is prone to suffer from stable COPD if the level of expression of a majority of the number of genes tested is altered in the sense that (i) the level of expression of DMBT1, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the sample from the subject is at least 3-fold (more preferably at least 5-fold, even more preferably at least 10-fold) increased as compared to the control expression level of the corresponding gene(s) and (ii) the level of expression of KIAA1199, TMSB15A, DPP6, SLC51B, NUDT11, PLA1A, HYAL2, CST6, ITGA10, CTHRC1, TAD1, FIBIN, BEX5, BEX1, ESM1 and/or GHRL in the sample from the subject is at least 3-fold (more preferably at least 5-fold, even more preferably at least 10-fold) decreased as compared to the control expression level of the corresponding gene(s).

In a further preferred embodiment of the method according to the third aspect of the invention, it is determined that the subject to be tested suffers from stable COPD or is prone to suffer from stable COPD if the level of expression of at least 70% (more preferably at least 80%, and even more preferably at least 90%) of the number of genes tested is altered in the sense that (i) the level of expression of DMBT1, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the sample from the subject is increased as compared to the control expression level of the corresponding gene(s) and (ii) the level of expression of KIAA1199, TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject is decreased as compared to the control expression level of the corresponding gene(s).

In a further preferred embodiment of the method according to the third aspect of the invention, it is determined that the subject to be tested suffers from stable COPD or is prone to suffer from stable COPD if the level of expression of at least 70% (more preferably at least 80%, and even more preferably at least 90%) of the number of genes tested is altered in the sense that (i) the level of expression of DMBT1, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the sample from the subject is at least 3-fold (more preferably at least 5-fold, even more preferably at least 10-fold) increased as compared to the control expression level of the corresponding gene(s) and (ii) the level of expression of KIAA1199, TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject is at least 3-fold (more preferably at least 5-fold, even more preferably at least 10-fold) decreased as compared to the control expression level of the corresponding gene(s).

In the method according to the fourth aspect of the invention, preferably, it is determined that the subject is prone to develop progressive COPD if the level of expression of a majority (i.e., more than 50%) of the number of genes tested is altered in the sense that (i) the level of expression of KIAA1199, GPR110, GDF15, RASGRF2, RND1, FGG, CEACAM5, HYAL2, AHRR, CXCL3, CYP1A1, CYP1B1, CYP1A2, CST6, NTRK2 and/or TAL1 in the sample from the subject is increased as compared to the control expression level of the corresponding gene(s) and (ii) the level of expression of DMBT1, ELF5, AZGP1, PRRX1, AQP3, COMP, ITGA10, CTHRC1, BEX1 and/or GHRL in the sample from the subject is decreased as compared to the control expression level of the corresponding gene(s).

In accordance with the fourth aspect, it is furthermore preferred that an alteration in the level of expression of at least 60%, more preferably at least 70%, even more preferably at least 80%, and still more preferably at least 90% of the number of genes tested—i.e., an alteration in the sense that (i) the level of expression of KIAA1199, GPR110, GDF15, RASGRF2, RND1, FGG, CEACAM5, HYAL2, AHRR, CXCL3, CYP1A1, CYP1B1, CYP1A2, CST6, NTRK2 and/or TAD in the sample from the subject is increased as compared to the control expression level of the corresponding gene(s) and (ii) the level of expression of DMBT1, ELF5, AZGP1, PRRX1, AQP3, COMP, ITGA10, CTHRC1, BEX1 and/or GHRL in the sample from the subject is decreased as compared to the control expression level of the corresponding gene(s)—is required for determining that the subject is prone to develop progressive COPD.

The decrease or increase in the level of expression of the marker gene(s) tested which is required for determining that the subject is prone to develop progressive COPD in accordance with the fourth aspect is preferably at least a 1.5-fold decrease or increase, more preferably at least a 2-fold decrease or increase, even more preferably at least a 3-fold decrease or increase, even more preferably at least a 5-fold decrease or increase, and yet even more preferably at least a 10-fold decrease or increase.

In a preferred embodiment of the method according to the fourth aspect of the invention, it is determined that the subject to be tested is prone to develop progressive COPD if the level of expression of a majority of the number of genes tested is altered in the sense that (i) the level of expression of KIAA1199, GPR110, GDF15, RASGRF2, RND1, FGG, CEACAM5, HYAL2, AHRR, CXCL3, CYP1A1, CYP1B1, CYP1A2, CST6, NTRK2 and/or TAL1 in the sample from the subject is at least 3-fold (more preferably at least 5-fold, even more preferably at least 10-fold) increased as compared to the control expression level of the corresponding gene(s) and (ii) the level of expression of DMBT1, ELF5, AZGP1, PRRX1, AQP3, COMP, ITGA10, CTHRC1, BEX1 and/or GHRL in the sample from the subject is at least 3-fold (more preferably at least 5-fold, even more preferably at least 10-fold) decreased as compared to the control expression level of the corresponding gene(s).

In a further preferred embodiment of the method according to the fourth aspect of the invention, it is determined that the subject to be tested is prone to develop progressive COPD if the level of expression of at least 70% (more preferably at least 80%, and even more preferably at least 90%) of the number of genes tested is altered in the sense that (i) the level of expression of KIAA1199, GPR110, GDF15, RASGRF2, RND1, FGG, CEACAM5, HYAL2, AHRR, CXCL3, CYP1A1, CYP1B1, CYP1A2, CST6, NTRK2 and/or TAL1 in the sample from the subject is increased as compared to the control expression level of the corresponding gene(s) and (ii) the level of expression of DMBT1, ELF5, AZGP1, PRRX1, AQP3, COMP, ITGA10, CTHRC1, BEX1 and/or GHRL in the sample from the subject is decreased as compared to the control expression level of the corresponding gene(s).

In a further preferred embodiment of the method according to the fourth aspect of the invention, it is determined that the subject to be tested is prone to develop progressive COPD if the level of expression of at least 70% (more preferably at least 80%, and even more preferably at least 90%) of the number of genes tested is altered in the sense that (i) the level of expression of KIAA1199, GPR110, GDF15, RASGRF2, RND1, FGG, CEACAM5, HYAL2, AHRR, CXCL3, CYP1A1, CYP1B1, CYP1A2, CST6, NTRK2 and/or TAL1 in the sample from the subject is at least 3-fold (more preferably at least 5-fold, even more preferably at least 10-fold) increased as compared to the control expression level of the corresponding gene(s) and (ii) the level of expression of DMBT1, ELF5, AZGP1, PRRX1, AQP3, COMP, ITGA10, CTHRC1, BEX1 and/or GHRL in the sample from the subject is at least 3-fold (more preferably at least 5-fold, even more preferably at least 10-fold) decreased as compared to the control expression level of the corresponding gene(s).

The present invention furthermore relates to the use of the gene DMBT1 as a marker in an in vitro diagnostic method of assessing the susceptibility of a subject to develop progressive COPD. In particular, in accordance with the fifth aspect, the invention relates to the use of a pair of primers for (i.e., binding to) a transcript of the gene DMBT1 in an in vitro diagnostic method of assessing the susceptibility of a subject to develop progressive COPD. Non-limiting examples of such an in vitro method are the methods according to the second aspect of the present invention. The transcript is preferably an mRNA of the gene DMBT1 (e.g., any one of the specific mRNAs of DMBT1 listed in Table 1 above) or a cDNA synthesized from the mRNA of the gene DMBT1 (e.g., a cDNA synthesized from any one of the specific mRNAs of DMBT1 listed in Table 1 above). The primers can be designed using methods known in the art (as also described, e.g., in Green et al., 2012) so as to allow the specific amplification/quantification of the transcript of the gene DMBT1. Furthermore, the primers are preferably DNA primers. The in vitro diagnostic method of assessing the susceptibility of a subject to develop progressive COPD, in which the pair of primers is to be used, preferably comprises a step of determining the expression level of the gene DMBT1 in a sample obtained from the subject. The preferred features/embodiments of the method according to the second aspect of the present invention as described herein, including in particular the preferred embodiments of determining expression levels, the preferred embodiments of the sample, and the preferred embodiments of the subject, also apply to the method in which the pair of primers is to be used.

In accordance with the fifth aspect, the present invention also relates to the use of a nucleic acid probe to (i.e., binding to) a transcript of the gene DMBT1 in an in vitro diagnostic method of assessing the susceptibility of a subject to develop progressive COPD. Non-limiting examples of such an in vitro method are the methods according to the second aspect of the present invention. The transcript is preferably an mRNA of the gene DMBT1 (e.g., any one of the specific mRNAs of DMBT1 listed in Table 1 above) or a cDNA synthesized from the mRNA of the gene DMBT1 (e.g., a cDNA synthesized from any one of the specific mRNAs of DMBT1 listed in Table 1 above). The nucleic acid probe comprises or consists of a nucleic acid capable of hybridizing with the above-mentioned transcript. The nucleic acid probe is preferably a single-stranded DNA probe or a single-stranded RNA probe, more preferably a single-stranded DNA probe. It is furthermore preferred that the nucleic acid probe (which may be, e.g., a single-stranded DNA or a single-stranded RNA, and is preferably a single-stranded DNA) is an oligonucleotide probe having, e.g., 10 to 80 nucleotides, preferably 15 to 60 nucleotides, more preferably 20 to 35 nucleotides, and even more preferably about 25 nucleotides. Such nucleic acid probes can be designed using methods known in the art (as also described, e.g., in Green et al., 2012) so as to allow the specific detection and quantification of the transcript of the corresponding gene. The in vitro diagnostic method of assessing the susceptibility of a subject to develop progressive COPD, in which the nucleic acid probe is to be used, preferably comprises a step of determining the expression level of the gene DMBT1 in a sample obtained from the subject. The preferred features/embodiments of the method according to the second aspect of the invention as described herein, including in particular the preferred embodiments of determining expression levels, the preferred embodiments of the sample, and the preferred embodiments of the subject, also apply to the method in which the nucleic acid probe is to be used.

In the fifth aspect, the invention further relates to the use of a microarray comprising a nucleic acid probe to (i.e., binding to) a transcript of the gene DMBT1 and optionally comprising nucleic acid probes to the transcripts of one or more further genes selected from KIAA1199, TMSB15A, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL in an in vitro diagnostic method of assessing the susceptibility of a subject to develop progressive COPD. The microarray preferably comprises nucleic acid probes to the transcript of DMBT1 and to the transcripts of at least one, more preferably at least two, even more preferably at least three of the above-mentioned further genes. Each of the transcripts is preferably an mRNA of the corresponding gene (including, e.g., any one of the corresponding specific mRNAs listed in Table 1 above) or a cDNA synthesized from the mRNA of the gene (including, e.g., a cDNA synthesized from any one of the corresponding specific mRNAs listed in Table 1 above). Each of the nucleic acid probes is preferably a single-stranded DNA probe or a single-stranded RNA probe, more preferably a single-stranded DNA probe. It is furthermore preferred that the nucleic acid probes (which may be, e.g., single-stranded DNA or single-stranded RNA, preferably single-stranded DNA) are oligonucleotide probes having, e.g., 10 to 80 nucleotides, preferably 15 to 60 nucleotides, more preferably 20 to 35 nucleotides, and even more preferably about 25 nucleotides. The in vitro diagnostic method of assessing the susceptibility of a subject to develop progressive COPD, in which the microarray is to be used, preferably comprises a step of determining the expression level of the gene DMBT1 and optionally of the one or more further genes in a sample obtained from the subject. The preferred features/embodiments of the method according to the second aspect of the invention as described herein, including in particular the preferred embodiments of determining expression levels, the preferred embodiments of the sample, and the preferred embodiments of the subject, also apply to the method in which the microarray is to be used.

In accordance with the fifth aspect, the invention is also directed to the use of an antibody against (i.e., binding to) the protein DMBT1 in an in vitro diagnostic method of assessing the susceptibility of a subject to develop progressive COPD. The antibody binds specifically to the protein DMBT1 and may be, e.g., a polyclonal antibody or a monoclonal antibody. Preferably, the antibody is a monoclonal antibody. The antibody may further be a full/intact immunoglobulin molecule or a fragment/part thereof (such as, e.g., a separated light or heavy chain, an Fab fragment, an Fab/c fragment, an Fv fragment, an Fab' fragment, or an $F(ab')_2$ fragment), provided that the fragment/part substantially retains the binding specificity of the corresponding full immunoglobulin molecule. The antibody may also be a modified and/or altered antibody, such as a chimeric or humanized antibody, a bifunctional or trifunctional antibody, or an antibody construct (such as a single-chain variable fragment (scFv) or an antibody-fusion protein). The antibody can be prepared using methods known in the art, as also described, e.g., in Harlow et al., 1998. For example, monoclonal antibodies can be prepared by methods such as the hybridoma technique (see, e.g., Köhler et al., 1975), the trioma technique, the human B-cell hybridoma technique (see, e.g., Kozbor et al., 1983) or the EBV-hybridoma technique (see, e.g., Cole et al., 1985). The protein DMBT1 may be, e.g., the specific DMBT1 protein listed in Table 1 above. The in vitro diagnostic method of assessing the susceptibility of a subject to develop progressive COPD, in which the antibody is to be used, preferably comprises a step of determining the amount of the protein DMBT1 in a sample obtained from the subject. The preferred features/embodiments of the method according to the second aspect of the invention as described herein, including in particular the preferred embodiments of determining the amount of a specific protein in a sample (as discussed in connection with the determination of translation levels), the preferred embodiments of the sample, and the preferred embodiments of the subject, also apply to the method in which the antibody is to be used.

Moreover, in accordance with the seventh aspect, the present invention relates to the use of a pair of primers for (i.e., binding to) a transcript of the gene DMBT1 in an in vitro method of diagnosing stable COPD in a subject or assessing the susceptibility of a subject to develop stable COPD. Non-limiting examples of such an in vitro method are the methods according to the third aspect of the present invention. The transcript is preferably an mRNA of the gene DMBT1 (e.g., any one of the specific mRNAs of DMBT1 listed in Table 1 above) or a cDNA synthesized from the mRNA of the gene DMBT1 (e.g., a cDNA synthesized from any one of the specific mRNAs of DMBT1 listed in Table 1 above). The primers can be designed using methods known in the art (as also described, e.g., in Green et al., 2012) so as to allow the specific amplification/quantification of the transcript of the gene DMBT1. Furthermore, the primers are preferably DNA primers. The in vitro method of diagnosing stable COPD in a subject or assessing the susceptibility of a subject to develop stable COPD, in which the pair of primers is to be used, preferably comprises a step of determining the expression level of the gene DMBT1 in a sample obtained from the subject. The preferred features/embodiments of the method according to the third aspect of the present invention as described herein, including in particular the preferred embodiments of determining expression levels, the preferred embodiments of the sample, and the preferred embodiments of the subject, also apply to the method in which the pair of primers is to be used.

In accordance with the seventh aspect, the present invention also relates to the use of a nucleic acid probe to (i.e., binding to) a transcript of the gene DMBT1 in an in vitro method of diagnosing stable COPD in a subject or assessing the susceptibility of a subject to develop stable COPD. Non-limiting examples of such an in vitro method are the methods according to the third aspect of the present invention. The transcript is preferably an mRNA of the gene DMBT1 (e.g., any one of the specific mRNAs of DMBT1 listed in Table 1 above) or a cDNA synthesized from the mRNA of the gene DMBT1 (e.g., a cDNA synthesized from any one of the specific mRNAs of DMBT1 listed in Table 1 above). The nucleic acid probe comprises or consists of a nucleic acid capable of hybridizing with the above-mentioned transcript. The nucleic acid probe is preferably a single-stranded DNA probe or a single-stranded RNA probe, more preferably a single-stranded DNA probe. It is furthermore preferred that the nucleic acid probe (which may be, e.g., a single-stranded DNA or a single-stranded RNA, and is preferably a single-stranded DNA) is an oligonucleotide probe having, e.g., 10 to 80 nucleotides, preferably 15 to 60 nucleotides, more preferably 20 to 35 nucleotides, and even more preferably about 25 nucleotides. Such nucleic acid probes can be designed using methods known in the art (as also described, e.g., in Green et al., 2012) so as to allow the specific detection and quantification of the transcript of the corresponding gene. The in vitro method of diagnosing stable COPD in a subject or assessing the susceptibility of a subject to develop stable COPD, in which the nucleic acid probe is to be used, preferably comprises a step of determining the expression level of the gene DMBT1 in a sample obtained from the subject. The preferred features/embodiments of the method according to the third aspect of the invention as described herein, including in particular the preferred embodiments of determining expression levels, the preferred embodiments of the sample, and the preferred embodiments of the subject, also apply to the method in which the nucleic acid probe is to be used.

In the seventh aspect, the invention further relates to the use of a microarray comprising a nucleic acid probe to (i.e., binding to) a transcript of the gene DMBT1 and optionally comprising nucleic acid probes to the transcripts of one or more further genes selected from KIAA1199, TMSB15A, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL in an in vitro method of diagnosing stable COPD in a subject or assessing the susceptibility of a subject to develop stable COPD. The microarray preferably comprises nucleic acid probes to the transcript of DMBT1 and to the transcripts of at least one, more preferably at least two, even more preferably at least three of the above-mentioned further genes. Each of the transcripts is preferably an mRNA of the corresponding gene (including, e.g., any one of the corresponding specific mRNAs listed in Table 1 above) or a cDNA synthesized from the mRNA of the gene (including, e.g., a cDNA synthesized from any one of the corresponding specific mRNAs listed in Table 1 above). Each of the nucleic acid probes is preferably a single-stranded DNA probe or a single-stranded RNA probe, more preferably a single-stranded DNA probe. It is furthermore preferred that the nucleic acid probes (which may be, e.g., single-stranded DNA or single-stranded RNA, preferably single-stranded DNA) are oligonucleotide probes having, e.g., 10 to 80 nucleotides, preferably 15 to 60 nucleotides, more preferably 20 to 35 nucleotides, and even more preferably about 25 nucleotides. The in vitro method of diagnosing stable COPD in a subject or assessing the susceptibility of a subject to develop stable COPD, in which the microarray is to be used, preferably comprises a step of determining the expression level of the gene DMBT1 and optionally of the one or more further genes in a sample obtained from the subject. The preferred features/embodiments of the method according to the third aspect of the invention as described herein, including in particular the preferred embodiments of determining expression levels, the preferred embodiments of the sample, and the preferred embodiments of the subject, also apply to the method in which the microarray is to be used.

In accordance with the seventh aspect, the invention is also directed to the use of an antibody against (i.e., binding to) the protein DMBT1 in an in vitro method of diagnosing stable COPD in a subject or assessing the susceptibility of a subject to develop stable COPD. The antibody binds specifically to the protein DMBT1 and may be, e.g., a polyclonal antibody or a monoclonal antibody. Preferably, the antibody is a monoclonal antibody. The antibody may further be a full/intact immunoglobulin molecule or a fragment/part thereof (such as, e.g., a separated light or heavy chain, an Fab fragment, an Fab/c fragment, an Fv fragment, an Fab' fragment, or an F(ab')2 fragment), provided that the fragment/part substantially retains the binding specificity of the corresponding full immunoglobulin molecule. The antibody may also be a modified and/or altered antibody, such as a chimeric or humanized antibody, a bifunctional or trifunctional antibody, or an antibody construct (such as a single-chain variable fragment (scFv) or an antibody-fusion protein). The antibody can be prepared using methods known in the art, as also described, e.g., in Harlow et al., 1998. For example, monoclonal antibodies can be prepared by methods such as the hybridoma technique (see, e.g., Köhler et al., 1975), the trioma technique, the human B-cell hybridoma technique (see, e.g., Kozbor et al., 1983) or the EBV-hybridoma technique (see, e.g., Cole et al., 1985). The protein DMBT1 may be, e.g., the specific DMBT1 protein listed in Table 1 above. The in vitro method of diagnosing stable COPD in a subject or assessing the susceptibility of a subject to develop stable COPD, in which the antibody is to be used, preferably comprises a step of determining the amount of the protein DMBT1 in a sample obtained from the subject. The preferred features/embodiments of the method according to the third aspect of the invention as described herein, including in particular the preferred embodiments of determining the amount of a specific protein in a sample (as discussed in connection with the determination of translation levels), the preferred embodiments of the sample, and the preferred embodiments of the subject, also apply to the method in which the antibody is to be used.

Furthermore, in accordance with the ninth aspect, the present invention relates to the use of a pair of primers for (i.e., binding to) a transcript of the gene DMBT1 in an in vitro diagnostic method of assessing the susceptibility of a subject suffering from stable COPD to develop progressive COPD involving the appearance of irreversible lung damage. Non-limiting examples of such an in vitro method are the methods according to the fourth aspect of the present invention. The transcript is preferably an mRNA of the gene DMBT1 (e.g., any one of the specific mRNAs of DMBT1 listed in Table 1 above) or a cDNA synthesized from the mRNA of the gene DMBT1 (e.g., a cDNA synthesized from any one of the specific mRNAs of DMBT1 listed in Table 1 above). The primers can be designed using methods known in the art (as also described, e.g., in Green et al., 2012) so as to allow the specific amplification/quantification of the transcript of the gene DMBT1. Furthermore, the primers are preferably DNA primers. The in vitro diagnostic method of assessing the susceptibility of a subject suffering from stable COPD to develop progressive COPD involving the appearance of irreversible lung damage, in which the pair of primers is to be used, preferably comprises a step of determining the expression level of the gene DMBT1 in a sample obtained from the subject. The preferred features/embodiments of the method according to the fourth aspect of the present invention as described herein, including in particular the preferred embodiments of determining expression levels, the preferred embodiments of the sample, and the preferred embodiments of the subject, also apply to the method in which the pair of primers is to be used.

In accordance with the ninth aspect, the present invention also relates to the use of a nucleic acid probe to (i.e., binding to) a transcript of the gene DMBT1 in an in vitro diagnostic method of assessing the susceptibility of a subject suffering from stable COPD to develop progressive COPD involving the appearance of irreversible lung damage. Non-limiting examples of such an in vitro method are the methods according to the fourth aspect of the present invention. The transcript is preferably an mRNA of the gene DMBT1 (e.g., any one of the specific mRNAs of DMBT1 listed in Table 1 above) or a cDNA synthesized from the mRNA of the gene DMBT1 (e.g., a cDNA synthesized from any one of the specific mRNAs of DMBT1 listed in Table 1 above). The nucleic acid probe comprises or consists of a nucleic acid capable of hybridizing with the above-mentioned transcript. The nucleic acid probe is preferably a single-stranded DNA probe or a single-stranded RNA probe, more preferably a single-stranded DNA probe. It is furthermore preferred that the nucleic acid probe (which may be, e.g., a single-stranded DNA or a single-stranded RNA, and is preferably a single-stranded DNA) is an oligonucleotide probe having, e.g., 10 to 80 nucleotides, preferably 15 to 60 nucleotides, more preferably 20 to 35 nucleotides, and even more preferably about 25 nucleotides. Such nucleic acid probes can be designed using methods known in the art (as also described, e.g., in Green et al., 2012) so as to allow the specific detection and quantification of the transcript of the corresponding gene. The in vitro diagnostic method of assessing the susceptibility of a subject suffering from stable COPD to develop progressive COPD involving the appearance of irreversible lung damage, in which the nucleic acid probe is to be used, preferably comprises a step of determining the expression level of the gene DMBT1 in a sample obtained from the subject. The preferred features/embodiments of the method according to the fourth aspect of the invention as described herein, including in particular the preferred embodiments of determining expression levels, the preferred embodiments of the sample, and the preferred embodiments of the subject, also apply to the method in which the nucleic acid probe is to be used.

In the ninth aspect, the invention further relates to the use of a microarray comprising a nucleic acid probe to (i.e., binding to) a transcript of the gene DMBT1 and optionally comprising nucleic acid probes to the transcripts of one or more further genes selected from KIAA1199, TMSB15A, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL in an in vitro diagnostic method of assessing the susceptibility of a subject suffering from stable COPD to develop progressive COPD involving the appearance of irreversible lung damage. The microarray preferably comprises nucleic acid probes to the transcript of DMBT1 and to the transcripts of at least one, more preferably at least two, even more preferably at least three of the above-mentioned further genes. Each of the transcripts is preferably an mRNA of the corresponding gene (including, e.g., any one of the corresponding specific mRNAs listed in Table 1 above) or a cDNA synthesized from the mRNA of the gene (including, e.g., a cDNA synthesized from any one of the corresponding specific mRNAs listed in Table 1 above). Each of the nucleic acid probes is preferably a single-stranded DNA probe or a single-stranded RNA probe, more preferably a single-stranded DNA probe. It is furthermore preferred that the nucleic acid probes (which may be, e.g., single-stranded DNA or single-stranded RNA, preferably single-stranded DNA) are oligonucleotide probes having, e.g., 10 to 80 nucleotides, preferably 15 to 60 nucleotides, more preferably 20 to 35 nucleotides, and even more preferably about 25 nucleotides. The in vitro diagnostic method of assessing the susceptibility of a subject suffering from stable COPD to develop progressive COPD involving the appearance of irreversible lung damage, in which the microarray is to be used, preferably comprises a step of determining the expression level of the gene DMBT1 and optionally of the one or more further genes in a sample obtained from the subject. The preferred features/embodiments of the method according to the fourth aspect of the invention as described herein, including in particular the preferred embodiments of determining expression levels, the preferred embodiments of the sample, and the preferred embodiments of the subject, also apply to the method in which the microarray is to be used.

In accordance with the ninth aspect, the invention is also directed to the use of an antibody against (i.e., binding to) the protein DMBT1 in an in vitro diagnostic method of assessing the susceptibility of a subject suffering from stable COPD to develop progressive COPD involving the appearance of irreversible lung damage. The antibody binds specifically to the protein DMBT1 and may be, e.g., a polyclonal antibody or a monoclonal antibody. Preferably, the antibody is a monoclonal antibody. The antibody may further be a full/intact immunoglobulin molecule or a fragment/part thereof (such as, e.g., a separated light or heavy chain, an Fab fragment, an Fab/c fragment, an Fv fragment, an Fab' fragment, or an F(ab')2 fragment), provided that the fragment/part substantially retains the binding specificity of the corresponding full immunoglobulin molecule. The antibody may also be a modified and/or altered antibody, such as a chimeric or humanized antibody, a bifunctional or trifunctional antibody, or an antibody construct (such as a single-chain variable fragment (scFv) or an antibody-fusion protein). The antibody can be prepared using methods known in the art, as also described, e.g., in Harlow et al., 1998. For example, monoclonal antibodies can be prepared by methods such as the hybridoma technique (see, e.g., Köhler et al., 1975), the trioma technique, the human B-cell hybridoma technique (see, e.g., Kozbor et al., 1983) or the EBV-hybridoma technique (see, e.g., Cole et al., 1985). The protein KIAA1199 may be, e.g., the specific DMBT1 protein listed in Table 1 above. The in vitro diagnostic method of assessing the susceptibility of a subject suffering from stable COPD to develop progressive COPD involving the appearance of irreversible lung damage, in which the antibody is to be used, preferably comprises a step of determining the amount of the protein DMBT1 in a sample obtained from the subject. The preferred features/embodiments of the method according to the fourth aspect of the invention as described herein, including in particular the preferred embodiments of determining the amount of a specific protein in a sample (as discussed in connection with the determination of translation levels), the preferred embodiments of the sample, and the preferred embodiments of the subject, also apply to the method in which the antibody is to be used.

In accordance with the sixth aspect, the present invention provides a method of treating COPD, the method comprising administering a drug against COPD to a subject that has been identified in a method according to the second aspect of the invention as being prone to develop progressive COPD. The invention likewise provides a drug against COPD for use in treating COPD in a subject that has been identified in a method according to the second aspect as being prone to develop progressive COPD. The invention also relates to the use of a drug against COPD in the preparation of a pharmaceutical composition for treating COPD in a subject that has been identified in a method according to the second aspect as being prone to develop progressive COPD. The subject referred to above is as defined in the methods according to the second aspect of the invention and, accordingly, is preferably a human.

Moreover, in accordance with the eighth aspect, the present invention provides a method of treating or preventing COPD, the method comprising administering a drug against COPD to a subject that has been identified in a method according to the third aspect of the invention as suffering from stable COPD or as being prone to suffer from stable COPD. It will be understood that a subject that has been identified as suffering from stable COPD can be treated by administering a drug against COPD, while a subject that has been identified as being prone to suffer from stable COPD can be prevented from developing COPD by administering a drug against COPD. The invention likewise provides a drug against COPD for use in treating or preventing COPD in a subject that has been identified in a method according to the third aspect as suffering from stable COPD or as being prone to suffer from stable COPD. The invention also relates to the use of a drug against COPD in the preparation of a pharmaceutical composition for treating or preventing COPD in a subject that has been identified in a method according to the third aspect as suffering from stable COPD or as being prone to suffer from stable COPD. The subject referred to above is as defined in the methods according to the third aspect of the invention and, accordingly, is preferably a human.

In accordance with the tenth aspect, the present invention provides a method of treating COPD, the method comprising administering a drug against COPD to a subject suffering from stable COPD, wherein the subject has been identified in a method according to the fourth aspect of the invention as being prone to develop progressive COPD. The invention likewise provides a drug against COPD for use in treating COPD in a subject suffering from stable COPD, wherein the subject has been identified in a method according to the fourth aspect as being prone to develop progressive COPD. The invention also relates to the use of a drug against COPD in the preparation of a pharmaceutical composition for treating COPD in a subject suffering from stable COPD, wherein the subject has been identified in a method according to the fourth aspect as being prone to develop progressive COPD. The subject referred to above is as defined in the methods according to the fourth aspect of the invention and, accordingly, is preferably a human.

The drug against COPD to be administered to a subject in accordance with the sixth, eighth or tenth aspect of the invention is not particularly limited and may be, for example, a $\beta_2$-agonist (such as, e.g., bitolterol, carbuterol, fenoterol, pirbuterol, procaterol, reproterol, rimiterol, salbutamol, levosalbutamol, terbutaline, tulobuterol, arformoterol, bambuterol, clenbuterol, formoterol, olodaterol, salmeterol, indacaterol, or a pharmaceutically acceptable salt of any of the aforementioned agents), a glucocorticoid (such as, e.g., beclometasone, betamethasone, budesonide, ciclesonide, flunisolide, fluticasone, mometasone, triamcinolone, or a pharmaceutically acceptable salt of any of the aforementioned agents), an anticholinergic or a muscarinic antagonist (such as, e.g., aclidinium bromide, glycopyrronium bromide, ipratropium bromide, oxitropium bromide, tiotropium bromide, or a pharmaceutically acceptable salt of any of the aforementioned agents), a mast cell stabilizer (such as, e.g., cromoglicate, nedocromil, or a pharmaceutically acceptable salt of any of the aforementioned agents), a xanthine derivative (such as, e.g., acefylline, ambuphylline, bamifylline, doxofylline, enprofylline, etamiphylline, proxyphylline, theobromine, theophylline, aminophylline, choline theophyllinate, or a pharmaceutically acceptable salt of any of the aforementioned agents), a leukotriene antagonist (such as, e.g., montelukast, pranlukast, zafirlukast, or a pharmaceutically acceptable salt of any of the aforementioned agents), a lipoxygenase inhibitor (such as, e.g., zileuton or a pharmaceutically acceptable salt thereof), a thromboxane receptor antagonist (such as, e.g., ramatroban, seratrodast, or a pharmaceutically acceptable salt of any of the aforementioned agents) a non-xanthine PDE4 inhibitor (such as, e.g., ibudilast, roflumilast, or a pharmaceutically acceptable salt of any of the aforementioned agents), or any other drug against COPD (such as, e.g., amlexanox, eprozinol, fenspiride, omalizumab, epinephrine, hexoprenaline, isoprenaline, isoproterenol, orciprenaline, metaproterenol, atropine, or a pharmaceutically acceptable salt of any of the aforementioned agents), or any combination thereof. A particularly preferred drug against COPD is roflumilast.

In the eleventh aspect, the present invention provides an in vitro method of monitoring the progression of COPD in a subject, the method comprising:

- determining the level of expression of one or more genes selected from NTRK2 and RASGRF2 in a first sample obtained from the subject;
- determining the level of expression of the one or more genes in a second sample obtained from the subject at a later point in time than the first sample;
- comparing the level of expression of the one or more genes in the second sample to the level of expression of the corresponding gene(s) in the first sample; and
- assessing (or determining) the progression of COPD in the subject, wherein a decrease in the level of expression of NTRK2 and/or RASGRF2 in the second sample as compared to the level of expression of the corresponding gene(s) in the first sample is indicative of an amelioration (i.e., an improvement) of COPD in the subject, and wherein an increase in the level of expression of NTRK2 and/or RASGRF2 in the second sample as compared to the level of expression of the corresponding gene(s) in the first sample is indicative of a worsening of COPD in the subject.

Figure 4A:
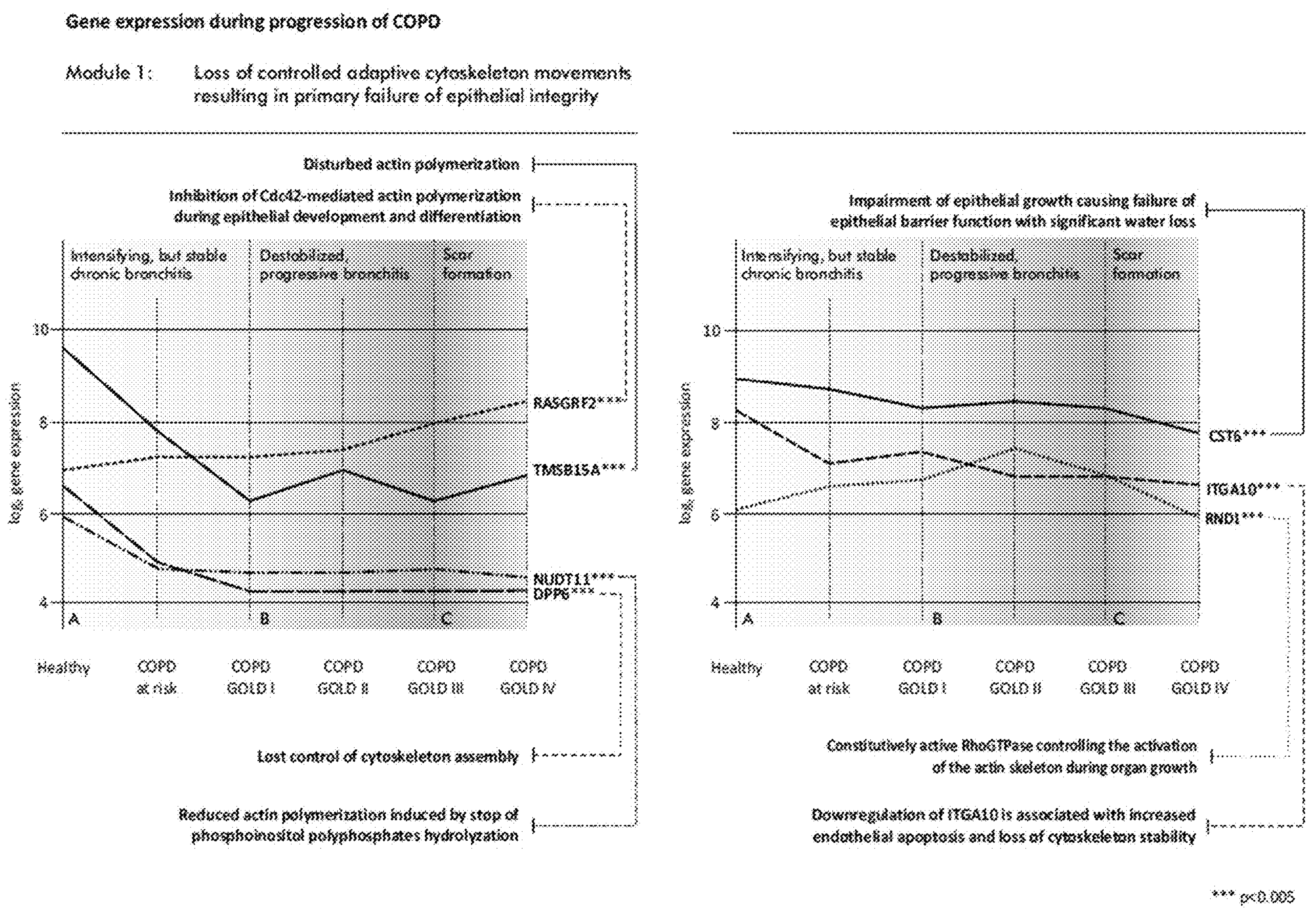
Figure 4B:
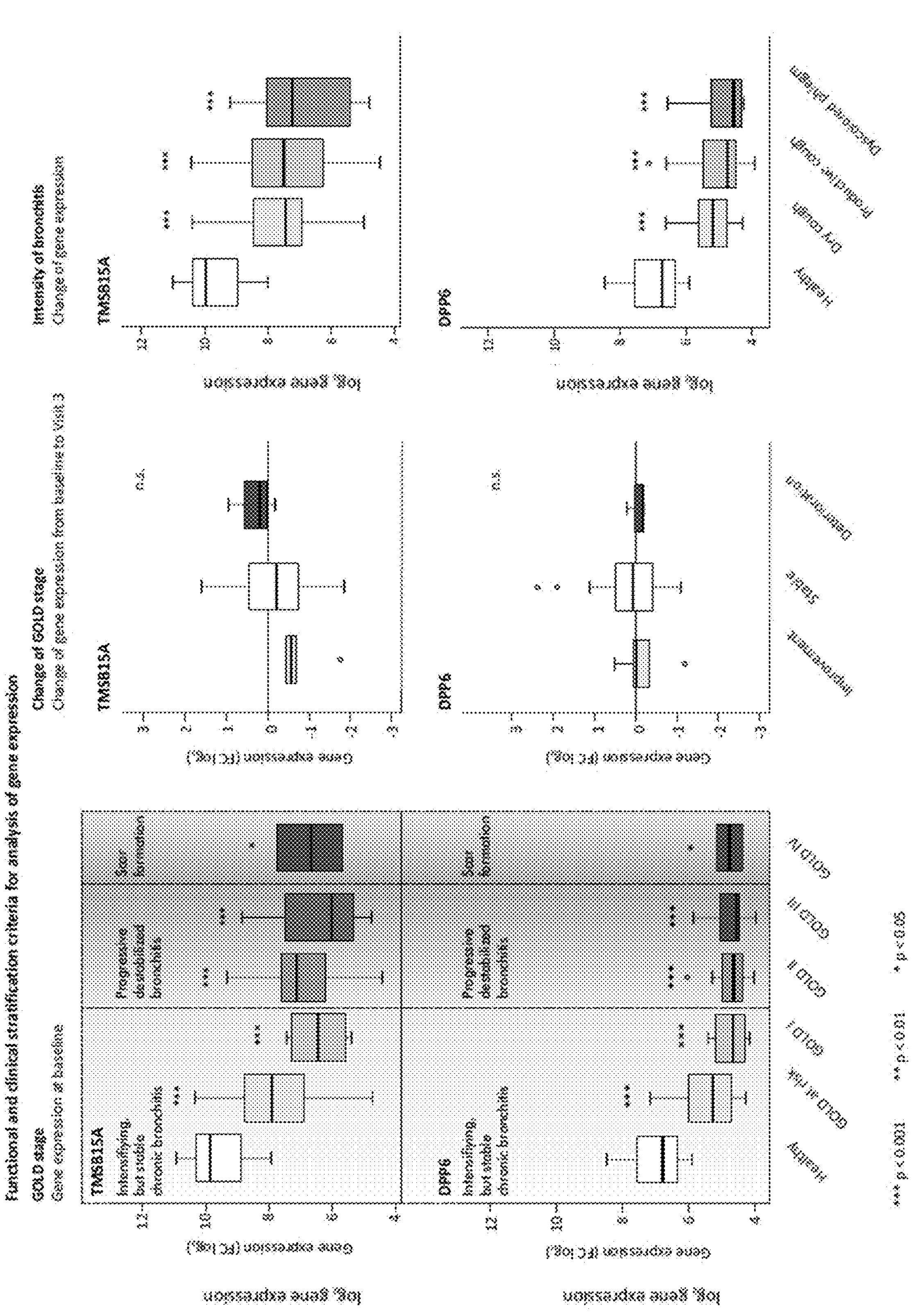
Figure 4C:
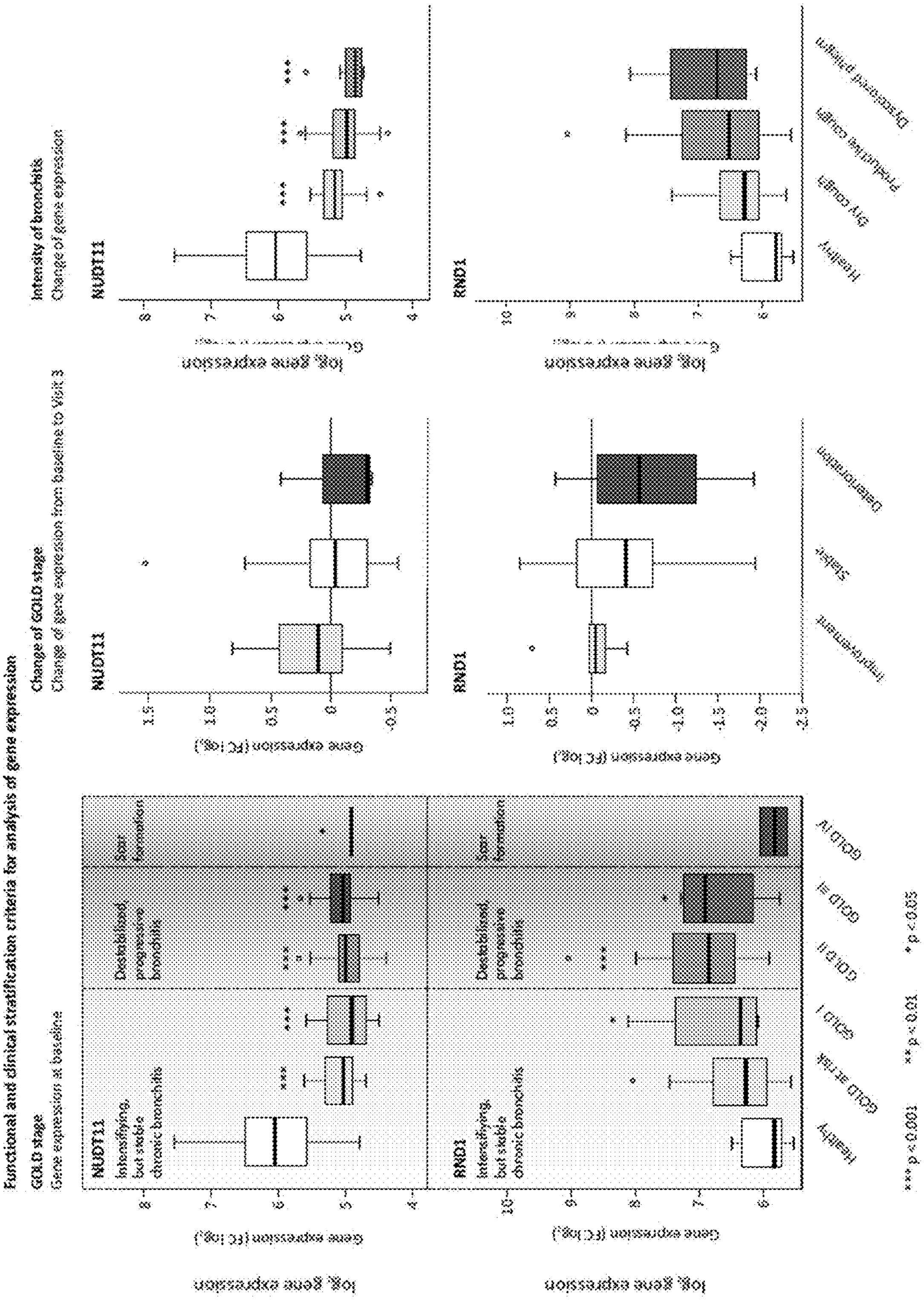
Figure 8A:
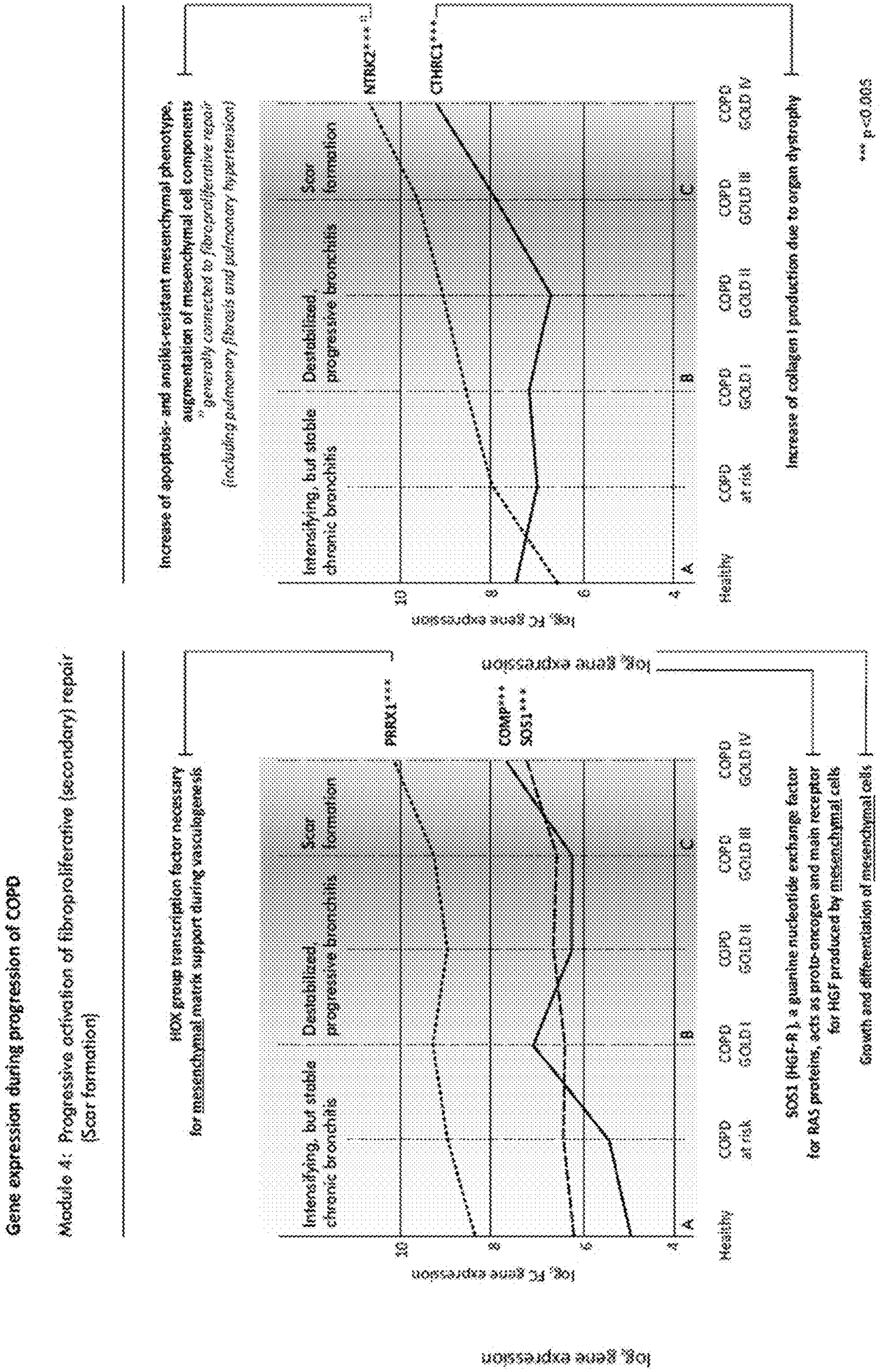

As demonstrated in Example 1 and shown in FIGS. 4A and 8A, a decrease in the level of expression of NTRK2 and/or RASGRF2 is indicative of an amelioration/improvement of COPD whereas an increase in the level of expression of these genes is indicative of a worsening of COPD. Monitoring the progression of COPD in a subject suffering from this disease can be useful, e.g., for assessing the prospects of success of a treatment, of a new medication, or of a new dosing regimen.

In the eleventh aspect, it is preferred that the level of expression of the gene NTRK2 and optionally of the gene RASGRF2 is determined. More preferably, the level of expression of the genes NTRK2 and RASGRF2 is determined.

The level of expression of the above-mentioned marker genes in the first sample and in the second sample according the eleventh aspect of the invention can be determined as described in connection with the methods of the second to fourth aspects of the invention. For example, the level of transcription or the level of translation of the marker gene(s) NTRK2 and/or RASGRF2 can be determined. It is preferred that the level of expression of the one or more genes selected from NTRK2 and RASGRF2 in the first sample and in the second sample is determined by determining the level of transcription of the corresponding gene(s). The level of transcription is preferably determined using qRT-PCT or a microarray.

The subject to be tested in the method according to the eleventh aspect of the invention is as defined in connection with the methods of the second to fourth aspects of the invention, and preferably is a human or a non-human mammal, more preferably a human. It is furthermore preferred that the subject to be tested/monitored in accordance with the eleventh aspect is a subject (preferably a human) that has been diagnosed as suffering from COPD (e.g., at the point in time when the first sample was obtained).

While the first sample and the second sample obtained from the subject can, in principle, be any tissue sample or serum from the subject, they should both originate from the same type of tissue of the subject (or should both be serum samples). Preferably, the first sample and the second sample are lung tissue samples. More preferably, the first sample and the second sample are transbronchial lung biopsy samples or they are bronchoalveolar lavage (BAL) samples.

The second sample has been obtained from the subject at a later point in time than the first sample. For instance, the second sample may have been obtained from the subject about 2 months to about 12 months, preferably about 3 months to about 9 months (e.g., about 3 months, or about 4 months, or about 5 months, or about 6 months, or about 7 months, or about 8 months, or about 9 months), and more preferably about 3 months to about 6 months after the first sample was obtained from the subject.

As used herein, the term "about" refers to ±10% of the indicated numerical value, and in particular to ±5% of the indicated numerical value. Whenever the term "about" is used, a specific reference to the exact numerical value indicated is also included. If the term "about" is used in connection with a parameter that is quantified in integers, such as the number of nucleotides in a given nucleic acid, the numbers corresponding to ±10% or ±5% of the indicated numerical value are to be rounded to the nearest integer. For example, the expression "about 25 nucleotides" refers to the range of 23 to 28 nucleotides, in particular the range of 24 to 26 nucleotides, and preferably refers to the specific value of 25 nucleotides.

It is to be understood that the present invention specifically relates to each and every combination of features and embodiments described herein, including any combination of general and/or preferred features/embodiments. In particular, the invention specifically relates to all combinations of preferred features (including all degrees of preference) of the methods and uses provided herein.

In this specification, a number of documents including patent applications, scientific literature and manufacturers' manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The invention is also described by the following illustrative figures. The appended figures show:

FIG. 1: Study design of the COPD-AUVA study conducted at the Vienna Medical University (see Example 1).

Figure 2:
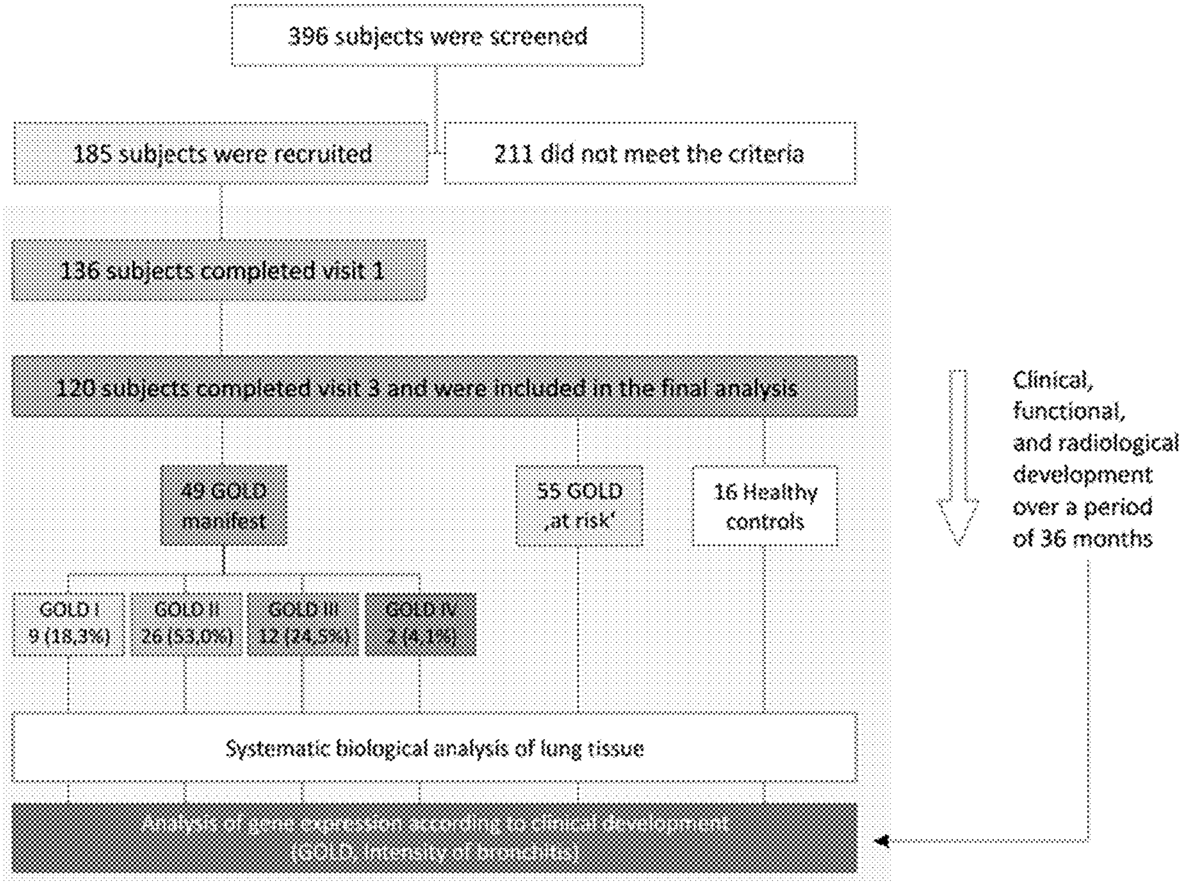

FIG. 2: Overview of the numbers of subjects of different disease states who underwent the COPD-AUVA study.

FIGS. 3A-D: Overview of healthy subjects (A) and of subjects with either chronic bronchitis but no signs of pulmonary obstruction (COPD "at risk"; "GOLD 0") at visit 1 (B) or with manifest COPD at visit 1 (C), as well as the development of COPD (severity according to GOLD criteria), bronchitis and smoking habits in these subjects over the period from visit 1 (day 0) to visit 2 (12 months) to visit 3 (36 months). The term "pack years" refers to a person's cigarette consumption calculated as the packs of cigarettes (each pack containing 20 cigarettes) smoked per day, multiplied by the length of cigarette consumption in years. (D) Clinical characteristics of participants in the COPD-AUVA study and changes between baseline and visit 3 (see Example 1).

FIGS. 4A-D: COPD Pathology module 1: Development of chronic bronchitis: Progressive inhibition of adaptive motility of mucosal cells caused by the inhibition of coordinated actin cytoskeleton movements.

Chronic bronchitis starts with the significant downregulation of genes that control assembly, polymerization, motility, stabilization and energy supply of F actin-mediated cytoskeleton movements (suppression of thymosin beta 15A (TMSB15A), dipeptidyl-peptidase 6 (DPP6), nudix (nucleoside diphosphate linked moiety X)-type motif 11 (NUDT11), and integrin alpha 10 (ITGA10)). At the same time, expression of the RASGRF2 gene known to inhibit Cdc42-mediated polymerization of actin during cellular movements is progressively increased during advancement of COPD (FIGS. 4A and 4D) indicating that the inhibition of cellular motility is not only a leading mechanism in early stages of COPD development, but also part of the progressive membrane destruction in later stages of COPD.

Of note, reduced expression of these genes is also connected to increasing intensity of bronchial inflammation. This characteristic expression pattern includes the SLC51B gene (FIG. 4D) which is as yet largely known for its capacity to transport steroid-precursor molecules in intestinal cells.

The compensatory activation of the GTPase RND1 (Rho family GTPase 1) best known for its ability to control the organization of the actin cytoskeleton in response to growth factor stimulation is just increased up to COPD GOLD stage II not only indicating a complete failure of actin-dependent cellular cytoskeleton organization in later stages of COPD, but also the loss of the regenerative capacity, as also demonstrated within Module 3 (see FIGS. 6A-6E). This in turn concurs rather well with the progressive downregulation of the cystatin M/E (CST6) gene being annotated with both functional differentiation of epithelial cells and maintenance of surface integrity.

As the coordinated action of these molecules is required for controlled movements of epithelial cells during pivotal processes, such as growth, intercalation and extrusion of cells within a cohesive cell layer system, the loss of these functions causes a profound disturbance of membrane integrity allowing for the development of non-specific bronchial inflammation that basically reflects all constituents of ventilated air including combustion products, such as cigarette smoke or welding fumes.

FIGS. 5A-H: COPD Pathology module 2: Bi-phasic activation of mucosal immunity.

Figure 5A:
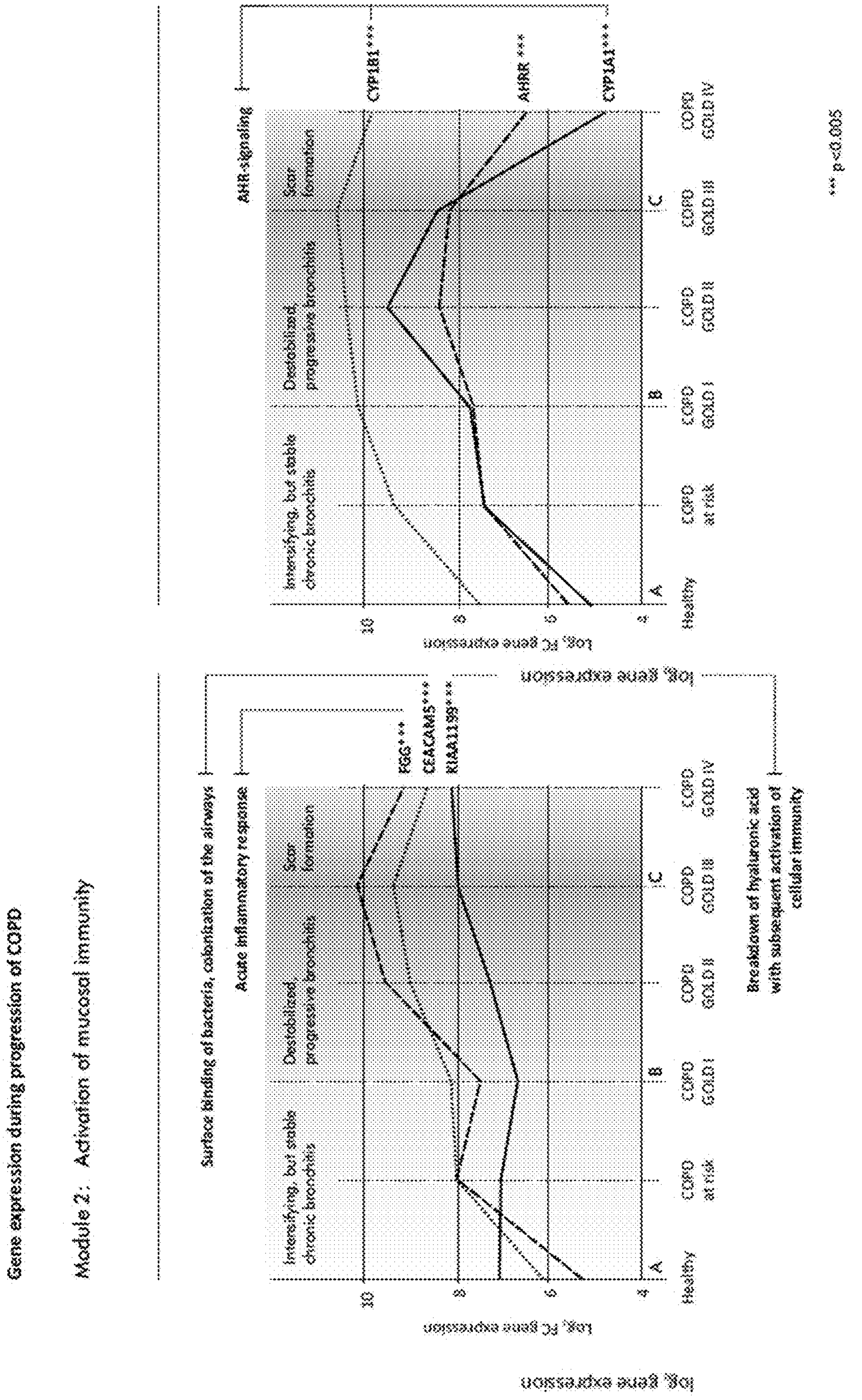
Figure 5B:
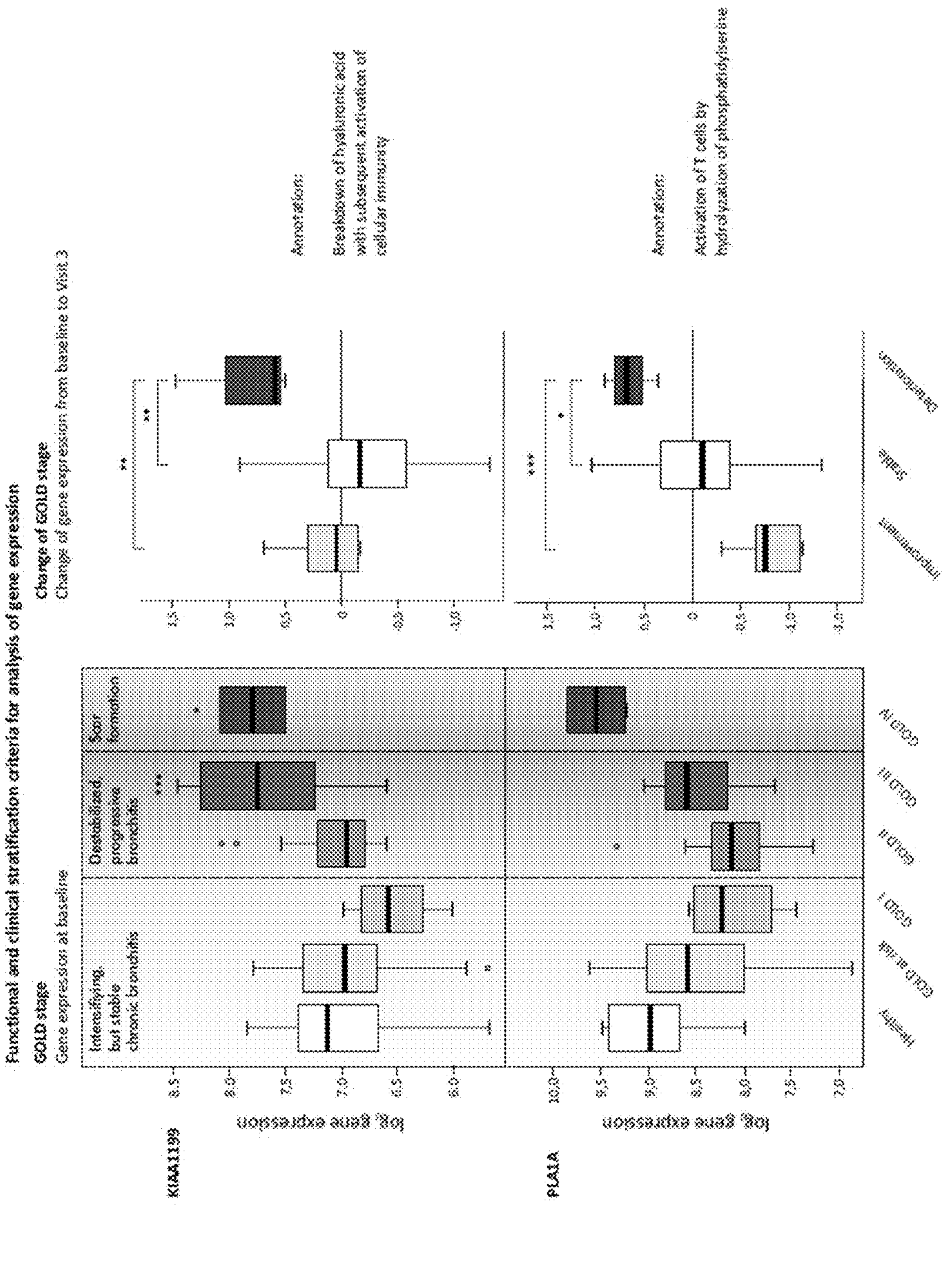
Figure 5C:
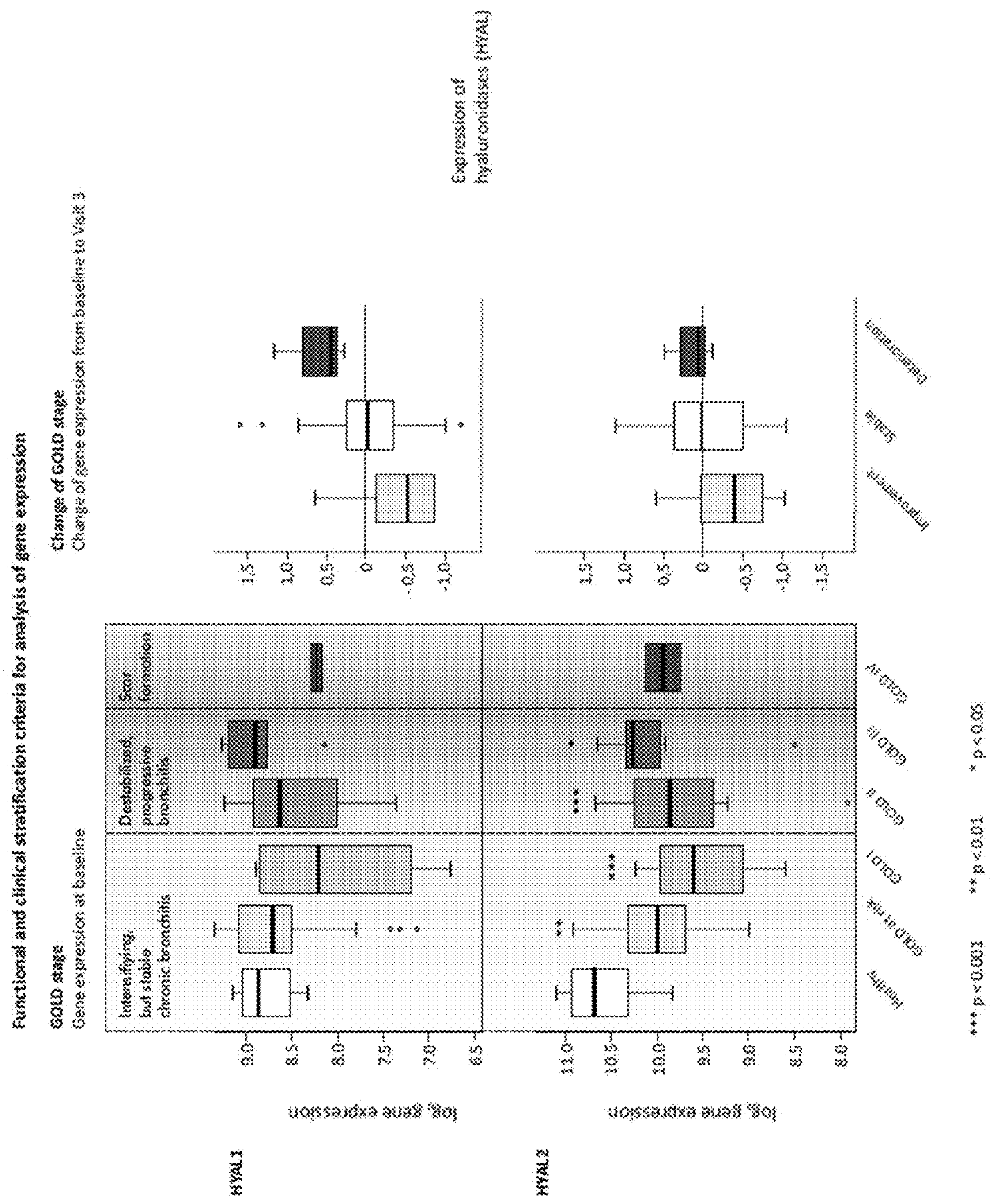
Figure 5D:
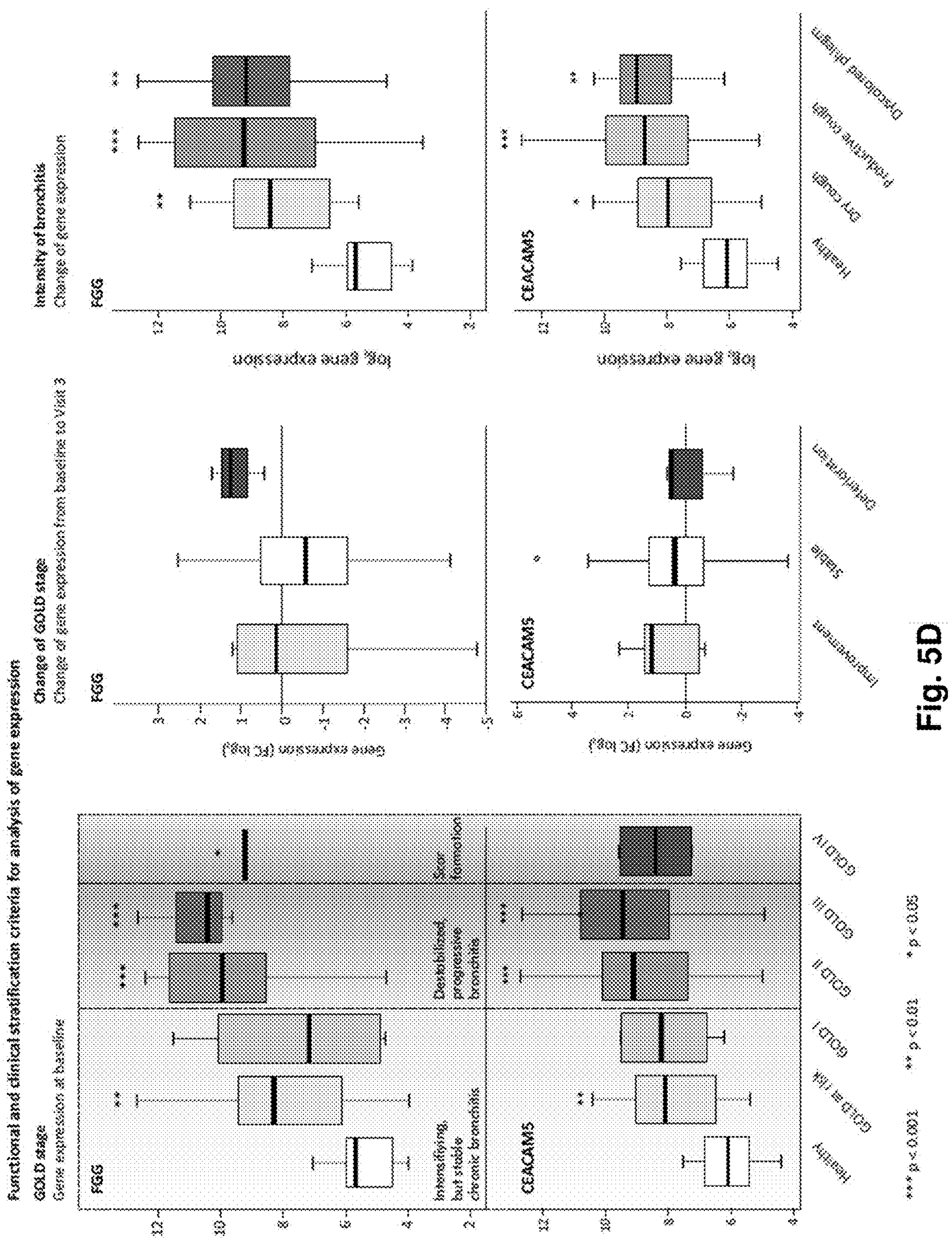
Figure 5E:
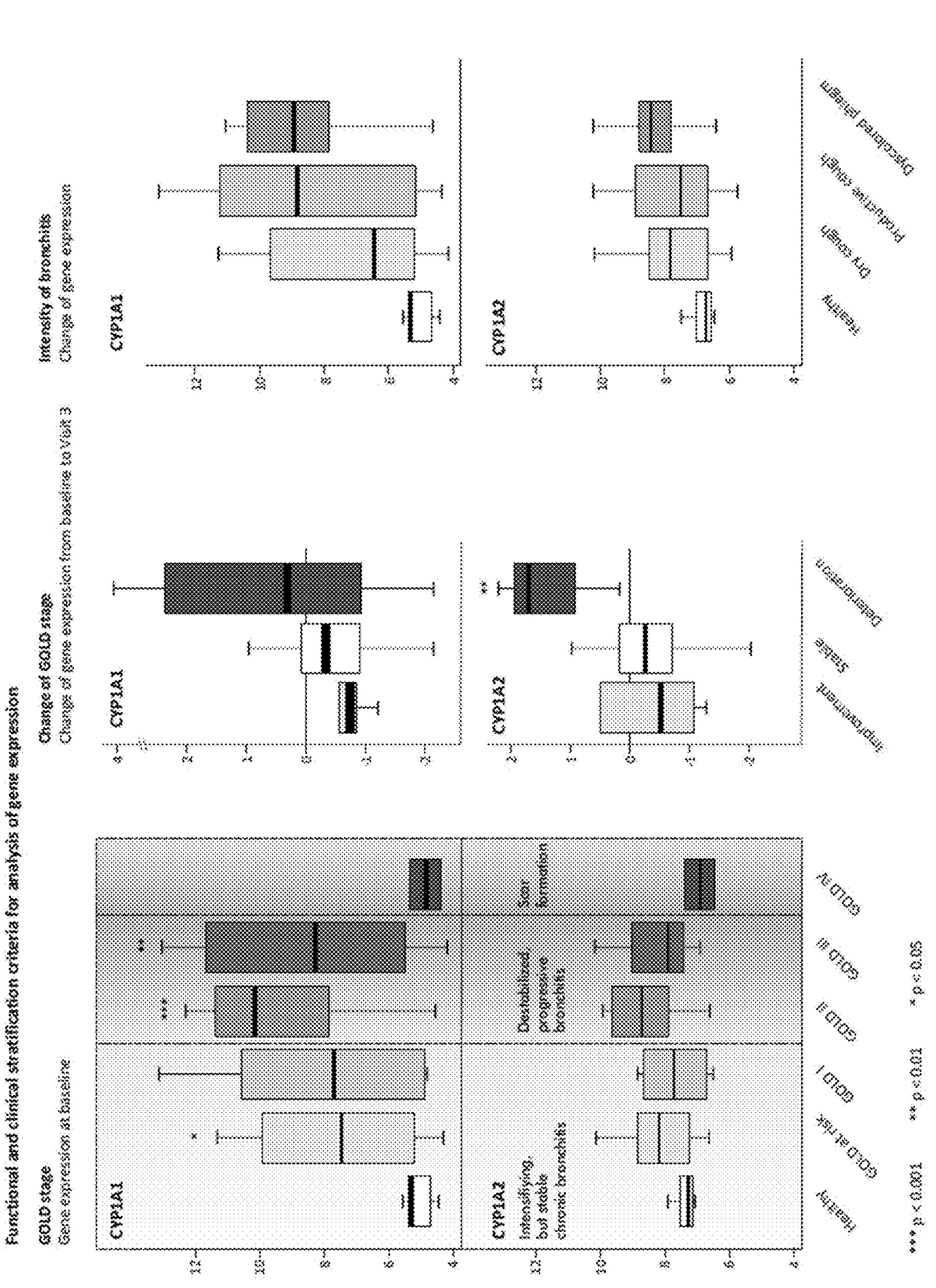
Figure 5F:
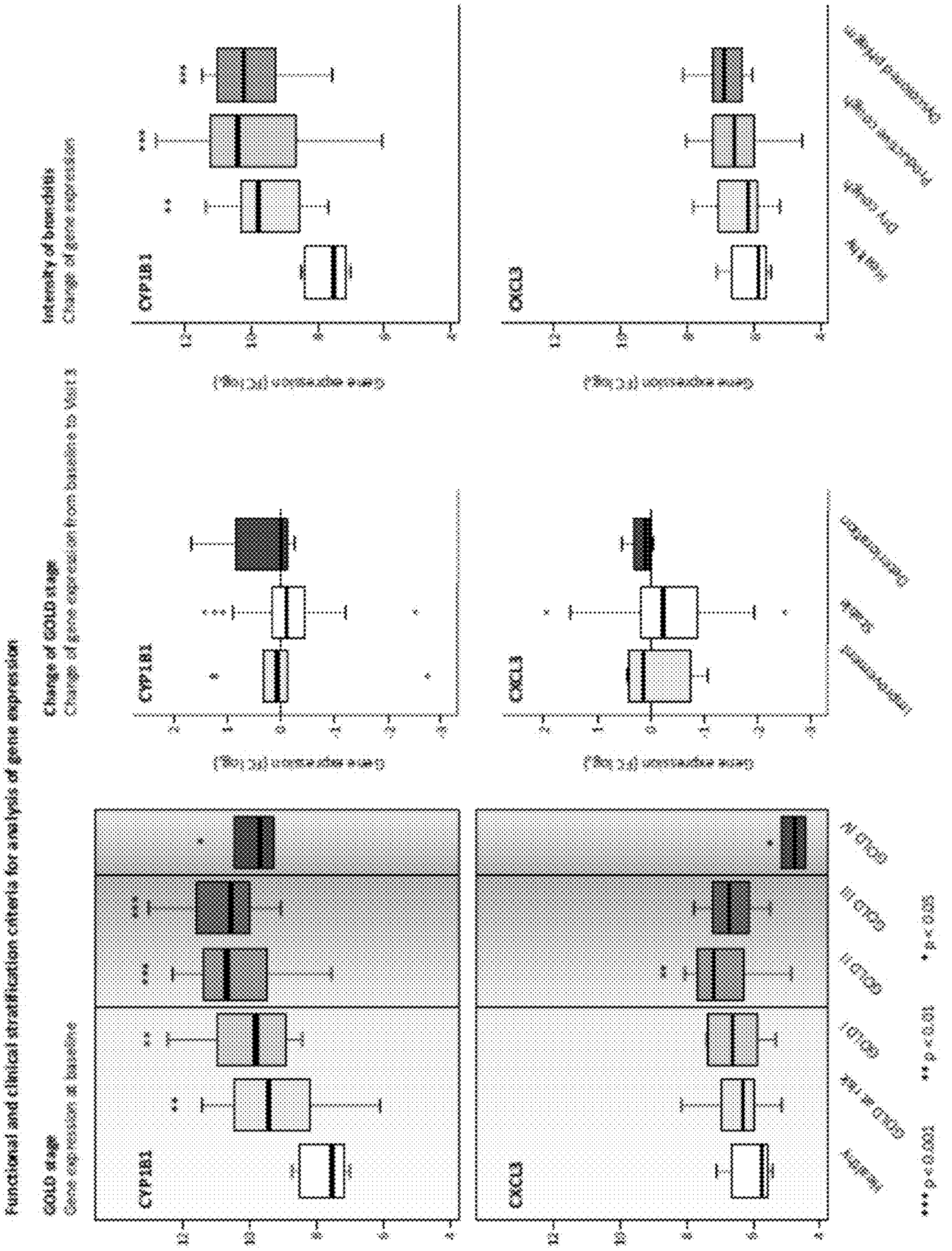
Figure 5G:
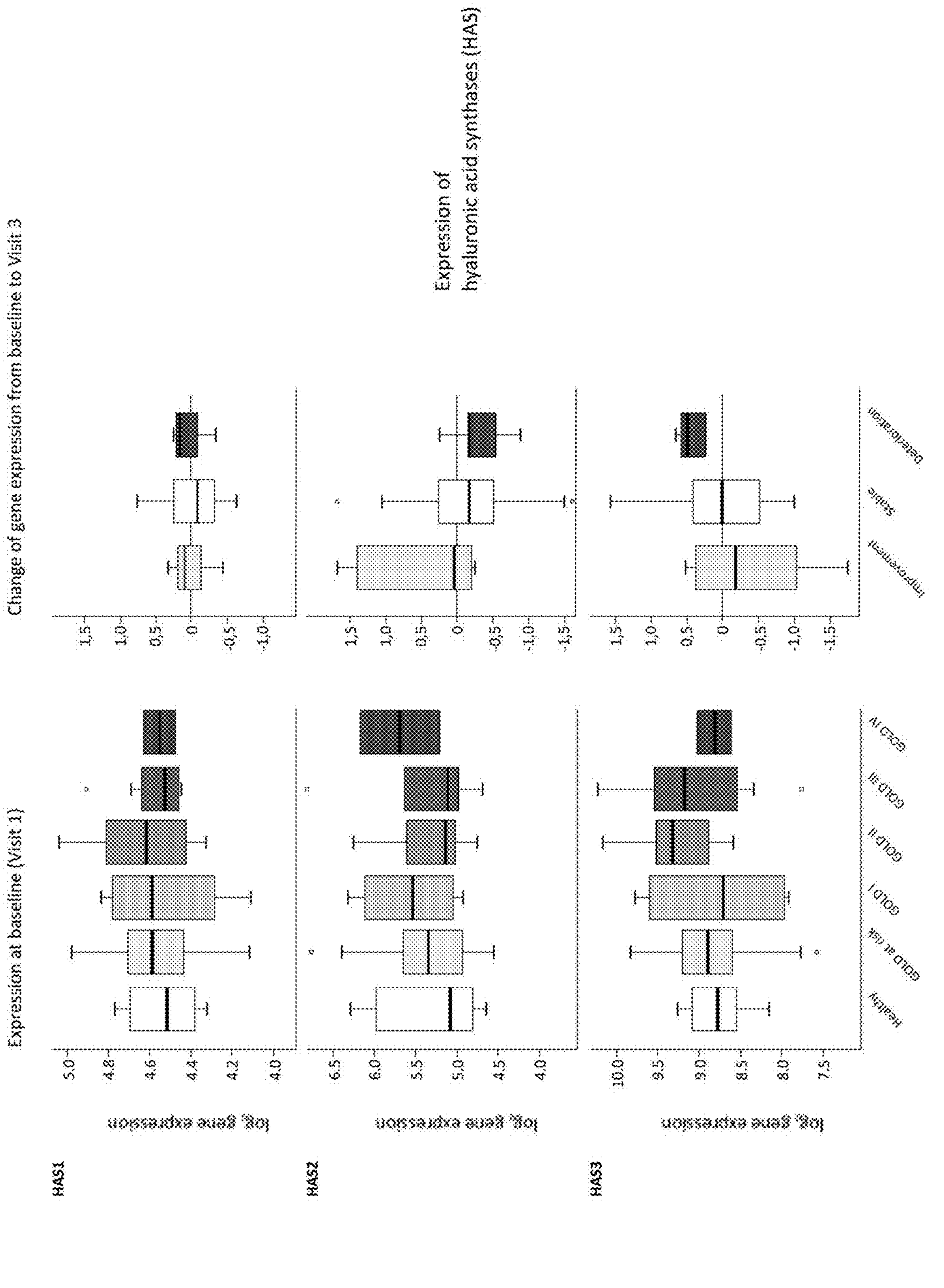
Figure 5H:
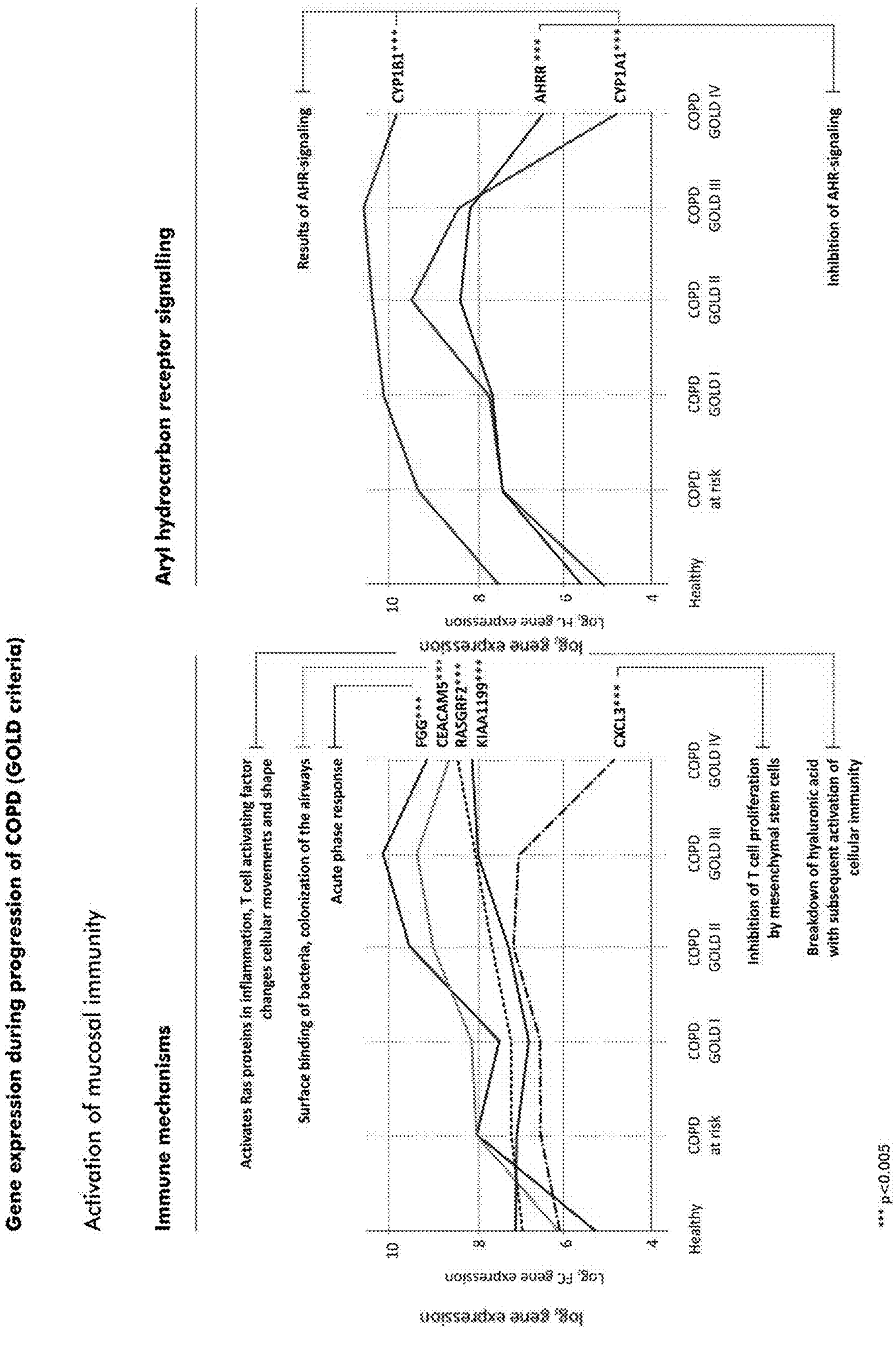

Driven by this loss of cellular cohesion, the bronchus develops a diverse mucosal immune response that combines mechanisms of acute inflammation, such as the expression of fibrinogen (FGG) (FIGS. 5A and 5D), the upregulation of carcinoembryonic antigen-related cell adhesion molecule 5 (CEACAM 5) (FIGS. 5A and 5D), and aryl hydrocarbon receptor (AHR) signaling, the latter characterized by increased expression of cytochrome P450, family 1, subfamily A polypeptide 1 (CYP1A1) and cytochrome P450, family 1, subfamily B polypeptide 1 (CYP1B1) (FIGS. 5A and 5E, 5F). Intensity of AHR signaling is significant, in spite of the increased compensatory expression of the aryl hydrocarbon receptor repressor gene (AHRR), most likely reflecting the continuous impact of smoke. As CEACAMs have recently been shown to act as surface receptors for gram-negative bacteria such as *Neisseria meningitidis, Haemophilus influenzae* and *Moraxella catarrhalis* being frequently found in progressive bronchitis, this mechanism is prone to contribute to episodes of intensified bronchial inflammation.

Figure 4D:
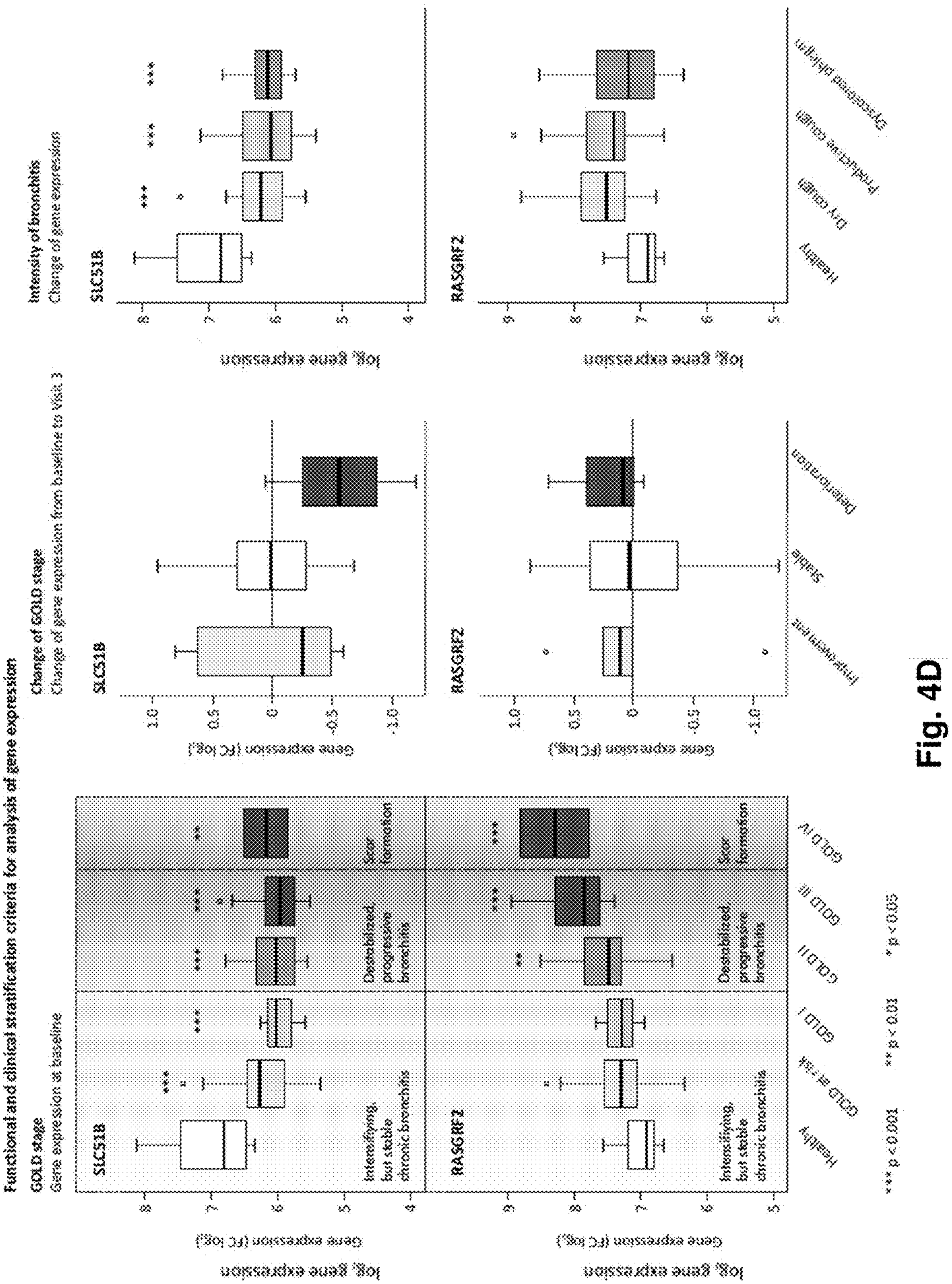

Nonetheless, neither FGG nor CEACAM5 expression causes short-term worsening of non-reversible pulmonary obstruction (FIG. 5D, middle panel), although the activation of both genes significantly contributes to the intensity of bronchial inflammation (FIG. 4D, right panel). This differs from CYP1A2, KIAA1199 and phospholipase A1 member A (PLA1A) expression (FIGS. 4*b* and *e*) that all correlate with a significant deterioration of pulmonary function. While CYP1A2 expression as part of a smoke-induced AHR signaling response fits well to the current perception of COPD development, the strong correlation of KIAA1199 and PLA1A expression with deterioration of pulmonary function according to GOLD criteria points towards another direction, the complete failure of the bronchial compartment system.

KIAA1199 has recently been demonstrated to activate matrix hyaluronidases while phospholipase A1 member A (PLA1A) is known to activate T cells in response to non-specific inflammatory stimulation. It has presently been found that the significant upregulation of KIAA1199 is characteristic for the second phase of increased bronchial inflammation in GOLD stages III and IV (FIG. 5B) which follows a phase of non-progressive bronchial inflammation characterizing GOLD stage I (FIG. 5A). Notably, during this stabilization phase both the expression of KIAA1199 and of PLA1A is reduced as well (FIG. 5B). Given the strong proinflammatory impact of a degradation of high molecular mass hyaluronan, these observations indicate that the final increase of inflammatory activity in COPD GOLD stage III and IV is the combined result of permanently disturbed epithelial integrity and a secondary destruction of the hyaluronan matrix within the bronchial wall by the activation of matrix hyaluronidases. This view is supported by the expression pattern of matrix hyaluronidase 2 (HYAL2) itself which represents the leading hyaluronan-degrading enzyme in humans (FIG. 5C).

FIGS. 6A-E: COPD Pathology module 3: The impact of intensified regenerative repair: temporary suspension of progressive bronchial inflammation.

Maintaining the structural integrity of the mucosa as well as upholding essential components of the bronchial wall is part of effective wound healing and as such an indispensable measure to prevent the intrusion of antigens, allergens and infectious agents into submucosal compartments. It is thus not surprising that various genes guiding functions of epithelial repair are upregulated in response to increased inflammation, as demonstrated in FIG. 6A. However, only a small group of these genes is significantly contributing to the temporary suspension of progressive bronchial inflammation in GOLD stage I, genes known to participate in epithelial regeneration and differentiation, bacterial defense and transepithelial water transport (FIGS. 6A-6C): a) deleted in malignant brain tumors 1 (DMBT1), b) zinc-binding alpha-2-glycoprotein 1 (AZGP1), and c) aquaporin 3 (AQP3). However, this regenerative impulse does not last long as expression of these genes decreases again once progression of inflammation resumes stressing the impact of KIAA1199 expression and matrix degradation on bronchial inflammation. Although further genes closely related to epithelial repair, such as stratifin (SFN), the G protein-coupled orphan receptor 110 (GPR110), the smoke-inducible growth differentiation factor 15 (GDF15), and E74-like factor 5 (ELF5) are expressed throughout a much longer period of COPD development (FIG. 6A), the effectiveness of this wound healing approach is evidently not sufficient to maintain bronchial integrity and to balance bronchial inflammation in the presence of epithelial disintegration and progressive hyaluronan breakdown.

Figure 6A:
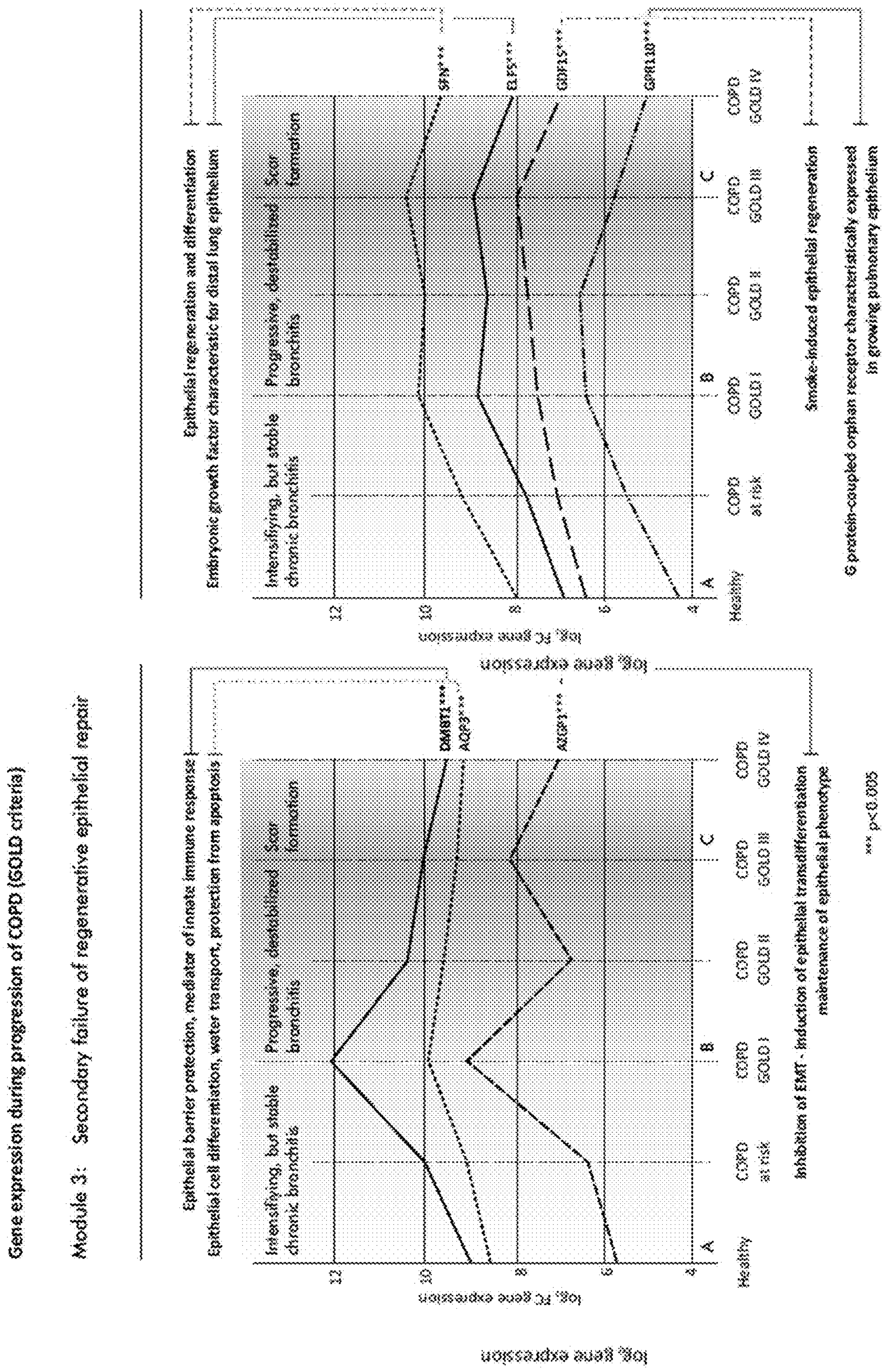
Figure 6B:
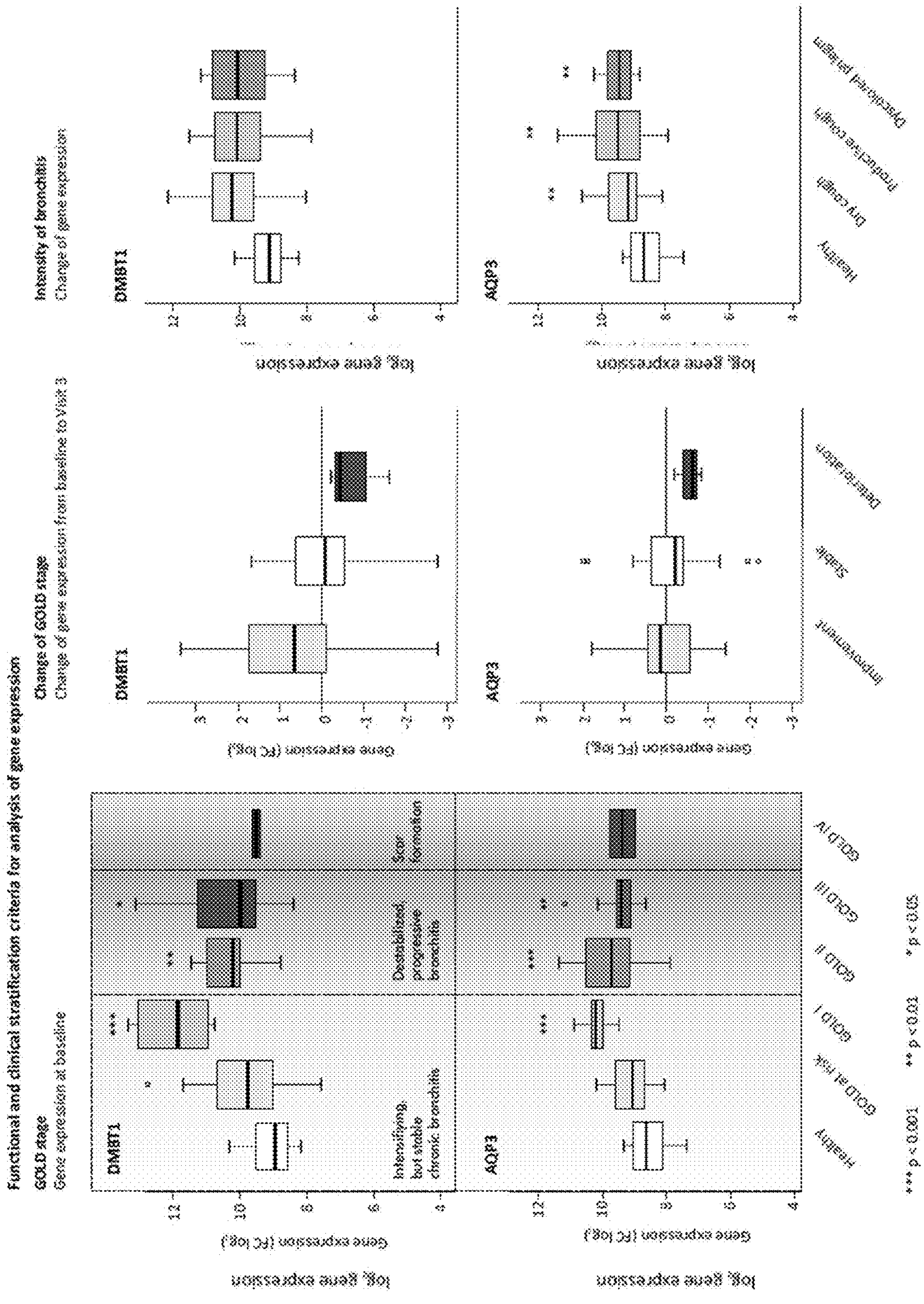
Figure 6C:
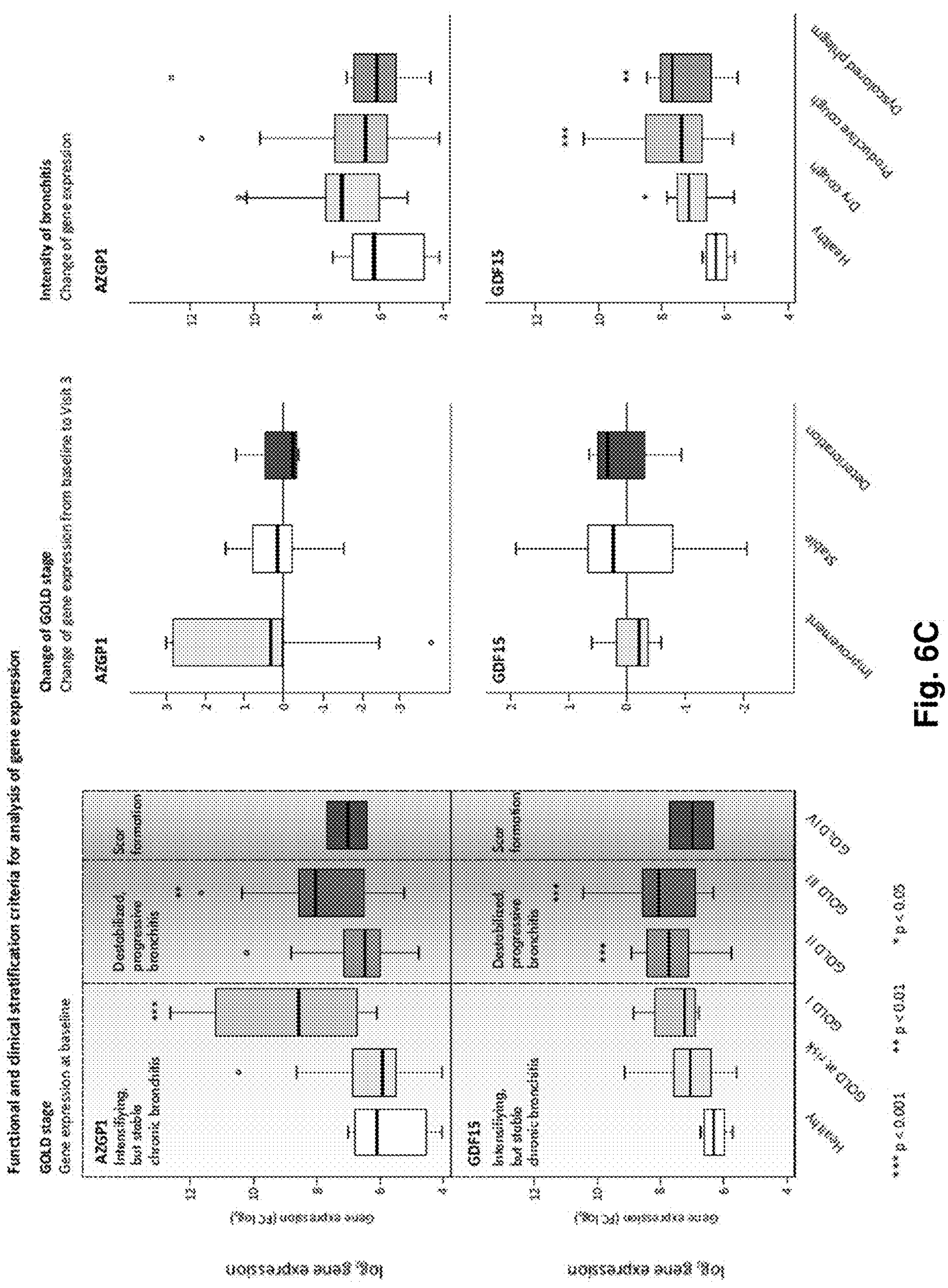
Figure 6D:
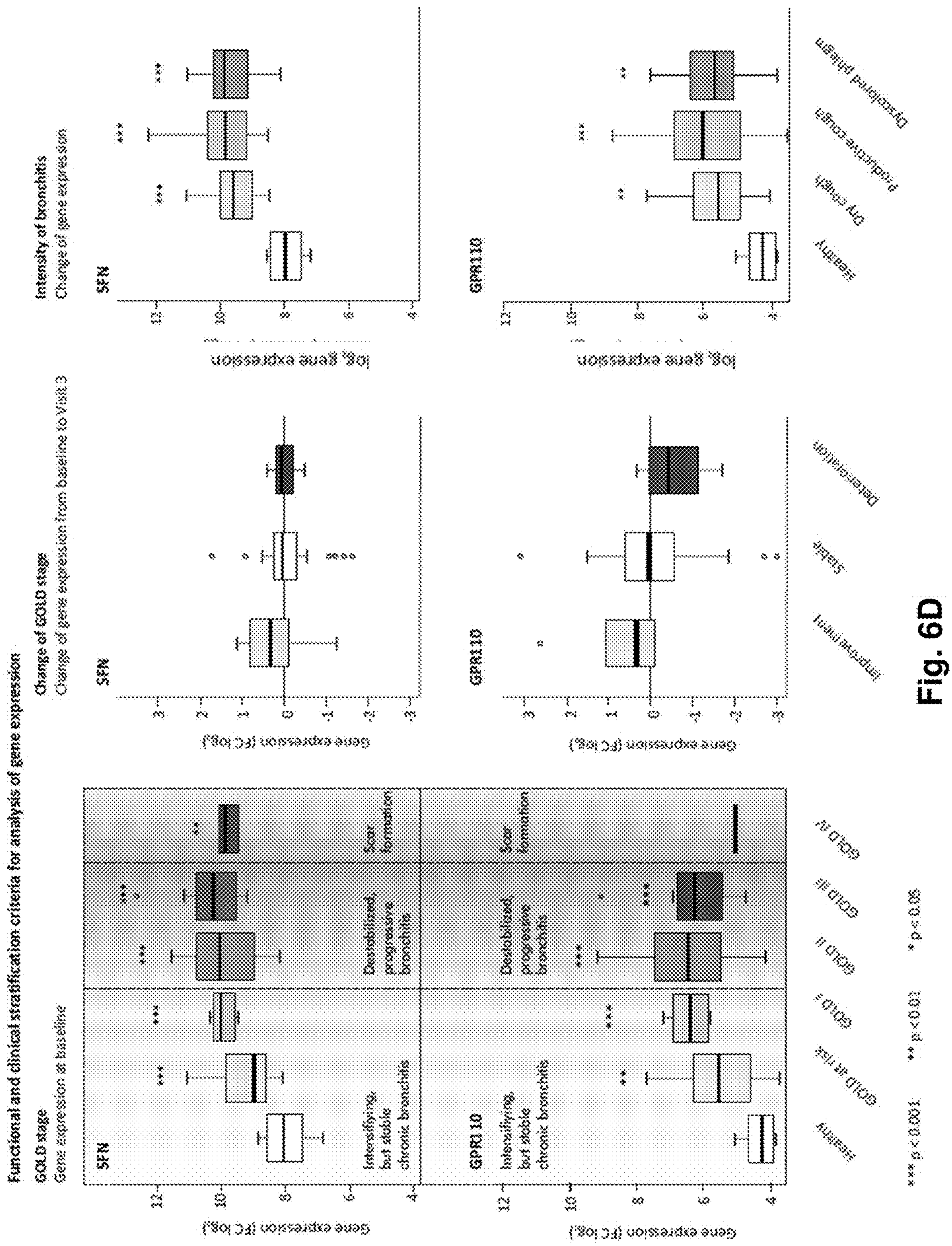
Figure 6E:
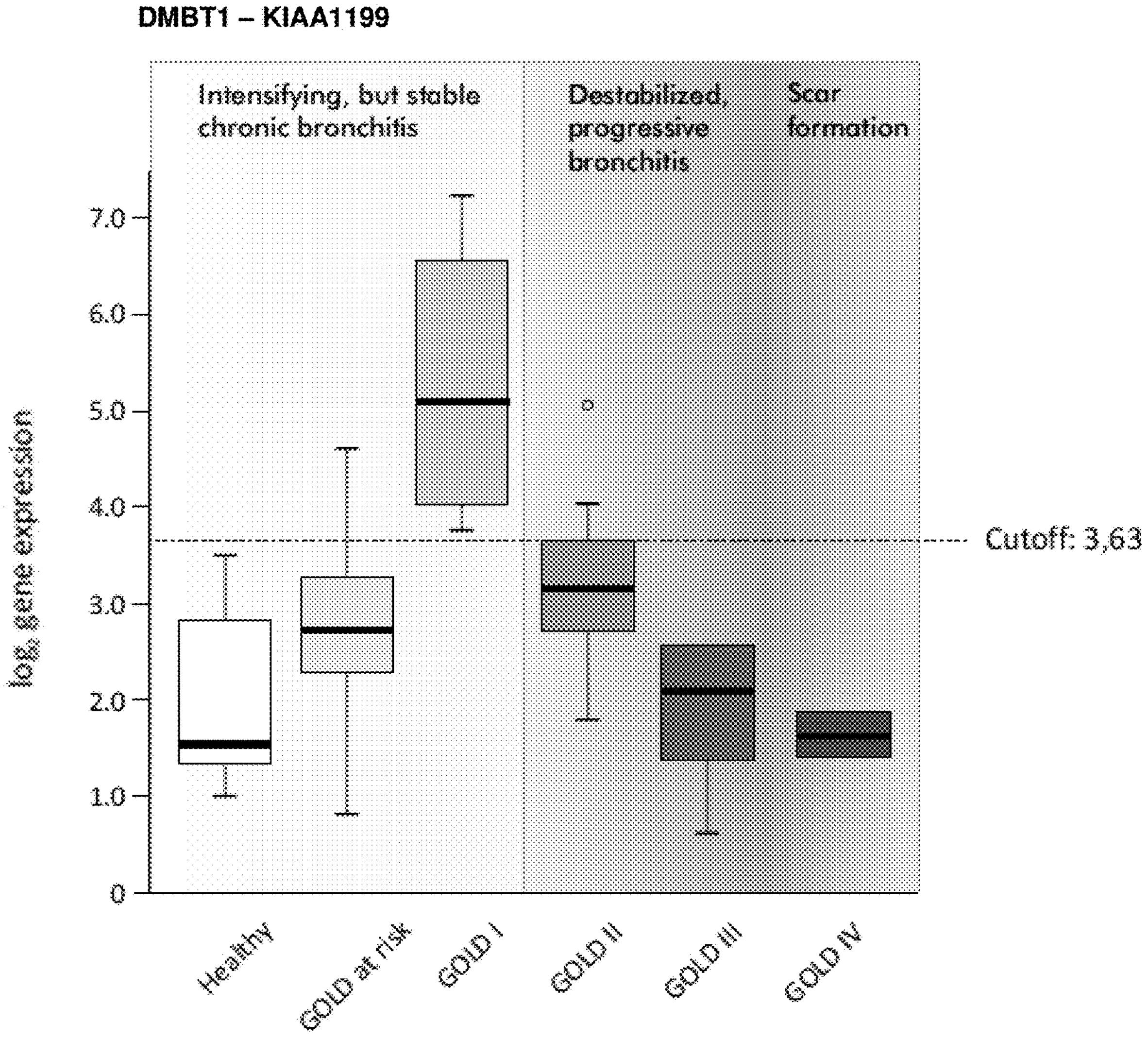

As a result, simultaneous measurement of DMBT1 and KIAA1199 gene expression is capable of discerning stable from progressive COPD (according to GOLD criteria), if the difference between DMBT1 and KIAA1199 expression exceeds a value of 3.63 (FIG. 6E). The importance of intensified KIAA1199 expression for progressive epithelial inflammation is further stressed by the fact that in chronic inflammatory wound healing of diabetic skin, expression of KIAA1199 is significantly upregulated, whereas in normal skin repair, KIAA1199 expression is reduced (see FIG. 8). It should also be noted that KIAA1199 expression in aged skin is in general significantly higher than in the skin from younger individuals ($p<0.01$).

Figure 7:
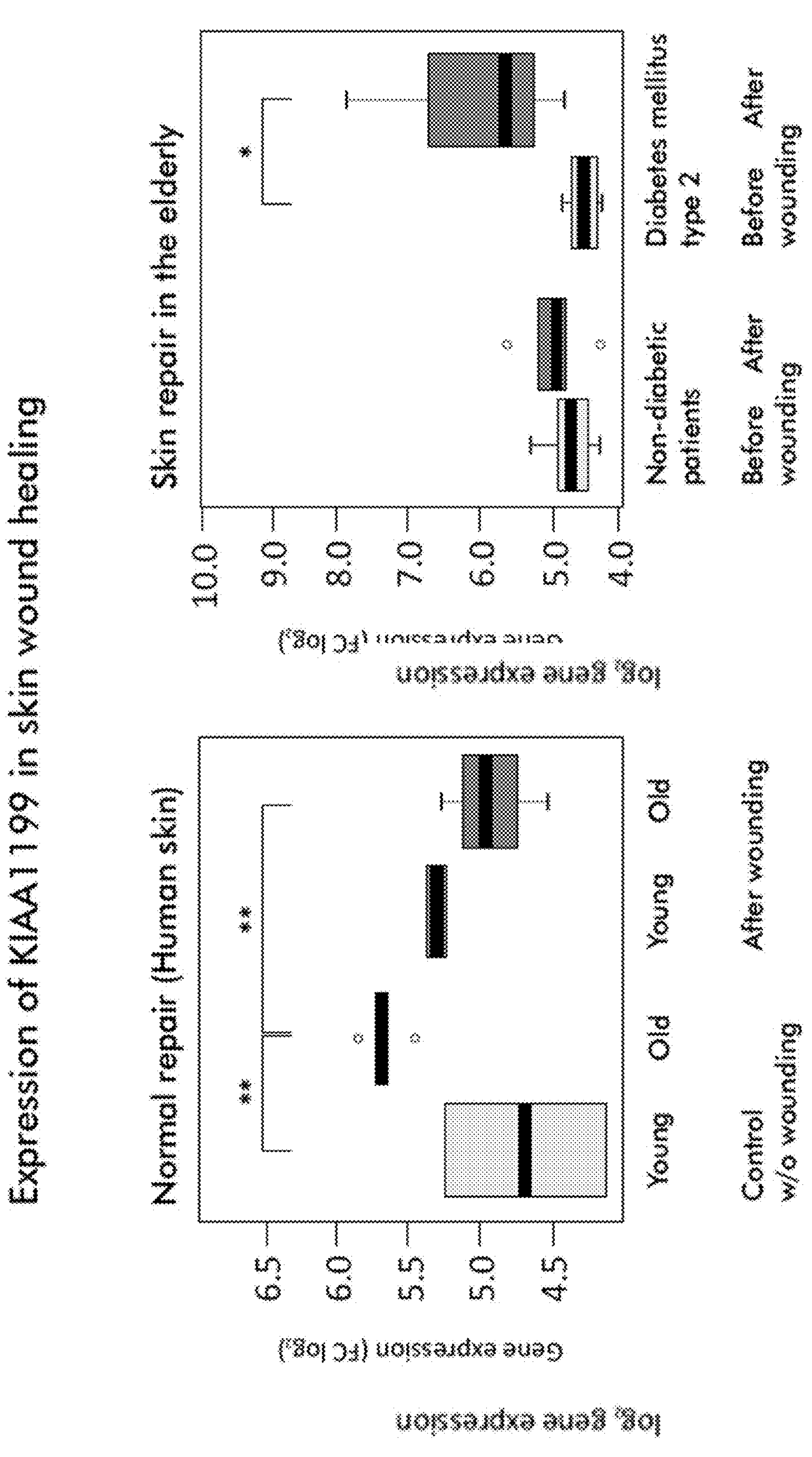

FIG. 7: Expression of KIAA1199 in skin wound healing.

Figure 8B:
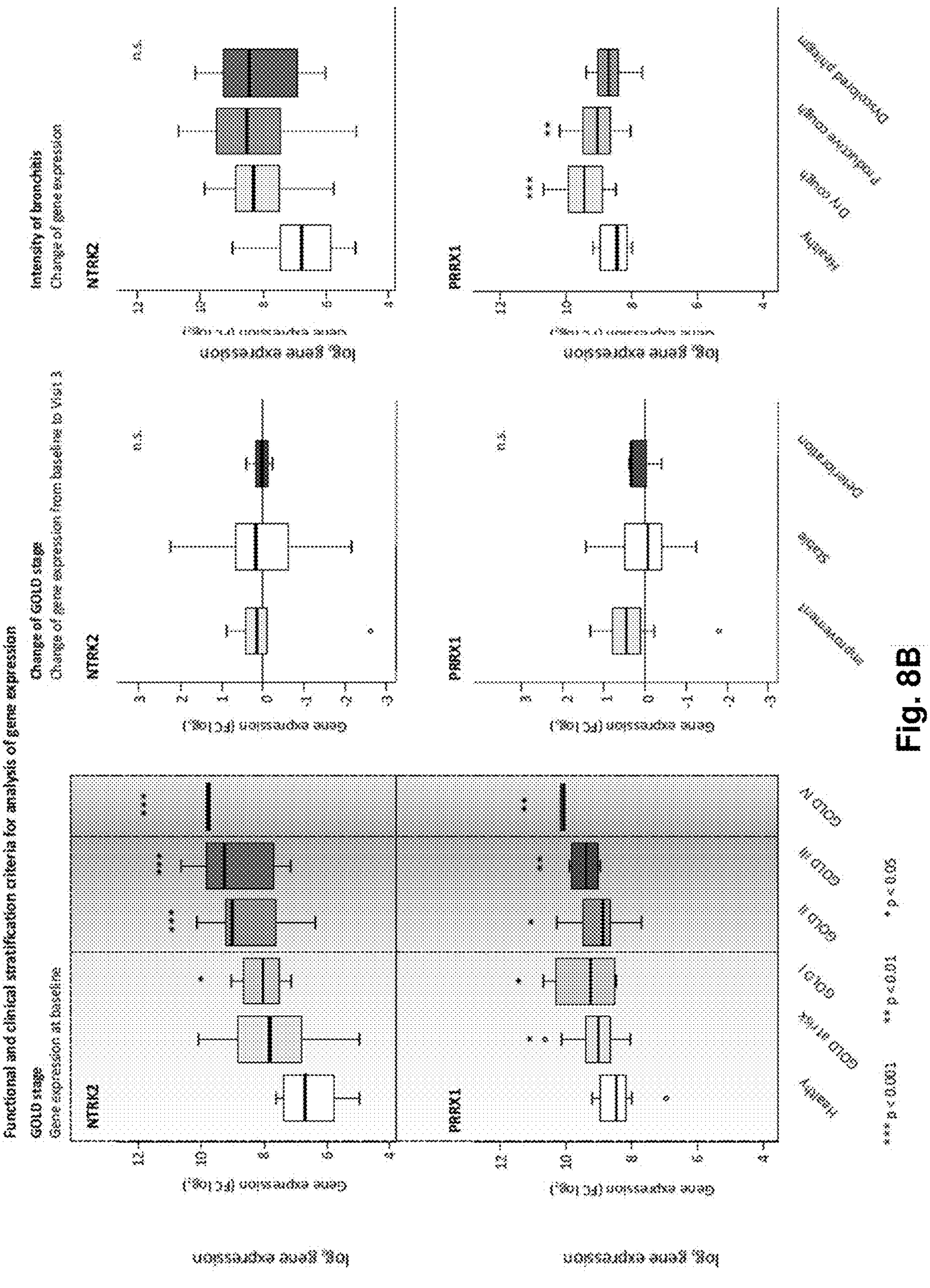
Figure 8C:
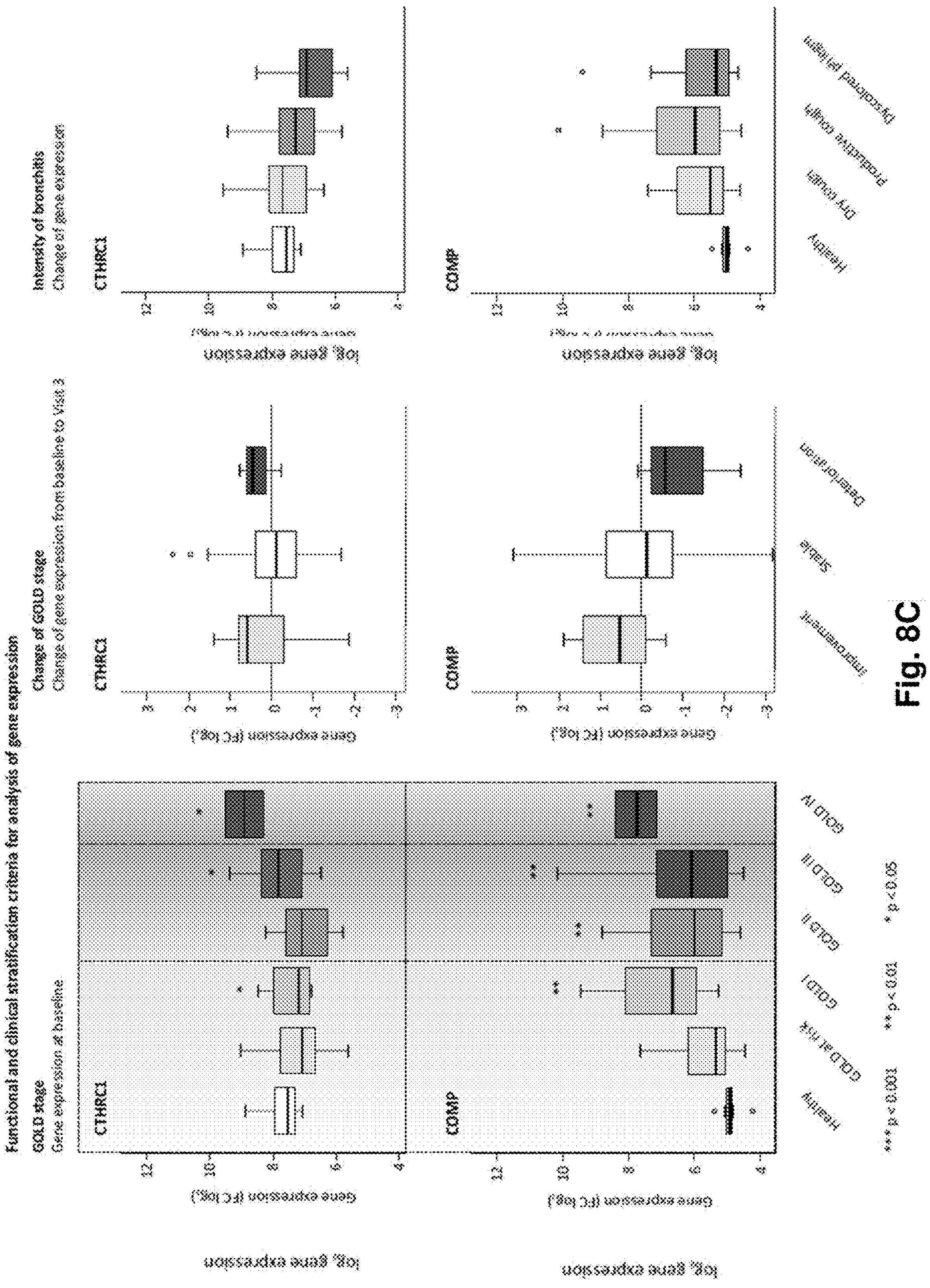

FIGS. 8A-D: COPD Pathology module 4: Scar formation by predominant mesenchymal repair as the result of regenerative failure in the presence of a prevailing structural deficit. As in any situation of prevailing unresolved repair that is not life-threatening, activation of "secondary" mesenchymal repair will serve as the exit strategy to remove the structural deficit and to terminate wound healing. During progression of COPD, coordinated gene activation in this regard can be divided into two categories: a) permanent support of mesenchymal repair (expression of NTRK2 and SOS1 genes) (FIGS. 8A and 8B), b) support of mesenchymal repair during both functional "primary" repair and non-functional "secondary" wound healing (expression of COMP, PRRX1 and CTHRC1 genes) (FIGS. 8A-8C).

Figure 8D:
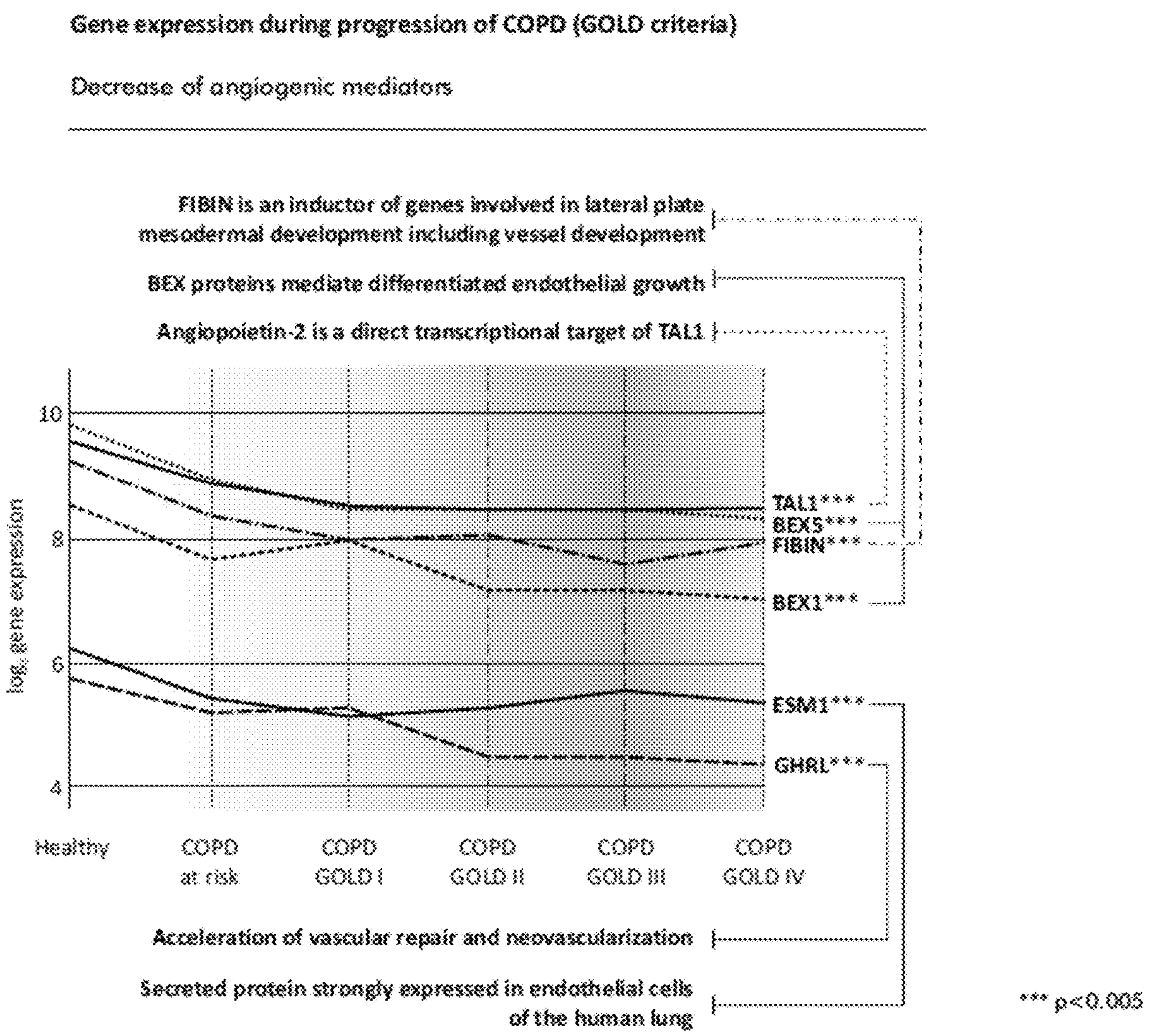

As in any form of predominantly mesenchymal repair, expression of genes controlling vascular growth and differentiation is progressively diminished. FIG. 8D provides a synopsis of the expression pattern and relevant annotations for all genes related to vascular outgrowth and repair which are significantly regulated during progression of COPD.

The invention will now be described by reference to the following examples which are merely illustrative and are not to be construed as a limitation of the scope of the present invention.

EXAMPLES

Example 1: Controlled Prospective Pilot Trial Aimed at Identifying Symptom-Based Molecular Metabolic Markers for Progressive COPD (Vienna COPD-AUVA Study)

Introduction

In the context of the present invention, a controlled prospective pilot trial aimed at the identification of symptom-based molecular metabolic markers for progressive COPD was conducted at the Vienna Medical University between 2007 and 2012. The Vienna COPD-AUVA study combined the assessment of validated clinical measures for COPD following in part the overall strategy of the ECLIPSE trial (Vestbo et al., 2011), the largest and most elaborate study addressing progress and variability of COPD.

For stratification of patients, a three-year analysis (day 0, 12 months, and 36 months) of symptom scoring (St. George Respiratory questionnaire, activity and symptom score), assessment of pulmonary function, cardiopulmonary exercise testing, and radiological evaluation by computer-assisted tomography (high-resolution mode) were combined with whole genome transcription analysis plus quantitative RT-PCR assessment and mass spectrometry proteomics. As shown in FIG. 1, the patients were grouped into three strata, two of which presented at the start of the study with regular lung function, either without any sign of a cardiopulmonary disease (healthy volunteers) or with symptoms of chronic bronchitis (COPD "at risk"), and a group of volunteers having symptoms of chronic bronchitis together with deteriorated lung function (COPD at GOLD stages I-IV).

Study visits were performed at base line and after 12 and 36 months, respectively. Each visit was performed on an ambulatory basis and included medical history, physical examination, pulmonary function tests (PFT), cardiopulmonary exercise tests (CPET), radiological assessment by computer-assisted tomography (CAT) scans and a bronchoscopy. On each visit, both personal and occupational history was taken as well as smoking history which comprised onset and duration of symptoms related to COPD, production of phlegm (frequency, quantity, and color), intensity of symptoms measured by the St. George Respiratory Questionnaire (SGRQ; activity and symptom score index) and assessment of life quality using the SF-36 questionnaire. The rate of exacerbations (frequency, number of hospitalizations, use of antibiotics, corticosteroids or combined treatment) and the individual medication were also recorded.

Pulmonary function tests (PFT) were taken at each visit and included blood drawings, body plethysmography, spirometry and quantitative measurement of pulmonary gas exchange at rest and during symptom-limited cardiopulmonary exercise testing (CPET). PFT was performed with an Autobox DL 6200 (Sensor Medics, Vienna, Austria), and CPET on a treadmill using the Sensormedics 2900 Metabolic Measurement Cart. Formulas for calculation of reference values were taken from Harnoncourt et al., 1982. Predicted values were derived from the reference values of the Austrian Society of Pneumology following the recommendations of the European Respiratory Society (Rabe et al., 2007).

Serum samples were analyzed for complete cellular blood count, electrolytes, glucose, C-reactive protein, fibrinogen, and coagulation parameters.

Prior to bronchoscopy, CAT scans encompassing high resolution-computed tomography (HRCT) were performed. Following additional informed consent on each visit, bronchoscopy was performed. During bronchoscopy, both bronchoalveolar lavage (BAL) samples and transbronchial biopsy samples (five per segment in each middle lobe) were taken.

Biological analysis was performed in transbronchial lung biopsies taken during bronchoscopy from two pulmonary localizations (5 each) of the middle-lobe after radiological assessment by computer-assisted tomography (CAT) scans including high-resolution scanning. CAT scans were used for the assessment of emphysema formation as well as for the exclusion of tumor development and infection. During the controlled observational period, combined assessment of clinical and molecular development was finally possible in 120 volunteers. Biomarkers were identified in each case by means of the individual changes of pulmonary function and clinical symptoms characteristic for the progression of COPD. As a result, this approach makes use of the well-known variability of clinical phenotypes in COPD and their variable course of progression while at the same time identifying the very set of biomolecules responsible for this type of disease progression.

Clinical Analysis

The study protocol was approved by the ethical committee of the Medical University of Vienna (ClinicalTrials.gov Identifier: NCT00618137). Following informed consent during screening, individuals were stratified at visit 1 (day 0) if they fulfilled the following criteria:

TABLE 2

Stratification of subjects at visit 1 (day 0).

| | Inclusion criteria | Occupational history |
|---|---|---|
| Healthy Controls | Age 18-70 years<br>No history or clinical findings suggestive of any disease<br>Never Smoker<br>Normal pulmonary function test at study entry | No occupation with increased exposure towards combustion products, particularly no welding or professional car driving |
| COPD, at risk' | Age 18-70 years<br>Chronic bronchitis according to WHO with repeated episodes of phlegm production<br>No history or clinical findings suggestive of bronchial asthma<br>Normal PFT according to GOLD criteria at study entry<br>Smoking history of at least 10 years<br>No history or clinical findings suggestive of cardiovascular or malign disease | Professional car driver or welder with increased occupational exposure towards combustion products of at least 10 years |
| COPD manifest | Age 18-70 years<br>Chronic bronchitis according to WHO with repeated episodes of phlegm production<br>No history or clinical findings suggestive of bronchial asthma<br>Pathological PFT according to GOLD criteria at study entry<br>Smoking history of at least 10 years<br>No history or clinical findings suggestive of cardiovascular or malign disease | Professional car driver or welder with increased occupational exposure towards combustion products of at least 10 years |

396 individuals were screened, 185 of whom met the study criteria. 136 participants finished visit 2 after 12 months, and 120 completed the final visit after 36 months of controlled observation. Throughout the study, all participants were residing and occupied in the greater Vienna area in order to ensure comparable environmental conditions. The control group consisted of 16 healthy volunteers who had never smoked (7 females and 9 males; mean age 36±12.2 years), as also shown in Table 2 above. None of the healthy participants developed any symptom of pulmonary disease during the study period. At the start of the study, 104 participants presented with clinical symptoms of chronic bronchitis according to WHO definition, 55 of whom did not have signs of non-reversible bronchial obstruction (GOLD "at risk"), while the other 49 participants showed bronchial obstruction ranging from GOLD stage I to IV as determined by PFT (see FIG. 3D). All participants in the COPD and COPD "at risk" groups were active cigarette smokers with a smoking history of more than 10 pack years, except for one welder who in addition to a daily expectoration of phlegm reported about frequent episodes of bronchial infection (>2 per year) without radiological signs of bronchiectasis. 64 participants were working as taxi or bus drivers (53%) and 40 active welders (33%) with a previous exposure to welding fumes of more than 10 years.

At visit 1, the majority of participants with manifest COPD had bronchial obstruction GOLD stage II and III (n=38), while the remaining subjects were in COPD GOLD stage I (n=9) and IV (n=2) (see FIG. 3D). Mean age in GOLD stages I and II was 50±9.5 and 56±10.4 yrs. respectively, compared to 52±9.0 yrs. in GOLD stage III and 63±11 yrs. in GOLD stage IV. 29% of the participants in the GOLD "at risk" group were already presenting with a continuous daily expectoration of sputum, and sputum was frequently discolored (yellow, green, brown) in 27%.

During controlled observation (36 months), 14 participants (12%) had a progression of disease according to GOLD, 7 (13%) in the GOLD "at risk" group, 1 (11%) in GOLD I, 3 (12%) in GOLD II, and 3 (25%) in GOLD III. Improvement of bronchial obstruction according to GOLD was observed in 13 individuals (5 participants in both GOLD stage I and II, and 3 cases in GOLD stage III and IV), mostly connected to a cessation of cigarette smoking.

As part of the observational design of the study, participants were not specifically encouraged to stop smoking. Accordingly, smoking habits changed only slightly: only 5 participants of the "COPD at risk" group (9%) and 2 participants in the "manifest COPD" group (4%) stopped smoking during the observational period, while 31% reduced cigarette smoking (data not shown). These changes did not significantly alter both occurrence and intensity of chronic bronchitis symptoms, as 27 participants (23%) demonstrated improvement and deterioration of cough and sputum production.

Biological/Molecular Analysis (Gene Transcription in Pulmonary Tissue)

RNAlater (Ambion, lifetechnologies) was used for tissue asservation. The lung biopsy material was disrupted using Lysing Matrix D ceramic balls in a Fastprep 24 system (MP Biomedical, Eschwege). A chaotropic lysis buffer (RLT, RNeasy Kit, Qiagen, Hilden) was used, followed by a phenol/chloroform extraction and subsequent clean up using the spin column approach of the RNeasy Mini Kit (Qiagen, Hilden) according to the manufacturer's manual, including a DNase I digestion on the chromatography matrix. RNA quantification was done spectrophotometrically using a NanoDrop 1000 device (Thermo Scientific) and quality control was performed on the Agilent 2100 Bioanalyzer. A cut off for the amount of 1 microgram and a RNA integrity number of 7.0 was chosen.

Total RNA samples were hybridized to Human Genome U133plus 2.0 array (Affymetrix, St. Clara, Calif.), interrogating 47,000 transcripts with more than 54,000 probe sets.

Array hybridization was performed according to the supplier's instructions using the "GeneChip® Expression 3' Amplification One-Cycle Target Labeling and Control reagents" (Affymetrix, St. Clara, Calif.). Hybridization was carried out overnight (16h) at 45° C. in the GeneChip® Hybridization Oven 640 (Affymetrix, St. Clara, Calif.). Subsequent washing and staining protocols were performed with the Affymetrix Fluidics Station 450. For signal enhancement, antibody amplification was carried out using a biotinylated anti-streptavidin antibody (Vector Laboratories, U.K.), which was cross-linked by a goat IgG (Sigma, Germany) followed by a second staining with streptavidin-phycoerythrin conjugate (Molecular Probes, Invitrogen). The scanning of the microarray was done with the GeneChip® Scanner 3000 (Affymetrix, St. Clara, Calif.) at 1.56 micron resolution.

The data analysis was performed with the MAS 5.0 (Microarray Suite statistical algorithm, Affymetrix) probe level analysis using GeneChip Operating Software (GCOS 1.4) and the final data extraction was done with the DataMining Tool 3.1 (Affymetrix, St. Clara, Calif.).

CEL files were imported and processed in R/Bioconductor (Gentleman et al., 2004). Briefly, data was preprocessed using quantile normalization (Gentleman et al., 2004) and combat (Johnson et al., 2007), linear models were calculated using limma (Smyth G K, 2005) and genes with a p-value of the f-statistics <5e-3 were called significant. Those genes were grouped into 20 clusters of co-regulated genes. The procedure of modeling and clustering was repeated for GOLD and phlegm as covariates.

For subsequent Gene Ontology (GO)-analysis it was necessary to separate the effects of GOLD and phlegm on gene expression. To this end, the GOLD classifications were grouped into "no COPD" (healthy and GOLD 0) and "COPD" (GOLD grades I-IV). Similarly, phlegm was reclassified into a "phlegm" group (productive or severe) and a "no phlegm" group (health or no/dry). Based on these reclassifications, gene expression was modeled using a 2×2 factorial design, resulting in five different lists of genes: (1) genes which are regulated with phlegm in the presence of COPD, (2) genes which are regulated with phlegm in the absence of COPD, (3) genes which are regulated with COPD in the presence of COPD, (4) genes which are regulated with COPD in the absence of COPD and finally (5) genes which are regulated differently with COPD, depending on whether there is phlegm or not.

These lists were annotated with respect to their biological functions as catalogued in the Gene Ontology (GO) database using the ClueGO plugin for the Cytoscape framework.

Results of Combined Clinical and Molecular Analysis

Activation of Epithelial Repair Mechanisms

Systematic analysis of the significant changes of gene expression during COPD development reveals a differentiated picture: As shown in FIGS. 6A to 6D, mechanisms of regeneration and repair commence as soon as the chronic inflammatory process in the peripheral bronchial tree is established. This is already the case in persistent or repeatedly manifesting bronchitis (COPD "at risk"). The functions associated with this kind of aberration from the normal equilibrium, in ontological terms still only potential COPD, include mediators involved in the regulation of embryonic epidermal and pulmonary growth, such as ELF5 (E74-like factor 5; ETS domain transcription factor) which confers spatially controlled outgrowth of epithelial structures (Metzger et al., 2008; Yaniw et al., 2005) as well as mucosal immunity of the lung (Lei et al., 2007). Not surprisingly, the expression of ELF5 is accompanied by a significant upregulation of stratifin (SFN) conferring increased epidermal regeneration and differentiation (Medina et al., 2007), yet also reduced deposition of matrix proteins including collagen I (Chavez-Muñoz et al., 2012) and reduced functions of non-specific surface immunity (Butt et al., 2012). This regenerative phase of repair involves not only the G protein-coupled orphan receptor GPR110 and the smoke-inducible growth differentiation factor 15 (GDF15) (Wu et al., 2012), a member of the bone morphogenic protein-transforming growth factor-beta superfamily, but also mediators directing differentiated epithelial repair, such as the zinc-binding alpha-2-glycoprotein 1 (AZGP1), and the DMBT1 gene (deleted in malignant brain tumors 1) which is strongly upregulated during acute but resolving bacterial inflammation in enteral epithelia during appendicitis (Kaemmerer et al., 2012), suggesting a functional relevance for mucosal defense (Diegelmann et al., 2012). The almost identical expression profile of DMBT1 and AZGP1, a mediator capable of inducing a strong epithelial transdifferentiation in tumor cells (Kong et al., 2010), suggests an as yet undefined combinatory effect of both mediators on cellular differentiation during epithelial regeneration. Notably, the expression of these genes is strongly increased in individuals with COPD GOLD I and decreases significantly with progression of COPD, as also shown in FIG. 6A. In line with this observation, all mediators conveying epithelial regeneration and differentiation were found to be significantly downregulated during the transition from COPD stage III to COPD stage IV.

Activation of mediators of regenerative repair was also found in individuals demonstrating significant symptoms of bronchial inflammation, as demonstrated by a uniform increase of gene expression of SFN, GPR110 (see also FIG. 6D), and aquaporin 3 (AQP3) (see FIG. 6A) being an additional mediator known to guide proliferation and differentiation of epithelial cells (Nakahigashi et al., 2011; Kim et al., 2010). However, expression of these factors did not further increase with an increase of severity of bronchial inflammation, much in contrast to mediators capable of intensifying inflammation on epithelial surfaces, such as the carcinoembryonic antigen-related cell adhesion molecule 5 (CEACAM5) (see FIGS. 5A and 5D), or factors being part of the preferentially mesenchymal wound healing response during inflammatory repair (Agarwal et al., 2012; Agarwal et al., 2013), such as the cartilage oligomeric matrix protein (COMP) (see FIGS. 8A and 8C). The study design allowed as well for the measurement of changes of gene expression occurring throughout the study period of 3 years, possibly indicating significant changes of repair during short-term progression of COPD. Here, a significant downregulation of GPR110 and DMBT1 genes correlating with deteriorated lung function according to GOLD was found, as also shown in FIGS. 6B and 6D. This decrease of regenerative gene activity started already in GOLD stage II, where it was accompanied by a striking increase of repair functions related to mesenchymal wound healing (see also FIG. 8).

Progressive Activation of Mesenchymal Repair

During later stages of COPD, expression of mediators favoring mesenchymal repair became increasingly prominent. This did not only relate to the increased expression of the COMP gene (see FIGS. 8A and 8C), but also to the expression of potent activators of mesenchymal stem cells, such as the son of sevenless homolog 1 (SOS1) gene, a guanine nucleotide exchange factor for RAS proteins acting as the cognate receptor for hepatocyte growth factor, and to the paired related homeobox 1 gene (PRRX1), a transcriptional co-activator of RAS transcription factors belonging to the HOX family of early differentiation factors able to induce mesenchymal outgrowth in liver cirrhosis (Jiang et al., 2008) as well as epithelial-to-mesenchymal transition (EMT) during cancer development (Ocaña et al., 2012). While their pattern of expression indicates that both COMP and PRRX1 genes take also part in the regenerative phase of wound healing characterizing GOLD stage I and II, their later increase during transition from GOLD stage III to IV suggests an additional involvement in the progressive scarring of the airways. Increased expression of pro-fibrotic factors is further demonstrated by the striking increase of expression of neurotrophic tyrosine kinase receptor type 2 (or tropomyosin receptor kinase B receptor; TrkB) (NTRK2). NTRK2/TrkB, thus far known to act as high affinity receptor for various neurotrophic growth factors during nerve development, is also capable of promoting resistance of mesenchymal cells towards apoptosis and anoikis (Frisch et al., 2013). The combined increase of profibrotic mediators includes as well the expression of the collagen triple helix repeat containing 1 gene (CTHRC1) capable of conferring fibrotic organ dystrophy (Spector et al., 2013). Notably, while the increased expression of CTHRC1 starts only at GOLD stage II, cumulative activation of NTRK2/TrkB is a hallmark throughout progression of COPD in general, suggesting a permanent contribution of NTRK2/TrkB signaling to the aberrant repair response in the peripheral airways during COPD development. This view is further supported by the observation that a disturbed TrkB axis may contribute to experimental pulmonary fibrosis (Avcuoglu et al., 2011).

With the exception of COMP expression, where clinical deterioration correlates with worsening of bronchial obstruction according to GOLD (see also FIG. 8C), neither increased long-term expression of NTRK2 (see also FIG. 8B), nor of PRRX1 (see also FIG. 8B) or CTHRC1 genes (see also FIG. 8C) demonstrate a comparable short-term impact on bronchial obstruction during the controlled 3-year observational study period. Corresponding results were obtained when assessing the correlation of gene expression with progressive bronchial inflammation: while the expression of all genes favoring mesenchymal repair is increased as a result of intensified bronchitis, significant changes were only found for the PRRX1 and CTHRC1 genes (see also FIGS. 8B and 8C).

Loss of Structural Integrity of Epithelial Surfaces

Unexpectedly, the present analysis revealed a very significant downregulation of expression of a group of genes which guide movement, distribution and activation of the cellular cytoskeleton and which, as a result, are likely to profoundly influence structural integrity and barrier function of the mucosal surface. The downregulation of these genes takes place already during establishment of chronic bronchitis, well before the establishment of bronchial obstruction according to GOLD, as also shown in FIG. 4A. The genes closely connected to this development are thymosin beta 15 A (TMSB15A), dipeptidyl-peptidase 6 (DPP6), nudix (nucleoside diphosphate linked moiety X)-type motif 11 (NUDT11), integrin alpha 10 (ITGA10), cystatin E/M (CST6), and PRICKLE2 (data not shown). Notably, the two genes most significantly decreased during progression of COPD, TMSB15A and DPP6, are also significantly downregulated in correlation with symptoms of increased bronchial inflammation (see also FIG. 4B). Beta thymosins are controllers of both composition and sequestration of the actin cytoskeleton (Hannappel, 2007; Huff et al., 2001; Malinda et al., 1999), by that influencing membrane structure, surface stability and cellular phenotype (Husson et al., 2010). One of the outcomes of elevated levels of beta thymosins during wound healing seems to be a protection from fibrotic aberrations of repair (De Santis et al., 2011), in part by preventing the expression of $\alpha$-smooth muscle stress fibers preventing them from a transdifferentiation into myofibroblasts most characteristic for fibrotic tissue development. Currently, little is known about the function of DPP6 in regenerative wound healing. However, DPP6, a member of the S9B family of membrane-bound serine proteases which is lacking any detectable protease activity, has recently been demonstrated to confer membrane stability and controlled outgrowth of cells during nerve development including close control of cell attachment and motility (Lin et al., 2013). Moreover, given its proven association with and control of membrane-bound ion channel expression and activation (Jerng et al., 2012), in particular of voltage-gated potassium channels, expression of DPP6 is also capable of controlling the resting membrane potential (Nadin et al., 2013), thereby controlling both activity and intracellular distribution of the actin cytoskeleton (Mazzochi et al., 2006; Chifflet et al., 2003).

Combined with the striking reduction of TMSB15A gene expression, the significant decrease of DPP6 expression suggests a severe disturbance of regular movement and distribution of the cellular actin skeleton, reducing physico-chemical integrity of the epithelial lipid bilayers. As this occurs already very early in COPD development, this finding could indicate an initiating and possibly predisposing mechanism leading to non-specific surface inflammation.

Cystatin M/E (CST6), on the other side, is an epithelium-specific protease inhibitor belonging to the cystatin family of secreted cysteine protease inhibitors indispensable for the physiological regulation of protease activity during growth and differentiation of epithelial structures. CST6 is expressed both in dermal and bronchial epithelia where it characterizes the status of functional differentiation (Zeeuwen et al., 2009). Significant downregulation of CST6 has already been shown to cause a marked disturbance of both surface integrity and differentiation status in the dermis of mice (Zeeuwen et al., 2010). Progressive downregulation of CST6 as observed during advancement of COPD is thus likely to destabilize the intricate balance between proteases and protease inhibitors, by that contributing to a loss of surface stability as well as cellular adhesion and differentiation in the regenerating bronchial epithelium. Within this context, significant downregulation of two other genes intricately involved in the regulation of cell adhesion and motility has also been observed, namely of integrin $\alpha 10$ (ITGA10) being part of differentiated mesenchymal structures, and the nudix (nucleoside diphosphate linked moiety X)-type motif hydrolase 11 (NUDT11), capable of hydrolyzing diphosphoinositol polyphosphates derived from cellular lipid bilayer structures, and diadenosine polyphosphates, mostly based on adenosine triphosphate (ATP).

The consequence of these changes in gene expression is expected to be a disintegration of the epithelial barrier function, probably starting on the cellular level (continuous shear stress within the cellular lipid bilayer due to uncoordinated accumulation and movements of the actin cytoskeleton attached to it), and aggravated by disintegration of the extracellular matrix composition itself. This is supported by the significant increase of gene expression of the KIAA1199 gene during progression of COPD from GOLD stage I to GOLD stage IV (see FIG. 5B). Increased expression of KIAA1199, in addition to mediating cellular attachment and contact inhibition (Tian et al., 2013), has just recently been demonstrated to cause the leakage of endoplasmatic reticulum (ER) contents into the cytosol of cancer cells (Evensen et al., 2013). Moreover, increased expression of KIAA1199 is capable of activating hyaluronidases (HAase), enzymes capable of degrading high-molecular mass hyaluronic acid (HMM-HA), one of the major constituents of the extracellular matrix (Toole, 2004). Biological responses triggered by hyaluronic acid (HA) depend on the HA polymer length. HMM-HA has strong anti-inflammatory properties (Kothapalli et al., 2007), whereas low-molecular-mass HA promotes inflammation and concomitant cellular proliferation (Pure et al., 2009). In support of this view, degradation of HA has been shown to trigger skin inflammation by generation of low molecular weight fragments of HA (Yoshida et al., 2013).

In line with this, expression of HA synthases (HAS1-3) is not changed during progression of COPD (see FIG. 5G), while the hyaluronidase 2 (HYAL2) gene is upregulated between GOLD stages I and III (see also FIG. 5C). Indeed, the pattern of expression of both HYAL1 and HYAL2 follows the expression pattern of KIAA1199, showing a downregulation during the most intense regenerative phase of repair in COPD progression (chronic bronchitis and COPD GOLD I). Upregulation of KIAA1199 in turn is synchronous to that of the PLA1A gene (see FIG. 5B) which is a phosphatidylserine-specific phospholipase expressed in macrophages stimulated by typical mechanisms of surface immunity, such as toll-like receptor 4 (TLR4) signaling (Wakahara et al., 2007). Both intensified KIAA1199 and PLA1A expression were found to be connected to short-term worsening of pulmonary function according to GOLD criteria (see also FIG. 5B).

Decrease of Pro-Angiogenic Mediators During Progression of COPD

Effective organ repair involves mechanisms concomitantly directing spatially controlled epithelial, mesenchymal and endothelial outgrowth. However, in contrast to gene functions contributing to epithelial and mesenchymal repair, gene expression promoting angiogenesis and vascular differentiation was found to decrease as soon as chronic bronchitis was present. During development of COPD (GOLD stage I and II), this pattern of gene expression proceeded significantly, as also shown in FIG. 8D. Even the increase of Bex1 and Ghrelin (GHRL) gene expression occurring at GOLD stage I is rather small and insignificant compared to gene functions aimed at the regeneration of epithelial outgrowth, such as DMBT1 and AZGP1. Some of the functions, such as FIBIN (fin bud initiation factor homolog), ESM1 (endothelial cell-specific molecule 1) and ghrelin (GHRL) are known to act, in part, as mediators in the early phases of organ development. For instance, FIBIN takes part in mesodermal lateral plate development (Wakahara et al., 2007) which is crucial for early vasculogenesis (Paffett-Lugassy et al., 2013), ESM1 mediates VEGF-A-dependent signaling (Zhang et al., 2012) and is typically expressed in growing vascular tissue which includes tumor angiogenesis (Zhang et al., 2012; Roudnicky et al., 2013; Chen et al., 2010) and regenerative wound healing (Béchard et al., 2001).

Ghrelin, on the other hand, is a typical marker of microvascular development (Li et al., 2007; Wang et al., 2012; Rezaeian et al., 2012) being vital for continuous epithelial oxygen and energy supply preventing excessive apoptosis characteristic for emphysema development (Mimae et al., 2013). BEX1 and BEX5 (Brain Expressed, X-Linked 1 and 5) are genes encoding adapter molecules interfering with p75NTR signaling events. p75NTR is one of the two receptors central to nerve growth factor (NGF) signaling. While BEX1 is known to induce sustained cell proliferation under conditions of growth arrest in response to NGF, much less is known about its possible involvement in angiogenesis and vessel formation, although NGF signaling itself is well-known to promote angiogenesis (Cantarella et al., 2002). One possible interaction could be that reduced BEX1 gene expression would increase p75NTR signaling efficacy causing increased endothelial apoptosis, as the blockade of p75NTR signaling significantly decreases endothelial apoptosis (Han et al., 2008; Caporali et al., 2008). The BEX5 promoter, in turn, contains regulatory binding sites for TAL1 (T-cell acute lymphocytic leukemia 1), a direct transcriptional activator of angiopoietin 2, which is significantly upregulated during angiogenesis (Deleuze et al., 2012). TAL1, however, is downregulated as well during progression of COPD, as also shown in FIG. 8D.

Stage-Dependent Activation of the Immune Response

Based on the significant changes of gene expression measured during progression of COPD, four sequential phases of gene expression were distinguished: Phase 1 is characterized by a rapid increase of genes involved in the acute immune response, such as fibrinogen (FGG) (Duvoix et al., 2013; Cockayne et al., 2012), and products of aryl hydrocarbon receptor (AHR) signaling, such as CYP1A1 (cytochrome P450, family 1, subfamily A, polypeptide 1) and CYP1B1 (cytochrome P450, family 1, subfamily B, polypeptide 1) expression, as also shown in FIGS. 5A to 5E. This includes as well an increased expression of carcinoembryonic antigen (CEA)-related cell adhesion molecules (CEACAMs), particularly of the CEACAM5 gene (see FIGS. 5A and 5D). At this early stage, still representing chronic bronchitis without significant changes of pulmonary function (COPD "at risk"), expression of genes mediating functions of primarily adaptive immunity, such as RASGRF2 (Ras protein-specific guanine nucleotide-releasing factor 2), KIAA1199 or CXCL3 was not significantly changed (see also FIGS. 5H and 5F). At phase 2 (representing GOLD stage I), expression of these genes remained stable or even decreased to some extent (see FIGS. 4A and 5A), probably reflecting the stabilizing outcome of regenerative repair efforts which was most intense at GOLD stage I (see also FIG. 6A). However, phase 3 which includes GOLD stages II and III was characterized by a significant increase of expression of all genes related to immunity including genes indicating increased AHR signaling, such as CYP1A1, CYP1A2 and CYP1B1 (see also FIGS. 5A, 5E and 5F). The latter ones most likely reflect the impact of cigarette smoking, all the more as three quarters of the participants were still actives smokers at this stage (see FIG. 3C). Increased gene expression reflecting intensified AHR signaling could be demonstrated in spite of elevated levels of the aryl hydrocarbon receptor repressor (AHRR) gene known to inhibit AHR signaling events, particularly during GOLD stages II and III.

Nonetheless, short-term analysis of gene expression addressing a development of COPD over a period of 3 years (see also FIGS. 5A and 5D, middle) indicates that the overall impact of AHR signaling on the deterioration of pulmonary function is more important than the additional expression of CEACAM5 which, comparable to FGG expression (see also FIG. 5D), seems to reflect the intensity of bronchitis much better. Phase 4 representing GOLD stage IV shows a striking downregulation of the majority of immune-related functions upregulated during earlier phases of COPD development, comparable to the regulation of genes controlling cellular regeneration and differentiation. Interestingly, however, this does not apply to the expression of KIAA1199 and RASGRF2 genes which are both upregulated even at GOLD stage IV, the latter one being again capable of influencing cellular movements by inhibition of the actin cytoskeleton (Calvo et al., 2011): RASGRF2 belongs to a group of activators of the GTPase RAS involved as well in the activation of T cells and required for the induction of NF-AT, IL-2 and TNF-α (Ruiz et al., 2007).

Within this context, the slow yet constant and highly significant upregulation of the guanine-nucleotide exchange factor (GEF) son of sevenless homolog 1 (SOS1) (see FIG. 8A), capable of continually activating RAS, could significantly contribute to the chronic inflammatory process facilitating the bronchial wall scarring characteristic for late stage COPD.

Members of the carcinoembryonic antigen-related cell adhesion molecule (CEACAM) family serve as cellular receptors for typical gram-negative bacteria frequently colonizing the surface of the human airways, such as *Neisseria meningitidis, Haemophilus influenzae* and *Moraxella catarrhalis* expressing opacity (Opa) proteins (Muenzner et al., 2010; Bookwalter et al., 2008; Muenzner et al., 2005). It was recently suggested that non-typable *Haemophilus influenzae* and *Moraxella catarrhalis* are able to increase the expression of their respective receptors on host cells (Klaile et al., 2013). However, no correlation between the expression of members of the CEACAM family and COPD was found under the conditions employed in that study. In the present study, only the expression of the CEACAM5 gene was significantly increased up to GOLD stage III, in that following the inflammatory reaction in general, while significantly decreasing afterwards in GOLD stage IV. This does not, however, exclude the aggravation of mucosal inflammation as a result of a persistent upregulation of CEACAM5, all the more as the expression of CEACAM5 was found to be increased in combination with a growing intensity of bronchial inflammation (see FIG. 5D).

CONCLUSIONS

Between 2007 and 2012, a controlled prospective pilot trial was conducted in finally 120 volunteers in order to identify metabolic markers indicative of the progression of COPD. By adopting parts of the design of the ECLIPSE trial (Vestbo et al., 2011), the largest and most elaborate study performed thus far to identify clinical markers describing both progress and variability of COPD, the Vienna COPD study combined controlled assessment of validated clinical measures with unsupervised assessment of genome-wide gene transcription in pulmonary tissue representing the focus of COPD pathology (Hogg J C, 2004 (b)). The correlation of gene expression with clinical development was based a) on the extent of non-reversible pulmonary obstruction at visit 1 (according to the Global Initiative for Obstructive Lung Disease; GOLD), b) on the worsening of non-reversible obstruction according to GOLD between visit 1 and 3 (covering a period of three years), and c) on symptoms indicative of an increasing intensity of bronchitis being recorded during structured clinical history at visits 1 and 3.

This analysis revealed changes of gene expression indicative of six major deviations from regular maintenance of pulmonary structure and defense: (1) Progressive loss of functions guiding epithelial and (2) vascular regeneration combined with (3) persistent and increasing activation of mechanism of fibroproliferative repair, together indicating a transition from regenerative to fibrotic repair during progression of COPD; (4) intensifying bronchial inflammation being antagonized at GOLD stage I when regenerative repair activity is highest, and culminating afterwards at GOLD stages II and III; (5) a complete loss of structural maintenance at GOLD stage IV connected to a finally failing immunity, both suggestive of the formation of scar tissue; and lastly, a rapid and persistent downregulation of functions controlling the intracellular distribution, aggregation and sequestration of actin polymers which form the cytoskeleton (6). The latter finding is of particular interest as the changes in the transcription of the corresponding genes, in particular the downregulation of TMSB15A, DPP6, NUDT11 and PRICKLE2, were already observed at GOLD stage 0 (COPD "at risk"), well before any change of pulmonary function was measurable. This striking loss occurs together with a significant increase of functions determining bronchial inflammation suggesting that these changes might be the first to predispose the bronchi to persistent inflammation. The outcome of such an early and simultaneous downregulation of the TMSB15A, DPP6, NUDT11 and PRICKLE2 genes will be discussed in the following.

Thymosin beta 15A (TMSB15A) belongs to the group of WH2 (WASP-homologue 2) domain binding proteins which are necessary for the depolymerization of actin filaments during cellular movements (Husson et al., 2010; Hertzog et al., 2004). Formation and rapid movement of actin filaments in turn are indispensable for processes such as cell division, intercalation and cellular extrusion. This applies as well to the regulation of apicobasal cell polarity (Nishimura et al., 2012), and even more important, to the formation and maintenance of tight and adherens junctions (Shen et al., 2005; Calautti et al., 2002). These complex membrane dynamics are not only an answer to external and internal stress, but also part of regular tissue growth and as such energy-dependent. The assembly of the actin skeleton is highly dynamic and creates a layer of epidermal cells acting as an impenetrable fluid-like shield composed of the constantly moving lipid border of the cells (Guillot et al., 2013). Thus, a persistent downregulation of TMSB15A is likely to prevent any fast adaptive arrangement of the surface lipid layers during cellular movements causing repeated perturbations of the epithelial barrier function.

DPP6, on the other hand, is known to stabilize the membrane potential by acting on membrane-bound potassium channels, and has also a profound impact on the organization of the actin cytoskeleton (Chifflet et al., 2003), supporting the perception of a failing barrier function. The same applies to the downregulation of NUDT11 gene expression. The nucleoside diphosphate linked moiety X (nudix)-type motif 11 (NUDT11) gene encodes a type 3 diphosphoinositol polyphosphate phosphohydrolase which generates energy-rich phosphates essential for vesicle trafficking, maintenance of cell-wall integrity in *Saccharomyces* and for the mediation of cellular responses to environmental salt stress (Dubois et al., 2002). As the adaptive assembly of F and G actin fibers within the cytoskeleton occurs in seconds, it is easily conceivable that energy-rich diphosphoinositol polyphosphates being integral constituents of any cell membrane will be utilized as rapidly accessible source of energy.

These findings point towards a synchronized dysregulation of genes necessary for upholding the epithelial barrier. Moreover, the downregulation of the PRICKLE2 gene was also shown to be vital for the formation of polarized epithelial layers during mouse embryogenesis (Tao et al., 2012). Decreased expression of all four genes (i.e., TMSB15A, DPP6, NUDT11 and PRICKLE2), however, was associated with significantly increased bronchial inflammation, suggesting a functional correlation between the downregulation of genes that guide functionally interrelated features of cytoskeleton assembly with the activation of bronchitis. This sheds a new light on the progression of bronchial inflammation as it indicates a direct connection between the loss of a protective epithelial shield and the aggravation of chronic bronchitis. Based on the physicochemical nature of such an effect, penetration of the epithelial membranes by any potential antigen or allergen is likely to be enhanced, particularly during intensified repair due to repeated smoke-induced damage or following viral infections. This could not only explain the remarkable heterogeneity of inflammatory conditions characteristic for COPD, but also the observation that the capacity to achieve intense cellular regeneration in spite of ongoing inflammation might be helpful in suppressing pro-inflammatory gene expression.

This view is further supported by the significant downregulation of the protease inhibitor cystatin M/E (CST6) during progression of COPD (see also FIG. 4A). CST6 is known to control the homeostasis of the stratum corneum, its deficiency in mice causing severe ichthyosis and neonatal lethality (Zeeuwen et al., 2009). The progressive loss of a protease inhibitor in later phases of COPD known to preserve the integrity of epithelial structures will most likely contribute to a failure of the protective barrier function, not only by a disintegration of the epithelial layer but also by facilitating the breakdown of the matrix itself.

In this context, the strong upregulation of the KIAA1199 gene which has been demonstrated to significantly increase the activity of matrix hyaluronidases, is probably equally important, as this upregulation is directly associated with a significant worsening of lung function, even within the relatively short observational period of the present study (see also FIG. 5B). It has recently been shown that matrix structures containing large amounts of high molecular mass hyaluronan as well as the inhibition of hyaluronidase activity protect against both inflammation and cancer progression (Tian et al., 2013). In summary, these findings provide the first conclusive evidence for a progressive breakdown of bronchial surface integrity during the course of COPD development causing growing non-specific bronchial inflammation that varies with frequency and intensity of the physicochemical assaults attacking the bronchial surfaces.

According to results described herein, the response to these assaults is a slow progressive scarring process in the peripheral bronchi, whereby the combined upregulation of CTHRC1, SOS1 and NTRK2 genes (see also FIG. 8A) is likely to indicate mechanisms of preferentially mesenchymal wound healing while the stage dependent expression of the PRRX1 and COMP genes suggests their participation in regular organ repair as well demonstrating the ambiguity between regular matrix support during regenerative repair and scar formation as a result of a progressive failure of the organ's regenerative repair capacity.

This fits well to the progressive downregulation of genes mainly controlling functions of regenerative growth of the vascular tree as demonstrated by the concomitant decrease of the expression of FIBIN, TAL1, BEX1/5, and Ghrelin (GHRL) genes (see also FIG. 8D). Here again, the increasing capacity of the peripheral lung to employ mechanisms of preferentially regenerative repair during GOLD stage I becomes evident as BEX1 and GHRL increase at this stage while progressively decreasing during further progression of COPD.

Thus, in the COPD AUVA study, the clinical progression of COPD has been successfully correlated with the biological analysis of gene expression in pulmonary tissue. In particular, it has been demonstrated that the expression of the genes KIAA1199, DMBT1, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and COMP is increased in pulmonary tissue samples from subjects prone to develop progressive COPD, while the expression of the genes TMSB15A, DPP6, SLC51B, NUDT11, PLA1A, HYAL2, CST6, ITGA10, CTHRC1, TAL1, FIBIN, BEX5, BEX1, ESM1 and GHRL is decreased in pulmonary tissue samples from subjects prone to develop progressive COPD, as compared to the expression of the corresponding genes in pulmonary tissue samples from healthy subjects. These molecular biomarkers can thus be used for assessing the susceptibility/proneness of a subject to develop progressive COPD in accordance with the present invention, particularly in the method of the second aspect of the invention. Moreover, it has also been demonstrated that the expression of the genes DMBT1, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and COMP is increased in pulmonary tissue samples from subjects suffering from or prone to suffer from stable COPD, while the expression of the genes KIAA1199, TMSB15A, DPP6, SLC51B, NUDT11, PLA1A, HYAL2, CST6, ITGA10, CTHRC1, TAL1, FIBIN, BEX5, BEX1, ESM1 and GHRL is decreased in pulmonary tissue samples from subjects suffering from or prone to suffer from stable COPD, as compared to the expression of the corresponding genes in pulmonary tissue samples from healthy subjects, indicating that these biomarkers are suitable for diagnosing stable COPD or assessing the susceptibility of a subject to develop stable COPD in accordance with the invention, particularly in the method of the third aspect of the invention.

REFERENCES

Agarwal P, et al. *J Biol Chem.* 2012; 287(27):22549-59. doi:10.1074/jbc.M111.335935.
Agarwal P, et al. *Matrix Biol.* 2013; 32(6):325-31. doi: 10.1016/j.matbio.2013.02.010.
Avcuoglu S, et al. *Am J Respir Cell Mol Biol.* 2011; 45(4):768-80. doi:10.1165/rcmb.2010-0195OC.
Béchard D, et al. *J Biol Chem.* 2001; 276(51):48341-9.
Bookwalter J E, et al. *Infect Immun.* 2008; 76(1):48-55.
Butt A Q, et al. *J Biol Chem.* 2012; 287(46):38665-79. doi:10.1074/jbc.M112.367490.
Calautti E, et al. *J Cell Biol.* 2002; 156:137-48.
Calvo F, et al. *Nat Cell Biol.* 2011; 13(7):819-26. doi: 10.1038/ncb2271.
Cantarella G, et al. *FASEB J.* 2002; 16(10):1307-9.
Caporali A, et al. *Circ Res.* 2008; 103(2):e15-26. doi: 10.1161/CIRCRESAHA.108.177386.
Chavez-Muñoz C, et al. *J Cell Biochem.* 2012; 113(8):2622-32. doi:10.1002/jcb.24137.
Chen L Y, et al. *J Int Med Res.* 2010; 38(2):498-510.
Chifflet S, et al. *Exp Cell Res.* 2003; 282(1):1-13.
Cockayne D A, et al. *PLoS One.* 2012; 7(6):e38629. doi: 10.1371/journal.pone.0038629.
Cole S P C, et al. *Monoclonal Antibodies and Cancer Therapy.* 1985; 27:77-96.
De Santis M, et al. *Respir Res.* 2011; 12:22. doi:10.1186/1465-9921-12-22.
Deleuze V, et al. *PLoS One.* 2012; 7(7):e40484. doi:10.1371/journal.pone.0040484.
Diegelmann J, et al. *J Biol Chem.* 2012; 287(1):286-98. doi:10.1074/jbc.M111.294355.
Ding C, et al. *J Biochem Mol Biol.* 2004; 37(1):1-10.
Dubois E, et al. *J Biol Chem.* 2002; 277:23755-63.
Duvoix A, et al. *Thorax.* 2013; 68(7):670-6. doi:10.1136/thoraxjnl-2012-201871.
Evensen N A, et al. *J Natl Cancer Inst.* 2013; 105(18):1402-16. doi:10.1093/jnci/djt224.
Frisch S M, et al. *J Cell Sci.* 2013; 126(Pt1):21-9. doi: 10.1242/jcs.120907.
Gentleman R, et al. *Genome Biology.* 2004; 5:R80.
Green, M R et al. *Molecular Cloning: A Laboratory Manual.* Cold Spring Harbor Laboratory Press. Fourth Edition. 2012. ISBN: 978-1936113422.
Guillot C, et al. *Science.* 2013; 340:1185-9.
Halbert R J, et al. *Eur Respir J.* 2006; 28:523-32.
Han Y, et al. *Biochem Biophys Res Commun.* 2008; 366(3): 685-91.
Han M K, et al. *Am J Respir Crit Care Med.* 2010; 182:598-604.
Hannappel E. *Ann N Y Acad Sci.* 2007; 1112:21-37. doi: 10.1196/annals.1415.018.
Harlow E, et al. Using Antibodies: A Laboratory Manual. Cold Spring Harbor Laboratory Press. 1998. ISBN: 978-0879695446.
Harnoncourt K, et al. *Osterreich Arzteztg.* 1982; 37:1640-2.
Hertzog M, et al. *Cell.* 2004; 117:611-623.
Hogg J C, et al. *N Engl J Med.* 2004; 350:2645-2653. (a)
Hogg J C. *Lancet.* 2004; 364:709-721. (b)
Huff T, et al. *Int J Biochem Cell Biol.* 2001; 33:205-220. doi:10.1016/51357-2725(00)00087-X.
Hurst J R, et al. *N Engl J Med.* 2010; 363:1128-1138.
Husson C, et al. *Ann N Y Acad Sci.* 2010; 1194:44-52. doi:10.1111/j.1749-6632.2010.05473.x.
Jerng H H, et al. *PLoS One.* 2012; 7(6):e38205. doi:10.1371/journal.pone.0038205.
Jiang F, et al. *Exp Biol Med* (Maywood). 2008; 233(3):286-96. doi:10.3181/0707-RM-177.
Johnson W E, et al. *Biostatistics.* 2007; 8(1):118-127.
Kaemmerer E, et al. *Histopathology.* 2012; 60(4):561-9.doi: 10.1111/j.1365-2559.2011.04159.x.
Kim N H, et al. *J Invest Dermatol.* 2010; 130(9):2231-9. doi:10.1038/jid.2010.99.
Klaile E, et al. *Respir Res.* 2013; 14:85. doi:10.1186/1465-9921-14-85.
Köhler G, et al. *Nature.* 1975; 256(5517):495-7.
Kong B, et al. *Oncogene.* 2010; 29(37):5146-58. doi: 10.1038/onc.2010.258.
Kothapalli D, et al. *J Cell Biol.* 2007; 176:535-44.
Kozbor D, et al. *Immunol Today.* 1983; 4(3):72-9.
Lei W, et al. *Am J Physiol Lung Cell Mol Physiol.* 2007; 293(5):L1359-68.
Li A, et al. *Biochem Biophys Res Commun.* 2007; 353(2): 238-43.
Lin L, et al. *Nat Commun.* 2013; 4:2270. doi:10.1038/ncomms3270.
Malinda K M, et al. *J Invest Dermatol.* 1999; 113(3):364-8. doi:10.1046/j.1523-1747.1999.00708.x.
Mazzochi C, et al. *Am J Physiol Renal Physiol.* 2006; 291(6):F1113-22.
Medina A, et al. *Mol Cell Biochem.* 2007; 305:255-64.
Metzger D E, et al. *Dev Biol.* 2008; 320(1):149-60. doi: 10.1016/j.ydbio.2008.04.038.
Mimae T, et al. *Thorax.* 2013. doi:10.1136/thoraxjnl-2013-203867.
Muenzner P, et al. *J Cell Biol.* 2005; 170(5):825-36. doi: 10.1083/jcb.200412151
Muenzner P, et al. *Science.* 2010; 329(5996):1197-201. doi:10.1126/science.1190892.
Murray C J L, et al. *Lancet.* 1997; 349:1498-504.
Nadin B M, et al. *PLoS One.* 2013; 8(4):e60831. doi: 10.1371/journal.pone.0060831.
Nakahigashi K, et al. *J Invest Dermatol.* 2011; 131(4):865-73. doi:10.1038/jid.2010.395.
Nishimura T, et al. *Cell.* 2012; 149(5):1084-97. doi:10.1016/j.cell.2012.04.021.
Ocaña O H, et al. *Cancer Cell.* 2012; 22(6):709-24. doi: 10.1016/j.ccr.2012.10.012.
Paffett-Lugassy N, et al. *Nat Cell Biol.* 2013; 15(11):1362-9. doi:10.1038/ncb2862.
Pauwels, R A et al. *Am J Respir Crit Care Med.* 2001; 163(5):1256-76.
Price D, et al. *Prim Care Respir J.* 2011; 20(1):15-22. doi:10.4104/perj.2010.00060.
Puré E, et al. *Cell Signal.* 2009; 21(5):651-5. doi:10.1016/j.cellsig.2009.01.024.
Rabe K F, et al. *Am J Respir Crit Care Med.* 2007; 176(6):532-55.

Rezaeian F, et al. *Am J Physiol Heart Circ Physiol.* 2012; 302(3):H603-10. doi:10.1152/ajpheart.00390.2010.
Roudnicky F, et al. *Cancer Res.* 2013; 73(3):1097-106. doi:10.1158/0008-5472.CAN-12-1855.
Ruiz S, et al. *Mol Cell Biol.* 2007; 27(23):8127-42.
Shen L, et al. *Mol Bio Cell.* 2005; 16:3919-36.
Smyth G K. limma: linear models for microarray data. In: Gentleman R, et al. Bioinformatics and Computational Biology Solutions using R and Bioconductor. 2005. Springer, New York, pages 397-420.
Spector I, et al. *Am J Pathol.* 2013; 182(3):905-16. doi:10.1016/j.ajpath.2012.11.004.
Tao H, et al. *Dev Biol.* 2012; 364(2):138-48. doi:10.1016/j.ydbio.2012.01.025.
Tian X, et al. *Nature.* 2013; 499(7458):346-9. doi:10.1038/nature12234.
Toole B P. *Nat Rev Cancer.* 2004; 4(7):528-39.
U S Burden of Disease Collaborators. *JAMA.* 2013; 310(6):591-608.
Vestbo J, et al. *N Engl J Med.* 2011; 365(13):1184-92.
Vestbo J, et al. *Am J Respir Crit Care Med.* 2013; 187(4):347-65. doi:10.1164/rccm.201204-0596P P.
Wang L, et al. *Peptides.* 2012; 33(1):92-100. doi:10.1016/j.peptides.2011.11.001.
Wakahara T, et al. *Dev Biol.* 2007; 303(2):527-35.
Wedzicha J A. *Thorax.* 2000; 55:631-632.
Wu Q, et al. *Innate Immun.* 2012; 18(4):617-26. doi:10.1177/1753425911429837.
Yaniw D, et al. *Cell Res.* 2005; 15(6):423-9.
Yoshida H, et al. *Proc Natl Acad Sci USA.* 2013; 110(14):5612-7. doi:10.1073/pnas.1215432110.
Zeeuwen P L J M, et al. *J Invest Dermatol.* 2009; 129:1327-38. doi:10.1038/jid.2009.40.
Zeeuwen P L J M, et al. *FASEB J.* 2010; 24:3744-55. doi:10.1096/fj.10-155879.
Zhang S M, et al. *Biotech Histochem.* 2012; 87(3):172-8. doi:10.3109/10520295.2011.577754.

The invention claimed is:

1. A method of identifying and treating a human subject that is prone to develop progressive COPD involving the appearance of irreversible lung damage, the method comprising the steps of:
   a) obtaining a lung sample from the human subject;
   b) assaying the level of transcription of DMBT1 and KIAA1199 in the lung sample obtained from the human subject;
   c) identifying the human subject as prone to develop progressive COPD based on a decreased level of transcription of DMBT1 and an increased level of transcription of KIAA1199 in the lung sample from the human subject as compared to the transcription levels of DMBT1 and KIAA1199 in a control subject suffering from stable COPD; and
   d) administering a drug against COPD to the human subject identified as prone to develop progressive COPD.

2. The method of claim 1, wherein the method further comprises:
   in step b), assaying the level of transcription of one or more further genes selected from the group consisting of ELF5, AZGP1, PRRX1, AQP3, GPR110, GDF15, RASGRF2, RND1, FGG, CEACAM5, HYAL2, AHRR, CXCL3, CYP1A1, CYP1B1, CYP1A2, CST6, NTRK2, COMP, ITGA10, CTHRC1, TAL1, BEX1 and GHRL in the lung sample obtained from the human subject;
   in step c), identifying the human subject as prone to develop progressive COPD based on increased levels of transcription of KIAA1199, GPR110, GDF15, RASGRF2, RND1, FGG, CEACAM5, HYAL2, AHRR, CXCL3, CYP1A1, CYP1B1, CYP1A2, CST6, NTRK2 and TAL1 and decreased levels of transcription of DMBT1, ELF5, AZGP1, PRRX1, AQP3, COMP, ITGA10, CTHRC1, BEX1 and GHRL in the lung sample from the human subject as compared to the transcription level of KIAA1199, GPR110, GDF15, RASGRF2, RND1, FGG, CEACAM5, HYAL2, AHRR, CXCL3, CYP1A1, CYP1B1, CYP1A2, CST6, NTRK2, TAL1, DMBT1, ELF5, AZGP1, PRRX1, AQP3, COMP, ITGA10, CTHRC1, BEX1 and GHRL in a control subject suffering from stable COPD.

3. The method of claim 2, wherein in step b) the level of transcription of at least one further gene selected from FGG, CYP1A1, CEACAM5, CTHRC1, NTRK2 and RASGRF2 is assayed in the lung sample obtained from the human subject.

4. The method of claim 2, wherein in step b) the level of transcription of at least one further gene selected from ELF5, AZGP1, PRRX1, AQP3, GPR110, GDF15, RASGRF2 and RND1 is assayed in the lung sample obtained from the human subject.

5. The method of claim 1, wherein the lung sample obtained from the human subject is a lung tissue sample.

6. The method of claim 1, wherein the lung sample obtained from the human subject is a transbronchial lung biopsy sample or a bronchoalveolar lavage sample.

7. The method of claim 1, wherein the level of transcription is assayed using a quantitative reverse transcriptase polymerase chain reaction.

8. The method of claim 1, wherein the level of transcription is assayed using a microarray.

9. The method of claim 1, wherein the drug against COPD is bitolterol, carbuterol, fenoterol, pirbuterol, procaterol, reproterol, rimiterol, salbutamol, levosalbutamol, terbutaline, tulobuterol, arformoterol, bambuterol, clenbuterol, formoterol, olodaterol, salmeterol, indacaterol, beclometasone, betamethasone, budesonide, ciclesonide, flunisolide, fluticasone, mometasone, triamcinolone, aclidinium bromide, glycopyrronium bromide, ipratropium bromide, oxitropium bromide, tiotropium bromide, cromoglicate, nedocromil, acefylline, ambuphylline, bamifylline, doxofylline, enprofylline, etamiphylline, proxyphylline, theobromine, theophylline, aminophylline, choline theophyllinate, montelukast, pranlukast, zafirlukast, zileuton, ramatroban, seratrodast, ibudilast, roflumilast, amlexanox, eprozinol, fenspiride, omalizumab, epinephrine, hexoprenaline, isoprenaline, isoproterenol, orciprenaline, metaproterenol, atropine, or a pharmaceutically acceptable salt of any of the aforementioned agents, or any combination thereof.

10. The method of claim 9, wherein the drug against COPD is roflumilast.

* * * * *